(12) United States Patent
Borriello et al.

(10) Patent No.: US 9,181,279 B2
(45) Date of Patent: *Nov. 10, 2015

(54) CYCLIC AMINE DERIVATIVES AS EP$_4$ RECEPTOR ANTAGONISTS

(75) Inventors: Manuela Borriello, Monza (IT); Sabrina Pucci, Bernareggio (IT); Luigi Piero Stasi, Monza (IT); Lucio Rovati, Monza (IT)

(73) Assignee: ROTTAPHARM BIOTECH S.R.L., Monza (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/130,451

(22) PCT Filed: Jul. 4, 2011

(86) PCT No.: PCT/EP2011/061226
§ 371 (c)(1),
(2), (4) Date: Dec. 31, 2013

(87) PCT Pub. No.: WO2013/004290
PCT Pub. Date: Jan. 10, 2013

(65) Prior Publication Data
US 2015/0087626 A1    Mar. 26, 2015

(51) Int. Cl.
*C07D 221/04* (2006.01)
*C07D 471/08* (2006.01)
*C07D 211/34* (2006.01)
*C07D 221/20* (2006.01)
*C07D 401/06* (2006.01)
*C07F 1/02* (2006.01)
*C07D 207/16* (2006.01)
*C07D 209/52* (2006.01)
*C07D 209/54* (2006.01)
*C07D 211/60* (2006.01)
*C07D 453/06* (2006.01)
*C07F 7/18* (2006.01)
*C07D 205/04* (2006.01)

(52) U.S. Cl.
CPC .............. *C07F 1/02* (2013.01); *C07D 205/04* (2013.01); *C07D 207/16* (2013.01); *C07D 209/52* (2013.01); *C07D 209/54* (2013.01); *C07D 211/34* (2013.01); *C07D 211/60* (2013.01); *C07D 221/04* (2013.01); *C07D 221/20* (2013.01); *C07D 401/06* (2013.01); *C07D 453/06* (2013.01); *C07D 471/08* (2013.01); *C07F 7/1852* (2013.01); *C07F 7/1856* (2013.01)

(58) Field of Classification Search
CPC .. C07D 207/34; C07D 213/64; C07D 333/68; C07D 211/88; C07D 211/22; C07D 255/41; C07D 209/52; C07D 211/60; C07D 221/04; C07D 471/08
USPC .................................................. 546/220, 221
See application file for complete search history.

(56) References Cited

FOREIGN PATENT DOCUMENTS

EP       2277858       1/2011
WO    2005105733     11/2005

OTHER PUBLICATIONS

International Preliminary Report on Patentability dated Jul. 22, 2013 corresponding to International Application No. PCT/EP2011/061226; 5 pages.
International Search Report dated Dec. 22, 2011 corresponding to International Application No. PCT/EP2011/061226; 4 pages.
Written Opinion dated Dec. 22, 2011 corresponding to International Application No. PCT/EP2011/061226; 4 pages.

*Primary Examiner* — Rita Desai
(74) *Attorney, Agent, or Firm* — Ohlandt Greeley Ruggiero & Perle L.L.P.

(57) ABSTRACT

There is described a novel group of cyclic amine derivative compounds, having an EP$_4$ receptor antagonistic activity and specifically pharmaceutical compounds which are useful for the treatment or alleviation of Prostaglandin E mediated diseases.

The present invention therefore relates to novel compounds which are selective antagonists of the EP$_4$ subtype of PGE$_2$ receptors with analgesic and antinflammatory activity, processes for their preparation, pharmaceutical compositions containing them and their use as medicaments, inter alia for the treatment or alleviation of Prostaglandin E mediated diseases such as acute and chronic pain, osteoarthritis, inflammation-associated disorder as arthritis, rheumatoid arthritis, cancer, migraine and endometriosis.

28 Claims, No Drawings

CYCLIC AMINE DERIVATIVES AS $EP_4$ RECEPTOR ANTAGONISTS

FIELD OF THE INVENTION

The present invention relates to novel cyclic amine derivative compounds, processes for their preparation, pharmaceutical compositions containing them and their use as medicaments, inter alia for the treatment or alleviation of Prostaglandin E mediated diseases such as acute and chronic pain, osteoarthritis, inflammation-associated disorder as arthritis, rheumatoid arthritis, cancer, migraine and endometriosis.

The cyclic amine derivative compounds of the invention are selective $EP_4$ receptor antagonists.

BACKGROUND OF THE INVENTION

A number of review articles describe the characterization and therapeutic relevance of the prostanoid receptors as well as the most commonly used selective agonists and antagonists; *Eicosanoids: From Biotechnology to therapeutic Applications*, Folco, Samuelson, Maclouf and Velo eds, Plenum Press, New York, 1996, chap. 14, 137-154; *"Molecular aspects of the structures and functions of the prostaglandin E receptors"*, Journal of Lipid Mediators and Cell Signalling, 1996, 14, 83-87; *"Function of prostanoid receptors: studies on knockout mice"*, Prostaglandins & other Lipid Mediators, 2002, 68-69, 557-573 and *"Prostanoid receptor antagonists: development strategies and therapeutic applications"*, British Journal of Pharmacology (2009), 158, 104-145. Prostaglandin $E_2$ ($PGE_2$) is a member of the prostanoid family with a variety of physiological effects, including mucosal protection, induction of gastric acid secretion in stomach, generation of fever, hyperalgesia, inflammation and immunity. These actions of prostaglandin $PGE_2$ are mediated by four G-protein-coupled $PGE_2$ receptors, $EP_1$, $EP_2$, $EP_3$ and $EP_4$. The prostaglandin $PGE_2$, in fact, has affinity for all of these EP receptors (SubTypes $EP_1$, $EP_2$, $EP_3$, $EP_4$, respectively).

The $EP_4$ receptor is a 7-transmembrane receptor whose activation is normally associated with elevation of intracellular cyclic adenosine monophosphate (cAMP) levels. $PGE_2$-activated $EP_4$ receptor signalling may be involved in various pathologic states, such as pain (in particular inflammatory, neuropathic and visceral), inflammation, neuroprotection, cancer, dermatitis, bone disease, immune system dysfunction promotion of sleep, renal regulation, gastric or enteric mucus secretion and duodenal bicarbonate secretion.

In The Journal of Immunology (2008, 181, 5082-5088) studies suggest that $PGE_2$ inhibits proteoglycan synthesis and stimulates matrix degradation in osteoarthritic chondrocytes via the $EP_4$ receptor. Targeting $EP_4$, rather than cyclooxygenase 2, could represent a future strategy for osteoarthritis disease modification.

In European Journal of Pharmacology (2008, 580, 116-121) studies suggest that that a pharmacological blockade of the prostanoid $EP_4$ receptor may represent a new therapeutic strategy in signs and symptomatic relief of osteoarthritis and/or rheumatoid arthritis.

Patent application publications WO2005021508, WO2005105732, WO2005105733, WO2007121578 and WO2009139373 disclose compounds as being useful in the treatment of prostaglandin mediated diseases.

SUMMARY OF THE INVENTION

One of the objects of the present invention is the provision of compounds having an $EP_4$ receptor antagonistic activity and specifically pharmaceutical compounds which are useful for the treatment or alleviation of Prostaglandin E mediated diseases.

The inventors of the present application have discovered novel compounds that are selective antagonists of the $EP_4$ subtype of $PGE_2$ receptors. Specifically, the compounds according to the invention are provided with analgesic and antinflammatory activity.

In accordance with a general aspect, the present invention provides a cyclic amine compound of Formula (I):

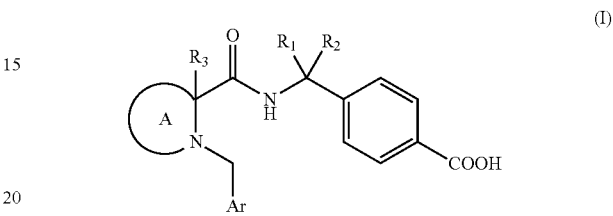

or a pharmaceutically acceptable salt or derivative thereof, wherein:

$R_1$ and $R_2$ are independently of each other hydrogen, linear or branched $C_{1-3}$ alkyl or are joined together to form a cyclopropyl ring;

A is selected from

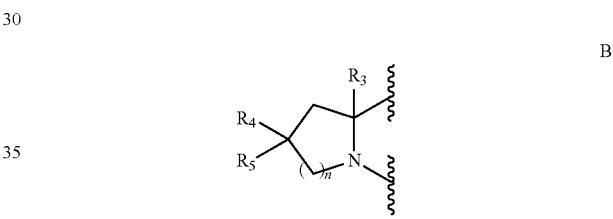

B

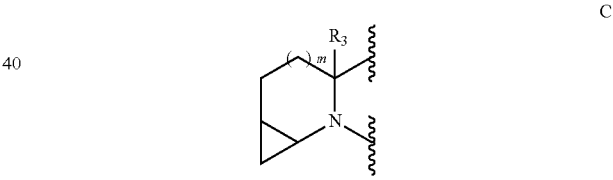

C

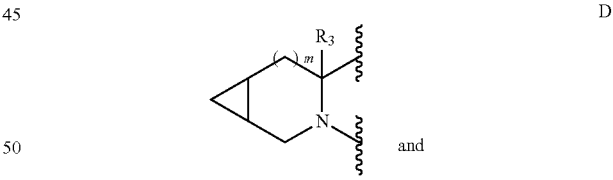

D and

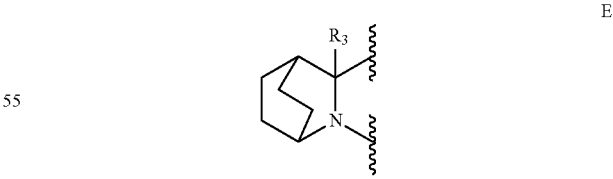

E wherein:
n=0, 1 or 2
m=0 or 1
$R_3$ is H or linear or branched $C_{1-3}$ alkyl
$R_4$ and $R_5$ are independently hydrogen, fluorine, linear or branched $C_{1-3}$ alkyl or joined together they form a cyclopropyl ring, Ar is phenyl having:
  i. in 4-position one substituent selected from the group consisting of halogen, cyano, trifluoromethyl, or
  ii. in 3-position one substituent selected from the group consisting of halogen, cyano, trifluoromethyl, provided that
    ii.a. when A is B, both $R_4$ and $R_5$ are fluorine, linear or branched $C_{1-3}$ alkyl or joined together they form a cyclopropyl ring,
    ii.b. A is C and m is 0
    ii.c. A is D and m is 1.

a 5-membered heteroaromatic ring containing 1 to 3 heteroatoms wherein said heteroatoms independently of each others are S, O or N; or a 6-membered heteroaromatic ring containing 1 to 3 N.

In certain embodiments, the 6-membered heteroaromatic ring is substituted, preferably in 4 position, with halogen, cyano or trifluoromethyl.

The term "halogen" as used herein refers to a fluorine, chlorine, bromine or iodine atom. In certain embodiments the halogen is chlorine or fluorine.

The term "$C_{1-3}$ alkyl" as used herein refers to a linear or branched saturated hydrocarbon group containing of 1 to 3 carbon atoms. Examples of such groups include methyl, ethyl, n-propyl, isopropyl.

In this invention compounds of Formula (I) may exist as R and S enantiomers and as racemic mixture. This invention includes in its scope of protection all the possible isomers and racemic mixtures. Wherever should be present further symmetry centres, this invention includes all the possible diastereoisomers and relative mixtures as well.

In another aspect the invention concerns a compound of Formula (I) as medicament, in particular it concerns its use for the treatment of pathologies where an antagonist of the $EP_4$ receptor is needed, such as the treatment of acute and chronic pain, inflammatory pain, osteoarthritis, inflammation-associated disorder as arthritis, rheumatoid arthritis, cancer endometriosis and migraine.

DETAILED DESCRIPTION OF THE INVENTION

The invention thus concerns, in a general aspect, cyclic amine derivatives of Formula (I):

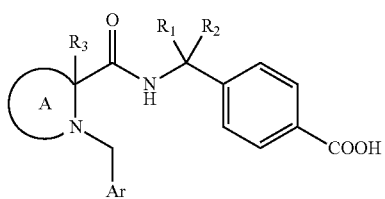
(I)

or a pharmaceutically acceptable salt thereof,
wherein:
  $R_1$ and $R_2$ are independently hydrogen, linear or branched $(C_{1-3})$alkyl or joined together they form a cyclopropyl ring;

A is selected from the group consisting of:

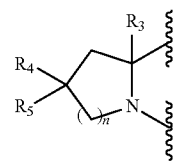
B

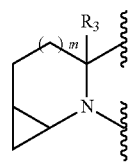
C

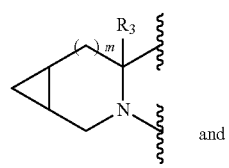
D
and

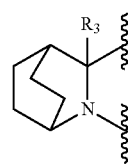
E wherein:
  n=0, 1 or 2
  m=0 or 1
  $R_3$ is H or linear or branched $C_{1-3}$ alkyl,
  $R_4$ and $R_5$ are independently hydrogen, fluorine, linear or branched $C_{1-3}$ alkyl or joined together they form a cyclopropyl ring,
  Ar is
  phenyl having:
    i. in 4-position one substituent selected from the group consisting of halogen, cyano, trifluoromethyl, or
    ii. in 3-position one substituent selected from the group consisting of halogen, cyano, trifluoromethyl, provided that
      ii.a. A is B, and both $R_4$ and $R_5$ are fluorine, linear or branched $C_{1-3}$ alkyl or are joined together to form a cyclopropyl ring,
      ii.b. A is C and m is 0,
      ii.c. A is D and m is 1.
  a 5-membered heteroaromatic ring containing 1 to 3 heteroatoms wherein said heteroatoms independently of each others are S, O or N; or
  a 6-membered heteroaromatic ring containing 1 to 3 N.

In certain embodiments Ar is phenyl substituted in 4 position with halogen, cyano, or trifluoromethyl.

In certain embodiments Ar is phenyl substituted in 4 position with trifluoromethyl.

In certain embodiments the heteroatom of the 5-membered heteroaromatic ring is N.

In certain embodiments, either the 5-membered heteroaromatic and the 6-membered heterocyclic rings are substituted with halogen, cyano or trifluoromethyl. In these embodiments said halogen preferably is fluorine or chlorine and according to an embodiment the halogen is fluorine.

Examples of a suitable 5-membered heteroaromatic ring containing 1 to 3 heteroatoms selected from S, O e N, include pyrrolyl, imidazolyl, pirazolyl, triazolyl, furanyl, oxazolyl, oxadiazolyl, thienyl, thiazolyl, thiadiazolyl and the like.

Examples of a 6-membered heteroaromatic ring containing 1 to 3 N include pyridyl, pyrimidinyl, pyrazinyl and triazinyl.

In one embodiment the 6-membered heteroaromatic ring is pyridyl. In this embodiment the pyridyl ring is substituted, preferably in 4 position, with halogen, cyano or trifluoromethyl.

It will be understood that, as used herein, references to the compounds of Formula (I) are meant to include the compounds of Formulae (IB), (IC), (ID), (IE) as described hereinafter, where appropriate.

In a first aspect of the invention, cyclic amine derivative of Formula (I) contains A which is the ring B.

In accordance with this aspect a subset of compounds of Formula (IB) is provided

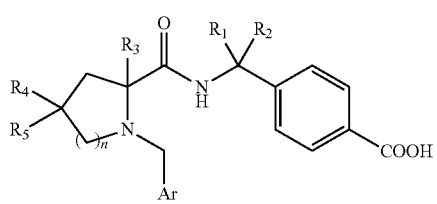

(IB)

and/or pharmaceutically acceptable derivatives or salts thereof, wherein:

n=0, 1 or 2

$R_1$ and $R_2$ are independently hydrogen, linear o branched $C_{1-3}$ alkyl, or joined together they form a cyclopropyl ring.

$R_3$ is H or linear or branched $(C_{1-3})$alkyl, $R_4$ and $R_5$ are independently hydrogen, fluorine, linear or branched $(C_{1-3})$alkyl or joined together they form a cyclopropyl ring, Ar is phenyl having:
  i. in 4-position one substituent selected from the group consisting of halogen, cyano, trifluoromethyl, or
  ii. in 3-position one substituent selected from the group consisting of halogen, cyano, trifluoromethyl, provided that both $R_4$ and $R_5$ are fluorine, linear or branched $C_{1-3}$ alkyl or joined together they form a cyclopropyl ring, a 5-membered heteroaromatic ring containing 1 to 3 heteroatoms wherein said heteroatoms independently of each others are S, O or N; or a 6-membered heteroaromatic ring containing 1 to 3 N.

In certain embodiments n is 1 or 2 and preferably is 2.

In accordance to certain embodiments $R_1$ and $R_2$ are joined together to form a cyclopropyl ring.

In certain embodiments $R_3$ is H or methyl and preferably is H.

In certain embodiments, $R_4$ and $R_5$ are independently hydrogen, fluorine, a linear or branched $C_{1-3}$ alkyl, tipically methyl, or joined together they form a cyclopropyl ring.

In certain embodiments $R_4$ and $R_5$ are both methyl.

In certain embodiments wherein Ar is phenyl, the halogen is fluorine or chlorine and according to specific embodiment the halogen is fluorine.

In certain embodiments, $R_4$ and $R_5$ are H and Ar is phenyl having in 4-position one substituent selected from the group consisting of halogen, cyano and trifluoromethyl.

In certain embodiments $R_4$ and $R_5$ are together, halogen, preferably fluorine, a linear or branched $C_{1-3}$ alkyl, or are fused to form a cyclopropyl and Ar is phenyl having in 3 or 4-position one substituent selected from the group consisting of halogen, cyano, trifluoromethyl.

In certain embodiments Ar is phenyl having in 3-position one substituent selected from trifluoromethyl or fluorine.

In certain embodiments, either the 5-membered heteroaromatic and the 6-membered heterocyclic rings are substituted with halogen, cyano or trifluoromethyl. In these embodiments said halogen preferably is fluorine or chlorine.

In certain embodiments the 6-membered heteroarocyclic ring is pyridyl.

In certain embodiments n is 1; $R_4$ and $R_5$ are independently selected from H, fluorine or methyl, or both $R_4$ and $R_5$ are fluorine or methyl.

In other embodiments n is 2, both $R_4$ and $R_5$ are fluorine.

According to an embodiment n is 2, $R_4$ and $R_5$ are joined together to form a cyclopropyl ring.

In certain embodiments n is 2, Ar is phenyl substituted in 4-position with one substituent selected from the group consisting of fluorine, chlorine, cyano, trifluoromethyl, preferably trifluoromethyl and $R_1$, $R_2$, $R_3$, $R_4$, $R_5$, are as defined above.

In a second aspect of the invention, the cyclic amine derivative of Formula (I) contains A which is the ring C.

In accordance with this aspect a subset of compounds of Formula (IC) is provided:

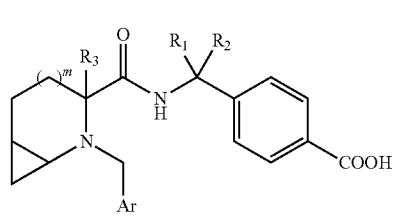

(IC)

and/or pharmaceutically acceptable salts or derivatives thereof, wherein m, $R_1$ $R_2$, $R_3$ and Ar are as above described in general, unless otherwise specified.

In certain embodiments m is 1.

In certain embodiments, $R_1$ and $R_2$ are independently hydrogen, linear or branched $C_{1-3}$ alkyl, tipically methyl, or joined together they form a cyclopropyl ring.

In certain embodiments $R_3$ is H or linear o branched $C_{1-3}$ alkyl, tipically methyl.

In certain embodiments $R_3$ is H.

In certain embodiments, Ar is phenyl having
  in 4-position one substituent selected from the group consisting of
    halogen, cyano, trifluoromethyl, wherein halogen typically is fluorine, or
  in 3-position one substituent selected from group consisting of halogen, cyano, trifluoromethyl, provided that m is 0;

In certain embodiments, either the 5-membered heteroaromatic and the 6-membered heterocyclic rings are substituted, preferably in 4 position, with halogen, cyano or trifluoromethyl.

In one embodiment the 6-membered heteroarocyclic ring is pyridyl.

In certain embodiments m is 0 and Ar is phenyl substituted in 4 position with fluorine, chlorine, cyano, or trifluoromethyl, preferably with trifluoromethyl, and $R_1$, $R_2$, $R_3$ are as defined above.

In a third aspect of the invention, the cyclic amine derivative of Formula (I) contains A which is the ring D.

In accordance with this aspect a subset of compounds of Formula (ID) is provided:

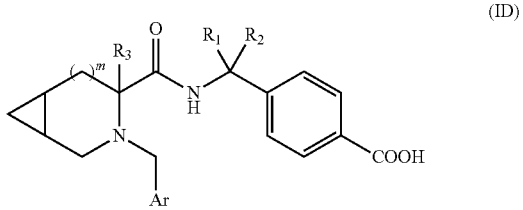

(ID)

and/or pharmaceutically acceptable derivatives or salts thereof, wherein m, $R_1$, $R_2$, $R_3$ and Ar are as above described in general, unless otherwise specified, In certain embodiments of this aspect, m is 1.

In certain embodiments, $R_1$ and $R_2$ are independently hydrogen, linear or branched $C_{1-3}$ alkyl, or joined together they form a cyclopropyl ring.

In certain embodiments $R_3$ is H or linear o branched $C_{1-3}$ alkyl, tipically methyl.

In certain embodiments $R_3$ is H.

In certain embodiments, Ar is phenyl, having
in 4-position one substituent selected from the group consisting of
halogen, cyano, trifluoromethyl,
in 3-position one substituent selected from group consisting of halogen,
cyano, trifluoromethyl, provided that m is 1.

In certain embodiments Ar is phenyl as defined above and having in one or both 2 and 6 positions a moiety selected from the group consisting of H, halogen, cyano, trifluoromethyl, or linear or branched $C_{1-3}$ alkyl.

In certain embodiments, either the 5-membered heteroaromatic and the 6-membered heterocyclic rings are substituted, preferably in 4 position, with halogen, cyano or trifluoromethyl.

In one preferred embodiment the 6-membered heteroarocyclic ring is pyridyl.

In certain embodiments m is 1 and Ar is phenyl substituted in 4 position with one substituent selected from the group consisting of halogens, cyano, trifluorormethyl, preferably trifluoromethyl and $R_1$, $R_2$, $R_3$ are as defined above.

In a fourth aspect of the invention, the cyclic amine derivative of Formula (I) contains A which is the ring E.

In accordance with this aspect a subset of compounds of Formula (IE) is provided:

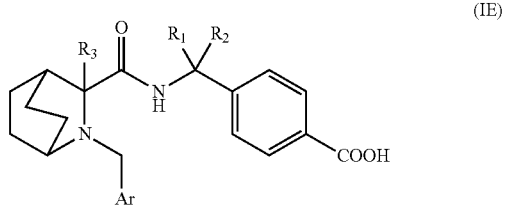

(IE)

and/or pharmaceutically acceptable derivatives or salts thereof, wherein $R_1$, $R_2$, $R_3$ and Ar are as above described in general, unless otherwise specified.

In certain embodiments, $R_1$ and $R_2$ are independently hydrogen, linear o branched $C_{1-3}$ alkyl, or joined together they form a cyclopropyl ring.

In certain embodiments $R_3$ is H or linear or branched $C_{1-3}$ alkyl, preferably $R_3$ is H.

In certain embodiments, Ar is phenyl, substituted in 4 position with one substituent selected from the group consisting of halogen, cyano and trifluoromethyl.

In certain embodiments, Ar is
phenyl, having in 4-position one substituent selected from the group consisting of halogen, cyano, trifluoromethyl.

In certain embodiments, Ar is phenyl, having in 4-position one substituent selected from the group consisting of halogen, cyano and trifluoromethyl.

In certain embodiments Ar is phenyl as defined above and having in one or both 2 and 6 positions a moiety selected from the group consisting of H, halogen, cyano, trifluoromethyl, or linear or branched $C_{1-3}$ alkyl.

In certain embodiments, either the 5-membered heteroaromatic and the 6-membered heterocyclic rings are substituted, preferably in 4 position, with halogen, cyano or trifluoromethyl.

In one preferred embodiment the 6-membered heteroarocyclic ring is pyridyl.

The term "pharmaceutically acceptable salts" as used herein, refers to salts prepared from pharmaceutically acceptable non-toxic bases or acids including inorganic or organic bases and inorganic or organic acids, quaternary ammonium salts and internally formed salts.

Salts derived from inorganic bases include aluminium, ammonium, calcium, copper, ferric, ferrous, lithium, magnesium, manganese salts, manganous, potassium, sodium, zinc, and the like. Preferred are the ammonium, calcium, magnesium, litium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethyl-aminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methyl-glucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula (I) are meant to also include the pharmaceutically acceptable salts or derivatives.

Furthermore, the compound of the formula (I) may form an acid addition salt or a salt with a base, depending on the kind of the substituents, and these salts are included in the present invention, as long as they are pharmaceutically acceptable salts.

The compounds (I) of the invention may be in crystalline forms. In certain embodiments, the crystalline forms of the compounds (I) are polymorphs.

The terms "the compound of the invention" and "the compounds of the present invention" refer to each of the compounds of formulae (I), (IB), (IC), (ID), (IE) and are meant to include their pharmaceutically acceptable salts, hydrates, solvates, and crystalline forms and also any suitable forms as illustrated hereinafter.

In certain embodiments, the compound of the Formula (I) may exist in the form of other tautomers or geometrical isomers in some cases, depending on the kinds of the substituents. In the present specification, the compound may be described in only one form of such isomers, but the present invention includes such isomers, isolated forms of the isomers, or a mixture thereof.

Furthermore, the compound of the Formula (I) may have asymmetric carbon atoms or axial asymmetries in some cases, and correspondingly, it may exist in the form of optical isomers such as an (R)-form, an (S)-form, and the like. The present invention includes both a mixture and an isolated form of these optical isomers.

Within the scope of the present invention are therefore included all stereoisomeric forms, including enantiomers, diastereoisomers, and mixtures thereof, including racemates and the general reference to the compounds of formulae (I), (IB), (IC), (ID), (IE) include all the stereoisomeric forms, unless otherwise indicated.

Additionally, the pharmaceutically acceptable prodrugs of the compound of the formula (I) are also included in the present invention. The pharmaceutically acceptable prodrug refers to a compound having a group which can be converted into an amino group, OH, CO2H, or the like, by solvolysis or under a physiological condition. Examples of the groups for forming a prodrug include those as described in Prog. Med., 5, 2157-2161 (1985) or "Pharmaceutical Research and Development" (Hirokawa Publishing Company, 1990), vol. 7, Drug Design, 163-198.

Additionally, the present invention in certain embodiments also includes various hydrates or solvates, and polymorphism of the compound of the formula (I) and a pharmaceutically acceptable salt thereof. Furthermore, the present invention also includes the compounds labelled with various radioactive isotopes or non-radioactive isotopes.

Compounds according to the present invention include examples 1-40 as shown herein below, or a pharmaceutically acceptable salt thereof.

In certain embodiments, the present invention provides a compound selected from the group consisting of:
lithium 4-((1S)-1-(1-(4-(trifluoromethyl)benzyl)piperidine-2-carboxamido)ethyl)benzoate lithium 4-((S)-1-((R)-1-(4-fluorobenzyl)piperidine-2-carboxamido)ethyl)benzoate
lithium 4-((S)-1-((R)-1-(4-(trifluoromethyl)benzyl)piperidine-2-carboxamido)ethyl)benzoate
lithium (R)-4-(1-(1-(4-(trifluoromethyl)benzyl)piperidine-2-carboxamido)cyclopropyl)benzoate
lithium (R)-4-(1-(1-(4-chlorobenzyl)piperidine-2-carboxamido)cyclopropyl)benzoate
lithium (R)-4-(1-(1-(4-cyanobenzyl)piperidine-2-carboxamido)cyclopropyl)benzoate
4-(1-(6-(4-(trifluoromethyl)benzyl)-6-azaspiro[2.5]octane-5-carboxamido)cyclopropyl)benzoic acid
4-(1-(6-((6-(trifluoromethyl)pyridin-3-yl)methyl)-6-azaspiro[2.5]octane-5-carboxamido)cyclopropyl)benzoic acid
4-(1-(6-(3-(trifluoromethyl)benzyl)-6-azaspiro[2.5]octane-5-carboxamido)cyclopropyl)benzoic acid
4-((1S)-1-(6-(4-(trifluoromethyl)benzyl)-6-azaspiro[2.5]octane-5-carboxamido)ethyl)benzoic acid
4-((1S)-1-(5-methyl-6-(4-(trifluoromethyl)benzyl)-6-azaspiro[2.5]octane-5-carboxamido)ethyl)benzoic acid
4-(1-(4,4-dimethyl-1-(4-(trifluoromethyl)benzyl)piperidine-2-carboxamido)cyclopropyl)benzoic acid
4-((1S)-1-(4,4-dimethyl-1-(4-(trifluoromethyl)benzyl)piperidine-2-carboxamido)ethyl)benzoic acid
4-((1S)-1-((2R)-4-fluoro-1-(4-(trifluoromethyl)benzyl)piperidine-2-carboxamido)ethyl)benzoic acid
4-(1-((2R)-4-fluoro-1-(4-(trifluoromethyl)benzyl)piperidine-2-carboxamido)cyclopropyl)benzoic acid
4-((S)-1-((R)-4,4-difluoro-1-(4-(trifluoromethyl)benzyl)piperidine-2-carboxamido)ethyl)benzoic acid
(R)-4-(1-(4,4-difluoro-1-(4-(trifluoromethyl)benzyl)piperidine-2-carboxamido)cyclopropyl)benzoic acid
4-(1-(4,4-difluoro-1-(4-(trifluoromethyl)benzyl)piperidine-2-carboxamido)cyclopropyl)benzoic acid
4-(1-(4,4-difluoro-1-(3-(trifluoromethyl)benzyl)piperidine-2-carboxamido)cyclopropyl)benzoic acid
4-(1-(4,4-difluoro-1-(3-(trifluoromethyl)benzyl)piperidine-2-carboxamido)cyclopropyl)benzoic acid
4-(1-(3-(4-(trifluoromethyl)benzyl)-3-azabicyclo[4.1.0]heptane-4-carboxamido)cyclopropyl)benzoic acid
4-(1-(3-(4-(trifluoromethyl)benzyl)-3-azabicyclo[4.1.0]heptane-4-carboxamido)cyclopropyl)benzoic acid
4-(1-(3-(4-(trifluoromethyl)benzyl)-3-azabicyclo[4.1.0]heptane-4-carboxamido)cyclopropyl)benzoic
4-(1-(3-(3-(trifluoromethyl)benzyl)-3-azabicyclo[4.1.0]heptane-4-carboxamido)cyclopropyl)benzoic acid
4-(1-((3R)-2-(4-(trifluoromethyl)benzyl)-2-azabicyclo[4.1.0]heptane-3-carboxamido)cyclopropyl)benzoic acid
4-((1S)-1-((3R)-2-(4-(trifluoromethyl)benzyl)-2-azabicyclo[4.1.0]heptane-3-carboxamido)ethyl)benzoic acid
lithium 4-((S)-1-((R)-1-(4-(trifluoromethyl)benzyl)pyrrolidine-2-carboxamido)ethyl)benzoate
lithium 4-((S)-1-((R)-1-(4-fluorobenzyl)pyrrolidine-2-carboxamido)ethyl)
4-(1-((1R,3R,5R)-2-(3-(trifluoromethyl)benzyl)-2-azabicyclo[3.1.0]hexane-3-carboxamido)cyclopropyl)benzoic acid
4-(1-((1R,3R,5R)-2-(4-(trifluoromethyl)benzyl)-2-azabicyclo[3.1.0]hexane-3-carboxamido)cyclopropyl)benzoic acid
4-(1-((3R)-2-(4-(trifluoromethyl)benzyl)-2-azabicyclo[3.1.0]hexane-3-carboxamido)cyclopropyl)benzoic acid
4-((1S)-1-((3R)-2-(4-(trifluoromethyl)benzyl)-2-azabicyclo[3.1.0]hexane-3-carboxamido)ethyl)benzoic acid
4-((1S)-1-((3R)-2-(4-(trifluoromethyl)benzyl)-2-azabicyclo[3.1.0]hexane-3-carboxamido)ethyl)benzoic acid
(R)-4-(1-(4,4-dimethyl-1-(4-(trifluoromethyl)benzyl)pyrrolidine-2-carboxamido)cyclopropyl)benzoic acid
4-((1S)-1-(1-(4-(trifluoromethyl)benzyl)azetidine-2-carboxamido)ethyl)benzoic acid
4-((1S)-1-(1-(4-(trifluoromethyl)benzyl)azetidine-2-carboxamido)ethyl)benzoic acid
4-((1S)-1-(3-(4-(trifluoromethyl)benzyl)-3-azabicyclo[3.1.0]hexane-2-carboxamido)ethyl)benzoic acid
4-(1-(3-(4-(trifluoromethyl)benzyl)-3-azabicyclo[3.1.0]hexane-2-carboxamido)cyclopropyl)benzoic acid
4-((1S)-1-(2-(4-(trifluoromethyl)benzyl)-2-azabicyclo[2.2.2]octane-3-carboxamido)ethyl)benzoic acid
4-(1-(2-(4-(trifluoromethyl)benzyl)-2-azabicyclo[2.2.2]octane-3-carboxamido)cyclopropyl)benzoic acid (R)-4-(1-(2-methyl-1-(4-(trifluoromethyl)benzyl)piperidine-2-carboxamido)cyclopropyl)benzoic acid
4-((S)-1-((R)-2-methyl-1-(4-(trifluoromethyl)benzyl)piperidine-2-carboxamido)ethyl)benzoic acid
(R)-4-(1-(2-methyl-1-(4-(trifluoromethyl)benzyl)pyrrolidine-2-carboxamido)cyclopropyl)benzoic acid
lithium 4-((S)-1-((2R,4S)-4-fluoro-1-(3-(trifluoromethyl)benzyl)pyrrolidine-2-carboxamido)ethyl)benzoate
4-((S)-1-((R)-4,4-difluoro-1-(4-(trifluoromethyl)benzyl)pyrrolidine-2-carboxamido)ethyl)benzoic acid Preferred compounds of the invention are selected from the group consisting of:
lithium(R)-4-(1-(1-(4-(trifluoromethyl)benzyl)piperidine-2-carboxamido)cyclopropyl)benzoate
4-(1-(6-(4-(trifluoromethyl)benzyl)-6-azaspiro[2.5]octane-5-carboxamido)cyclopropyl)benzoic acid
4-((1S)-1-(6-(4-(trifluoromethyl)benzyl)-6-azaspiro[2.5]octane-5-carboxamido)ethyl)benzoic acid
4-((1S)-1-(4,4-dimethyl-1-(4-(trifluoromethyl)benzyl)piperidine-2-carboxamido)ethyl)benzoic acid
4-(1-(3-(4-(trifluoromethyl)benzyl)-3-azabicyclo[4.1.0]heptane-4-carboxamido)cyclopropyl)benzoic
4-(1-((3R)-2-(4-(trifluoromethyl)benzyl)-2-azabicyclo[4.1.0]heptane-3-carboxamido)cyclopropyl)benzoic acid
4-((1S)-1-((3R)-2-(4-(trifluoromethyl)benzyl)-2-azabicyclo[4.1.0]heptane-3-carboxamido)ethyl)benzoic acid
lithium 4-((S)-1-((R)-1-(4-(trifluoromethyl)benzyl)pyrrolidine-2-carboxamido)ethyl)benzoate
4-(1-((1R,3R,5R)-2-(3-(trifluoromethyl)benzyl)-2-azabicyclo[3.1.0]hexane-3-carboxamido)cyclopropyl)benzoic acid
4-(1-((1R,3R,5R)-2-(4-(trifluoromethyl)benzyl)-2-azabicyclo[3.1.0]hexane-3-carboxamido)cyclopropyl)benzoic acid A further aspect of this invention concerns a process for the preparation of a compound of Formula (I) comprising the following steps represented in the general scheme below:

GENERAL SCHEME

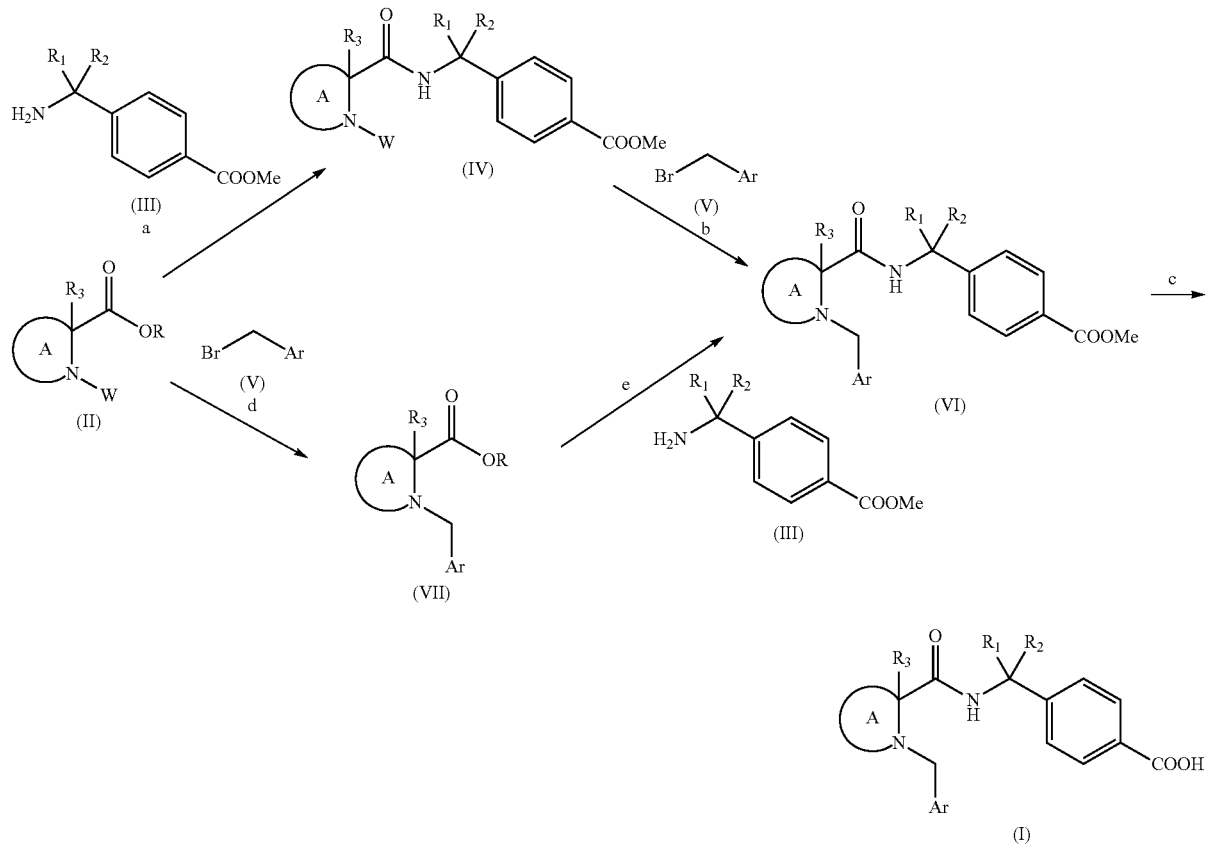

4-((S)-1-((R)-4,4-difluoro-1-(4-(trifluoromethyl)benzyl)piperidine-2-carboxamido)ethyl)benzoic acid
(R)-4-(1-(4,4-difluoro-1-(4-(trifluoromethyl)benzyl)piperidine-2-carboxamido)cyclopropyl)benzoic acid
4-(1-(4,4-difluoro-1-(4-(trifluoromethyl)benzyl)piperidine-2-carboxamido)cyclopropyl)benzoic acid
4-(1-(4,4-difluoro-1-(3-(trifluoromethyl)benzyl)piperidine-2-carboxamido)cyclopropyl)benzoic acid
4-(1-(4,4-difluoro-1-(3-(trifluoromethyl)benzyl)piperidine-2-carboxamido)cyclopropyl)benzoic acid a) reacting a compound of formula (II) with a compound of formula (III) in the presence of a coupling reagent and a base thus obtaining a compound of Formula (IV);
b) reacting a compound (IV) with compound of (V) in presence of a suitable base thus obtaining a compound of Formula (VI);
c) hydrolysing an ester compound (VI) with strong bases such us lithium hydroxide in a suitable solvent system such as 1,4-dioxane/H$_2$O, thus obtaining a compound of Formula (I);

d) reacting a compound (II) with a compound of (V) in presence of a suitable base thus obtaining a compound of Formula (VII);

e) reacting a compound of formula (VII) with a compound of formula (III) in the presence of a coupling reagent and in the presence of a base thus obtaining a compound of Formula (VI).

In the above general scheme:

A, $R_1$, $R_2$, $R_3$, Ar are as defined in formula (I),

R is selected from the group consisting of hydrogen, linear or branched $C_{1-3}$ alkyl and benzyl groups, W is selected from the group consisting of hydrogen, benzyl group and t-Butyl carbamate group, It will be appreciated that compounds of formula (II), (IV) and (VII), may be converted into other compounds of formula (II), (IV) and (VII), by synthetic methods known to the skilled person in the art.

Examples of such conversion reactions are:

i) Compounds of formula (II) wherein R is $C_{1-3}$ alkyl, may be prepared by reacting corresponding compounds wherein R is hydrogen with alcohols, for example ethanol, in the presence of a suitable reactive reagent such as thionyl chloride.

ii) Compounds of formula (II), when R is hydrogen, may be prepared by hydrolysis of the corresponding compounds of formula (II), wherein R is $C_{1-3}$ alkyl. The hydrolysis is carried out in the presence of a base, for example lithium hydroxide, typically in presence of a suitable ether system, such as aqueous 1,4-dioxane.

iii) Compounds of formula (IV) wherein W is hydrogen, may be prepared by corresponding compounds of formula (IV) wherein W is benzyl group, by hydrogenolysis or by reacting compound formula (IV), wherein W is t-Butyl carbamate group, with trifluoroacetic acid.

iv) Compounds of formula (VII), when R is hydrogen, may be prepared by hydrolysis of the corresponding compounds of formula (VII), wherein R is $C_{1-3}$ alkyl. The hydrolysis is carried out in the presence of a base, for example lithium hydroxide in aqueous 1,4-dioxane.

Method Of Synthesis

As above shown, according to a further aspect of this invention there is provided a process for the preparation of compound of formula (I).

In a more detailed way, the compounds of the present invention may be prepared according to the following schemes.

Unless otherwise indicated $R_1$, $R_2$, $R_3$, W and Ar in the reaction schemes and discussion that follow are as defined above, in formula (I).

The term "protecting group", as used hereinafter, means an amino protecting group which is selected from typical amino protecting groups as described in Protective Groups in Organic Synthesis edited by T. W. Greene et al. (John Wiley & Sons, 1999);

Compounds of formula (I) may be prepared by hydrolysis reaction of ester compounds of formula (VI) according to the reaction scheme 1.

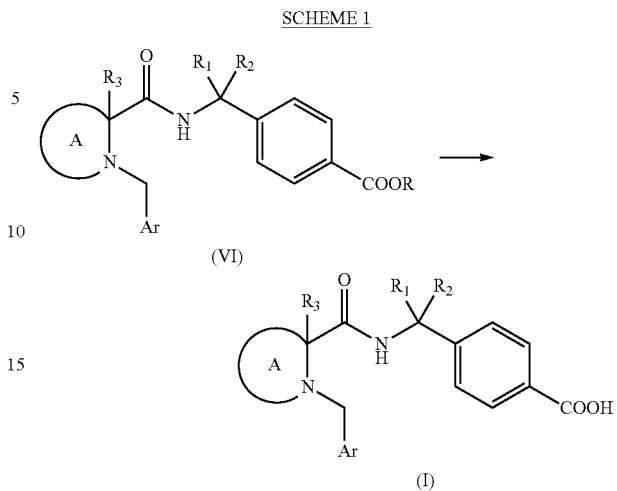

Hydrolysis can be carried out in presence of a base, for example lithium hydroxide in a suitable solvent such as in aqueous 1,4-dioxane.

In certain embodiments, this reaction may be carried out at room temperature.

Compounds of formula (VI) may be prepared according to reaction scheme 2.

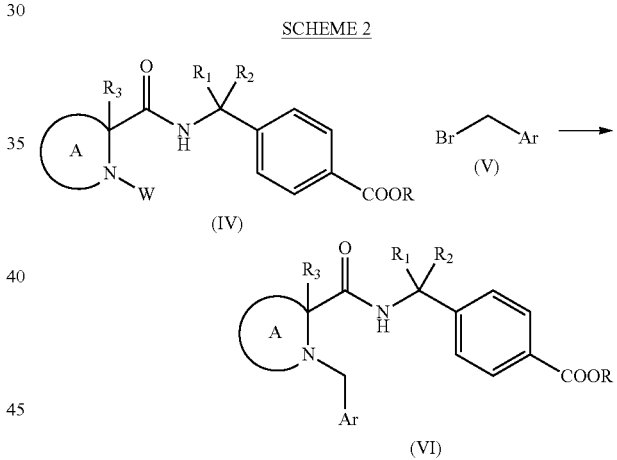

Compounds of formula (IV), wherein W is hydrogen, may be reacted with compounds of formula (V) in the presence of a suitable base, such as cesium carbonate and in a suitable solvent such as acetonitrile. In certain embodiments the reaction is carried out at room temperature or in others by heating, for example at 60° C.

Compounds of formula (IV), wherein W is hydrogen, may be prepared from corresponding compounds of formula (IV) wherein W preferably is benzyl group or t-butyl carbamate group.

In certain embodiments wherein W is t-butyl carbamate, the deprotection step can be carried out in presence of trifluoroacetic acid in a suitable solvent such as dichloromethane.

In other embodiments wherein W is a benzyl group, the deprotection step can be carried out by hydrogenolysis typically in a suitable solvent such as ethanol.

Compounds of formula (IVa) may be prepared according to reaction scheme 3.

SCHEME 3

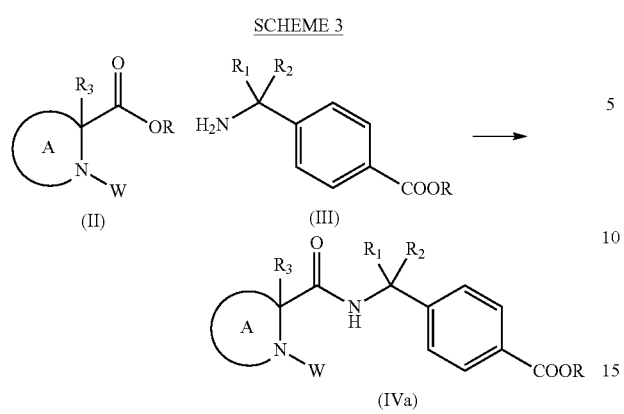

In certain embodiments, the compounds of formula (II), wherein R is hydrogen and W is a benzyl group or t-butyl carbamate, are reacted with compounds of formula (III) in the presence of a suitable coupling reagent, for example selected from (2-(6-Chloro-1H-benzotriazole-1-yl)-1,1,3,3-tetramethylaminium hexafluorophosphate) (HCTU), O-(7-Azabenzotriazol-1-yl)-N,N,N',N'-tetramethyluronium hexafluorophosphate (HATU), (1-Ethyl-3-(3-dimethyllaminopropyl) carbodiimide hydrochloride) and 1-Hydroxybenzotriazole and mixtures thereof. Typically, the reaction is carried out in an aprotic solvent, for example a halohydrocarbon, such as dichloromethane, N,N-dimethylformamide, or acetonitrile or mixture thereof, typically at room temperature, in presence of a suitable base, such as N,N-diisopropylamine.

Compounds of formula (III) are known, for example from the International Patent applications WO 2005105733 and WO2008104055.

Alternatively compound of formula (VI) may be prepared according to reaction scheme 4.

SCHEME 4

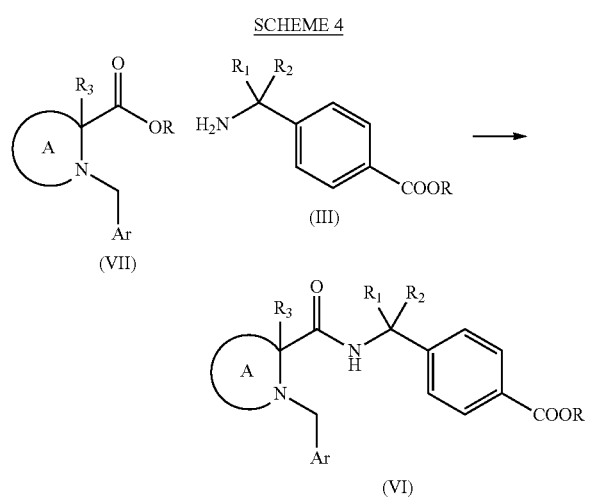

In certain embodiments, the compounds of formula (VII), wherein R is H, are reacted with compounds of formula (III) in the presence of a suitable coupling reagent, for example selected from (2-(6-Chloro-1H-benzotriazole-1-yl)-1,1,3,3-tetramethylaminium hexafluorophosphate) (HCTU), O—(7-Azabenzotriazol-1-yl)-N,N,N',N'-tetramethyluronium hexafluorophosphate (HATU), (1-Ethyl-3-(3-dimethyllaminopropyl)carbodiimide hydrochloride) and 1-Hydroxybenzotriazole or mixtures thereof.

In certain embodiments the reaction is carried out in an aprotic solvent, for example a halohydrocarbon, such as dichloromethane, N,N-dimethylformamide, or acetonitrile or mixtures thereof, typically at room temperature, in presence of a suitable base.

In certain embodiments, the compounds of formula (VII), wherein R is hydrogen, may be prepared by hydrolysis of the corresponding compounds of formula (VII), wherein R is C(1-3) alkyl. In certain embodiments, the hydrolysis is carried out in the presence of a base for example lithium hydroxide, typically in suitable solvent such as aqueous 1,4-dioxane.

In certain embodiments, the compounds of formula (VII) may be prepared according to reaction scheme 5.

SCHEME 5

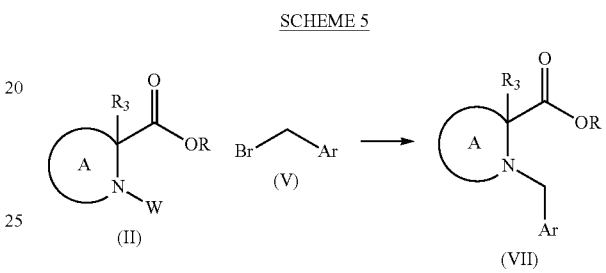

In certain embodiments, the compounds of formula (II), wherein R is C(1-3) alkyl and W is a benzyl group or t-butyl carbamate, may be reacted with compounds of formula (V) in the presence of a suitable base such as cesium carbonate and a suitable solvent such as acetonitrile. In certain embodiments the reaction is carried out at room temperature, in other embodiments the reaction is carried out under heating, for example at around 60° C.

In certain embodiments the compounds of formula (II) wherein A is D, R is hydrogen, W is t-butyl carbamate and m is 1, may be prepared according to the reaction scheme 6.

SCHEME 6

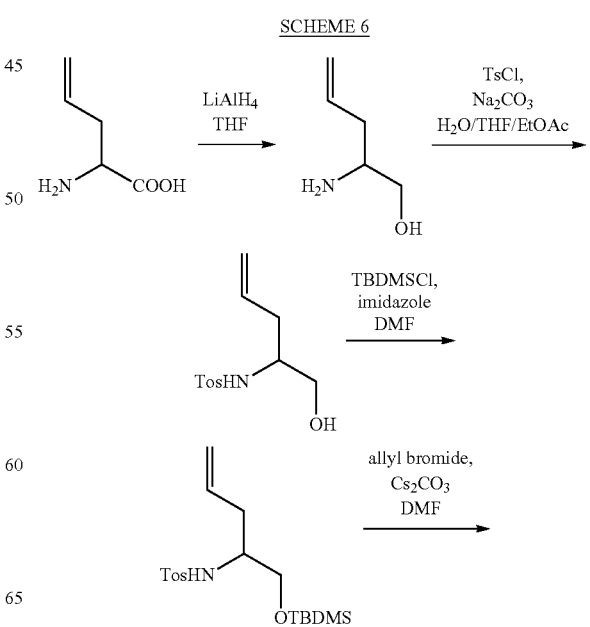

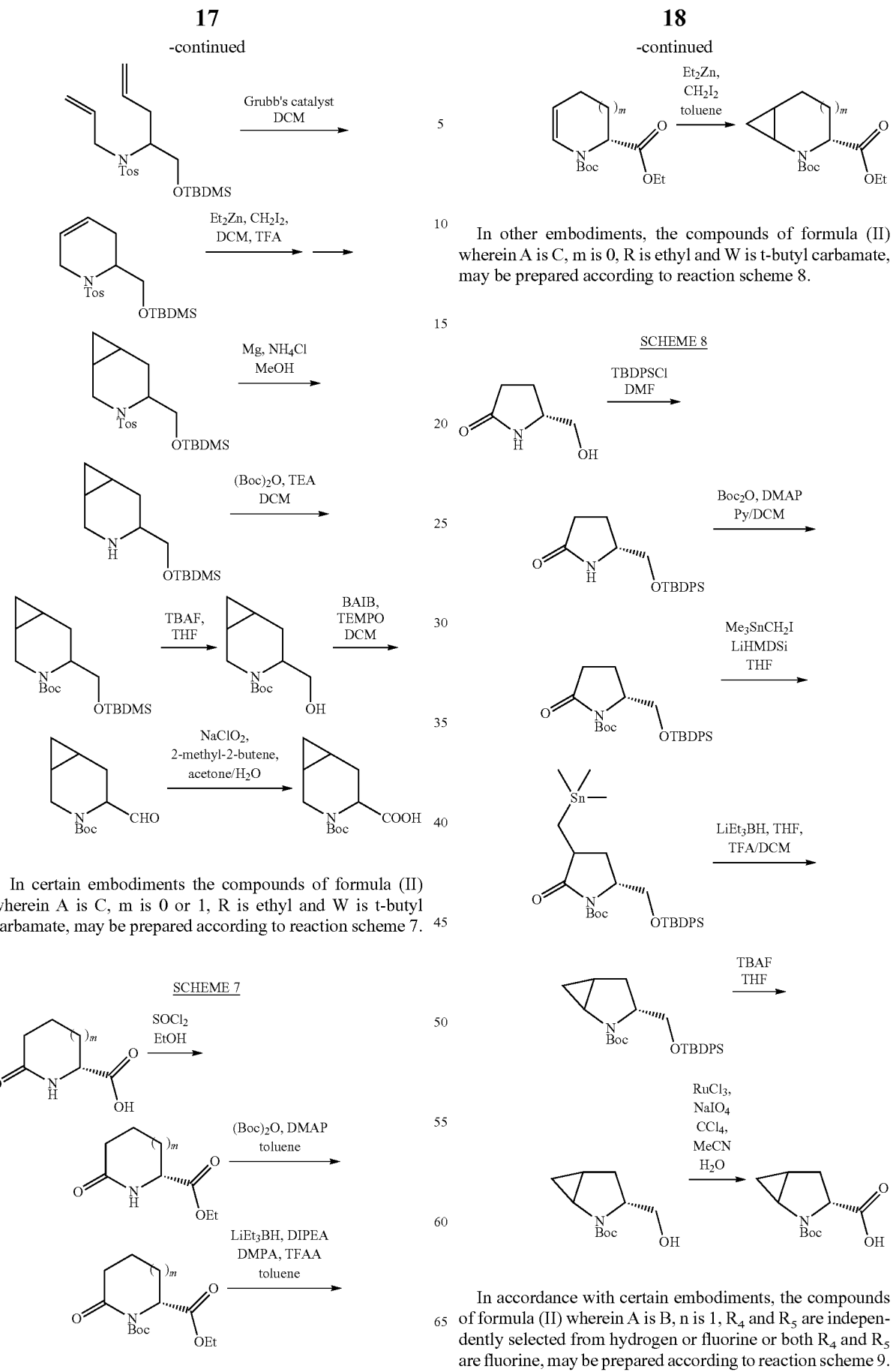

In other embodiments, the compounds of formula (II) wherein A is C, m is 0, R is ethyl and W is t-butyl carbamate, may be prepared according to reaction scheme 8.

In certain embodiments the compounds of formula (II) wherein A is C, m is 0 or 1, R is ethyl and W is t-butyl carbamate, may be prepared according to reaction scheme 7.

In accordance with certain embodiments, the compounds of formula (II) wherein A is B, n is 1, $R_4$ and $R_5$ are independently selected from hydrogen or fluorine or both $R_4$ and $R_5$ are fluorine, may be prepared according to reaction scheme 9.

SCHEME 9

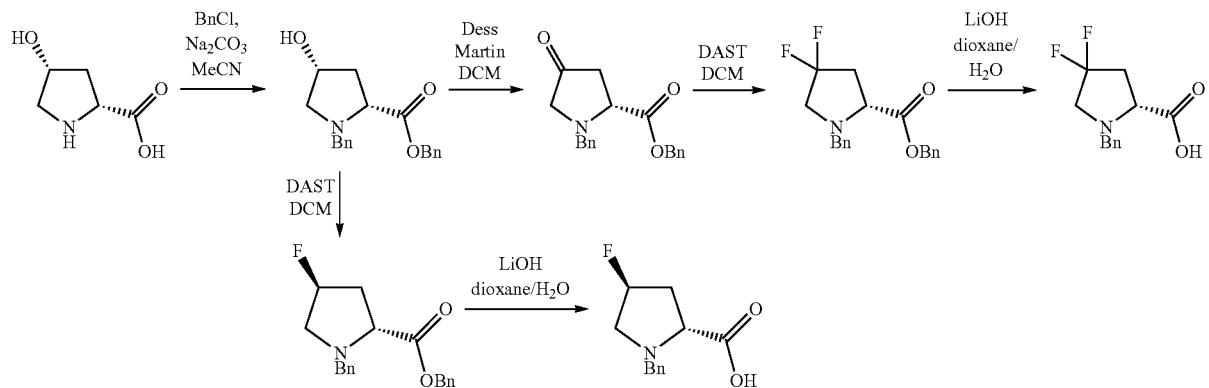

In certain embodiments the compounds of formula (II) wherein A is B, n is 1, $R_4$ and $R_5$ are methyl, R and $R_3$ are hydrogen and W is t-butyl carbamate, may be prepared according synthetic route described in scheme 10.

SCHEME 10

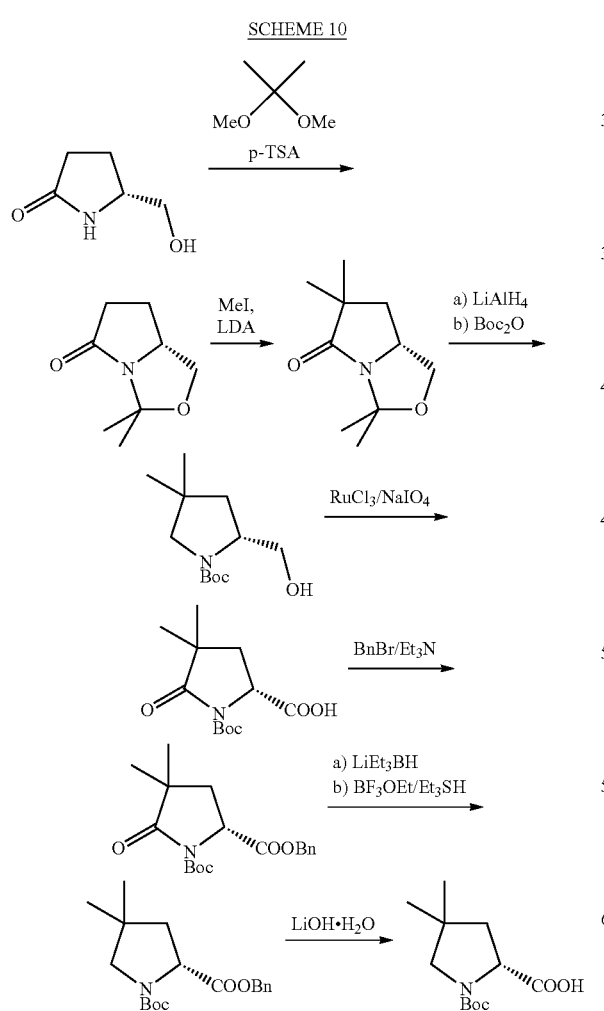

In accordance with certain embodiments, the compounds of formula (II) wherein A is B, W, R, $R_4$ and $R_5$ are hydrogen, n is 0, 1 and 2, $R_3$ is methyl, may be prepared according synthetic route described in scheme 11.

SCHEME 11

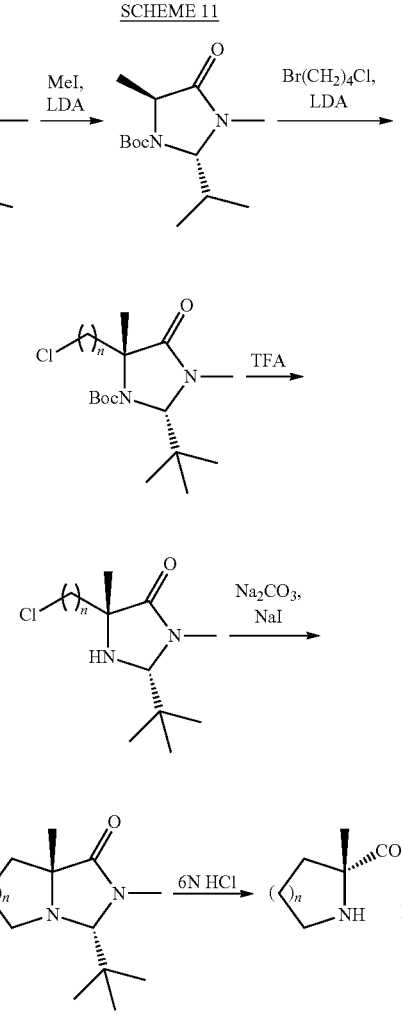

Scheme 12 describes an alternative synthetic route to products of formula (II) wherein A is B, W, $R_4$ and $R_5$ are hydrogen, n is 1, R and $R_3$ are methyl.

SCHEME 12

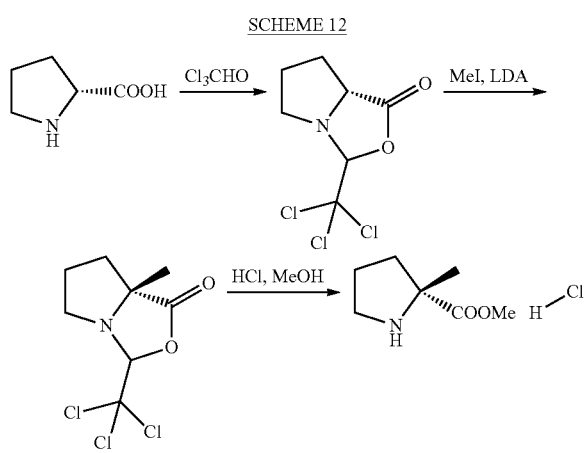

According to certain embodiments of the invention, the compounds (I) are obtained using a simple process, easy to scale-up and avoiding lengthy and expensive preparation steps, obtaining high yield of a stable pharmaceutical grade compound of formula (I).

Typically, the various methods described above may be useful for the introduction of the desired group at any stage in the stepwise formation of the required compound, and it will appreciated that these general methods can be combined in different way in such multi-stage processes. Typically, the sequence of the reactions in multi-stage processes are chosen so that the reaction conditions used do not affect groups in the molecule which are in the final product.

In certain embodiments where an enantiomer of a compound of the general formula (I) is required, this may be obtained by resolution of a corresponding enantiomeric mixture of such compound of formula (I) by using conventional methods such as by chiral HPLC procedure.

In certain embodiments the compounds of general formula (I) are in the form of salts, specifically pharmaceutically acceptable salts. These salts may be obtained using conventional methods, for example by reacting the compound having general formula (I) in the form of a free base with a suitable acid in a suitable solvent for example an alcohol, such as ethanol or an ether such as diethyl ether or an ester such as ethyl acetate.

In certain embodiments the compounds of general formula (I) may be isolated in association with solvent molecules for example by evaporation or crystallisation from a suitable solvent to provide the corresponding solvates.

The Inventors have found that the general family of the compounds of formula (I) as well the sub-families of the compounds of formulae (IB), (IC), (ID), (IE) as above, have affinity for and are specific antagonists of $PGE_2$ receptors, in particular of $EP_4$ subtype of $PGE_2$ receptors.

The compounds of general formula (I) and the specific compounds of (IB), (IC), (ID), (IE) are useful in the treatment of Prostaglandin E mediated conditions or diseases.

Thus, according to an additional aspect the invention concerns compounds of Formulae (I), (IB), (IC), (ID), (IE) for use as a medicament the treatment of pathologies or disorders where an antagonist of the $EP_4$ receptor is needed.

In certain embodiments the pathologies or disorders are selected from acute and chronic pain, inflammatory pain, osteoarthritis, inflammation-associated disorder such as arthritis, rheumatoid arthritis, cancer endometriosis and migraine.

In certain embodiments, the compounds of the invention are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention are useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

Compounds of the invention are also useful in the treatment of immunological diseases such as autoimmune diseases, immunological deficiency diseases or organ transplantation. The compounds of the invention are also effective in increasing the latency of HIV infection.

Compounds of the invention are also useful in the treatment of diseases of abnormal platelet function (e.g. occlusive vascular diseases).

Compounds of the invention are also useful for the preparation of a drug with diuretic action.

Compounds of the invention are also useful in the treatment of impotence or erectile dysfunction.

Compounds of the invention are also useful in the treatment of bone disease characterized by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis. In a further aspect, compounds of the invention may be useful in inhibiting bone resorption and/or promoting bone generation.

Compounds of the invention are also useful for attenuating the hemodynamic side effects of NSAIDs and COX-2 inhibitors.

Compounds of the invention are also useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

Compounds of the invention are also useful in the treatment of neurodegenerative diseases and neurodegeneration such as dementia, particularly degenerative dementia (including senile dementia, Alzheimer's disease, Pick's disease, Huntingdon's chores, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of Formula (I), (IB), (IC), ID) and (IE) are also useful in the treatment of neuroprotection and in the treatment of neurodegeneration following stroke, cardiac arrest, pulmonary bypass, traumatic brain injury, spinal cord injury or the like. Compounds of the invention are also useful for the treatment of stroke and multiple sclerosis.

Compounds of the invention are also useful in the treatment of tinnitus.

Compounds of the invention are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

Compounds of the invention are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

Compounds of the invention are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

Compounds of the invention are also useful for treating or preventing a neoplasia in a subject in need of such treatment or prevention. The term "treatment" includes partial or total inhibition of the neoplasia growth, spreading or metastasis, as well as partial or total destruction of the neoplastic cells and/or symptoms associated with neoplasia including pain, anorexia or weight loss. The term also includes the use of compounds as sensitizing agents for other chemotherapies. The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia. The term "subject" for purposes of treatment includes any human or mammal subject who has any one of the known neoplasias, and preferably is a human subject. For methods of prevention, the subject is any human or animal subject, and preferably is a human subject who is at risk for obtaining a neoplasia. The subject may be at risk due to exposure to carcinogenic agents, being genetically predisposed to have the neoplasia, and the like. The term "neoplasia" includes both benign and cancerous tumors, growths and polyps. Thus, the compounds of the invention are useful for treating or preventing benign tumors, growths and polyps including squamous cell papilloma, basal cell tumor, transitional cell papilloma, adenoma, gastrinoma, cholangiocellular adenoma, hepatocellular adenoma, renal tubular adenoma, oncocytoma, glomus tumor, melanocyte nevus, fibroma, myxoma, lipoma, leiomyoma, rhabdomyoma, benign teratoma, hemangioma, osteoma, chondroma and meningioma. The compounds of the invention are also useful for treating or preventing cancerous tumors, growths and polyps including squamous cell carcinoma, basal cell carcinoma, transitional cell carcinoma, adenocarcinoma, malignant gastrinoma, cholangiocelleular carcinoma, hepatocellular carcinoma, renal cell carcinoma, malignant melanoma, fibrosarcoma, myxosarcoma, liposarcoma, leimyosarcoma, rhabdomyosarcoma, malignant teratoma, hemangiosarcoma, Kaposi sarcoma, lymphangiosarcoma, ostreosarcoma, chondrosarcoma, malignant meningioma, non-Hodgkin lymphoma, Hodgkin lymphoma and leukemia. For purposes of this specification, "neoplasia" includes brain cancer, bone cancer, epithelial cell-derived neoplasia (epithelial carcinoma), basal cell carcinoma, adenocarcinoma, gastrointestinal cancer such as lip cancer, mouth cancer, esophageal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that affect epithelial, mesenchymal or blood cells throughout the body. The compounds of the invention are useful for treating or preventing any of the aforementioned cancers. The compounds of the invention are useful for treating or preventing benign and cancerous tumors, growths and polyps of the following cell types: squamous epithelium, basal cells, transitional epithelium, glandular epithelium, G cells, bile ducts epithelium, hepatocytes, tubules epithelium, melanocytes, fibrous connective tissue, cardiac skeleton, adipose tissue, smooth muscle, skeletal muscle, germ cells, blood vessels, lymphatic vessels, bone, cartilage, meninges, lymphoid cells and hematopoietic cells. The compounds can be used to treat subjects having adenomatous polyps, including those with familial adenomatous polyposis (FAP). Additionally, the compounds can be used to prevent polyps from forming in patients at risk of FAP. Preferably, the compounds of the invention are useful for treating or preventing the following cancers: colorectal, esophagus stomach, breast, head and neck, skin, lung, liver, gall bladder, pancreas, bladder, endometrium cervix, prostate, thyroid and brain.

It is to be understood that reference to a treatment includes both treatment of established symptoms and prophylactic treatment, unless explicitly stated otherwise.

In a further aspect, the present invention concerns a compound of Formulae (I), (IB), (IC), (ID), (IE) for use as a medicament.

In another aspect the invention provides a pharmaceutical composition comprising a compound of Formula (I) (IB), (IC), (ID), (IE) and a pharmaceutically acceptable carrier.

The compound of Formula (I) may be used in combination with a pharmaceutically acceptable carrier and, optionally, with suitable excipients, to obtain pharmaceutical compositions.

The term "pharmaceutically acceptable carrier" means solvents, carrier agents, diluting agents and the like which are used in the administration of compounds of the invention.

In certain embodiments, the pharmaceutical compositions of the invention may be in solid or liquid form.

The pharmaceutical compositions in solid form may contain suitable excipients such as fillers, lubricants, binding agents, wetting agents, disintegrants, colorants and flavouring agents and mixtures thereof. For example the tablets may contain pre-gelatinised starch, microcrystalline cellulose, sodium glycolate starch, talc, lactose, magnesium stearate, sucrose, stearic acid, mannitol.

The pharmaceutical compositions in liquid form, typically may be provided as solutions, suspensions, emulsion, syrups, elixir. Typically, the compositions in liquid form may contain suspending agents, emulsifying agents, carriers, preservatives and colorants, flavouring agents.

Typically, the pharmaceutical compositions of the invention can be administered by parenteral, oral, buccal, sublingual, nasal, rectal, topical or transdermal administration. Pharmaceutical compositions for oral administration are generally preferred.

The pharmaceutical compositions of the invention suitable for the oral administration typically, will be discrete units in solid form such as in the form of tablets, capsules, cachets, powders, granules, lozenges, patches, suppositories, pellets, or in liquid form such as liquid preparations, injectable or infusible solutions or suspensions.

The pharmaceutical compositions for parenteral administration typically include sterile preparations in the forms of solutions or suspensions. In certain embodiments the compositions for parenteral administration are aqueous based solution suitable for injection or infusion. In certain embodiments such compositions for parenteral administration includes one or more adjuvants such as buffering agents, preservatives, antibacterial agents, surfactants and mixtures thereof.

The pharmaceutical compositions for topical administration may be formulated as creams, pastes, oils, ointments, emulsions, foams, gels, drops, spray solutions and transdermal patches.

In certain embodiments the pharmaceutical composition of the invention includes 0.1 to 99% by weight of the compound of formula (I) as active ingredient. In certain embodiments the amount of the compound of formula (I) is 1 to 30% by weight.

The dosage of the compound of formula (I) to be administered depends on the severity of the disease, the weight, the age and general conditions of the patient in need of treatment.

For example a suitable unit dosage may vary of from 0.01 to 1000 mg or typically of 1.0 to 300 mg to be administered one or more in a day, for example twice a day usually at regular intervals. The duration of the therapy depends on the severity of the illness and general condition of the patients and may be varied by the physician an extended for certain weeks or months.

According to another aspect, the use of a compounds of the general formula (I) for the manufacture of a medicament for the treatment of pathologies or diseases which require the administration of an antagonist of the $EP_4$ receptor, such as the treatment of inflammatory pain, osteoarthritis, arthritis.

In accordance to certain embodiments, the present invention provides for a pharmaceutical composition comprising a compound of formula (I) or (IB), (IC), (ID), (IE), in association with an additional active ingredient and a pharmaceutically acceptable excipient.

Said additional active ingredients may be an additional compound of formula (I) or a different chemical entity having similar or different activity.

In certain embodiments said additional active ingredients is selected from the antinflammatory compounds, such as FANS or cortisonic compounds.

The invention will be now detailed by means of the following examples relating to the preparation of some embodiments of the compounds of the invention and to the evaluation of their activity against $EP_4$ receptor.

The following Descriptions relating to intermediate products and Examples illustrating the preparation of certain compounds of formula (I) or salts thereof follow below. The descriptions illustrate the preparation of intermediates used to make compounds of formula (I) or salts thereof.

In the procedures that follow, after each starting material, reference to a description is provided. This is provided merely for assistance to the skilled chemist. The starting material may not necessarily have been prepared from the Description referred to. The stereochemistry of Descriptions and Examples has been assigned on the assumption that the absolute configuration centres are retained. Relative stereochemistry has been determined by using NMR Nuclear Overhauser Effect Spectroscopy (NOESY) experiments, as for example in the descriptions D73a, D73b, D140a and D140b.

When a chiral HPLC separation of a racemic mixture was accomplished, it has been decide to use the term enantiomer 1 or enantiomer 2 depending on the retention time in the corresponding chiral HPLC separation. The term enantiomer 1 is used for the single stereoisomer with the minor retention time in the conditions of the chiral separation. Conversely the term enantiomer 2 is used for the single stereoisomer with the major retention time in the conditions of the chiral separation.

When a chiral HPLC separation or a separation by flash chromatography of a diastereoisomeric mixture was accomplished, it has been decide to use the term diastereoisomer 1 or diastereoisomer 2 depending on the retention time in the corresponding chiral HPLC separation or on the retention time in the corresponding flash chromatography column. The term diastereoisomer 1 is used for the single diastereoisomer with the minor retention time in the conditions of the chiral separation or the first eluting in flash chromatography column. Conversely the term diastereoisomer 2 is used for the single diastereoisomer with the major retention time in the conditions of the chiral separation or the second eluting in flash chromatography column.

The yields are calculated assuming that products were 100% pure if not stated otherwise.

Compound are named using ChemBioDraw Ultra 12.0 (CambridgeSoft Corp., 100 CambridgePark Drive, Cambridge, Mass. 02140)

Reagents used in the following examples were commercially available from various suppliers (for example Sigma- Aldrich, Acros, Matrix scientific, Manchester or Apollo) and used without further purifications.

Reactions in anhydrous environment were run under a positive pressure of dry N2 and solvents were used in dry form.

For reaction involving microwave irradiation, an Initiator 2.5 System was used.

Purification was performed using Biotage automatic flash chromatography systems (Sp1 and Isolera systems), Companion CombiFlash (ISCO) automatic flash chromatography, Flash Master or Vac Master systems.

Flash chromatography was carried out on silica gel 230-400 mesh (supplied by Merck AG Darmstadt, Germany), Varian Mega Be-Si pre-packed cartridges, pre-packed Biotage silica cartridges (e.g. Biotage SNAP-Si cartridges), Waters PoraPak RXN RP cartridges, Biotage SNAP-C18.

SPE-Si cartridges are silica solid phase extraction columns.

PoraPakRXN RP cartridges are polimer based reverse phase resin.

Biotage SNAP C18 Gold cartridges are silica based reverse phase column.

SPE-SCX cartridges are ion exchange solid phase extraction columns supplied by Varian. The eluent used with SPE-SCX cartridges is dichloromethane and methanol or only methanol followed by 2N ammonia solution in methanol. The collected fractions are those eluted with ammonia solution in methanol.

Thin layer chromatography was carried out using Merck TLC plates Kieselgel 60F-254, visualized with UV light, aqueous permanganate solution, iodine vapours.

Proton Nuclear Magnetic Resonance $^1$H NMR) spectra were recorded on Bruker Avance 400 MHz instrument and on Bruker Avance III plus 400 MHz. TMS was used as internal standard. Chemical shifts are reported in ppm ($\delta$) using the residual solvent line as internal standard. Splitting patterns are designated as: s, singlet; d, doublet; t, triplet; q, quartet; m, multiplet; b, broad signal. The NMR spectra were recorded at temperature ranging from 25° C. to 90° C. When more than one conformer was detected the chemical shifts of the most abundant one is usually reported.

In the analytical characterisation of the described compounds "MS" refers to Mass Spectra taken by Direct infusion Mass or to a mass Spectra associated with peaks taken by UPLC/MS or HPLC/MS analysis, where the Mass Spectrometer used is as mentioned below.

Direct infusion Mass Spectra (MS) were run on a Ion Trap Thermo LCQ classic spectrometer, operating in positive ES (+) and negative ES (−) ionization mode using different columns and operating procedures listed below:

Phenomenex Gemini-NX C18 column (100×2 mm, 3 μm particle size), column T=35° C. Mobile phase: A (water+0.1% formic acid)/B (acetonitrile+0.1% formic acid), Gradient: 10% B at t=0 min up to 90% B at t=12 min using different gradient curves, flow rate: 0.3 ml/min;

Acquity™ UPLC-BEH C18 column (50×21 mm, 1.7 μM particle size), column T=35° C. Mobile phase: A (water+0.1% formic acid)/B (acetonitrile+0.1% formic acid), Gradient: 5% B at t=0 min up to 100% B at t=4.5 min, using different gradient curves, flow rate: 0.5 ml/min;

Zorbax SB C18 column (2.1×50 mm, 3.5 μm particle size) column T=35° C. Mobile phase: A (water+0.1% formic acid)/B (acetonitrile+0.1% formic acid), Gradient: 10% B at t=0 min up to 90% B at t=12 min using different gradient curves, flow rate: 0.4 ml/min.

HPLC spectra were performed on a Waters Alliance 2965 instrument equipped with a Waters 2996 UV-Vis detector using a Phenomenex Luna C18 column (150×4.6 mm, 5 μm particle size). [Mobile phase: different mixtures of acetonitrile/methanol/KH2PO4 (20 mM pH 2.5); Elution time: 35 min; column T=30° C.; flow rate=0.6 ml/min. UV detection wavelength range from 220 up to 300 nm]

Total ion current (TIC) and DAD UV chromatografic traces together with MS and UV spectra were taken on a UPLC/MS Acquity™ system equipped with 2996 PDA detector and coupled to a Waters Micromass ZQ™ Mass Spectrometer operating in positive or negative electrospray ionisation mode. UPLC analysis were performed using an Acquity™ UPLC-BEH C18 column (50×21 mm, 1.7 μM particle size), column T=35° C. Mobile phase: A (water+0.1% formic acid)/B (acetonitrile+0.1% formic acid), Gradient: 5% B at t=0 min, up to 100% B at t=2 min or 4.5 min using different gradient curves, flow rate: 0.5 ml/min.

LCMS were taken on a quadrupole Mass spectrometer on Agilent LC/MSD 1200 Series using Column: Welchrom XB-C18 (50×4.6 mm, 5 μm) operating in ES (+) or (−) ionization mode at T=30° C. and with a flow rate=1.5 ml/min.

HPLC spectra for chiral purity determinations were performed on Agilent 1200 instrument and UV detector DAD G1315D using a Daicel Chiralpack IC column [5 μm particle size (250×4.6 mm)] or a Daicel Chiralpack AD-H column [5 μm particle size (250×4.6 mm)] or a DAICEL OD-H [5 μm particle size (250×4.6 mm)] or a Regis Welk 01 (SS) [5 μm particle size (250×4.6 mm)] and the following general isocratic conditions: Mobile phases: A: n-heptane or n-hexane from 90% to 50% (+0.1% DEA or +0.2% TFA) B: ethanol or IPA from 10% to 50%; time: up to 60 min of elution; Column Temperature: 30° C.; flow rate: 0.5 ml/min.

Purifications by means of preparative chiral HPLC were performed on Shimadzu Preparative Liquid Chromatograph LC-8A apparatus and UV detector SPD-20A using a Daicel Chiralpack IC column [(250×4.6 mm), 5 μm particle size] or a Daicel Chiralpack AD-H column [(250×4.6 mm), 5 μm particle size] and the following general isocratic conditions: Mobile phase: premixed mixture of n-heptane or n-hexane from 90% to 50%, and ethanol or IPA from 10% to 50% (+0.1% DEA or +0.2% TFA); time: up to 60 min of elution; Column Temperature: RT; flow rate: 10 ml/min.

Specific Mobile phase and operating conditions will be specified each time.

Abbreviations

BAIB—bis(acetoxy)iodobenzene
$BF_3 \cdot OEt_2$—Boron trifluoride diethyl etherate
$Boc_2O$—Di-tert-butyl dicarbonate
cHex—Cyclohexane
s-BuLi—sec-Butyllithium
t-Buli—tert-Butyllithium
DAST—Diethylaminosulfur trifluoride
1,2 DCE—1,2-Dichloroethane
DCM—dichloromethane
DEA—diethylamine
DMAP—4-Dimethylaminopyridine
DMF—Dimethylformamide
DIPEA—N,N-Diisopropylethylamine
EDC HCl—1-ethyl-3-(3-dimethylaminopropyl) carbodiimide)
EtOAc—Diethylacetate
$Et_2O$—Diethylether
$Et_3SiH$—Triethylsilane
HATU—O-(7-azabenzotriazol-1-yl)-N,N,N',N'-tetramethyluronium hexafluorophosphate
HBTU—O-Benzotriazole-N,N,N',N'-tetramethyl-uronium hexafluoro-phosphate HCTU—(2-(6-Chloro-1H-benzotriazole-1-yl)-1,1,3,3-tetramethylaminium hexafluorophosphate)
HOBT—N-Hydroxybenzotriazole
IPA—2-propanol
LDA—Lithium diisopropylamide
LiEt$_3$BH—Lithium triethylborohydride
LiHMDS—Lithium bis(trimethylsilyl)amide
MeCN—Acetonitrile
MTBE—Methyl tert-butyl ether
NaBH(OAc)$_3$—Sodium triacetoxyborohydride
NaBH$_4$—Sodium borohydride
PTSA—p-Toluene sulfonic acid
Py—Pyridine
RT—Room Temperature
TBAF—Tetra-n-butylammonium fluoride
TBDMSCI—tert-Butyldimethylsilyl chloride
TBDPSCI—tert-butyldiphenylsilyl chloride
TEA—Triethylamine
TEMPO—2,2,6,6-Tetramethylpiperidinyloxy
TFA—Trifluoroacetic acid
TFAA—Trifluoroacetic anhydride
TMEDA—Tetramethylethylenediamine
TMSCHN2—Trimethylsilyldiazomethane
p-TSA—p-Toluenesulfonic acid
THF—Tetrahydrofuran

DESCRIPTIONS

Description 1

6-(tert-butoxycarbonyl)-6-azaspiro[2.5]octane-5-carboxylic acid (racemic mixture) (D1)

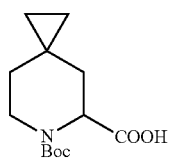 [SMILES: CC(C)(C)OC(=O)N1CCC2(CC2)CC1C(=O)O]

To a solution of tert-butyl 6-azaspiro[2.5]octane-6-carboxylate (2.1 g, 9.9 mmol; for preparation see published International Patent application WO2011006960) in dry Et$_2$O (40 ml), cooled to −78° C., TMEDA (3.6 ml, 23.85 mmol) was added followed by addition of sec-BuLi 1.4M sol in cHex (17.04 ml, 23.85 mmol). The reaction mixture was stirred at −78° C. for 1.5 hrs then slowly warmed at −25° C. and further stirred at this temperature for 30 min. The solution was cooled to −78° C. and quenched by bubbling dry ice into the reaction mixture via cannula for 15 min. The solution was then further stirred for 15 min the allowed to slowly warm to RT prior addition of NH$_4$Cl sat sol (40 ml). Phases were separated then the aqueous was acidified to pH~3 by addition of citric acid 1M sol and extracted with EtOAc. Collected organic phases after drying and solvent evaporation afforded a residue which was purified by SPE-Si cartridge (50 g) eluting with a mixture DCM/MeOH from 100/0 to 98/2. Collected fractions after solvent evaporation afforded the title compound (D1) (1.93 g).

MS: (ES/+) m/z: 254.1 [MH$^-$] C13H21NO4 requires 255.15

$^1$H NMR (400 MHz, CHCl3-d) δ (ppm 10.62 (br. s, 1 H), 5.15-4.70 (m, 1 H), 4.23-3.86 (m, 1 H), 3.37-3.02 (m, 1 H), 2.29-2.14 (m, J=5.4, 13.0 Hz, 1 H), 2.02-1.85 (m, J=3.4 Hz, 1 H), 1.67-1.54 (m, 1 H), 1.49 (br. s., 9 H), 0.88-0.77 (m, 1 H), 0.52-0.25 (m, 4 H).

Description 2

N-benzyl-1-phenylethanaminium 6-(tert-butoxycarbonyl)-6-azaspiro[2.5]octane-5-carboxylate (single unknown enantiomer) (D2)

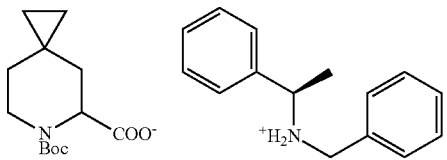

To an ice cooled solution of 6-(tert-butoxycarbonyl)-6-azaspiro[2.5]octane-5-carboxylic acid (racemic mixture) (D1) (41 g, 160.8 mmol) in anhydrous MeOH (400 ml) (R)—N-benzyl-1-phenylethanamine (34 g, 160.8 mmol) was added and the resulting reaction mixture was stirred at 0° C. for 1.5 hrs. The reaction mixture was warmed at RT and further stirred for 5 hours. Solvent was evaporated in vacuo to afford (R)—N-benzyl-1-phenylethanaminium 6-(tert-butoxycarbonyl)-6-azaspiro[2.5]octane-5-carboxylate (racemic salt) (75 g). To a solution of the above compound (75 g, 160.8 mmol) in anhydrous EtOH (400 ml), H$_2$O (1.2 L) was added and the resulting suspension was warmed to reflux until the mixture turned into clear solution. The mixture was cooled slowly to 50° C. until formation of a precipitate which was filtered at 50° C. The aqueous layer was extracted with EtOAc twice, and the collected organic layers were dried over anhydrous Na$_2$SO$_4$, filtered and evaporated in vacuo to afford 20 g of salt which was recrystallized from H$_2$O/EtOH (300/100 ml) at 50° C. to afford the title compound (D2) (10 g).

Description 3

6-(tert-butoxycarbonyl)-6-azaspiro[2.5]octane-5-carboxylic acid (single unknown enantiomer) (D3)

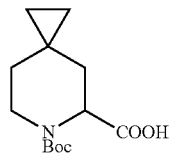

To a suspension of N-benzyl-1-phenylethanaminium 6-(tert-butoxycarbonyl)-6-azaspiro[2.5]octane-5-carboxylate (single unknown enantiomer) (D2) (10 g, 24 mmol) in EtOAc (100 mL) stirred at 0° C. was slowly added aqueous HCl 0.5N (100 ml) saturated with NaCl. After addition was completed, dissolution was observed. The organic layer was decanted, washed with saturated NaCl, dried (Na$_2$SO$_4$) and evaporated in vacuo to afford 5 g of acid which was recrystallized from petroleum ether/EtOAc (60 ml/20 ml) to afford the tile compound (D3) (2.8 g) as white solid.

Description 4

6-tert-butyl 5-methyl 6-azaspiro[2.5]octane-5,6-dicarboxylate (racemic mixture) (D4)

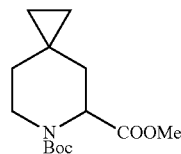 [SMILES: COC(=O)C1CC2(CCN1C(=O)OC(C)(C)C)CC2]

To an ice cooled solution of 6-(tert-butoxycarbonyl)-6-azaspiro[2.5]octane-5-carboxylic acid (racemic mixture) (D1) (500 mg, 0.78 mmol) in Et$_2$O/MeOH (10/5 ml), TMSCHN$_2$ 2M sol in Et$_2$O (1.5 ml, 2.94 mmol) was added and the resulting mixture was stirred 2 hrs at 0° C. then 18 hrs at RT. After solvent evaporation the crude residue was loaded onto SPE-Si cartridge (10 g) eluting with DCM. Collected fractions after solvent evaporation afforded the title compound (D4) (420 mg) as a clear oil.

MS: (ES/+) m/z: 170 [MH-Boc$^+$] C14H23NO4 requires 269.16

$^1$H NMR (400 MHz, CHCl3-d) δ (ppm): 5.07-4.63 (m, 1 H), 4.16-3.88 (m, 1 H), 3.74 (br. s., 3 H), 3.34-3.04 (m, 1 H), 2.18 (dd, J=6.0, 13.6 Hz, 1 H), 2.02-1.81 (m, 1H), 1.61-1.37 (m, 10 H), 0.81 (br. s., 1 H), 0.44-0.19 (m, 4 H)

Description 5

6-tert-butyl 5-methyl 5-methyl-6-azaspiro[2.5]octane-5,6-dicarboxylate (D5)

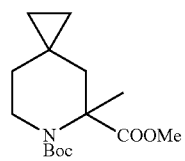 [SMILES: COC(=O)C1(C)CC2(CCN1C(=O)OC(C)(C)C)CC2]

6-tert-butyl 5-methyl 6-azaspiro[2.5]octane-5,6-dicarboxylate (D4) (420 mg, 1.56 mmol) was dissolved in THF (25 ml) and the solution was cooled at −78° C. prior addition of LDA 2M sol in THF/heptane (1.16 ml, 2.34 mmol). The red solution was left stirring at −78° C. for 40 min before adding iodomethane (0.146 ml, 2.34 mmol). The reaction was allowed to warm to RT and left stirring for 3 hrs. The resulting yellow-orange solution was treated with NH$_4$Cl sat. sol. (5 ml) and extracted with Et$_2$O (3×50 ml). Collected organic phases were washed with NaCl sat. sol. and dried over Na$_2$SO$_4$. Collected organics after solvent evaporation, afforded a residue which was purified by Biotage SNAP-Si (25 g) eluting with DCM. Collected fractions after solvent evaporation afforded the title compound (D5) (320 mg)

MS: (ES/+) m/z: 306.3 [MH+Na$^+$] C15H25NO4 requires 283.18

$^1$H NMR (400 MHz, CHCl3-d) δ (ppm): 4.03-3.85 (m, 1 H), 3.73 (s, 3 H), 3.28-3.11 (m, 1 H), 2.33-2.14 (m, 1 H), 2.01-1.85 (m, 1 H), 1.45 (s, 12 H), 1.17-1.09 (m, 1 H), 0.56-0.41 (m, 2 H), 0.40-0.21 (m, J=6.2 Hz, 3 H).

Description 6

6-(tert-butoxycarbonyl)-5-methyl-6-azaspiro[2.5]octane-5-carboxylic acid (D6)

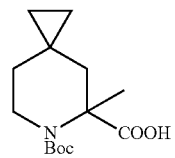 [SMILES: CC(C)(C)OC(=O)N1CCC2(CC2)CC1(C)C(=O)O]

6-tert-butyl 5-methyl 5-methyl-6-azaspiro[2.5]octane-5,6-dicarboxylate (D5) (320 mg, 1.13 mmol) was partitioned between dioxane/water (8/8 ml) prior addition of LiOH H$_2$O (190 mg, 4.52 mmol). The mixture was stirred at RT for 18 hrs then heated at 150° C. under microwave irradiation 40 min (4 cycles of 10 min each). Organic solvent was evaporated off and the aqueous solution washed with EtOAc (2×10 ml), acidified to pH~4 with citric acid sat. sol. and extracted with EtOAc (3×10 ml). The organic phases were washed with NaCl sat. sol, dried over Na$_2$SO$_4$ and evaporated to reduced pressure to afford the title compound (D6) (114 mg).

MS: (ES/+) m/z: 292 [MH+Na$^+$] C14H23NO4 requires 269.16

$^1$H NMR (400 MHz, CHCl3-d) δ (ppm): 4.01-3.88 (m, 1 H), 3.24-3.11 (m, 1 H), 2.41-2.30 (m, 1 H), 2.04-1.91 (m, 1 H), 1.47 (s, 12 H), 1.16 (d, J=13.2 Hz, 2 H), 0.51 (br. s., 2 H), 0.37 (d, J=6.4 Hz, 2 H).

Description 7

2-aminopent-4-en-1-ol (D7)

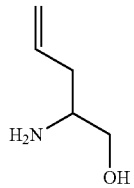

To an ice cooled solution of (±)-2-Amino-4-pentenoic acid (6 g, 0.052 mmol; available from Fluka #05960) in THF (250 ml), LiAlH$_4$ (2.37 g, 0.065 mmol) was added portionwise. The resulting reaction mixture was allowed to warm to RT then stirred overnight. Water (2.36 g), NaOH 1M (3.56 g) and water (7.2 g) were added in sequence to the reaction mixture previously cooled at 0° C. The precipitate was filtered off and the phases were separated. The aqueous layer was evaporated under reduced pressure to afford a yellow-brown oil (5 g). The previously filtered solid was treated with boiling THF (500 ml) for 30 min prior filtration. The filtrate was evaporated and the resulting residue was taken up in water and extracted with DCM (3×200 ml). After solvent evaporation, a yellow-brown oil (3.3 g) was isolated. Both obtained oils were collected together to afford a single batch of the desired compound (D7) (8.3 g).

MS: (ES/+) m/z: 102.1 [MH$^+$] C5H11NO requires 101.08

¹H NMR (400 MHz, DMSO-d) δ (ppm): 5.91-5.73 (m, 2 H), 5.08-4.92 (m, 4 H), 3.34-3.25 (m, 1 H), 3.16-3.11 (m, 1 H), 2.72-2.61 (m, 1 H), 2.19-2.02 (m, 1 H), 1.96-1.83 (m, 1 H).

Description 8

N-(1-hydroxypent-4-en-2-yl)-4-methylbenzenesulfonamide (D8)

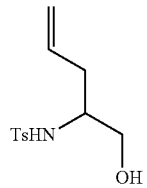

A solution of Na₂CO₃ (9.22 g, 86.92 mmol) in water (50 ml) was left under stirring at RT for 20 min prior addition of 2-aminopent-4-en-1-ol (D7) (8.3 g) and EtOAc (160 ml). After 30 minutes stirring, a solution of p-toluenesulfonyl chloride (12.9 g, 67.85 mmol) in EtOAc/THF (24/24 ml) was added over 15 minutes. The reaction mixture was stirred at RT for a weekend. Water (30 ml) and EtOAc (100 ml) were added to the reaction mixture, the phases were separated and the aqueous layer was extracted with EtOAc (2×80 ml). The combined organic phases were evaporated and the residue was purified by Biotage SNAP-Si (100 g) cartridge eluting with a mixture cHex/EtOAc from 80/20 to 50/50. Collected fractions after solvent evaporation afforded the title compound (D8) (5.5 g)

MS: (ES/+) m/z: 256.1 [MH⁺] C12H17NO3S requires 255.09

¹H NMR (400 MHz, CHCl3-d) δ (ppm): 7.82-7.75 (m, 2 H), 7.37-7.30 (m, J=8.8 Hz, 2 H), 5.57-5.44 (m, 1 H), 5.05 (s, 1 H), 5.04-4.98 (m, 1 H), 4.79 (d, J=7.3 Hz, 1 H), 3.65-3.59 (m, 1 H), 3.59-3.52 (m, 1 H), 3.36-3.22 (m, 1 H), 2.46 (s, 3 H), 2.28-2.14 (m, 2 H).

Description 9

N-(1-((tert-butyldiphenylsilyl)oxy)pent-4-en-2-yl)-4-methylbenzenesulfonamide (D9)

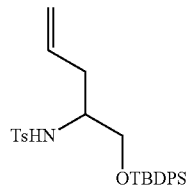

To a solution of N-(1-hydroxypent-4-en-2-yl)-4-methylbenzenesulfonamide (D8) (6.5 g, 25.45 mmol) in DMF (95 ml), imidazole (4.5 g, 66.17 mmol) and TBDPSCI (7.9 ml, 30.54 mmol) were added and the reaction was stirred at RT for 3 hrs. The mixture was diluted with brine (50 ml) and extracted with EtOAc (3×60 ml). The combined organic phases after solvent evaporation afforded a residue which was purified by Biotage SNAP-Si (100 g) cartridge eluting with a mixture cycloexane/EtOAc from 100/0 to 80/20. Collected fractions after solvent evaporation afforded the title compound (D9) (13 g).

MS: (ES/+) m/z: 494.2 [MH⁺] C28H35NO3SSi requires 493.21

¹H NMR (400 MHz, CHCl3-d) δ (ppm): 7.76-7.20 (m, 14 H), 5.64-5.43 (m, 1 H), 5.02 (s, 1 H), 5.00-4.94 (m, 1 H), 4.76 (d, J=7.8 Hz, 1 H), 3.62-3.54 (m, 1 H), 3.50-3.40 (m, 1 H), 3.39-3.25 (m, 1 H), 2.43 (s, 3 H), 2.34 (t, J=6.8 Hz, 2 H), 1.07-1.01 (m, 9 H).

Description 10

N-allyl-N-(1-((tert-butyldiphenylsilyl)oxy)pent-4-en-2-yl)-4-methylbenzenesulfonamide (D10)

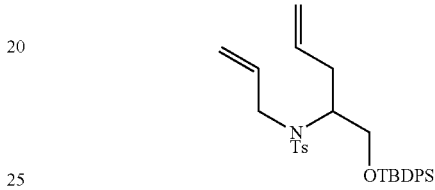

To a solution of N-(1-((tert-butyldiphenylsilyl)oxy)pent-4-en-2-yl)-4-methylbenzenesulfonamide (D9) (13 g, 26.33 mmol) in DMF (80 ml), Cs₂CO₃ (12.86 g, 39.49 mmol) and allyl bromide (1.8 ml, 21.06 mmol) were added and the mixture was stirred at RT for 4 hrs. The reaction mixture was diluted with water (40 ml) and extracted with EtOAc (3×60 ml). The combined organic phases were evaporated and the resulting residue was was purified by Biotage SNAP-Si (100 g) cartridge eluting with a mixture cycloexane/EtOAc from 100/0 to 90/10. Collected fractions after solvent evaporation afforded the title compound (D10) (10.7 g).

MS: (ES/+) m/z: 534.2 [MH⁺] C31H39NO3SSi requires 533.24

¹H NMR (400 MHz, CHCl3-d) δ (ppm): 7.72-7.67 (m, J=8.3 Hz, 2 H), 7.64-7.57 (m, 4 H), 7.50-7.43 (m, 2 H), 7.43-7.35 (m, 4 H), 7.23-7.17 (m, J=8.3 Hz, 2 H), 5.79 (tdd, J=6.4, 10.4, 17.0 Hz, 1 H), 5.55 (tdd, J=6.8, 10.3, 17.1 Hz, 1 H), 5.14-4.89 (m, 4 H), 4.03-3.92 (m, 2 H), 3.87-3.78 (m, 1 H), 3.71-3.60 (m, 2 H), 2.50-2.42 (m, 1 H), 2.40 (s, 3 H), 2.33-2.23 (m, 1 H), 1.04 (s, 9 H).

Description 11

2-(((tert-butyldiphenylsilyl)oxy)methyl)-1-tosyl-1,2,3,6-tetrahydropyridine (D11)

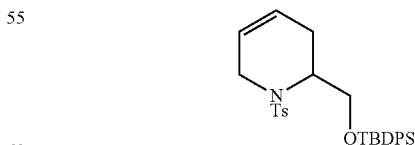

To a solution of N-allyl-N-(1-((tert-butyldiphenylsilyl)oxy)pent-4-en-2-yl)-4-methylbenzenesulfonamide (D10) (7.12 g, 13.33 mmol) in DCM (64 ml), Grubb's catalyst (1.09 g, 1.32 mmol) was added and the mixture was stirred at RT overnight. After solvent evaporation, the residue was loaded on KP-Si (100 g) cartridge eluting with a mixture cHex/

EtOAc from 100/0 to 90/10. Collected fractions after solvent evaporation afforded the title compound (D11) (8.9 g).

MS: (ES/+) m/z: 506.2 [MH$^+$] C29H35NO3SSi requires 505.74

$^1$H NMR (400 MHz, CHCl3-d) δ (ppm): 7.67-7.58 (m, 6 H), 7.50-7.35 (m, 6 H), 7.18 (d, J=7.8 Hz, 2 H), 5.60 (dd, J=2.0, 5.4 Hz, 1 H), 5.55 (br. s., 1 H), 4.32 (d, J=7.8 Hz, 1 H), 4.04 (d, J=18.1 Hz, 1 H), 3.63-3.53 (m, 2 H), 3.51-3.41 (m, 1 H), 2.40 (s, 3 H), 2.33-2.24 (m, 1 H), 2.22-2.11 (m, 1 H), 1.05 (s, 9 H).

Description 12

4-(((tert-butyldiphenylsilyl)oxy)methyl)-3-tosyl-3-azabicyclo[4.1.0]heptane (racemic mixture) (D12)

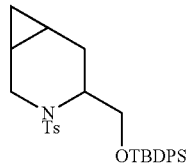

To an ice cooled solution of diethylzinc 1M in hexane (93.64 ml) in DCM (50 ml) TFA (7.17 ml, 93.64 mmol) was added dropwise. After 20 min stirring, diiodomethane (7.54 ml, 93.64 mmol) was added and the mixture stirred for further 20 min. A solution of 2-(((tert-butyldiphenylsilyl)oxy)methyl)-1-tosyl-1,2,3,6-tetrahydropyridine (D11) (5.92 g, 11.7 mmol) in DCM (25 ml) was added then the reaction mixture was allowed to warm to RT and stirred for 6 hrs. A solution of diethylzinc 1M in hexane (93.64 ml), TFA (7.17 ml, 93.64 mmol) and diiodomethane (7.54 ml, 93.64 mmol) in DCM (50 ml) was prepared as described above and added to the previous mixture at 0° C. The resulting reaction mixture was allowed to warm to RT and stirred overnight. NH4Cl solution (100 ml) was added to the reaction mixture, the phases were separated and the aqueous layer was extracted twice with EtOAc (2×60 ml). After solvent evaporation, the residue was was purified by Biotage SNAP-Si (2100 g) cartridge eluting with a mixture cHex/EtOAc from 100/0 to 95/05. Collected fractions after solvent evaporation afforded the title compound (D12) (5.12 g).

MS: (ES/+) m/z: 520.2 [MH$^+$] C30H37NO3SSi requires 519.23

$^1$H NMR (400 MHz, CHCl3-d) δ (ppm): 7.68-7.61 (m, 4 H), 7.61-7.55 (m, J=7.8 Hz, 2 H), 7.50-7.35 (m, 6 H), 7.21-7.15 (m, J=8.3 Hz, 2 H), 3.92-3.83 (m, 1 H), 3.71-3.59 (m, 2 H), 3.42-3.26 (m, 2 H), 2.40 (s, 3H), 2.26 (ddd, J=1.5, 8.3, 14.7 Hz, 1 H), 1.41 (td, J=5.3, 14.3 Hz, 1 H), 1.11-1.03 (m, 9 H), 0.93-0.82 (m, 1 H), 0.82-0.71 (m, 1 H), 0.70-0.58 (m, 1 H), 0.03 (q, J=4.9 Hz, 1 H)

Description 13

4-(((tert-butyldiphenylsilyl)oxy)methyl)-3-azabicyclo[4.1.0]heptane (racemic mixture) (D13)

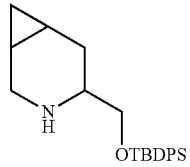

To a solution of 4-(((tert-butyldiphenylsilyl)oxy)methyl)-3-tosyl-3-azabicyclo[4.1.0]heptane (D12) (3.12 g, 6 mmol) in MeOH (430 ml), under a nitrogen atmosphere, magnesium turnings (previously flame dried) (8.46 g, 348 mmol) and NH4Cl (8.9 g, 168 mmol) were added sequentially and the mixture was stirred at 23° C. Two further additions of magnesium (4.3 g), each one after 2 hrs stirring, were done. DCM (210 ml) and NH4Cl sat. sol. (285 ml) were added to the reaction mixture. The formed emulsion was filtered through a celite pad. The organic layer was separated and washed with brine (2×55 ml). The combined organic layers were evaporated and the resulting residue was purified by SPE-SCX (20 g) cartridge. Collected ammonia fractions after solvent evaporation afforded the title compound (D13) (1.65 g).

MS: (ES/+) m/z: 365.7 [MH$^+$] C23H31 NOSi requires 365.22

$^1$H NMR (400 MHz, CHCl3-d) δ (ppm): 7.67 (d, J=6.8 Hz, 4 H), 7.49-7.36 (m, 6 H), 3.64-3.51 (m, 3 H), 2.82 (dd, J=2.7, 12.5 Hz, 1 H), 2.40 (tdd, J=3.9, 7.5, 11.1 Hz, 1 H), 1.72 (dd, J=3.9, 13.2 Hz, 1 H), 1.57 (ddd, J=5.6, 11.1, 13.1 Hz, 1 H), 1.19-0.99 (m, 11 H), 0.67 (dt, J=4.6, 8.7 Hz, 1 H), 0.21 (q, J=5.4 Hz, 1 H).

Description 14 tert-butyl 4-(((tert-butyldiphenylsilyl)oxy)methyl)-3-azabicyclo[4.1.0]heptane-3-carboxylate (racemic mixture) (D14)

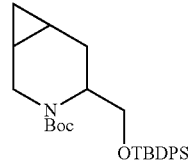

To a solution of 4-(((tert-butyldiphenylsilyl)oxy)methyl)-3-azabicyclo[4.1.0]heptane (D13) (1.65 g, 4.51 mmol) and TEA (1.25 ml, 9.02 mmol) in DCM (30 ml), Boc2O (1.08 g, 4.96 mmol) was added and the reaction mixture was stirred at RT for 1 h. The solution was diluted with H2O (50 ml), washed with 1N HCl (2×35 ml) then with NaHCO3 sat. sol. (2×35 ml). The combined organic layers were evaporated in vacuo and the resulting residue was loaded on SPE-Si cartridges (50 g) and eluted with a mixture cycloexane/EtOAc from 100/0 to 90/10. Collected fractions after solvent evaporation afforded the title compound (D14) (2.10 g).

MS: (ES/+) m/z: 488.2 [MH+Na$^+$] C28H39NO3Si requires 465.7

$^1$H NMR (400 MHz, DMSO-d6) δ (ppm): 7.62 (ddd, J=2.0, 3.9, 5.9 Hz, 4 H), 7.54-7.36 (m, 6 H), 4.09-3.84 (m, 1 H), 3.74 (d, J=12.2 Hz, 1 H), 3.70-3.55 (m, 2 H), 3.32-3.26 (m, 1 H), 2.09-1.81 (m, 1 H), 1.63 (ddd, J=3.4, 6.8, 14.7 Hz, 1 H), 1.40-1.25 (m, 9 H), 1.00 (s, 9 H), 0.88 (br. s., 2 H), 0.63-0.47 (m, 1 H), −0.02 (d, J=3.9 Hz, 1 H).

Description 15 tert-butyl 4-(hydroxymethyl)-3-azabicyclo[4.1.0]heptane-3-carboxylate (racemic mixture) (D15)

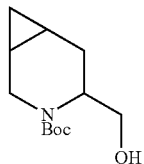 [SMILES: CC(C)(C)OC(=O)N1CC2CC2CC1CO]

To a solution of tert-butyl 4-(((tert-butyldiphenylsilyl)oxy)methyl)-3-azabicyclo[4.1.0]heptane-3-carboxylate (D14) (2.10 g, 4.5 mmol) in THF (80 ml), TBAF 1M sol. in THF (9.01 ml) was added and the reaction mixture was stirred at RT for 18 hrs. Solvents were evaporated in vacuo and the resulting residue was purified on SPE-Si (5 g) cartridge eluting with a mixture cHex/EtOAc from 90/10 to 40/60. Collected fractions after solvent evaporation afforded the title compound (D15) (0.93 g).

MS: (ES/+) m/z: 172.1 [MH-56$^+$] C12H21NO3 requires 277.15

$^1$H NMR (400 MHz, DMSO-d6) δ (ppm): 4.66 (br. s., 1 H), 3.78 (br. s., 1 H), 3.71 (d, J=13.7 Hz, 1 H), 3.47-3.31 (m, 2 H), 3.28 (br. s., 1 H), 1.96-1.83 (m, 1 H), 1.59-1.49 (m, 1H), 1.42-1.34 (m, 9 H), 0.89 (s, 2 H), 0.59 (dt, J=4.4, 8.3 Hz, 1 H), −0.08 (q, J=4.9 Hz, 1 H).

Description 16 tert-butyl 4-formyl-3-azabicyclo[4.1.0]heptane-3-carboxylate (racemic mixture) (D16)

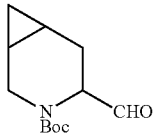

To a solution of tert-butyl 4-(hydroxymethyl)-3-azabicyclo[4.1.0]heptane-3-carboxylate (D15) (820 mg, 3.6 mmol) and TEMPO (112.7 mg, 0.72 mmol) in DCM (8 ml), BAIB (1.27 g, 3.96 mmol) was added and the resulting mixture was stirred at RT 4 hrs. The reaction mixture was diluted with DCM (35 ml), washed with Na$_2$S$_2$O$_3$ sat sol (35 ml) and extracted with DCM (2×35 ml). The combined organic extracts were washed with NaHCO$_3$ sat sol (35 ml) and brine (35 ml), dried and evaporated under reduce pressure. The remaining residue was loaded on SPE-Si (25 g) cartridge and eluted with a mixture cHex/EtOAC from 95/05 to 80/20. Collected fractions after solvent evaporation afforded the title compound (D16) (0.62 g).

MS: (ES/+) m/z: 170.1 [MH-56$^+$] C12H19NO3 requires 225.14

$^1$H NMR (400 MHz, DMSO-d6) δ (ppm): 9.46 (d, J=19.1 Hz, 1 H), 4.13-3.95 (m, 1 H), 3.75-3.60 (m, 1 H), 3.59-3.35 (m, 1 H), 2.30-2.19 (m, 1 H), 1.76-1.59 (m, 1 H), 1.47-1.29 (m, 9 H), 1.14-0.84 (m, 2 H), 0.62 (dt, J=4.9, 8.3 Hz, 1 H), 0.24-0.05 (m, 1 H).

Description 17

3-(tert-butoxycarbonyl)-3-azabicyclo[4.1.0]heptane-4-carboxylic acid (racemic mixture) (D17)

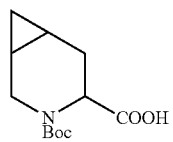 [SMILES: CC(C)(C)OC(=O)N1CC2CC2CC1C(=O)O]

To a mixture of tert-butyl 4-formyl-3-azabicyclo[4.1.0]heptane-3-carboxylate (D16) (615 mg, 2.73 mmol) in acetone/water (30/20 ml) NaH$_2$PO$_4$.2H$_2$O (426 mg, 2.73 mmol), 2-methyl-2-butene (1.3 ml, 12.28 mmol) and NaClO$_2$ (864 mg, 9.55 mmol) were added and the reaction mixture was stirred at RT overnight. Solvents were evaporated in vacuo and the remaining residue was taken up into EtOAc (10 ml) and water (10 ml). Phases were separated and the aqueous layer was extracted with EtOAc (2×10 ml). The combined organic extracts after solvent evaporation afforded the title compound (D17) (0.5 g).

MS: (ES/+) m/z: 264.1 [MH+Na$^+$] C12H19NO4 requires 241.13

$^1$H NMR (400 MHz, DMSO-d6) δ (ppm): 12.51 (br. s., 1 H), 4.25-4.01 (m, 1 H), 3.65-3.51 (m, 1 H), 3.37 (dd, J=4.6, 13.4 Hz, 1 H), 2.31-2.16 (m, 1H), 1.81-1.67 (m, 1 H), 1.42-1.32 (m, 9 H), 1.12-0.85 (m, 2 H), 0.67-0.53 (m, 1 H), 0.19-0.04 (m, 1 H).

Description 18

(R)-ethyl 6-oxopiperidine-2-carboxylate (D18)

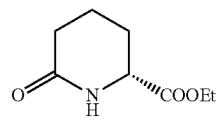

A 2-necked flask was charged with EtOH (60 ml) and cooled to −5° C. Thionyl chloride (2.8 ml, 38.4 mmol) was added dropwise in a manner that the temperature did not exceed 0° C. D-6-oxopipecolic acid (5 g, 34.9 mmol, available from Fluorochem #040124) was added in portions and the resulting mixture was left warming to RT and stirred for 18 hrs. EtOH was evaporated down to 15% of its volume and toluene (60 ml) was added followed by addition of TEA (10.6 ml, 76.8 mmol) in a manner that the temperature did not exceed 10° C. The slurry was left stirring for 30 min, before filtering the white salt. The filtrate was evaporated in vacuo and the resulting residue was re-dissolved in Et$_2$O (80 ml). The white solid formed was filtrated off and the filtrate was evaporated in vacuo to afford the title compound (D18) (6.4 g)

MS: (ES/+) m/z: 172.1 [MH$^+$] C8H13NO3 requires 171.09

$^1$H NMR (400 MHz, CHCl3-d) δ (ppm): 7.34-7.09 (m, 2 H), 6.51 (br. s., 1 H), 4.24 (q, J=7.2 Hz, 2 H), 4.08 (t, J=5.9 Hz, 1 H), 2.51-2.29 (m, 3 H), 2.26-2.12 (m, 1 H), 2.02-1.70 (m, 3 H).

Description 19

(R)-1-tert-butyl 2-ethyl 6-oxopiperidine-1,2-dicarboxylate (D19)

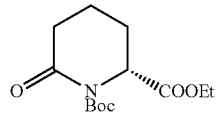

(R)-ethyl 6-oxopiperidine-2-carboxylate (D18) (5.97 g, 34.9 mmol) was dissolved in toluene (30 ml) prior addition of DMAP (213 mg, 1.74 mmol). After 10 minutes, a solution of Boc$_2$O (7.61 g, 34.9 mmol) in toluene (20 ml) was added dropwise and the resulting mixture left stirring at RT for 7 hrs. Boc$_2$O (1.52 g, 6.97 mmol) was added and the mixture further stirred for 18 hrs. The reaction mixture was then charged with half-saturated NaHCO$_3$ solution (100 ml) and stirred for 10 min before separating the two phases. The separated organic phase was washed with water (2×50 ml), dried over Na$_2$SO$_4$ and evaporated in vacuo to afford the title compound (D19) (9.06 g).

MS: (ES/+) m/z: 294.1 [MH+Na$^+$] C13H21NO5 requires 271.14

$^1$H NMR (400 MHz, CHCl3-d) δ (ppm): 4.77-4.63 (m, 1 H), 4.24 (dd, J=2.7, 7.1 Hz, 2 H), 2.68-2.42 (m, 2 H), 2.26-2.13 (m, 1 H), 2.12-1.97 (m, 1 H), 1.88-1.69 (m, 2 H), 1.59-1.44 (m, 9 H), 1.30 (t, J=7.1 Hz, 3 H).

Description 20

(R)-1-tert-butyl 2-ethyl 3,4-dihydropyridine-1,2(2H)-dicarboxylate (D20)

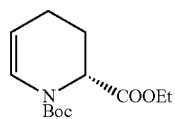

A solution of (R)-1-tert-butyl 2-ethyl 6-oxopiperidine-1,2-dicarboxylate (D19) (0.5 g, 1.84 mmol) in toluene (5 ml) was cooled at –50° C. LiEt$_3$BH 1M solution in THF (1.93 ml, 1.93 mmol) was added dropwise in a manner that the reaction temperature did not exceed –45° C. After complete addition the mixture was stirred at –45° C. for 30 minutes. DIPEA (1.38 ml, 7.92 mmol) was added to the reaction maintaining the temperature below –45° C. followed by the addition of DMAP (3.4 mg, 0.027 mmol). The reaction mixture was then charged with TFAA (0.3 ml, 2.11 mmol) keeping the temperature below –45° C. After complete addition, the reaction mixture was warmed to 20-25° C. within one hour and kept for an additional 4 hrs at this temperature. Reaction mixture was quenched by slow addition of water. Phases were separated and the organics washed with water, dried over Na$_2$SO$_4$ and concentrated to obtain a clear oil, which was used as such to be subjected to the same procedure once again to afford the title compound (D20) (260 mg).

MS: (ES/+) m/z: 278.1 [MH+Na$^+$] C13H21NO4 requires 255.15

$^1$H NMR (400 MHz, CHCl3-d) δ (ppm): 6.98-6.71 (m, 1 H), 4.99-4.86 (m, 1 H), 4.86-4.65 (m, 1 H), 4.32-4.12 (m, 2 H), 2.44-2.24 (m, 1 H), 2.08-1.76 (m, 3 H), 1.65-1.44 (m, 9 H), 1.38-1.17 (m, 3 H).

Description 21

3R)-2-tert-butyl 3-ethyl 2-azabicyclo[4.1.0]heptane-2,3-dicarboxylate (diastereoisomers mixture) (D21)

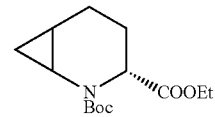

To a solution of (R)-1-tert-butyl 2-ethyl 3,4-dihydropyridine-1,2(2H)-dicarboxylate (D20) (260 mg, 1.02 mmol) in toluene (5 ml), cooled to –30° C., diethyl zinc 1M solution in heptane (2.04 ml, 2.04 mmol) was added dropwise followed by addition of diiodomethane (0.33 ml, 4.07 mmol) in toluene (1 ml). (During reactant additions the reaction temperature was maintained between –25° C. and –30° C.). The reaction mixture was stirred at –20° C. for 24 hrs. Diethyl zinc 1M solution in heptane (2.04 ml, 2.04 mmol) and diiodomethane (0.33 ml, 4.07 mmol) were added and the reaction left stirring at –20° C. for other 24 hrs. The reaction was quenched with half saturated NaHCO$_3$ (10 ml) and left stirring for 30 min. The white precipitate was filtered off. The organic phase was washed with water (2×20 ml), dried over Na$_2$SO$_4$ and evaporated in vacuo to afford the title compound (D21) (600 mg) used as such without purification.

MS: (ES/+) m/z: 292.1 [MH+Na$^+$] C14H23NO4 requires 269.16

Description 22

3R)-2-(tert-butoxycarbonyl)-2-azabicyclo[4.1.0]heptane-3-carboxylic acid (diastereoisomers mixture) (D22)

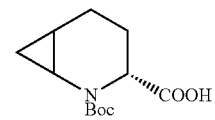

(3R)-2-tert-butyl 3-ethyl 2-azabicyclo[4.1.0]heptane-2,3-dicarboxylate (D21) (600 mg, 2.22 mmol) was partitioned between dioxane (10 ml) and water (5 ml) prior addition of LiOH H$_2$O (370 mg, 8.9 mmol). The mixture was stirred at RT for 18 hrs. Water (10 ml) and LiOH H$_2$O (740 mg, 18 mmol) were added and the mixture left at RT for 66 h. Dioxane was evaporated off and remaining aqueous was washed with Et$_2$O (3×20 ml). Aqueous solution was acidified with acetic acid up to pH 4 and extracted with EtOAc (3×30 ml). Collected organics were washed with NaCl sat., dried over Na$_2$SO$_4$ and evaporated in vacuo to afford the title compound (D22) (210 mg).

MS: (ES/+) m/z: 264.1 [MH+Na$^+$] C12H19NO4 requires 241.13

Description 23

(R)-ethyl 5-oxopyrrolidine-2-carboxylate (D23)

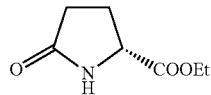 [SMILES: CCOC(=O)[C@H]1CCC(=O)N1]

To a solution of (R)-5-oxopyrrolidine-2-carboxylic acid (10 g, 69.84 mmol; available from Aldrich#422614) in EtOH (100 ml) cooled at −5° C., thionyl chloride (10 ml, 139.68 mmol) was added and the resulting mixture was stirred at RT for 3 hrs. Solvents were evaporated in vacuo and the resulting residue was taken up with EtOAc (350 ml), washed with water/TEA (40/12 ml), then with water (40 ml). Collected organics were dried over $Na_2SO_4$ and evaporated to afford a residue that was loaded on a SNAP-Si cartridge (50 g) and eluted with a mixture DCM/EtOAc from 90/10 to 50/50. Collected fractions after solvent evaporation afforded a first batch of title compound (D23) (6.4 g). The aqueous were saturated with NaCl and extracted with EtOAc (400 ml). The organic was washed with water (20 ml) dried over $Na_2SO_4$ and evaporated in vacuo to afford a second batch of title compound (D23) (3.7 g).

$^1$H NMR (400 MHz, CHCl3-d) δ (ppm): 6.58 (br. s., 1 H), 4.29-4.17 (m, 3 H), 2.53-2.29 (m, 3 H), 2.28-2.17 (m, 1 H), 1.35-1.22 (m, 3 H).

Description 24

(R)-1-tert-butyl 2-ethyl 5-oxopyrrolidine-1,2-dicarboxylate (D24)

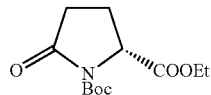 [SMILES: CCOC(=O)[C@H]1CCC(=O)N1C(=O)OC(C)(C)C]

To a solution of (R)-ethyl 5-oxopyrrolidine-2-carboxylate (D23) (10 g, 63.62 mmol) in toluene (50 ml), DMAP (390 mg, 3.2 mmol) was added before addition, after 10 min, of a solution of $Boc_2O$ (13.9 g, 63.62 mmol) in toluene (50 ml). The reaction mixture was stirred at RT overnight then diluted with EtOAc (200 ml), charged with half-saturated $NaHCO_3$ solution (60 ml) and stirred for 10 min. Phases were separated and the organics washed with water (40 ml), dried over $Na_2SO_4$ and evaporated in vacuo to afford a residue which was triturated in heptane. After filtration and drying under reduced pressure, 13.7 g of title compound (D24) were isolated.

MS: (ES/+) m/z: 280 [MH+Na$^+$] C12H19NO5 requires 257.13

$^1$H NMR (400 MHz, CHCl3-d) δ (ppm): 4.68-4.57 (m, 1 H), 4.26 (q, J=7.3 Hz, 2 H), 2.72-2.58 (m, 1 H), 2.57-2.43 (m, 1 H), 2.42-2.26 (m, 1 H), 2.12-1.99 (m, 1 H), 1.52 (s, 9 H), 1.32 (t, J=7.1 Hz, 3 H).

Description 25

(R)-1-tert-butyl 2-ethyl 2,3-dihydro-1H-pyrrole-1,2-dicarboxylate (D25)

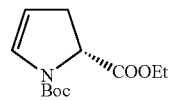

To a solution of (R)-1-tert-butyl 2-ethyl 5-oxopyrrolidine-1,2-dicarboxylate (D24) (14.3 g, 55.58 mmol) in toluene (100 ml) cooled at −50° C., LiEt$_3$BH 1M sol in THF (58.4 ml, 58.36 mmol) was added dropwise maintaining the reaction temperature below −45° C. After complete addition the mixture was stirred at −45° C. for 30 min. DIPEA (42 ml, 239 mmol), DMAP (102 mg, 0.83 mmol) and TFAA (8.9 ml, 63.92 mmol) were added sequentially maintaining the reaction temperature below −45° C. After complete addition, the reaction mixture was warmed to 20-25° C. within one hour and kept for an additional 2 hrs at this temperature. The reaction mixture was slowly charged with water (8 ml) so that the temperature did not exceed 5° C. and diluted with EtOAc (50 ml). Aqueous and organic phases were then separated and the organics washed again with water (8 ml), dried over $Na_2SO_4$ and evaporated to obtain residue which was purified by Biotage SNAP-Si cartridge (50 g) eluting with cHex/EtOAc from 90/10 to 50/50. Collected fractions, after solvent evaporation afforded the title compound (D25) (10.4 g).

MS: (ES/+) m/z: 264 [MH+Na$^+$] C12H19NO4 requires 241.13

$^1$H NMR (400 MHz, CHCl3-d) δ (ppm): 6.73-6.44 (m, 1 H), 4.93 (d, J=19.1 Hz, 1 H), 4.73-4.49 (m, 1 H), 4.36-4.09 (m, 2 H), 3.19-2.94 (m, 1 H), 2.77-2.54 (m, 1 H), 1.57-1.37 (m, 9 H), 1.37-1.18 (m, 3 H).

Description 26

3R)-2-tert-butyl 3-ethyl 2-azabicyclo[3.1.0]hexane-2,3-dicarboxylate (diastereoisomers mixture) (D26)

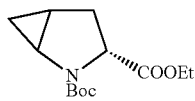

A flamed three-necked flask was charged with diethyl zinc solution 1.0 M in hexane (62 ml, 62 mmol) and toluene (100 ml). The resulting solution was cooled to −10° C. and charged dropwise with diiodomethane (5 ml, 62 mmol) and stirred at 0° C. for 10 min. The reaction mixture was cooled to −10° C., charged with a solution of (R)-1-tert-butyl 2-ethyl 2,3-dihydro-1H-pyrrole-1,2-dicarboxylate (D25) (5 g, 21 mmol) in toluene (30 ml) and kept at 0° C. After 6 h the mixture was quenched with half saturated $NaHCO_3$ (80 ml); a white precipitate was formed which was filtered off and washed with AcOEt (500 ml). Aqueous and organic phase was separated and the organic phase washed with water (60 ml), dried over Na₂SO₄ and evaporated to afford 4.5 g of yellow oil. This material dissolved in toluene (30 ml) was added, over a period of 45 min, to a solution of diethylzinc 1M in hexane (62 ml), and diiodomethane (5 ml) in toluene (100 ml) prepared as described above (T=−10° C.) and the resulting mixture was stirred at 0° C. for 4 hrs. After 4 h the mixture was quenched with half saturated NaHCO₃ (80 ml); a white precipitate was formed which was filtered off and washed with AcOEt (500 ml). Aqueous and organic phase were separated and the organic phase washed with water (60 ml), dried over Na₂SO₄ and evaporated to afford 3.85 g of yellow oil which was loaded on a SPE-Si cartridge (50 g) and eluted with a mixture cHex/AcOEt 95/5. Collected fractions after solvent evaporation afforded the title compound (D26) (1.19 g) as diastereoisomer mixture with syn-anti ratio 8/2.

MS: (ES/+) m/z: 278 [MH+Na⁺] C13H21NO4 requires 255.15

¹H NMR (400 MHz, CHCl3-d) δ (ppm): 4.66-4.46 (m, 1 H), 4.26-3.93 (m, 5 H), 3.62-3.40 (m, 2 H), 2.70-2.50 (m, 1 H), 2.42-2.17 (m, 2 H), 2.10-1.99 (m, 1 H), 1.69-1.58 (m, 2 H), 1.56-1.40 (m, 18 H), 1.32-1.21 (m, 6 H), 0.96-0.64 (m, 3 H), 0.48 (br. s., 1 H).

Description 27

3R)-2-(tert-butoxycarbonyl)-2-azabicyclo[3.1.0]hexane-3-carboxylic acid (diastereoisomer mixture) (D27)

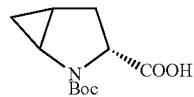

To a mixture of (3R)-2-tert-butyl 3-ethyl 2-azabicyclo [3.1.0]hexane-2,3-dicarboxylate (D26) (diastereoisomer mixture) (3.4 g, 13.3 mmol) in dioxane (15 ml) and water (15 ml), LiOH H₂O (2.2 g, 53 mmol). The mixture was stirret at RT for 18 h. Dioxane was evaporated off and water was washed with Et₂O (2×40 ml) then the pH was adjusted to ~4 by addition of citric acid and the resulting aqueous phase was extacted with DCM (200 ml), washed with water (20 ml), dried over Na₂SO₄ and evaporated in vacuo to afford the title compound (D27) (2.75 g) as diastereoisomer mixture with syn-anti ratio 10/2.

MS: (ES/+) m/z: 226 [M⁻] C11H17NO4 requires 227.12

¹H NMR (400 MHz, DMSO-d6) δ (ppm): 12.69-12.41 (m, 2 H), 4.45-4.32 (m, 1 H), 3.89 (br.s. 1 H), 3.42-3.32 (m, 2 H), 2.65-2.54 (m, 1 H), 2.35-2.24 (m, 1 H), 2.09 (m, 1 H), 1.95-1.73 (m, 1 H), 1.60-1.46 (m, 2 H), 1.44-1.30 (m, 18 H), 0.76-0.60 (m, 3 H), 0.46 (dt, J=2.4, 4.9 Hz, 1 H).

Description 28

(R)-5-(((tert-butyldiphenylsilyl)oxy)methyl)pyrrolidin-2-one (D28)

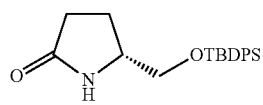

To an ice cooled solution of R-(5)-hydroxymethyl-2pyrrolidinone (4 g, 34.7 mmol; available from Aldrich#366358) in DMF (30 ml), imidazole (2.6 g, 38.2 mmol) and TBDPSiCl (9.4 ml, 38.2 mmol) were added and the resulting mixture was stirred at RT for 3 hrs. After solvent evaporation, water was added and the mixture extracted with MTBE (2×50 ml). Collected organics were washed with NaCl sat., dried over Na₂SO₄ and evaporated. The residue was purified by Biotage SNAP-Si column (50 g) eluting with a mixture Et₂O/Acetone from 100/0 to 80/20. Collected fractions after solvent evaporation afforded the title compound (D28) (9.75 g)

¹H NMR (400 MHz, CHCl3-d) δ (ppm): 7.72-7.59 (m, 4 H), 7.53-7.37 (m, 6 H), 5.82 (br. s., 1 H), 3.83 (dd, J=4.2, 5.1 Hz, 1 H), 3.69-3.61 (m, 1H), 3.53 (dd, J=7.8, 10.3 Hz, 1 H), 2.42-2.28 (m, 2 H), 1.80-1.60 (m, 2 H), 1.13-1.01 (m, 9 H).

Description 29

(R)-tert-butyl 2-(((tert-butyldiphenylsilyl)oxy)methyl)-5-oxopyrrolidine-1-carboxylate (D29)

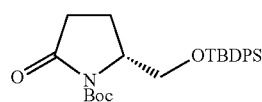

To an ice cooled solution of (R)-5-(((tert-butyldiphenylsilyl)oxy)methyl)pyrrolidin-2-one (D28) (8 g, 22.6 mmol) in DCM (40 ml), pyridine (2.5 ml) and DMAP (0.55 g, 4.52 mmol) were added followed by addition of Boc₂O (4.98 g, 22.8 mmol). The solution was left warming to RT. After 3 hrs stirring, Boc₂O (1.48 g, 6.78 mmol) was added and the mixture stirred for 18 hrs. NH₄Cl sat sol (30 ml) was added then the mixture was acidified to pH~4 by addition of 2N HCl. The organic phase was separated and the aqueous extracted with MTBE. The organic phases were collected and washed sequentially with H₃PO₄, water and brine then dried and evaporated. Combined organics after solvent evaporation were purified by Biotage SNAP-Si column (25 g) eluting with Et₂O. Collected fractions after solvent evaporation afforded the title compound (D29) (8 g).

MS: (ES/+) m/z: 454.4 [MH⁺] C26H35NO4Si requires 453.65

¹H NMR (400 MHz, CHCl3-d) δ (ppm): 7.64 (dd, J=7.0, 12.9 Hz, 4H), 7.51-7.36 (m, 6 H), 4.28-4.19 (m, 1 H), 3.96-3.86 (m, 1 H), 3.79-3.66 (m, 1 H), 2.87-2.72 (m, 1 H), 2.52-2.38 (m, 1 H), 2.23-2.08 (m, 2 H), 1.46 (s, 9 H), 1.07 (s, 9 H).

Description 30

(5R)-tert-butyl 5-(((tert-butyldiphenylsilyl)oxy)methyl)-2-oxo-3-((trimethylstannyl)methyl)pyrrolidine-1-carboxylate (diastereoisomer mixture) (D30)

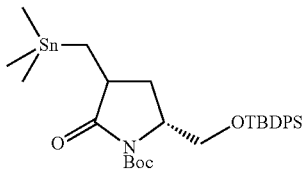

To a solution of (R)-tert-butyl 2-(((tert-butyldiphenylsilyl) oxy)methyl)-5-oxopyrrolidine-1-carboxylate (D29) (6 g, 13.23 mmol) in THF (80 ml) cooled at −70° C., LiHMDS 1M solution in THF (17.2 ml) was added dropwise over a period of minutes. The reaction was kept at −78° C. for 1 h before adding (iodomethyl)trimethylstannane (6.04 g, 19.84 mmol) over a period of 5 minutes. The mixture was allowed to warm at −35 and stirred at this temperature for 2 hrs. NH₄Cl sat. sol (15 ml) was added and the mixture diluted with EtOAc (40 ml). The organic layer was separated and the aqueous phase acidified to pH~4 with 0.5N HCl and the latter re-extracted with EtOAc (3×50 ml). The organic phases were combined, dried over Na₂SO₄ and evaporated in vacuo. The residue was purified by Biotage SNAP-Si (50 g) eluting with a mixture cHex/EtOAc from 100/0 to 90/10. Collected fractions after solvent evaporation afforded the title compound (D30) as diastereoisomer mixture (3.2 g).

¹H NMR (400 MHz, CHCl3-d) δ (ppm): 7.69-7.59 (m, 8 H), 7.46-7.38 (m, 12 H), 4.16-4.09 (m, 2 H), 4.09-4.01 (m, 1 H), 3.86 (d, J=4.4 Hz, 2 H), 3.75-3.69 (m, 1 H), 3.05-2.90 (m, 1 H), 2.69-2.56 (m, 1 H), 2.45-2.33 (m, 2 H), 1.82-1.70 (m, 2 H), 1.44 (s, 9 H), 1.41 (s, 9 H), 1.28 (s, 1 H), 1.23-1.13 (m, 1 H), 1.08 (s, 9 H), 1.06 (s, 9 H), 0.99-0.94 (m, 1 H), 0.94-0.86 (m, 1 H), 0.24-0.04 (m, 18 H)

Description 31

3R)-tert-butyl 3-(((tert-butyldiphenylsilyl)oxy)methyl)-2-azabicyclo[3.1.0]hexane-2-carboxylate (diastereoisomers mixture) (D31)

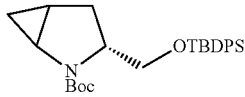

To a solution of (5R)-tert-butyl 5-(((tert-butyldiphenylsilyl)oxy)methyl)-2-oxo-3-((trimethylstannyl)methyl)pyrrolidine-1-carboxylate (D30) (3.1 g, 6.86 mmol) in THF (200 ml) cooled at −78° C., LiEt₃BH 1M sol in THF (17.2 ml) was added dropwise. The reaction was left at −78° C. for 2 hrs then water (50 ml) and the reaction extracted with Et₂O (3×100 ml). The organic phases were combined, dried over Na₂SO₄ and evaporated in vacuo to afford a residue which was dissolved in DCM (120 ml) and cooled at 0° C. TFA (1.31 ml, 17.2 mmol) was added and the reaction was stirred 10 min at this temperature. K₂CO₃ sat sol (100 ml) was added and the mixture extracted with DCM (3×100 ml). The organic phases were collected, dried over Na₂SO₄ and evaporated in vacuo to afford a residue which was purified by BiotageSNAP-Si column (50 g) eluting with a mixture cHex/EtOAc 95/5. Collected fractions after solvent evaporation afforded the title compound (D31) (2.1 g).

MS: (ES/+) m/z: 474.4 [MH+Na⁺] C27H37NO3Si requires 451.25

¹H NMR (400 MHz, CHCl3-d) δ ppm: 7.78-7.56 (m, 4 H), 7.48-7.35 (m, 6 H), 3.88 (br. s., 1 H), 3.73 (br. s., 1 H), 3.21 (br. s., 1 H), 2.44-2.28 (m, 1 H), 2.11-1.98 (m, 1 H), 1.52 (br. s., 2 H), 1.45 (s, 9 H), 1.08 (s, 9 H), 0.97-0.77 (m, 1 H), 0.37 (br. s., 1 H).

Description 32

3R)-tert-butyl 3-(hydroxymethyl)-2-azabicyclo[3.1.0]hexane-2-carboxylate (diastereoisomers mixture) (D32)

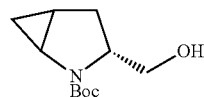

To a solution of (3R)-tert-butyl 3-(((tert-butyldiphenylsilyl)oxy)methyl)-2-azabicyclo[3.1.0]hexane-2-carboxylate (D31) (2.1 g, 4.6 mmol) in THF (130 ml), TBAF 1M sol in THF (9.2 ml) was added and the solution was stirred at RT for 18 hours. Solvent was evaporated and the residue purified by Biotage SNAP-Si column (50 g), eluting with DCM/Et₂O from 100/0 to 80/20. Collected fractions after solvent evaporation afforded the title compound (D32) (490 mg).

MS: (ES/+) m/z: 236.3 [MH+Na⁺] C11H19NO3 requires 213.14

¹H NMR (400 MHz, CHCl3-d) δ (ppm): 3.78-3.67 (m, 1 H), 3.65-3.61 (m, 2 H), 3.28 (dt, J=2.4, 6.1 Hz, 1 H), 3.23-2.89 (br. s., 1 H), 2.17 (dd, J=8.3, 13.2 Hz, 1 H), 1.88-1.78 (m, 1 H), 1.54-1.43 (m, 10 H), 0.78-0.69 (m, 1 H), 0.42 (dt, J=2.4, 5.3 Hz, 1 H).

Description 33

3R)-2-(tert-butoxycarbonyl)-2-azabicyclo[3.1.0]hexane-3-carboxylic acid (diastereoisomers mixture) (D33)

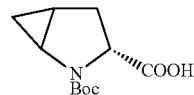

To a solution of (3R)-tert-butyl 3-(hydroxymethyl)-2-azabicyclo[3.1.0]hexane-2-carboxylate (D32) (440 mg, 2.06 mmol) in a mixture MeCN/CCl₄/H₂O (6/6/9 ml), sodium periodate (1.76 g, 8.25 mmol) was added and the reaction stirred vigorously for 5 min before addition of Ruthenium trichloride (12.8 mg, 0.062 mmol). The resulting solution was stirred 18 hrs at RT then quenched by addition of isopropanol (6 ml). The resulting black mixture was diluted with Et₂O (50 ml) and filtered through a celite pad. The filtrate was evaporated and the residue was dissolved in water, the pH was adjusted to pH~9-10 with K₂CO₃ and the aqueous was washed with Et₂O (3×30 ml). Aqueous was then acidified to pH~4-5 and re-extracted with EtOAc (3×30 ml). Collected organics after solvent evaporation afforded the title compound (D33) (216 mg).

MS: (ES/+) m/z: 250.2 [MH⁺] C11H17NO4 requires 227.12

Description 34

(R)-3,3-dimethyltetrahydropyrrolo[1,2-c]oxazol-5(3H-1)-one (D34)

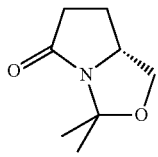

To a stirred suspension of (R)-(−)-5-(hydroxymethyl)pyrrolidin-2-one (2 g, 17.4 mmol; available from Aldrich#366358) and p-TSA (16 mg, 0.08 mmol) in toluene (50 ml), 2,2-dimethoxypropane (6.4 ml, 52.1 mmol) was added in one portion and the reaction mixture refluxed for 2 hrs. The reaction flask was equipped with a Dean Stark apparatus then 2,2-dimethoxypropane (6.4 ml, 52.1 mmol) was added and the reaction was refluxed overnight. Solvent was evaporated in vacuo affording the title compound (D34) (2.4 g).

MS: (ES/+) m/z: 156.1 [MH$^+$] C8H13NO2 requires 155.09

$^1$H NMR (400 MHz, CHCl3-d) δ (ppm): 4.26 (ddd, J=2.7, 5.9, 9.0 Hz, 1 H), 4.14-4.02 (m, 1 H), 3.53-3.37 (m, 1 H), 2.88-2.71 (m, 1 H), 2.62-2.47 (m, 1H), 2.27-2.11 (m, 1 H), 1.86-1.69 (m, 1 H), 1.67 (d, J=2.9 Hz, 3 H), 1.47 (d, J=2.9 Hz, 3 H).

Description 35

(R)-3,3,6,6-tetramethyltetrahydropyrrolo[1,2-c]oxazol-5(3H)-one (D35)

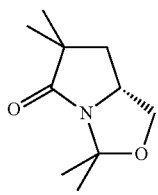

To a solution of (R)-3,3-dimethyltetrahydropyrrolo[1,2-c]oxazol-5(3H)-one (D34) (1.3 g, 8.37 mmol) in dry THF (120 ml) cooled to −78° C., LDA 2M sol in THF/heptane (6.28 ml, 12.6 mmol) was added. The red solution was stirred at this temperature for 40 min before adding iodomethane (0.78 ml, 12.6 mmol). The reaction mixture was warmed to RT (40 min) then cooled to −78° C. prior addition of LDA 2M sol in THF/heptane (6.28 ml, 12.6 mmol). The mixture was stirred at −78° C. for 1 h before adding iodomethane (0.78 ml, 12.6 mmol) then the mixture was slowly warmed to RT and stirred overnight. The resulting solution was treated with NH4Cl sat sol (10 ml) and extracted with Et2O (3×10 ml). The organic phases were collected and washed with NaCl sat. sol, dried over Na2SO4 and evaporated in vacuo to afford the title compound (D35) (1.2 g).

MS: (ES/+) m/z: 184.1 [MH$^+$] C10H17NO2 requires 183.13

$^1$H NMR (400 MHz, CHCl3-d) δ (ppm): 4.24-4.10 (m, 2 H), 3.42 (t, J=8.6 Hz, 1 H), 2.04 (dd, J=5.9, 12.2 Hz, 1 H), 1.68 (s, 3 H), 1.60 (dd, J=3.2, 8.6 Hz, 1 H), 1.49 (s, 3 H), 1.26 (s, 3 H), 1.21 (s, 3 H).

Description 36

(R)-5-(hydroxymethyl)-3,3-dimethylpyrrolidin-2-one (D36)

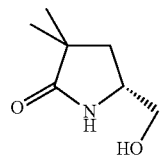

To a stirred suspension of (R)-3,3,6,6-tetramethyltetrahydropyrrolo[1,2-c]oxazol-5(3H)-one (D35) (714 mg, 3.89 mmol) in MeOH (15 ml), p-TSA (74 mg, 0.39 mmol) was added and the resulting mixture was heated at reflux for 2 hrs. Solvent was evaporated off and the residue was loaded on SPE-SCX cartridge (5 g). The cartridge was washed with MeOH (3 column volume). The methanolic phase was collected and evaporated to afford the title compound (D36) (690 mg)

MS: (ES/+) m/z: 144.1 [MH$^+$] C7H13NO2 requires 143.09

$^1$H NMR (400 MHz, CHCl3-d) δ (ppm): 3.91-3.82 (m, 1 H), 3.77 (dd, J=2.4, 11.6 Hz, 1 H), 3.51-3.44 (m, 2 H), 2.02 (dd, J=7.5, 12.7 Hz, 1 H), 1.71 (dd, J=7.8, 12.7 Hz, 1 H), 1.24 (s, 6 H).

Description 37

(R)-tert-butyl 2-(hydroxymethyl)-4,4-dimethylpyrrolidine-1-carboxylate (D37)

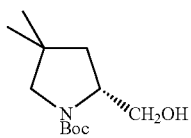

To an ice cooled suspension of LiAlH4 (219 mg, 5.78 mmol) in THF (10 ml) under N2, a solution of (R)-5-(hydroxymethyl)-3,3-dimethylpyrrolidin-2-one (D36) (690 mg, 4.82 mmol) in THF (10 ml) was added dropwise. The reaction was allowed to warm to RT over 30 min then refluxed for 5 hrs. LiAlH4 (219 mg, 5.78 mmol) was added to the mixture and the reaction stirred for 18 hrs then a further addition of LiAlH4 (219 mg, 5.78 mmol) was done and the reaction refluxed for additional 5 hrs. The reaction mixture was cooled to 0° C. prior sequentially addition of water (0.87 ml), 15% NaOH (0.87 ml) and water (2.58 ml). The resulting slurry solution was filtered off; the filtrated was diluted with water (10 ml) and basified to pH~12 with Na2CO3 before adding dropwise a solution of Boc2O (1.37 g, 6.26 mmol) in THF (10 ml). The resulting mixture was stirred for 24 hrs then extracted with EtOAc (3×30 ml). The organic phases were washed with NaCl sat., dried onto Na2SO4 and evaporated in vacuo to afford the title compound (D37) (435 mg).

MS: (ES/+) m/z: 252.2 [MH+Na$^+$] C12H23NO3 requires 229.17

$^1$H NMR (400 MHz, CHCl3-d) δ (ppm): 5.25-5.09 (m, 1 H), 4.13-3.99 (m, 1 H), 3.62 (d, J=7.9 Hz, 2 H), 3.39-3.23 (m, 1 H), 3.08-2.92 (m, 1 H), 1.87-1.73 (m, 1 H), 1.49 (s, 9 H), 1.38-1.25 (m, 1 H), 1.09 (s, 3 H), 1.03 (s, 3 H)

Description 38

(R)-1-(tert-butoxycarbonyl)-4,4-dimethyl-5-oxopyrrolidine-2-carboxylic acid (D38)

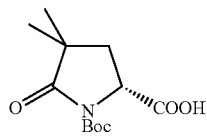 [SMILES: CC(C)(C)OC(=O)N1C(=O)C(C)(C)C[C@@H]1C(=O)O]

To a solution of (R)-tert-butyl 2-(hydroxymethyl)-4,4-dimethylpyrrolidine-1-carboxylate (D37) (385 mg, 1.68 mmol) in CH$_3$CN/CCl$_4$/H$_2$O (6/6/9 ml) NaIO$_4$ (1.43 g6.71 mmol) was added and the resulting mixture was stirred vigorously for 5 min before addition of RuCl$_3$ (10 mg, 0.05 mmol). The resulting brown solution was stirred 18 hrs at RT then the reaction was quenched with isopropanol (0.6 ml) and diluted with Et$_2$O (10 ml). The mixture was filtered through a celite pad and the filtrate was washed with Et$_2$O (4×20 ml) then with DCM (2×5 ml). Collected organic phases after drying over Na$_2$SO$_4$ and solvent evaporation afforded the title compound (D38) (293 mg).

MS: (ES/+) m/z: 280.2 [MH+Na$^+$] C12H19NO5 requires 257.13

$^1$H NMR (400 MHz, CHCl3-d) δ (ppm): 4.63-4.54 (m, 1 H), 2.34-2.22 (m, 1 H), 2.04-1.95 (m, 1 H), 1.53 (s, 9 H), 1.25 (d, J=4.9 Hz, 6 H).

Description 39

(R)-2-benzyl 1-tert-butyl 4,4-dimethyl-5-oxopyrrolidine-1,2-dicarboxylate (D39)

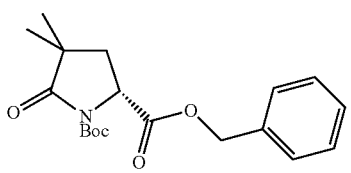 [SMILES: CC(C)(C)OC(=O)N1C(=O)C(C)(C)C[C@@H]1C(=O)OCc1ccccc1]

To a solution of (R)-1-(tert-butoxycarbonyl)-4,4-dimethyl-5-oxopyrrolidine-2-carboxylic acid (D38) (320 mg, 1.24 mmol) in acetone (10 ml), TEA (0.35 ml, 2.49 mmol) and benzyl bromide (0.23 ml, 1.86 mmol) were added and the resulting mixture was stirred at RT for 18 hrs. TEA (0.35 ml, 2.49 mmol) and benzyl bromide (0.23 ml, 1.86 mmol) were added and the reaction stirred for 24 hrs prior addition of further TEA (0.35 ml, 2.49 mmol) and benzyl bromide (0.23 ml, 1.86 mmol). The final mixture was then refluxed for 18 hrs. Solvents were evaporated off and the resulting residue was re-dissolved in EtOAc, washed with water (3×10 ml), dried over Na$_2$SO$_4$ and evaporated in vacuo to afford a residue that was purified by Biotage SNAP-Si column (25 g) eluting with a mixture DCM/EtOAc from 100/0 to 90/10. Collected fractions after solvent evaporation afforded the title compound (D39) (260 mg).

MS: (ES/+) m/z: 248.2 [MH-Boc$^+$] C19H25NO5 requires 347.17

$^1$H NMR (400 MHz, CHCl3-d) δ (ppm): 7.38 (br. s., 5 H), 5.25 (d, J=1.0 Hz, 1 H), 5.20 (d, J=1.0 Hz, 1 H), 4.63-4.55 (m, 1 H), 2.27-2.18 (m, 1 H), 1.95-1.87 (m, 1 H), 1.47 (s, 9 H), 1.20 (d, J=14.5 Hz, 6 H).

Description 40

(R)-2-benzyl 1-tert-butyl 4,4-dimethylpyrrolidine-1,2-dicarboxylate (D40)

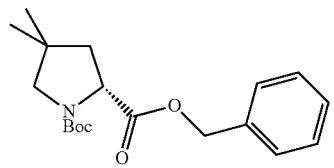 [SMILES: CC1(C)C[C@H](C(=O)OCc2ccccc2)N(C(=O)OC(C)(C)C)C1]

To a solution of (R)-2-benzyl 1-tert-butyl 4,4-dimethyl-5-oxopyrrolidine-1,2-dicarboxylate (D39) (210 mg, 0.6 mmol) in THF (10 ml) cooled at −78° C., LiEt$_3$BH 1M sol in THF (0.6 ml) was added and the mixture stirred 2 hrs at −78° C. The reaction was warmed to 0° C. and quenched with slow addition of NaHCO$_3$ sat sol (4 ml) and 1 drop of H$_2$O$_2$. Stirring was continued for 20 min then THF was removed under reduced pressure and the remaining residue was taken up in water (5 ml) and extracted with DCM (3×10 ml). The organic phases were collected, dried over Na$_2$SO$_4$ and evaporated in vacuo. The obtained residue was dissolved in DCM (10 ml) and cooled at −78° C. under N$_2$. Et$_3$SiH (0.09 ml, 0.6 mmol) was added followed by addition of BF$_3$.OEt$_2$ (0.1 ml, 0.63 mmol) and the reaction stirred 30 min, prior further addition of Et$_3$SiH (0.09 ml, 0.6 mmol) and BF$_3$.OEt$_2$ (0.1 ml, 0.63 mmol). The final reaction mixture was stirred at −78° C. for 3 hrs then quenched by the slow addition of saturated NaHCO$_3$ and water. The reaction mixture was extracted with DCM (3×10 ml), the organic layers washed with NaCl sat sol, dried over Na$_2$SO$_4$ and evaporated to afford the title compound (D40) (168 mg).

MS: (ES/+) m/z: 356.3 [MH+Na$^+$] C19H27NO4 requires 333.19

Description 41

(R)-1-(tert-butoxycarbonyl)-4,4-dimethylpyrrolidine-2-carboxylic acid (D41)

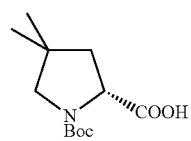 [SMILES: CC1(C)C[C@H](C(=O)O)N(C(=O)OC(C)(C)C)C1]

To a mixture of (R)-2-benzyl 1-tert-butyl 4,4-dimethylpyrrolidine-1,2-dicarboxylate (D40) (198 mg, 0.59 mmol) in dioxan/water (4/4 ml), LiOH.H$_2$O (100 mg, 2.37 mmol) was added and the mixture was left stirring at RT for 18 hrs. Organic solvent was evaporated off and the reaction mixture was diluted with water (8 ml), washed with Et$_2$O (2×10 ml), acidified with acetic acid to pH~4-5 and extracted with Et$_2$O (3×10 ml). The organic phases were collected, dried over Na$_2$SO$_4$ and evaporated in vacuo to afford the title compound (D41) (84 mg).

MS: (ES/+) m/z: 144.1 [MH-Boc⁺] C12H21NO4 requires 243.15

¹H NMR (400 MHz, CHCl3-d) δ (ppm): 4.51-4.20 (m, 1 H), 3.45-3.05 (m, 2 H), 2.32-1.81 (m, 2 H), 1.62-1.39 (m, 9H), 1.19-1.03 (m, 6H)

Description 42 methyl 3-azabicyclo[3.1.0]hexane-2-carboxylate hydrochloride (racemic mixture) (D42)

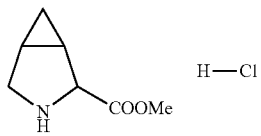

To an ice cooled solution of 3-azabicyclo[3.1.0]hexane-2-carboxylic acid (racemic mixture with relative stereochemistry syn) (500 mg, 3.93 mmol; available from ABCR#AB156920), thionyl chloride (0.57 ml, 7.86 mmol) was added dropwise and the resulting mixture was stirred at RT overnight. Solvent evaporation under reduced pressure afforded the title compound (D42) 700 mg) as racemic mixture with relative stereochemistry syn.

MS: (ES/+) m/z: 142.1 [MH-Boc⁺] C7H11NO2 requires 141.08

¹H NMR (400 MHz, METHANOL-d4) δ (ppm): 4.67 (d, J=4.2 Hz, 1 H), 3.90 (s, 3 H), 3.54 (d, J=3.6 Hz, 1 H), 3.51-3.42 (m, 1 H), 2.23-2.10 (m, 1 H), 1.94 (d, J=3.4 Hz, 1 H), 0.86 (d, J=7.5 Hz, 1 H), 0.61 (d, J=6.0 Hz, 1 H).

Description 43

(2S,5S)-tert-butyl 2-(tert-butyl)-3,5-dimethyl-4-oxoimidazolidine-1-carboxylate (D43)

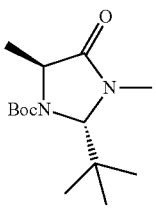

To a solution of (S)-tert-butyl 2-(tert-butyl)-3-methyl-4-oxoimidazolidine-1-carboxylate (0.5 g, 1.95 mmol; available from Aldrich#337595) in dry THF (15 ml) cooled to −78° C., LDA 2M in THF/heptane (0.97 ml, 1.95 mmol) was added and the reaction mixture stirred at this temperature for 40 min before adding iodomethane (0.146 ml, 2.34 mmol). The reaction was allowed to warm to RT and stirred for 18 hrs. The reaction mixture was cooled again at −78° C. then LDA 2M in THF/hepatane (0.3 ml) and iodomethane (0.04 ml, 0.6 mmol) were added in sequence. The mixture was allowed to reach RT and further stirred for 5 hrs. The resulting solution was treated with NH4Cl sat sol (5 ml) and extracted with Et2O. The organic phases were collected and washed with NaCl sat sol, dried over Na2SO4 and evaporated in vacuo to afford a residue which was purified by Biotage SNAP-Si column (25 g) eluting with cHex/Et2O 60/40. Collected fractions after solvent evaporation afforded the title compound (D43) (430 mg).

MS: (ES/+) m/z: 271.2 [MH⁺] C14H26N2O3 requires 270.19

Description 44

(2S,5R)-tert-butyl 2-(tert-butyl)-5-(4-chlorobutyl)-3,5-dimethyl-4-oxoimidazolidine-1-carboxylate (D44)

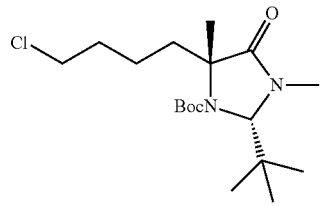 [SMILES: CN1C(=O)[C@@](C)(CCCCCl)N(C(=O)OC(C)(C)C)[C@H]1C(C)(C)C]

To a solution of (2S,5S)-tert-butyl 2-(tert-butyl)-3,5-dimethyl-4-oxoimidazolidine-1-carboxylate (D43) (430 mg, 1.59 mmol) in dry THF (15 ml) cooled to −78° C., LDA 2M in THF/heptane (1.2 ml, 2.38 mmol) was added and the reaction mixture stirred at this temperature for 40 min before adding 1-bromo-4-chloro-butane (0.27 ml, 2.38 mmol). The reaction was allowed to warm to RT and left stirring for 3 hrs. The resulting solution was treated with NH4Cl sat sol (5 ml) and extracted with Et2O (3×10 ml). The organic phases were collected and washed with NaCl sat sol, dried over Na2SO4 and evaporated in vacuo to afford a residue which was purified by Biotage SNAP-Si column (25 g) eluting with cHex/Et2O 60/40. Collected fractions after solvent evaporation afforded the title compound (D44) (465 mg).

MS: (ES/+) m/z: 361.3 [MH⁺] C18H33ClN2O3 requires 360.22

¹H NMR (400 MHz, CHCl3-d) δ (ppm): 3.56-3.37 (m, 2 H), 3.02 (s, 3 H), 2.28-2.15 (m, 1 H), 1.86-1.60 (m, 4 H), 1.51 (s, 11 H), 1.28-0.80 (m, 12 H).

Description 45

2R,5R)-2-(tert-butyl)-5-(4-chlorobutyl)-3,5-dimethylimidazolidin-4-one (D45)

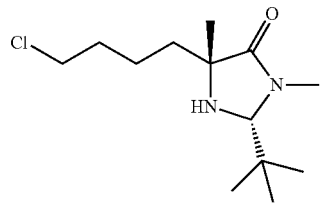 [SMILES: CN1C(=O)[C@@](C)(CCCCCl)N[C@H]1C(C)(C)C]

To an ice cooled of (2S,5R)-tert-butyl 2-(tert-butyl)-5-(4-chlorobutyl)-3,5-dimethyl-4-oxoimidazolidine-1-carboxylate (D44) (465 mg, 1.28 mmol) in dry DCM (2 ml), TFA (1 ml, 12.8 mmol) was added and the solution stirred for 12 hrs at RT. The reaction mixture was treated with NaHCO3 sat sol with vigorous stirring until pH~7. The resulting mixture was poured into water and the aqueous phase extracted with DCM (3×10 ml), dried over Na2SO4 and evaporated in vacuo to afford the title compound (D45) (310 mg).

MS: (ES/+) m/z: 261.2 [MH$^+$] C13H25ClN2O requires 260.22

$^1$H NMR (400 MHz, CHCl3-d) δ (ppm): 4.11 (s, 1 H), 3.54 (t, J=6.5 Hz, 2 H), 2.94 (s, 3 H), 1.86-1.73 (m, 2 H), 1.59 (br. s., 5 H), 1.33 (s, 3 H), 1.01 (s, 9 H).

Description 46

3R,8aR)-3-(tert-butyl)-2,8a-dimethylhexahydroimidazo[1,5-a]pyridin-1(5H)-one (D46)

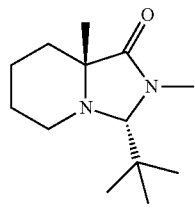 [SMILES: CN1C(=O)[C@@]2(C)CCCCN2[C@H]1C(C)(C)C]

To a solution of (2R,5R)-2-(tert-butyl)-5-(4-chlorobutyl)-3,5-dimethylimidazolidin-4-one (D45) (310 mg, 1.18 mmol) in dry MeCN (4 ml), anhydrous Na$_2$CO$_3$ (63 mg, 0.6 mmol) and NaI (178 mg, 1.18 mmol) were added sequentially. The solution was heated at 80° C. for 12 hrs. The reaction was allowed to cool at RT, poured into water (10 ml) and extracted with Et$_2$O (3×10 ml). The organic phases were collected, washed with NaCl sat sol, dried over Na$_2$SO$_4$ and evaporated in vacuo to afford the title compound (D46) (220 mg)

MS: (ES/+) m/z: 225.2 [MH$^+$] C13H24N2O requires 224.19

$^1$H NMR (400 MHz, CHCl3-d) δ (ppm): 4.10-3.90 (m, 1 H), 3.79 (d, J=5.3 Hz, 1 H), 3.74-3.60 (m, 1 H), 3.02 (br. s., 3 H), 2.97-2.79 (m, 1 H), 1.95-1.32 (m, 11 H), 1.10 (br. s., 6 H).

Description 47

(R)-2-methylpiperidine-2-carboxylic acid hydrochloride (D47)

(3R,8aR)-3-(tert-butyl)-2,8a-dimethylhexahydroimidazo[1,5-a]pyridin-1(5H)-one (D46) (220 mg, 0.98 mmol) was dissolved in HCl 6M (2 ml) into a thick-walled glass tube which was sealed and heated at 108° C. for 70 hrs. The reaction was cooled and the extracted with DCM (3×5 ml). The aqueous solution was evaporated to afford the title compound (D47) (180 mg).

MS: (ES/+) m/z: 144.1 [MH$^+$] C7H13NO2 requires 143.09

$^1$H NMR (400 MHz, METHANOL-d4) δ (ppm): 3.27 (br. s., 2 H), 2.57 (s, 3 H), 2.32-2.21 (m, 1 H), 1.91-1.68 (m, 4 H), 1.57 (m, 1 H).

Description 48

7aR)-3-(trichloromethyl)tetrahydropyrrolo[1,2-c]oxazol-1(3H)-one (D48)

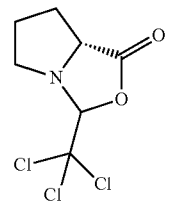

To a solution of D-proline (0.4 g, 3.48 mmol) in MeCN (8 ml) the trifluoroacetaldehyde (0.68 ml, 6.94 mmol) was added and the resulting mixture was stirred at RT for 8 hrs. Solvents were evaporated and the residue was triturated with diethyl ether. After solvent filtration and drying, 0.23 g of title compound (D48) was isolated.

MS: (ES/+) m/z: 244.0 [MH$^+$] C7H8Cl3NO2 requires 242.96

$^1$H NMR (400 MHz, CHCl3-d) δ (ppm): 4.15 (dd, J=4.5, 8.6 Hz, 1 H), 3.52-3.36 (m, J=7.0, 7.0, 10.5 Hz, 1 H), 3.22-3.07 (m, 1 H), 2.33-2.20 (m, 1 H), 2.19-2.08 (m, 1 H), 1.96 (quind, J=5.9, 12.1 Hz, 1 H), 1.84-1.69 (m, 1 H), 1.61 (br. s., 1 H).

Description 49

7aR)-7a-methyl-3-(trichloromethyl)tetrahydropyrrolo[1,2-c]oxazol-1(3H)-one (D49)

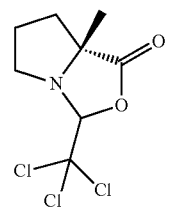

To a solution of (7aR)-3-(trichloromethyl)tetrahydropyrrolo[1,2-c]oxazol-1(3H)-one (D48) (0.2 g, 0.82 mol) in THF (10 ml) cooled at −78° C. LDA 2M sol in THF/heptane (0.58 ml, 1.17 mol) was added and the mixture stirred 30 min. Diiodomethane (0.185 ml, 2.97 mol) was added and the temperature was allowed to warm to −40° C. over a period of 2 hrs then left at this temperature for an additional hour. The resulting mixture was partitioned between DCM and H$_2$O. The aqueous phase was extracted with DCM (2×10 ml); the organic phases were collected, dried over Na$_2$SO$_4$ and evaporated in vacuo. The residue was purified by SPE-Si cartridge (25 g) eluting with DCM. Collected fractions after solvent evaporation afforded title compound (D49) in mixture (4:1) with starting material (110 mg).

MS: (ES/+) m/z: 258.0 [MH$^+$] C8H10Cl3NO2 requires 256.98

Description 50

(R)-methyl 2-methylpyrrolidine-2-carboxylate hydrochloride (D50)

To a solution of (7aR)-7a-methyl-3-(trichloromethyl)tetrahydropyrrolo[1,2-c]oxazol-1(3H)-one (D49) (0.11 g, 0.42 mol) in dry MeOH (2 ml), HCl 1M sol in MeOH (0.3 ml, 0.85 mol) was added and the mixture refluxed under a constant current of nitrogen for 1 h. Solvent was evaporated to afford the title compound (D50) 60 mg.

MS: (ES/+) m/z: 144.1 [MH+] C7H13NO2 requires 143.09

General Procedure for Amides Preparation

Method A

Selected acid (1 eq), HOBT.H$_2$O (1 eq) and EDC.HCl (1.5 eq) were suspended in DCM and the resulting mixture was stirred 1 h at RT. A solution of a selected amine (1 eq) and TEA (1 eq) in DCM was added and the mixture was stirred at RT for 1/48 hrs. Solvents were evaporated in vacuo and the resulting residue was re-dissolved in DCM. The mixture was then added to a saturated aqueous solution of NaHCO$_3$ and extracted with dichloromethane. The organic phase was dried over Na$_2$SO$_4$ and the solvent was removed under reduced pressure. The crude material was purified on SPE-Si cartridge or SNAP-Si column eluting with a mixture of DCM/MeOH 98:2 or DCM/EtOAc from 100:0 to 70:30 affording the title amide compound.

Method B

To a solution of selected acid (1 eq) in DMF, HATU (1.2 eq) and DIPEA (2.5 eq) were added in sequence. The mixture was stirred 30 min before addition of the selected amine (1.2 eq). The mixture was left stirring at RT for 18 hrs. The reaction was partitioned between EtOAc and H$_2$O and the aqueous phase was washed with EtOAc. The organic phases were collected and washed several times with H$_2$O, dried over Na$_2$SO$_4$ and evaporated under reduced pressure. The crude material was purified on SPE-Si cartridge or Biotage SNAP-Si column eluting with a mixture of DCM/EtOAc from 100:0 to 80:20 affording the title amide compound.

Method C

To a solution of selected acid (1 eq) in DMF, HCTU (1.1 eq) and DIPEA (2.5 eq) were added in sequence and the resulting mixture was stirred 30 min before adding the selected amine (1.1 eq). The mixture was left stirring at RT for 1-18 hrs then the reaction mixture was partitioned between EtOAc and H$_2$O and the organic phase was separated. The aqueous phase was washed with EtOAc. All the collected organic phases were washed with NaCl sat. sol., dried over Na$_2$SO$_4$ and the solvent was removed under reduced pressure. The residue was purified on SPE-Si cartridge or Biotage SNAP-Si column eluting with a mixture of DCM/EtOAc from 100:0 to 95:5 affording the title amide compound.

Description 51 tert-butyl 2-(((S)-1-(4-(methoxycarbonyl)phenyl)ethyl)carbamoyl) piperidine-1-carboxylate (diastereoisomers mixture) (D51)

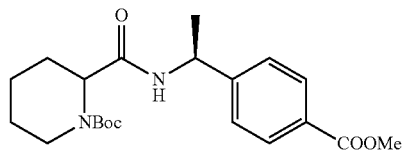 [SMILES: COC(=O)c1ccc([C@H](C)NC(=O)C2CCCCN2C(=O)OC(C)(C)C)cc1]

The title compound (D51) (1.95 g) was prepared according to the general procedure for amides preparation (Method A) starting from 1-(tert-butoxycarbonyl)piperidine-2-carboxylic acid (1.17 g, available from Sigma Aldrich #495875), and (S)-methyl 4-(1-aminoethyl)benzoate hydrochloride (1.1 g, for preparation see published International Patent application WO 2005/105733). Reaction time: 18 hrs.

MS: (ES/+) m/z: 391.3 [MH+] C21H30N2O5 requires 390.22 Chiral HPLC [Phenomenex Lux Cellulose-1; Mobile phase A: 90% n-hexane (+0.1% DEA), B: 10% IPA; DAD: 237 nm]: Peak 1 retention time: 11.6 min; peak 2 retention time:16.16 min.

$^1$H NMR (400 MHz, CHCl3-d) δ (ppm): 8.01 (d, 4H) 7.36 (t, 4 H) 6.12-6.82 (m, 2 H) 5.17 (br. s., 2 H) 4.74 (br. s., 2 H) 3.81-4.25 (m, 8 H) 2.81 (br. s., 1 H) 2.66 (t, 1 H) 2.28 (br. s., 2 H) 1.42-1.75 (m, 4 H).

Description 52

(R)-tert-butyl 2-(((S)-1-(4-(methoxycarbonyl)phenyl)ethyl)carbamoyl) piperidine-1-carboxylate (D52)

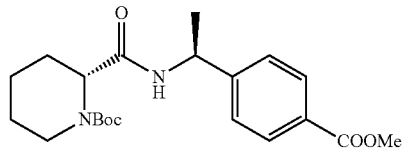 [SMILES: COC(=O)c1ccc([C@H](C)NC(=O)[C@H]2CCCCN2C(=O)OC(C)(C)C)cc1]

The title compound (D52) (405 mg) was prepared according to the general procedure for amides preparation (Method A) starting from (R)-1-(tert-butoxycarbonyl)piperidine-2-carboxylic acid (250 mg, available from Sigma Aldrich #516341), and (S)-methyl 4-(1-aminoethyl)benzoate hydrochloride (235 mg). Reaction time: 18 hrs.

MS: (ES/+) m/z: 391.3 [MH+] C21H30N2O5 requires 390.22

Chiral HPLC [Phenomenex Lux Cellulose-1; Mobile phase A: 90% n-hexane (+0.1% DEA), B: 10% EtOH; DAD: 237 nm]: Peak retention time: 9.6 min.

$^1$H NMR (400 MHz, CHCl3-d) δ (ppm): 8.02 (d, J=8.3 Hz, 2 H), 7.36 (d, J=7.8 Hz, 2 H), 6.75-6.40 (m, 1 H), 5.23-5.11 (m, 1 H), 4.81-4.70 (m, 1 H), 4.10-3.95 (m, 1 H), 3.93 (s, 3 H), 2.72-2.60 (m, 1 H), 2.36-2.20 (m, 1 H), 1.67-1.61 (m, 1 H), 1.58-1.47 (m, 15 H), 1.46-1.36 (m, 1 H).

Description 53

(R)-tert-butyl 2-((1-(4-(methoxycarbonyl)phenyl)cyclopropyl)carbamoyl)piperidine-1-carboxylate (D53)

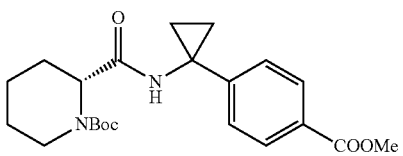 [SMILES: COC(=O)c1ccc(C2(NC(=O)[C@H]3CCCCN3C(=O)OC(C)(C)C)CC2)cc1]

The title compound (D53) (650 mg) was prepared according to the general procedure for amides preparation (Method A) starting from (R)-1-(tert-butoxycarbonyl)piperidine-2-carboxylic acid (500 mg, available from Sigma Aldrich #516341), and methyl 4-(1-aminocyclopropyl)benzoate hydrochloride (470 mg). Reaction time: 18 hrs.

MS: (ES/+) m/z: 403 [MH$^+$] C22H30N2O5 requires 402.22

Chiral HPLC [DAICEL OD-H; Mobile phase A: 80% n-hexane (+0.1% DEA), B: 20% IPA; DAD: 248 nm]: Peak retention time: 13.04 min.

$^1$H NMR (400 MHz, CHCl3-d) δ (ppm): 7.96 (d, J=8.1 Hz, 2 H), 7.24 (d, J=8.1 Hz, 2 H), 7.02-6.74 (m, 1 H), 4.81-4.68 (m, 1 H), 4.19-4.00 (m, 1 H), 3.92 (s, 3 H), 2.88-2.69 (m, 1 H), 2.39-2.17 (m, 1 H), 1.66 (br. s., 3 H), 1.52 (s, 9 H), 1.34 (d, J=18.6 Hz, 6 H).

Description 54 tert-butyl 5-((1-(4-(methoxycarbonyl)phenyl)cyclopropyl)carbamoyl)-6-azaspiro[2.5]octane-6-carboxylate (racemic mixture) (D54)

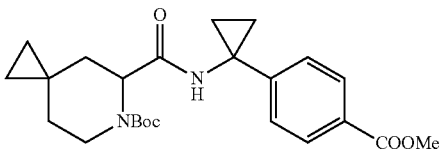

The title compound (D54) (290 mg) was prepared according to the general procedure for amides preparation (Method B) starting from 6-(tert-butoxycarbonyl)-azaspiro[2.5]octane-5-carboxylic acid (D1) (200 mg) and methyl 4-(1-aminocyclopropyl)benzoate hydrochloride (214 mg). Reaction time: 18 hrs.

MS: (ES/+) m/z: 429 [MH$^+$] C24H32N2O5 requires 428.52

$^1$H NMR (400 MHz, CHCl3-d) δ (ppm): 7.97 (d, J=8.1 Hz, 2 H), 7.28 (d, J=2.7 Hz, 2 H), 6.76 (br. s., 1 H), 4.90-4.76 (m, 1 H), 4.17 (br. s., 1H), 3.92 (s, 3H), 3.08-2.88 (m, 1 H), 2.05-1.99 (m, 1 H), 1.97-1.86 (m, 1H), 1.83-1.75 (m, 1 H), 1.51 (s, 9 H), 1.45-1.31 (m, 4 H), 0.88-0.79 (m, 1 H), 0.60-0.44 (m, 1 H), 0.43-0.27 (m, 2 H), 0.28-0.20 (m, 1 H).

Description 55 tert-butyl 5-((1-(4-(methoxycarbonyl)phenyl)cyclopropyl)carbamoyl)-6-azaspiro[2.5]octane-6-carboxylate (single unknown enantiomer) (D55)

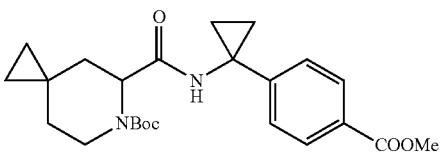 [SMILES: COC(=O)c1ccc(C2(NC(=O)C3CC4(CCN3C(=O)OC(C)(C)C)CC4)CC2)cc1]

6-(tert-butoxycarbonyl)-6-azaspiro[2.5]octane-5-carboxylic acid (D3) (16 g, 62.6 mol) HOBT.H2O (9.59 g, 62.6 mol) and EDC.HCl (18.00 g, 94 mol) were suspended in DCM (225 ml) and the resulting mixture was stirred 30 min at RT. A solution of methyl 4-(1-aminocyclopropyl)benzoate hydrochloride (14.3 g, 62.6 mol) and TEA (8.73 ml, 62.6 mol) in DCM (96 ml) was added and the mixture was stirred at RT for 3 hrs. The solution was washed with water (1×100 ml), NaHCO3 (2×100 ml) citric acid 1M (1×100 ml), sat NaCl (500 ml), dried over Na2SO4 and evaporated to afford a yellow solid 29 g which was triturated in a mixture Et2O/cHex 9/1 to afford the title compound (D55) (19.7 g).

MS: (ES/+) m/z: 429.3 [MH$^+$] C24H32N2O5 requires 428.52

$^1$H NMR (400 MHz, CHCl3-d) δ (ppm): 7.97 (d, J=8.3 Hz, 2 H), 7.28 (d, 5 H ubder solvent), 6.74 (br. s., 1 H), 4.96-4.70 (m, 1 H), 4.32-4.11 (m, 1 H), 3.92 (s, 3 H), 3.08-2.88 (m, 1 H), 2.12-1.97 (m, 1 H), 1.97-1.84 (m, 1 H), 1.84-1.73 (m, 1 H), 1.52 (s, 9 H), 1.43-1.31 (m, 4 H), 0.90-0.77 (m, 1 H), 0.62-0.46 (m, 1 H), 0.43-0.29 (m, 2 H), 0.28-0.19 (m, 1 H).

Description 56 tert-butyl 5-(((S)-1-(4-(methoxycarbonyl)phenyl)ethyl)carbamoyl)-6-azaspiro[2.5]octane-6-carboxylate (diastereoisomers mixture) (D56)

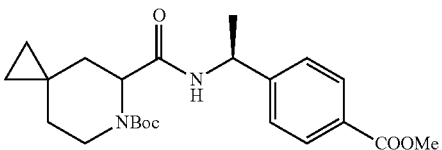 [SMILES: COC(=O)c1ccc([C@H](C)NC(=O)C2CC3(CCN2C(=O)OC(C)(C)C)CC3)cc1]

The title compound (D56) (130 mg) was prepared according to the general procedure for amides preparation (Method A) starting from 6-(tert-butoxycarbonyl)-azaspiro[2.5]octane-5-carboxylic acid (D1) (80 mg) and (S)-methyl 4-(1-aminoethyl)benzoate hydrochloride (67.6 mg). Reaction time: 18 hrs.

MS: (ES/+) m/z: 317 [MH-Boc$^+$] C23H32N2O5 requires 416.23

Chiral HPLC [Phenomens LUX-1; Mobile phase A: 90% n-hexane (+0.1% DEA), B: 10% IPA; DAD: 248 nm]: Peak 1 retention time: 13.01 min, peak 2 retention time: 19.4 min.

$^1$H NMR (400 MHz, CHCl3-d) δ (ppm): 8.03 (t, 4 H) 7.39 (dd, 4 H) 6.29 (br. s., 2 H) 5.16-5.28 (m, 2 H) 4.82 (br. s., 2 H) 4.14 (d, 1 H) 3.93 (d, 6 H) 3.00 (br. s., 1 H) 2.84-2.95 (m, 1 H)

2.01 (dt, 2 H) 1.73-1.96 (m, 4 H) 1.41-1.57 (m, 24 H) 0.72-0.95 (m, 3 H) 0.58 (d, 1 H) 0.21-0.45 (m, 6 H) 0.09 (br. s., 1 H).

Description 57 tert-butyl 5-(((S)-1-(4-(methoxycarbonyl)phenyl)ethyl)carbamoyl)-5-methyl-6-azaspiro[2.5]octane-6-carboxylate (diastereoisomers mixture) (D57)

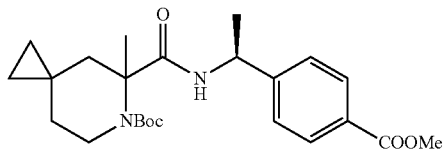

The title compound (D57) (25 mg) was prepared according to the general procedure for amides preparation (Method A) starting from 6-(tert-butoxycarbonyl)-5-methyl-6-azaspiro[2.5]octane-5-carboxylic acid (D6) (57 mg) and (S)-methyl 4-(1-aminoethyl)benzoate hydrochloride (46 mg). EDC.HCl: 1.1 eq, Reaction time: 48 hrs.

MS: (ES/+) m/z: 431 [MH$^+$] C24H34N2O5 requires 430.25

$^1$H NMR (400 MHz, CHCl3-d) δ (ppm): 8.09-7.94 (m, 2 H), 7.52-7.31 (m, 2 H), 5.33-5.07 (m, 1 H), 3.93 (s, 3 H), 3.91-3.79 (m, 1 H), 3.28-2.83 (m, 1 H), 2.07 (s, 1 H), 1.98-1.84 (m, 1 H), 1.66-1.42 (m, 12 H), 1.36-1.29 (m, 3 H), 1.19 (d, J=13.9 Hz, 1 H), 1.00-0.74 (m, 1 H), 0.65-0.12 (m, 4 H).

Description 58 tert-butyl 2-((1-(4-(methoxycarbonyl)phenyl)cyclopropyl)carbamoyl)-4,4-dimethylpiperidine-1-carboxylate (racemic mixture) (D58)

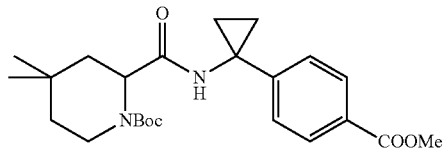 [SMILES: COC(=O)c1ccc(C2(NC(=O)C3CC(C)(C)CCN3C(=O)OC(C)(C)C)CC2)cc1]

The title compound (D58) (250 mg) was prepared according to the general procedure for amides preparation (Method C) starting from 1-(tert-butoxycarbonyl)-4,4-dimethylpiperidine-2-carboxylic acid (320 mg; described in *J. Med. Chem.* 1997, 40, 2491-2501) and methyl 4-(1-aminocyclopropyl)benzoate hydrochloride (312 mg). Reaction time: 18 hrs MS: (ES/+) m/z: 431.4 [MH$^+$] C24 H34N2O5 requires 430.25

$^1$H NMR (400 MHz, CHCl3-d) δ (ppm): 7.96 (d, J=8.2 Hz, 2 H), 7.32-7.29 (m, 2 H), 6.82-6.59 (m, 1 H), 4.65 (d, J=4.4 Hz, 1 H), 4.02 (br. s., 1 H), 3.92 (s, 3 H), 3.00 (d, J=10.6 Hz, 1 H), 2.18 (d, J=12.9 Hz, 1 H), 1.50 (s, 9 H), 1.43-1.29 (m, 7 H), 0.96 (s, 3 H), 0.84 (s, 3 H).

Description 59 tert-butyl 2-(((S)-1-(4-(methoxycarbonyl)phenyl)ethyl)carbamoyl)-4,4-dimethylpiperidine-1-carboxylate (diastereoisomers mixture) (D59)

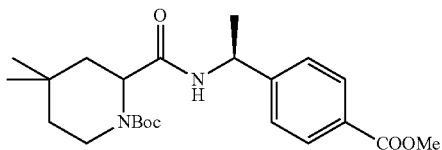 [SMILES: COC(=O)c1ccc([C@H](C)NC(=O)C2CC(C)(C)CCN2C(=O)OC(C)(C)C)cc1]

The title compound (D59) (230 mg) was prepared according to the general procedure for amides preparation (Method C) starting from 1-(tert-butoxycarbonyl)-4,4-dimethylpiperidine-2-carboxylic acid (320 mg; described in *J. Med. Chem.* 1997, 40, 2491-2501) and (S)-methyl 4-(1-aminoethyl)benzoate hydrochloride (295 mg). Reaction time: 18 hrs MS: (ES/+) m/z: 419.4 [MH$^+$] C23H34N2O5 requires 418.25

Description 60

(R)-tert-butyl 2-(((S)-1-(4-(methoxycarbonyl)phenyl)ethyl)carbamoyl)-4-oxopiperidine-1-carboxylate (D60)

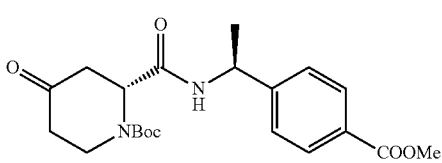 [SMILES: COC(=O)c1ccc([C@H](C)NC(=O)[C@H]2CC(=O)CCN2C(=O)OC(C)(C)C)cc1]

The title compound (D60) (300 mg) was prepared according to the general procedure for amides preparation (Method C) starting from (R)-1-(tert-butoxycarbonyl)-4-oxopiperidine-2-carboxylic acid (200 mg; available from Aldrich#701130) and (S)-methyl 4-(1-aminoethyl)benzoate hydrochloride (195 mg). Reaction time: 1 h MS: (ES/+) m/z: 405.5 [MH$^+$] C21H28N2O6 requires 404.19

$^1$H NMR (400 MHz, CHCl3-d) δ (ppm): 7.99 (d, J=7.6 Hz, 2 H), 7.32 (d, J=7.9 Hz, 2 H), 7.25-7.09 (m, 1 H), 5.17-5.02 (m, 1 H), 5.02-4.85 (m, 1 H), 3.93 (s, 3 H), 3.89-3.73 (m, 1 H), 3.57-3.36 (m, 1 H), 2.66-2.46 (m, 2 H), 2.46-2.31 (m, 1 H), 1.51 (br. s., 13 H).

Description 61

(2R)-tert-butyl 4-hydroxy-2-(((S)-1-(4-(methoxycarbonyl)phenyl)ethyl)carbamoyl)piperidine-1-carboxylate (D61) (diastereoisomer mixture)

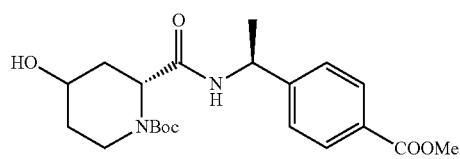 [SMILES: COC(=O)c1ccc([C@H](C)NC(=O)[C@H]2CC(O)CCN2C(=O)OC(C)(C)C)cc1]

To an ice cooled solution of (R)-tert-butyl 2-(((S)-1-(4-(methoxycarbonyl)phenyl)ethyl)carbamoyl)-4-oxopiperidine-1-carboxylate (D60) (300 mg, 0.75 mmol) in MeOH (25 ml) under nitrogen, NaBH₄ (142 mg, 3.75 mmol) was added portionwise and the resulting mixture was stirred at RT for 18 hrs. The mixture was diluted with water (10 ml) and extracted with EtOAc (3×10 ml). The organic phases were collected, washed with NaCl sat. (20 ml) dried over Na₂SO₄ and evaporated in vacuo to afford the title compound (D61) (261 mg).

MS: (ES/+) m/z: 407.2 [MH⁺] C21H30N2O6 requires 406.21

Description 62

(2R)-tert-butyl 4-fluoro-2-(((S)-1-(4-(methoxycarbonyl)phenyl)ethyl)carbamoyl)piperidine-1-carboxylate (diastereoisomer mixture) (D62)

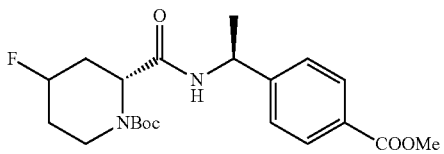 [SMILES: COC(=O)c1ccc([C@H](C)NC(=O)[C@H]2CC(F)CCN2C(=O)OC(C)(C)C)cc1]

A solution of (2R)-tert-butyl 4-hydroxy-2-(((S)-1-(4-(methoxycarbonyl)phenyl)ethyl)carbamoyl)piperidine-1-carboxylate (D61) (261 mg, 0.64 mmol) in DCM (10 ml) cooled at −20° C. was treated with DAST (0.17 ml, 1.28 mmol) and the reaction mixture stirred 1 h at −20° C. then at RT for 18 hrs. DAST (0.17 ml, 1.28 mmol) was added and the mixture further stirred 24 hrs. The reaction was quenched with NaHCO₃ sat. sol. and extracted with DCM (3×10 ml), dried over MgSO₄ and evaporated in vacuo. The residue was loaded onto a SPE-Si cartridge (20 g) eluting with a mixture DCM/EtOAc 90/10. Collected fractions after solvent evaporation afforded the title compound (D62) (89 mg)

¹H NMR (400 MHz, CHCl3-d) δ (ppm): 7.96 (d, J=8.2 Hz, 2 H), 7.21 (d, J=8.1 Hz, 2 H), 5.27-4.96 (m, 1 H), 4.96-4.80 (m, 1 H), 4.20-4.02 (m, 1 H), 3.92 (s, 3 H), 2.97-2.77 (m, 1 H), 2.63-2.47 (m, 1 H), 2.07 (s, 1 H), 1.75-1.46 (m, 12 H), 1.44-1.21 (m, 4 H).

Description 63

(R)-tert-butyl 2-((1-(4-(methoxycarbonyl)phenyl)cyclopropyl)carbamoyl)-4-oxopiperidine-1-carboxylate (D63)

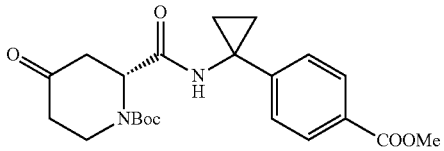 [SMILES: COC(=O)c1ccc(C2(NC(=O)[C@H]3CC(=O)CCN3C(=O)OC(C)(C)C)CC2)cc1]

The title compound (D63) (295 mg) was prepared according to the general procedure for amides preparation (Method C) starting from (R)-1-(tert-butoxycarbonyl)-4-oxopiperidine-2-carboxylic acid (200 mg) and methyl 4-(1-aminocyclopropyl)benzoate hydrochloride (206 mg). Reaction time: 18 hrs MS: (ES/+) m/z: 417.5 [MH⁺] C22H28N2O6 requires 416.19

¹H NMR (400 MHz, CHCl3-d) δ (ppm): 7.95 (d, J=7.9 Hz, 2 H), 7.51-7.37 (m, 1H), 7.22 (d, J=7.6 Hz, 2 H), 4.97-4.80 (m, 1 H), 3.92 (s, 4 H), 3.66-3.54 (m, 1H), 2.58 (d, J=5.6 Hz, 2 H), 2.52-2.37 (m, 1 H), 1.55 (s, 9 H), 1.46-1.24 (m, 5 H)

Description 64

(2R)-tert-butyl 4-hydroxy-2-((1-(4-(methoxycarbonyl)phenyl)cyclopropyl)carbamoyl)piperidine-1-carboxylate (diastereoisomer mixture) (D64)

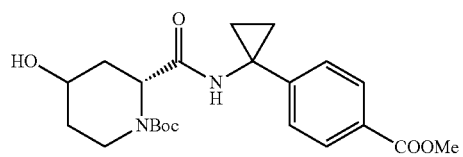 [SMILES: COC(=O)c1ccc(C2(NC(=O)[C@H]3CC(O)CCN3C(=O)OC(C)(C)C)CC2)cc1]

The title compound (D64) (266 mg) was prepared according to the experimental procedure described in Description 61 starting from starting from (R)-tert-butyl 2-((1-(4-(methoxycarbonyl)phenyl)cyclopropyl)carbamoyl)-4-oxopiperidine-1-carboxylate (D63) (300 mg, 0.72 mmol).

MS: (ES/+) m/z: 419.2 [MH⁺] C22H30N2O6 requires 418.21

Description 65

(2R)-tert-butyl 4-fluoro-2-((1-(4-(methoxycarbonyl)phenyl)cyclopropyl)carbamoyl)piperidine-1-carboxylate (diastereoisomer mixture) (D65)

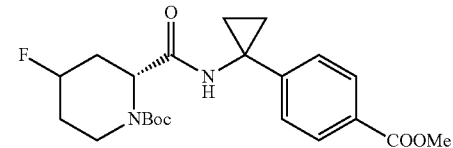 [SMILES: COC(=O)c1ccc(C2(NC(=O)[C@H]3CC(F)CCN3C(=O)OC(C)(C)C)CC2)cc1]

The title compound (D65) (39 mg) was prepared according to the experimental procedure described in Description 59 starting from starting from (2R)-tert-butyl 4-hydroxy-2-((1-(4-(methoxycarbonyl)phenyl)cyclopropyl)carbamoyl)piperidine-1-carboxylate (D64) (266 mg, 0.63 mmol).

¹H NMR (400 MHz, CHCl3-d) δ (ppm): 8.00 (d, J=7.8 Hz, 2 H), 7.34-7.26 (m, 2 H), 5.18-5.03 (m, 1 H), 4.96-4.86 (m, 1 H), 4.08-3.96 (m, 1 H), 3.93 (s, 3 H), 2.77-2.64 (m, 1 H), 2.64-2.49 (m, 1 H), 2.05-1.96 (m, 1 H), 1.73-1.53 (m, 3 H), 1.53-1.44 (m, 13 H).

Description 66

(R)-tert-butyl 4,4-difluoro-2-(((S)-1-(4-(methoxycarbonyl)phenyl)ethyl)carbamoyl)piperidine-1-carboxylate (D66)

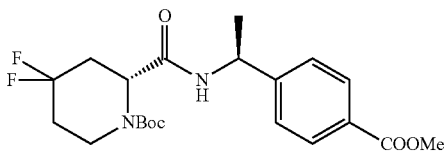 [SMILES: COC(=O)c1ccc([C@H](C)NC(=O)[C@H]2CC(F)(F)CCN2C(=O)OC(C)(C)C)cc1]

A solution of (R)-tert-butyl 2-(((S)-1-(4-(methoxycarbonyl)phenyl)ethyl)carbamoyl)-4-oxopiperidine-1-carboxylate (D60) (300 mg, 0.74 mmol) in DCM (30 ml) cooled at −20° C. was treated with DAST (0.49 ml, 3.71 mmol) and the reaction mixture stirred 1 h at −20° C. and at RT for 18 hrs. The reaction was quenched with NaHCO$_3$ sat. sol. and extracted with DCM (3×5 ml), dried over MgSO$_4$ and evaporated in vacuo. The residue was loaded onto a SPE-Si cartridge (15 g) eluting with a mixture DCM/EtOAc from 100/0 to 95/5. Collected fractions after solvent evaporation afforded the title compound (D66) (98 mg)

MS: (ES/+) m/z: 427.4 [MH$^+$] C21H28F2N2O5 requires 426.45

Description 67

(R)-tert-butyl 4,4-difluoro-2-((1-(4-(methoxycarbonyl)phenyl)cyclopropyl)carbamoyl)piperidine-1-carboxylate (single enantiomer) (D67)

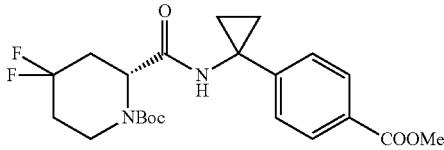 [SMILES: COC(=O)c1ccc(C2(NC(=O)[C@H]3CC(F)(F)CCN3C(=O)OC(C)(C)C)CC2)cc1]

The title compound (D67) (68 mg) was prepared according to the experimental procedure described in Description 66 starting from starting from (R)-tert-butyl 2-((1-(4-(methoxycarbonyl)phenyl)cyclopropyl)carbamoyl)-4-oxopiperidine-1-carboxylate (D63) (295 mg, 0.70 mmol).

MS: (ES/+) m/z: 339.4 [MH-Boc$^+$] C22H28F2N2O5 requires 438.20

$^1$H NMR (400 MHz, CHCl3-d) δ (ppm): 7.96 (d, J=8.1 Hz, 2 H), 7.22 (d, J=8.1 Hz, 2 H), 6.67 (br. s., 1 H), 5.06-4.93 (m, 1 H), 4.33-4.22 (m, 1 H), 3.91 (s, 4 H), 3.26-3.05 (m, 1 H), 3.05-2.88 (m, 1 H), 2.01-1.85 (m, 2 H), 1.59-1.31 (m, 13 H)

Description 68 tert-butyl 4,4-difluoro-2-((1-(4-(methoxycarbonyl)phenyl)cyclopropyl)carbamoyl)piperidine-1-carboxylate (racemic mixture) (D68)

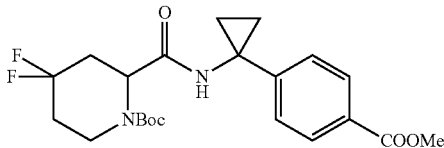 [SMILES: COC(=O)c1ccc(C2(NC(=O)C3CC(F)(F)CCN3C(=O)OC(C)(C)C)CC2)cc1]

The title compound (D68) (688 mg) was prepared according to the general procedure for amides preparation (Method C) starting from 1-(tert-butoxycarbonyl)-4,4-difluoropiperidine-2-carboxylic acid (600 mg; described in WO2010148197) and methyl 4-(1-aminocyclopropyl)benzoate hydrochloride (566.5 mg). Reaction time: 5 hrs MS: (ES/+) m/z: 439.2 [MH$^+$] C22H28F2N2O5 requires 438.46 Chiral HPLC [Daicel IC; Mobile phase A: 70% n-heptane (+0.1% DEA), B: 30% EtOH; DAD: 248 nm]: Peak 1 retention time: 11.46 min; Peak 2 retention time: 13.48 min.

$^1$H NMR (400 MHz, CHCl3-d) δ (ppm): 7.97 (d, J=8.3 Hz, 2 H), 7.23 (d, J=8.3 Hz, 2 H), 6.63 (s, 1 H), 4.97 (d, J=6.8 Hz, 1 H), 4.29 (br. s., 1 H), 3.92 (s, 3 H), 3.20-3.06 (m, 1 H), 3.04-2.89 (m, 1 H), 2.13-1.83 (m, 3 H), 1.52 (s, 9 H), 1.47-1.32 (m, 4 H).

Description 69 tert-butyl 4-((1-(4-(methoxycarbonyl)phenyl)cyclopropyl)carbamoyl)-3-azabicyclo[4.1.0]heptane-3-carboxylate (racemic mixture) (D69)

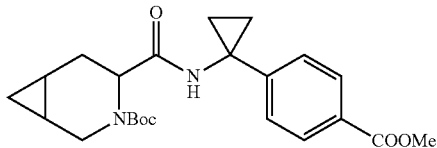 [SMILES: COC(=O)c1ccc(C2(NC(=O)C3CC4CC4CN3C(=O)OC(C)(C)C)CC2)cc1]

The title compound (D69) (270 mg) was prepared according to the general procedure for amides preparation (Method A) starting from 3-(tert-butoxycarbonyl)-3-azabicyclo[4.1.0]heptane-4-carboxylic acid (D17) (200 mg) and methyl 4-(1-aminocyclopropyl)benzoate hydrochloride (157 mg). HOBT.H$_2$O: 1.2 eq; Reaction time: 3 hrs.

MS: (ES/+) m/z: 415.2 [MH$^+$] C23H30N2O5 requires 414.22

Chiral HPLC [Daicel AD-H; Mobile phase A: 60% n-heptane (+0.1% DEA), B: 40% IPA; DAD: 248 nm]: Peak 1 retention time: 13.36 min, peak 2 retention time: 19.18 min.

$^1$H NMR (400 MHz, DMSO-d6) δ (ppm): 8.64-8.47 (m, 1 H), 7.89-7.70 (m, 2 H), 7.28 (d, J=7.8 Hz, 2 H), 4.04-3.92 (m, 1 H), 3.83 (s, 3 H), 3.77-3.62 (m, 1 H), 3.47-3.20 (m, 1 H, under water peak), 2.22-2.12 (m, 1 H), 1.83-1.66 (m, 1 H), 1.45-1.34 (m, 9 H), 1.30-1.06 (m, 5 H), 0.85 (br. s., 1 H), 0.61 (d, J=4.9 Hz, 1 H), 0.19 (d, J=3.9 Hz, 1 H).

Description 70

(3R)-tert-butyl 3-((1-(4-(methoxycarbonyl)phenyl)cyclopropyl)carbamoyl)-2-azabicyclo[4.1.0]heptane-2-carboxylate (diastereoisomers mixture) (D70)

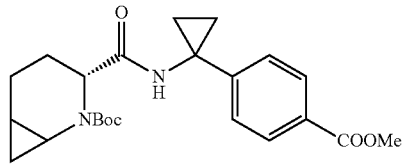 [SMILES: COC(=O)c1ccc(C2(NC(=O)[C@H]3CCC4CC4N3C(=O)OC(C)(C)C)CC2)cc1]

The title compound (D70) (28 mg) was prepared according to the general procedure for amides preparation (Method C) starting from (3R)-2-(tert-butoxycarbonyl)-2-azabicyclo[4.1.0]heptane-3-carboxylic acid (D22) (100 mg) and methyl 4-(1-aminocyclopropyl)benzoate hydrochloride (103 mg). Reaction time: 1 h MS: (ES/+) m/z: 415.3 [MH$^+$] C24H30N2O5 requires 414.22

¹H NMR (400 MHz, CHCl3-d) δ (ppm): 7.95 (d, J=7.7 Hz, 2 H), 7.34-7.14 (m, 2 H), 4.67-4.14 (m, 1 H), 3.91 (br. s., 3 H), 2.99-2.76 (1 H under residual solvent), 2.27-1.08 (m, 18 H), 0.88 (d, J=7.3 Hz, 1 H), 0.53-0.20 (m, 1 H).

Description 71

(3R)-tert-butyl 3-(((S)-1-(4-(methoxycarbonyl)phenyl)ethyl)carbamoyl)-2-azabicyclo[4.1.0]heptane-2-carboxylate (diastereoisomers mixture) (D71)

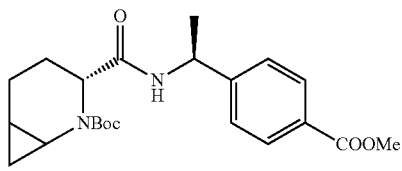 [SMILES: COC(=O)c1ccc([C@H](C)NC(=O)[C@H]2CCC3CC3N2C(=O)OC(C)(C)C)cc1]

The title compound (D71) (46 mg) was prepared according to the general procedure for amides preparation (Method C) starting from (3R)-2-(tert-butoxycarbonyl)-2-azabicyclo[4.1.0]heptane-3-carboxylic acid (D22) (100 mg) and (S)-methyl 4-(1-aminoethyl)benzoate hydrochloride (115 mg). Reaction time: 1 h MS: (ES/+) m/z: 403.2 [MH⁺] C22H30N2O5 requires 402.22

¹H NMR (400 MHz, CHCl3-d) δ (ppm): 8.01 (d, J=6.4 Hz, 2 H), 7.38 (d, J=6.9 Hz, 2 H), 5.28-5.04 (m, 1 H), 4.66-4.21 (m, 1 H), 3.93 (s, 3 H), 3.06-2.66 (m, 1 H), 2.25-1.11 (m, 17 H), 1.02-0.64 (m, 1 H), 0.56-0.15 (m, 1 H).

Description 72

(R)-tert-butyl 2-(((S)-1-(4-(methoxycarbonyl)phenyl)ethyl)carbamoyl) pyrrolidine-1-carboxylate (D72)

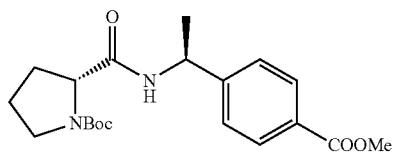 [SMILES: COC(=O)c1ccc([C@H](C)NC(=O)[C@H]2CCCN2C(=O)OC(C)(C)C)cc1]

The title compound (D72) (815 mg) was prepared according to the general procedure for amides preparation (Method A) starting from (R)-1-(tert-butoxycarbonyl)pyrrolidine-2-carboxylic acid (500 mg, available from Sigma Aldrich #433818), and (S)-methyl 4-(1-aminoethyl)benzoate hydrochloride (501 mg). Reaction time: 18 hrs MS: (ES/+) m/z: 377 [MH⁺] C20H28N2O5 requires 376.20

Chiral HPLC [Phenomenex Lux Cellulose-1; Mobile phase A: 70% n-hexane (+0.1% DEA), B: 30% EtOH; DAD: 254 nm]: Peak retention time: 7.93 min.

¹H NMR (400 MHz, CHCl3-d) δ (ppm): 8.00 (d, J=7.3 Hz, 2 H), 7.80-7.53 (m, 1 H), 7.35 (d, J=8.3 Hz, 2 H), 5.15 (br. s., 1 H), 4.35 (br. s., 1 H), 3.93 (s, 3 H), 3.37 (br. s., 2 H), 2.07 (s, 4 H), 1.50 (s, 12 H).

Description 73a and 73b (1R,3R,5R)-tert-butyl 3-((1-(4-(methoxycarbonyl)phenyl)cyclopropyl)carbamoyl)-2-azabicyclo[3.1.0]hexane-2-carboxylate (syn diastereoisomer) (D73a) and (1S,3R,5S)-tert-butyl 3-((1-(4-(methoxycarbonyl)phenyl)cyclopropyl)carbamoyl)-2-azabicyclo[3.1.0]hexane-2-carboxylate (anti diastereoisomer) (D73b)

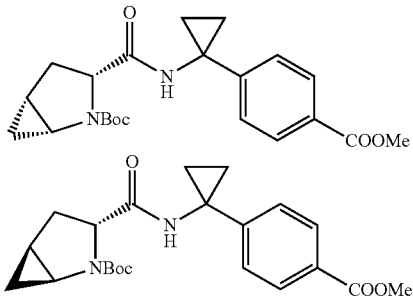

To a solution of (3R)-2-(tert-butoxycarbonyl)-2-azabicyclo[3.1.0]hexane-3-carboxylic acid (syn-anti diastereoisomer mixture 10/2) (D27) (3.06 g, 13.5 mmol) in dry DMF (15 ml) under N2 atmosphere HOBT.H2O (2.06 g, 13.46 mmol), EDC.HCl (3.87 g, 20.20 mmol), methyl 4-(1-aminocyclopropyl)benzoate hydrochloride (3.06 g, 13.46 mmol) and TEA (4.7 ml, 33.7 mmol) were added in sequence. The mixture was stirred for 2 hrs at RT, then the solvent was evaporated in vacuo and the residue taken up in AcOEt (500 ml), washed twice with water (50 ml), dried over Na2SO4 and evaporated to afford a residue which was loaded on a SNAP-Si cartridge (100 g) and eluted with a mixture DCM/AcOEt from 10/0 to 9/1. Collected fractions after solvent evaporation afforded the two diastereoisomer (D73a) (2.55 g) and (D73b) (880 mg).

(D73a) (syn diastereoisomer)
MS: (ES/+) m/z: 401.4 [MH⁺] C22H28N2O5 requires 400.20

¹H NMR (400 MHz, DMSO-d6) δ (ppm): 8.70 (s, 1 H), 7.90-7.76 (m, 2 H), 7.34-7.19 (m, 2 H), 4.52-4.35 (m, 1 H), 3.84 (s, 3 H), 3.43-3.32 (m, 1 H), 2.67-2.39 (m, 1 H), 1.88-1.74 (m, 1 H), 1.52-1.33 (m, 10 H), 1.27-1.12 (m, 4 H), 1.09-0.92 (m, 1 H), 0.66-0.53 (m, 1 H).

(D73b) (anti diastereoisomer)
MS: (ES/+) m/z: 401.4 [MH⁺] C22H28N2O5 requires 400.20

¹H NMR (400 MHz, DMSO-d6) δ (ppm): 8.69-8.52 (s, 1 H), 7.90-7.73 (m, 2 H), 7.35-7.19 (m, 2 H), 3.93-3.75 (m, 4 H), 3.36-3.30 (m, 1 H), 2.35-2.19 (m, 1 H), 2.12-2.02 (m, 1 H), 1.90-1.74 (m, 1 H), 1.47-1.30 (m, 9 H), 1.25-1.07 (m, 4 H), 0.73 (td, J=5.4, 8.8 Hz, 1 H), 0.39 (br. s., 1 H).

Description 74a and 74b (3R)-tert-butyl 3-(((S)-1-(4-(methoxycarbonyl)phenyl)ethyl)carbamoyl)-2-azabicyclo[3.1.0]hexane-2-carboxylate (diastereoisomer mixture) (D74a) and 3-(((S)-1-(4-(methoxycarbonyl)phenyl)ethyl)carbamoyl)-2-azabicyclo[3.1.0]hexane-2-carboxylate (single diastereoisomer) (D74b)

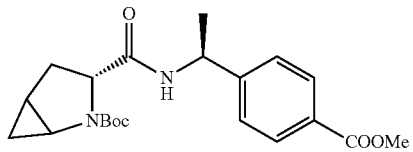 [SMILES: COC(=O)c1ccc([C@H](C)NC(=O)[C@H]2CC3CC3N2C(=O)OC(C)(C)C)cc1]

The title compounds (D74a) (15 mg) and (D74b) (65 mg) were prepared according to the general procedure for amides preparation (Method C) starting from (3R)-2-(tert-butoxycarbonyl)-2-azabicyclo[3.1.0]hexane-3-carboxylic acid (D33) (108 mg) and methyl 4-(1-aminocyclopropyl)benzoate hydrochloride (113 mg). Reaction time: 18 hrs.

(D74a) (diastereoisomer mixture)

$^1$H NMR (400 MHz, CHCl3-d) δ (ppm): 8.00 (d, J=8.1 Hz, 4 H), 7.36 (d, J=8.1 Hz, 4 H), 5.27-5.05 (m, 2 H), 4.13 (2 H, under residual solvent), 3.92 (s, 6 H), 3.35-3.12 (m, 2 H), 2.65-2.38 (m, 2 H), 2.35-2.12 (m, 2 H), 1.69-1.58 (m, 2H), 1.49 (s, 24 H), 0.94-0.74 (m, 2 H), 0.50-0.34 (m, 2 H)

(D74b) (single diastereoisomer)

MS: (ES/+) m/z: 289.3 [MH-Boc$^+$] C21H28N2O5 requires 388.20

$^1$H NMR (400 MHz, CHCl3-d) δ (ppm): 8.01 (d, J=8.0 Hz, 2 H), 7.37 (d, J=8.0 Hz, 2 H), 5.23-5.07 (m, 1 H), 4.22-4.06 (m, 1 H), 3.93 (s, 3 H), 3.33-3.18 (m, 1 H), 2.62-2.42 (m, 1 H), 2.32-2.12 (m, 1 H), 1.67-1.57 (m, 1 H), 1.50 (s, 12 H), 0.90-0.79 (m, 1 H), 0.47-0.36 (m, 1 H)

Description 75

(R)-tert-butyl 2-((1-(4-(methoxycarbonyl)phenyl) cyclopropyl)carbamoyl)-4,4-dimethylpyrrolidine-1-carboxylate (D75)

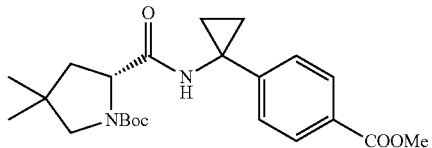 [SMILES: COC(=O)c1ccc(C2(NC(=O)[C@H]3CC(C)(C)CN3C(=O)OC(C)(C)C)CC2)cc1]

The title compound (D75) (94 mg) was prepared according to the general procedure for amides preparation (Method C) starting from (R)-1-(tert-butoxycarbonyl)-4,4-dimethylpyrrolidine-2-carboxylic acid (D41) (84 mg) and methyl 4-(1-aminocyclopropyl)benzoate hydrochloride (79 mg). HCTU: 1.05 eq; Reaction time: 2 hrs.

MS: (ES/+) m/z: 417.3 [MH$^+$] C23H32N2O5 requires 416.23

$^1$H NMR (400 MHz, CHCl3-d) δ (ppm): 8.04 (s, 1 H), 7.95 (d, J=8.0 Hz, 2 H), 7.28 (s, 2 H, under solvent), 4.32 (br. s., 1 H), 3.91 (s, 3 H), 3.65-3.25 (m, 1 H), 3.08 (d, J=10.7 Hz, 1 H), 2.35-2.07 (m, 1 H), 1.95-1.74 (m, 1 H), 1.49 (br. s., 9 H), 1.34 (d, J=12.3 Hz, 4 H), 1.18-0.95 (m, 6 H).

Description 76 methyl 4-((1S)-1-(1-benzylazetidine-2-carboxamido) ethyl)benzoate (diastereoisomers mixture) (D76)

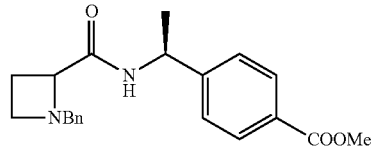 [SMILES: COC(=O)c1ccc([C@H](C)NC(=O)C2CCN2Cc2ccccc2)cc1]

The title compound (D76) (98 mg) was prepared according to the general procedure for amides preparation (Method C) starting from 1-benzylazetidine-2-carboxylic acid (100 mg, available from Apollo#OR7040) and (S)-methyl 4-(1-aminoethyl)benzoate hydrochloride (113 mg). Reaction time: 1 h MS: (ES/+) m/z: 353.3 [MH$^+$] C21H24N2O3 requires 352.18

$^1$H NMR (400 MHz, CHCl3-d) δ (ppm): 8.02 (d, J=8.1 Hz, 2 H), 7.94 (d, J=8.1 Hz, 2 H), 7.39-7.21 (m, 14 H), 7.06 (d, J=8.1 Hz, 2 H), 5.07-4.87 (m, 2 H), 3.93 (s, 6 H), 3.78-3.67 (m, 3 H), 3.65-3.56 (m, 3 H), 3.44 (d, J=8.1 Hz, 2 H), 3.11 (d, J=8.0 Hz, 2 H), 2.48 (br. s., 2 H), 2.15 (br. s., 1 H), 2.07 (s, 1 H), 1.47 (d, J=6.9 Hz, 3 H), 1.16 (d, J=6.9 Hz, 3 H).

General Procedure for Substituted Benzyl Amines Preparation

To a solution of selected cyclic amino-acid, cyclic amino-ester or cyclic amino-amide (1 eq) in ACN, Na$_2$CO$_3$ or Cs$_2$CO$_3$ (1.2-8 eq) and selected benzyl bromide (2 eq) were added sequentially and the resulting mixture was heated at 60-68° C. for 4-24 hrs or stirred at RT 18 hrs. After filtration of solids, the filtrate was evaporated in vacuo. The resulting residue was taken up in EtOAc and the organic phase was washed with water, dried over Na$_2$SO$_4$ and evaporated in vacuo. The crude material was purified on SPE-Si cartridge or Biotage SNAP-Si column eluting with mixtures of cHex/EtOAc or cHex/DCM or DCM/EtOAc affording the title substituted benzyl amine compound.

Description 77 methyl 3-(4-(trifluoromethyl)benzyl)-3-azabicyclo [3.1.0]hexane-2-carboxylate (syn relative stereochemistry) (D77)

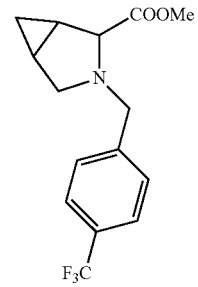 [SMILES: COC(=O)C1C2CC2CN1Cc1ccc(C(F)(F)F)cc1]

The title compound (D77) (345 mg) was prepared according to the general procedure for substituted benzyl amines preparation starting from methyl 3-azabicyclo[3.1.0]hexane-2-carboxylate hydrochloride (D42) (300 mg). (Na$_2$CO$_3$: 6 eq; reaction time: 18 hrs; 68° C.)

MS: (ES/+) m/z: 300.0 [MH$^+$] C15H16F3NO2 requires 299.11

$^1$H NMR (400 MHz, CHCl3-d) δ (ppm): 7.57 (d, J=7.8 Hz, 2 H), 7.46 (d, J=7.6 Hz, 2 H), 3.96 (d, J=13.4 Hz, 1 H), 3.74 (s, 3 H), 3.52-3.41 (m, 2 H), 3.00 (d, J=7.5 Hz, 1 H), 2.49 (d, J=4.9 Hz, 1 H), 1.72 (d, J=3.1 Hz, 1 H), 1.50-1.36 (m, 1 H), 1.11-0.96 (m, 1 H), 0.41 (d, J=4.7 Hz, 1 H).

Description 78 ethyl 2-(4-(trifluoromethyl)benzyl)-2-azabicyclo [2.2.2]octane-3-carboxylate (D78)

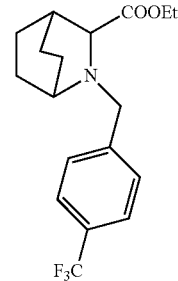 [SMILES: CCOC(=O)C1C2CCC(CC2)N1Cc1ccc(C(F)(F)F)cc1]

The title compound (D78) (430 mg) was prepared according to the general procedure for substituted benzyl amines preparation starting from ethyl 2-azabicyclo[2.2.2]octane-3-carboxylate (300 mg; for preparation see published International Patent application US2005009808). (Cs₂CO₃: 3 eq; reaction time: 18 hrs; 68° C.)

MS: (ES/+) m/z: 342 [MH⁺] C18H22F3NO2 requires 341.16

Description 79

(R)-4-(trifluoromethyl)benzyl 2-methyl-1-(4-(trifluoromethyl)benzyl)piperidine-2-carboxylate (D79)

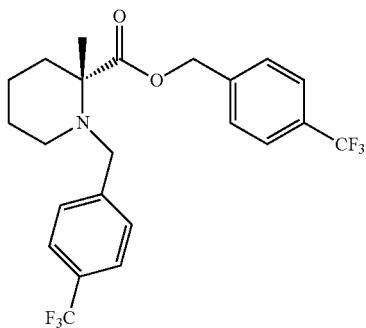 [SMILES: C[C@]1(C(=O)OCc2ccc(C(F)(F)F)cc2)CCCCN1Cc1ccc(C(F)(F)F)cc1]

The title compound (D79) (70 mg) was prepared according to the general procedure for substituted benzyl amines preparation starting from (R)-2-methylpiperidine-2-carboxylic acid (D47) (60 mg) and 4-(Trifluoromethyl)benzyl bromide (0.126 ml). (Na₂CO₃: 8 eq; reaction time 48 hrs; 68° C.)

MS: (ES/+) m/z: 460.3 [MH⁺] C23H23F6NO2 requires 459.16

¹H NMR (400 MHz, CHCl3-d) δ (ppm): 7.78-7.40 (m, 8 H), 5.24 (d, J=4.3 Hz, 2 H), 4.00 (d, J=15.4 Hz, 1 H), 3.82-3.53 (m, 2 H), 2.79-2.56 (m, 1 H), 2.55-2.39 (m, 1 H), 2.31-2.11 (m, 1 H), 1.72-1.45 (m, 7 H)

Description 80

(R)-methyl 2-methyl-1-(4-(trifluoromethyl)benzyl)pyrrolidine-2-carboxylate (D80)

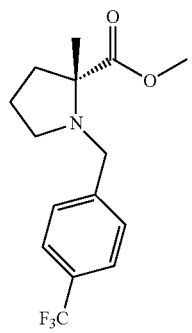 [SMILES: COC(=O)[C@@]1(C)CCCN1Cc1ccc(C(F)(F)F)cc1]

The title compound (D80) (50 mg) was prepared according to the general procedure for substituted benzyl amines preparation starting from (R)-methyl 2-methylpyrrolidine-2-carboxylate hydrochloride (D50) (60 mg) and 4-(Trifluoromethyl)benzyl bromide (0.126 ml). (Na₂CO₃: 4 eq; reaction time 18 hrs; 68° C.)

MS: (ES/+) m/z: 302.2 [MH⁺] C15H18F3NO2 requires 301.13

Description 81

2R,4R)-3-(trifluoromethyl)benzyl 4-hydroxy-1-(3-(trifluoromethyl)benzyl)pyrrolidine-2-carboxylate (D81)

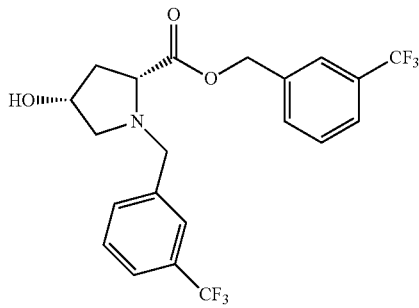 [SMILES: O=C(OCc1cccc(C(F)(F)F)c1)[C@H]1C[C@@H](O)CN1Cc1cccc(C(F)(F)F)c1]

The title compound (D81) (1.02 g) was prepared according to the general procedure for substituted benzyl amines preparation starting from cis-4-Hydroxy-D-proline (4.0 g; available from Aldrich#H5877) and 3-(Trifluoromethyl)benzyl bromide (9.37 ml). (Na₂CO₃: 2.5 eq; Reaction time: 24 hrs; 60° C.).

MS: (ES/+) m/z: 448.2 [MH⁺] C21H19F6NO3 requires 447.13

¹H NMR (400 MHz, CHCl3-d) δ (ppm): 7.70-7.34 (m, 8 H), 5.28-5.06 (m, 2 H), 4.51 (br. s., 1 H), 4.02 (d, J=13.3 Hz, 1 H), 3.81-3.64 (m, 2 H), 3.34 (dd, J=5.4, 10.1 Hz, 1 H), 2.52 (dd, J=2.9, 10.1 Hz, 1 H), 2.30 (td, J=7.0, 13.6 Hz, 1 H), 2.23-2.10 (m, 1 H), 1.76 (br. s., 1 H).

Description 82

2R,4S)-3-(trifluoromethyl)benzyl 4-fluoro-1-(3-(trifluoromethyl)benzyl)pyrrolidine-2-carboxylate (D82)

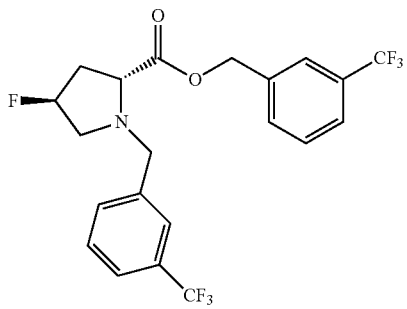 [SMILES: O=C(OCc1cccc(C(F)(F)F)c1)[C@H]1C[C@H](F)CN1Cc1cccc(C(F)(F)F)c1]

A solution of (2R,4R)-3-(trifluoromethyl)benzyl 4-hydroxy-1-(3-(trifluoromethyl)benzyl)pyrrolidine-2-carboxylate (D81) (200 mg, 0.45 mmol) in DCM (20 ml) cooled at −20° C. was treated with DAST (0.148 ml, 1.11 mmol) and the mixture was first stirred 1 h at −20° C. then 18 hrs at RT. The reaction was quenched with NaHCO₃ sat. sol. and the aqueous phase extracted with DCM (3×5 ml), dried over MgSO₄ and evaporated. The residue was purified by Biotage SNAP-Si column (25 g) eluting with petroleum ether/EtOAc from 90/10 to 80/20. Collected fractions, after solvent evaporation afforded the title compound (D82) (110 mg)

MS: (ES/+) m/z: 450.2 [MH$^+$] C21H18F7NO2 requires 449.12

Chiral HPLC [Daicel OD-H; Mobile phase A: 80% n-hexane (+0.1% DEA); B: 20% IPA; DAD: 265 nm]: Peak retention time: 10.82 min.

$^1$H NMR (400 MHz, CHCl3-d) δ (ppm): 7.77-7.36 (m, 8 H), 5.37-5.04 (m, 3 H), 4.14 (d, J=13.3 Hz, 1 H), 3.77-3.58 (m, 1 H), 3.46 (br. s., 1 H), 3.38-3.17 (m, 1 H), 2.86-2.49 (m, 2 H), 2.49-2.25 (m, 1 H).

Description 83

(R)-3-(trifluoromethyl)benzyl 4-oxo-1-(3-(trifluoromethyl)benzyl)pyrrolidine-2-carboxylate (D83)

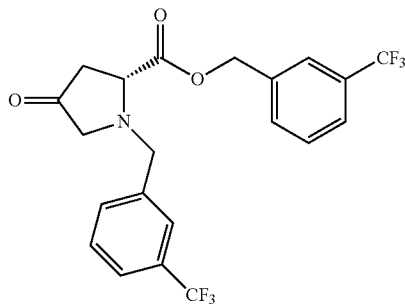 [SMILES: O=C1C[C@H](C(=O)OCc2cccc(C(F)(F)F)c2)N(Cc2cccc(C(F)(F)F)c2)C1]

A solution of (2R,4R)-3-(trifluoromethyl)benzyl 4-hydroxy-1-(3-(trifluoromethyl)benzyl)pyrrolidine-2-carboxylate (D81) (469 mg, 1.05 mmol) in dry DCM (10 ml) was treated with Dess-Martin periodinane (0.57 mg, 1.34 mmol) and stirred at RT 4 hrs. The reaction was quenched with 10% aqueous sodium sulphite solution (10 ml) and extracted with EtOAc (3×10 ml). The organic phases were collected, washed with NaCl sat. sol, dried over Na$_2$SO$_4$ and evaporated to afford a residue which was purified by SPE-Si cartridge (10 g) eluting with a mixture cHex/EtOAc 90/10. Collected fractions after solvent evaporation afforded the title compound (D83) (290 mg).

MS: (ES/+) m/z: 446.2 [MH$^+$] C21H17F6NO3 requires 445.11

$^1$H NMR (400 MHz, CHCl3-d) δ (ppm): 7.75-7.37 (m, 8 H), 5.25 (s, 2 H), 4.06-3.87 (m, 2 H), 3.78 (d, J=13.4 Hz, 1 H), 3.36 (d, J=17.1 Hz, 1 H), 3.06 (d, J=17.1 Hz, 1 H), 2.80 (dd, J=7.9, 18.1 Hz, 1 H), 2.69-2.47 (m, 1 H).

Description 84

(R)-3-(trifluoromethyl)benzyl 4,4-difluoro-1-(3-(trifluoromethyl)benzyl)pyrrolidine-2-carboxylate (D84)

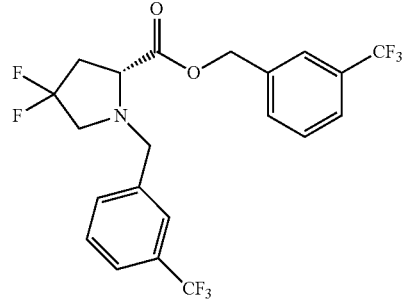 [SMILES: O=C(OCc1cccc(C(F)(F)F)c1)[C@H]1CC(F)(F)CN1Cc1cccc(C(F)(F)F)c1]

A solution of (R)-4-(trifluoromethyl)benzyl 4-oxo-1-(4-(trifluoromethyl)benzyl)pyrrolidine-2-carboxylate (D83) (90 mg, 0.20 mmol) in DCM (10 ml) cooled at −20° C. was treated with DAST (0.133 ml, 1.01 mmol) and the mixture was first stirred 1 h at −20° C. then 18 hrs at RT. The reaction was quenched with NaHCO$_3$ sat. sol. and the aqueous phase extracted with DCM (3×5 ml), dried over MgSO$_4$ and evaporated. The residue was purified by SPE-Si cartridge (10 g) eluting with cHex/DCM 50/50. Collected fractions, after solvent evaporation afforded the title compound (D84) (87 mg)

MS: (ES/+) m/z: 468.2 [MH$^+$] C21H17F8NO2 requires 467.11

$^1$H NMR (400 MHz, CHCl3-d) δ (ppm): 7.78-7.36 (m, 8 H), 5.31-5.14 (m, 2 H), 4.07 (d, J=13.4 Hz, 1 H), 3.77-3.59 (m, 2 H), 3.37 (q, J=12.2 Hz, 1 H), 2.91 (td, J=10.9, 16.4 Hz, 1 H), 2.75-2.43 (m, 2 H).

General Procedure for t-Butyl Carbamate (Boc) Cleavage

To an ice cooled solution of Boc protected amine in DCM a 3:1 mixture TFA:DCM was added and the resulting mixture was stirred at RT 1 h prior evaporation of solvents. The residue was loaded onto SPE-SCX cartridge. The collected ammonia fractions after solvent evaporation afforded the title compounds.

Description 85 methyl 4-((1S)-1-(piperidine-2-carboxamido)ethyl) (diastereoisomers mixture) (D85)

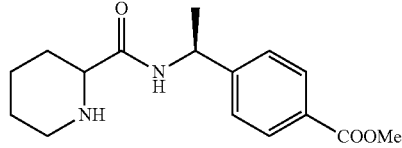 [SMILES: COC(=O)c1ccc([C@H](C)NC(=O)C2CCCCN2)cc1]

The title compound (D85) (1.37 g) was prepared according to the general procedure for t-Butyl carbamate (Boc) cleavage starting from tert-butyl 2-(((S)-1-(4-(methoxycarbonyl)phenyl)ethyl)carbamoyl) piperidine-1-carboxylate (D51) (1.95 g).

MS: (ES/+) m/z: 291.3 [MH$^+$] C16H22N2O3 requires 290.16

$^1$H NMR (400 MHz, CHCl3-d) δ (ppm): 8.01 (d, 2 H) 7.38 (d, 2 H) 7.13-7.27 (m, 1 H) 5.08-5.24 (m, 1 H) 3.93 (s, 3 H) 3.22-3.38 (m, 1 H) 3.05 (d, 1 H) 2.72 (t, 1 H) 2.50 (br. s., 1 H) 1.98 (d, 1 H) 1.80 (d, 1 H) 1.60 (br. s., 1 H) 1.50 (d, 3 H) 1.38-1.48 (m, 3 H).

Description 86 methyl 4-((S)-1-((R)-piperidine-2-carboxamido) ethyl)benzoate (D86)

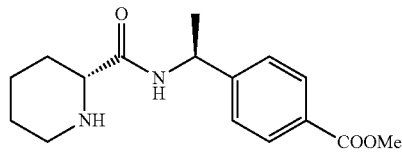 [SMILES: COC(=O)c1ccc([C@H](C)NC(=O)[C@H]2CCCCN2)cc1]

The title compound (D86) (286 mg) was prepared according to the general procedure for t-Butyl carbamate (Boc) cleavage starting from (R)-tert-butyl 2-(((S)-1-(4-(methoxycarbonyl)phenyl)ethyl)carbamoyl) piperidine-1-carboxylate (D52) (405 mg).

MS: (ES/+) m/z: 291.3 [MH+] C16H22N2O3 requires 290.16

Chiral HPLC [Phenomenex Lux Cellulose-1; Mobile phase A: 90% n-hexane (+0.1% DEA), B: 10% EtOH; DAD: 237 nm]: Peak retention time: 15.93 min.

¹H NMR (400 MHz, CHCl3-d) δ (ppm): 8.02 (d, 2 H) 7.39 (d, 2 H) 7.15 (d, 1 H) 5.17 (t, 1 H) 3.93 (s, 3 H) 3.17-3.33 (m, 1 H) 3.03 (d, 1 H) 2.71 (br. s., 1 H) 1.89-2.08 (m, 1 H) 1.72-1.86 (m, 1 H) 1.54-1.67 (m, 2 H) 1.50 (d, 3 H) 1.30-1.46 (m, 3 H).

Description 87

(R)-methyl 4-(1-(piperidine-2-carboxamido)cyclopropyl)benzoate (D87)

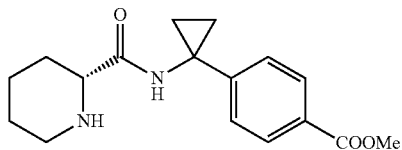 [SMILES: COC(=O)c1ccc(C2(NC(=O)[C@H]3CCCCN3)CC2)cc1]

The title compound (D87) (490 mg) was prepared according to the general procedure for t-Butyl carbamate (Boc) cleavage starting from (R)-tert-butyl 2-((1-(4-(methoxycarbonyl)phenyl)cyclopropyl)carbamoyl) piperidine-1-carboxylate (D53) (650 mg).

MS: (ES/+) m/z: 303.2 [MH+] C17H22N2O3 requires 302.16

Description 88 methyl 4-(1-(6-azaspiro[2.5]octane-5-carboxamido)cyclopropyl)benzoate (racemic mixture) (D88)

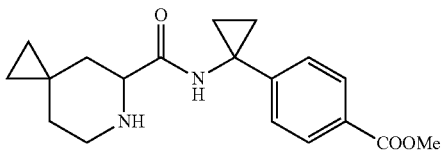 [SMILES: COC(=O)c1ccc(C2(NC(=O)C3CC4(CCN3)CC4)CC2)cc1]

The title compound (D88) (230 mg) was prepared according to the general procedure for t-Butyl carbamate (Boc) cleavage starting from tert-butyl 5-((1-(4-(methoxycarbonyl)phenyl)cyclopropyl)carbamoyl)-6-azaspiro[2.5]octane-6-carboxylate (racemic mixture) (D54) (290 mg).

MS: (ES/+) m/z: 329.3 [MH+] C19H24N2O3 requires 328.18

¹H NMR (400 MHz, CHCl3-d) δ (ppm): 8.08 (br. s., 1 H), 7.92 (d, J=8.2 Hz, 2 H), 7.19 (d, J=8.1 Hz, 2 H), 3.91 (s, 3 H), 3.74 (d, J=9.4 Hz, 1 H), 3.11 (d, J=12.0 Hz, 1 H), 2.98-2.84 (m, 1 H), 2.02-1.78 (m, 2 H), 1.39-1.24 (m, 5 H), 0.88 (d, J=13.5 Hz, 1 H), 0.51-0.32 (m, 3 H), 0.26 (d, J=6.1 Hz, 1 H).

Description 89 methyl 4-(1-(6-azaspiro[2.5]octane-5-carboxamido)cyclopropyl)benzoate 2,2,2-trifluoroacetate (single unknown enantiomer) (D89)

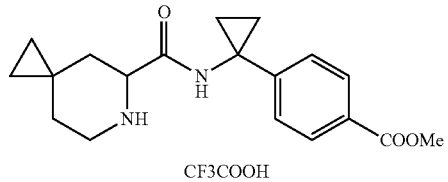 [SMILES: COC(=O)c1ccc(C2(NC(=O)C3CC4(CCN3)CC4)CC2)cc1 ; "CF3COOH"]

tert-butyl 5-((1-(4-(methoxycarbonyl)phenyl)cyclopropyl)carbamoyl)-6-azaspiro[2.5]octane-6-carboxylate (D55) (19.7 g) was dissolved in DCM (220 ml) before adding TFA (35 ml). The reaction was stirred at RT for 18 hrs. After solvent evaporation the title compound (D89) (27 g) was isolated.

MS: (ES/+) m/z: 329.3 [MH+] C19H24N2O3 requires 328.18

¹H NMR (400 MHz, CHCl3-d) δ (ppm): 9.89-9.40 (m, 1 H), 7.94 (d, J=7.9 Hz, 2 H), 7.79-7.51 (m, 1 H), 7.12 (d, J=7.9 Hz, 2 H), 4.41 (br. s., 1 H), 3.94 (s, 3 H), 3.47-3.27 (m, J=10.5 Hz, 1 H), 3.24-3.02 (m, 1 H), 2.16 (t, J=12.6 Hz, 1 H), 2.12-2.06 (m, 1 H), 1.44-1.17 (m, 5 H), 0.93 (d, J=14.2 Hz, 1 H), 0.67-0.31 (m, 4 H).

Description 90 methyl 4-(1-(6-azaspiro[2.5]octane-5-carboxamido)cyclopropyl)benzoate (single unknown enantiomer) (D90)

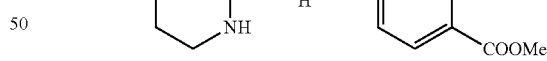

The title compound (D90) (310 mg) was prepared according to the general procedure for t-Butyl carbamate (Boc) cleavage starting from tert-butyl 5-((1-(4-(methoxycarbonyl)phenyl)cyclopropyl)carbamoyl)-6-azaspiro[2.5]octane-6-carboxylate (D55) (405 mg).

MS: (ES/+) m/z: 329.2 [MH+] C19H24N2O3 requires 328.18

¹H NMR (400 MHz, CHCl3-d) δ (ppm): 7.95 (d, J=8.2 Hz, 2 H), 7.80-7.61 (m, 1 H), 7.24 (d, J=8.2 Hz, 2 H), 3.91 (s, 3 H), 3.61-3.47 (m, 1 H), 3.19-3.05 (m, 1 H), 2.99-2.81 (m, 1 H), 1.98-1.72 (m, 2 H), 1.33 (d, J=5.7 Hz, 5 H), 1.03-0.88 (m, 1 H), 0.38 (d, J=6.0 Hz, 3 H), 0.34-0.21 (m, 1 H).

Description 91 methyl 4-((1S)-1-(6-azaspiro[2.5]octane-5-carboxamido)ethyl)benzoate (diastereoisomers mixture) (D91)

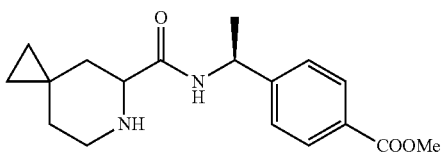 [SMILES: COC(=O)c1ccc([C@H](C)NC(=O)C2CC3(CCN2)CC3)cc1]

The title compound (D91) (96 mg) was prepared according to the general procedure for t-Butyl carbamate (Boc) cleavage starting from tert-butyl 5-(((S)-1-(4-(methoxycarbonyl)phenyl)ethyl)carbamoyl)-6-azaspiro[2.5]octane-6-carboxylate (D56) (130 mg).

MS: (ES/+) m/z: 317 [MH-Boc$^+$] C18H24N2O3 requires 316.18

Chiral HPLC [Phenomens LUX-1; Mobile phase A: 90% n-hexane (+0.1% DEA), B: 10% IPA; DAD: 248 nm]: Peak 1 retention time: 13.6 min, peak 2 retention time: 15.7 min.

$^1$H NMR (400 MHz, CHCl3-d) δ (ppm): 8.02 (dd, 4 H) 7.40 (d, 4 H) 7.18 (t, 2 H) 5.17 (t, 2 H) 3.93 (s, 6 H) 3.36 (ddd, 2 H) 2.97-3.16 (m, 2H) 2.74-2.93 (m, 2H) 1.64-1.87 (m, 5 H) 1.45-1.55 (d, 7 H) 1.34 (t, 2 H) 0.91 (d, 2 H) 0.17-0.49 (m, 8 H)

Description 92 methyl 4-((1S)-1-(5-methyl-6-azaspiro[2.5]octane-5-carboxamido)ethyl)benzoate (diastereoisomers mixture) (D92)

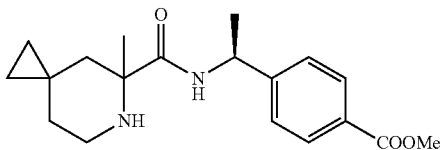 [SMILES: COC(=O)c1ccc([C@H](C)NC(=O)C2(C)CC3(CCN2)CC3)cc1]

The title compound (D92) (19 mg) was prepared according to the general procedure for t-Butyl carbamate (Boc) cleavage starting from tert-butyl 5-(((S)-1-(4-(methoxycarbonyl)phenyl)ethyl)carbamoyl)-5-methyl-6-azaspiro[2.5]octane-6-carboxylate (D57) (25 mg)

MS: (ES/+) m/z: 331.3 [MH$^+$] C19H26N2O3 requires 330.19

$^1$H NMR (400 MHz, CHCl3-d) δ (ppm): 8.07-7.94 (m, 2 H), 7.92-7.74 (m, 1 H), 7.49-7.33 (m, 2 H), 5.15 (t, J=7.1 Hz, 1 H), 3.92 (s, 3 H), 3.25-2.72 (m, 3 H), 1.94 (t, J=12.7 Hz, 1 H), 1.55-1.46 (m, 3 H), 1.37-1.24 (m, 3 H), 1.01-0.81 (m, 2 H), 0.62-0.18 (m, 4 H).

Description 93 methyl 4-(1-(4,4-dimethylpiperidine-2-carboxamido)cyclopropyl)benzoate (D93)

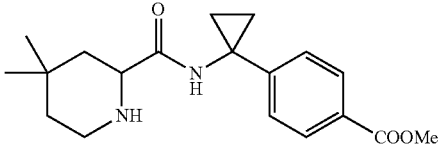 [SMILES: COC(=O)c1ccc(C2(NC(=O)C3CC(C)(C)CCN3)CC2)cc1]

The title compound (D93) (150 mg) was prepared according to the general procedure for t-Butyl carbamate (Boc) cleavage starting from tert-butyl 2-((1-(4-(methoxycarbonyl)phenyl)cyclopropyl)carbamoyl)-4,4-dimethylpiperidine-1-carboxylate (D58) (250 mg)

MS: (ES/+) m/z: 331.3 [MH$^+$] C19H26N2O3 requires 330.19

$^1$H NMR (400 MHz, CHCl3-d) δ (ppm): 7.95 (d, J=8.2 Hz, 2 H), 7.47 (br. s., 1 H), 7.24 (d, J=8.3 Hz, 2 H), 3.91 (s, 3 H), 3.39 (dd, J=2.7, 11.5 Hz, 1 H), 3.00-2.78 (m, 2 H), 1.78-1.67 (m, 3 H), 1.33 (d, J=6.7 Hz, 4 H), 1.29-1.20 (m, 1 H), 0.98 (d, J=5.2 Hz, 6 H).

Description 94 methyl 4-((1S)-1-(4,4-dimethylpiperidine-2-carboxamido)ethyl)benzoate (diastereoisomers mixture) (D94)

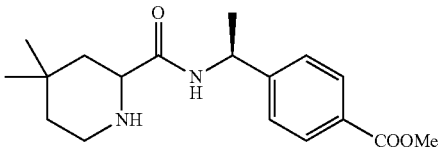 [SMILES: COC(=O)c1ccc([C@H](C)NC(=O)C2CC(C)(C)CCN2)cc1]

The title compound (D94) (150 mg) was prepared according to the general procedure for t-Butyl carbamate (Boc) cleavage starting from tert-butyl 2-(((S)-1-(4-(methoxycarbonyl)phenyl)ethyl)carbamoyl)-4,4-dimethylpiperidine-1-carboxylate (diastereoisomers mixture) (D59) (230 mg)

MS: (ES/+) m/z: 319.3 [MH$^+$] C18H26N2O3 requires 318.25

$^1$H NMR (400 MHz, CHCl3-d) δ (ppm): 8.09-7.96 (m, 2 H), 7.40 (d, J=7.0 Hz, 2H), 5.15 (br. s., 1 H), 3.93 (s, 3 H), 3.48 (d, J=12.1 Hz, 1 H), 2.95 (br. s., 2 H), 1.82-1.69 (m, 1 H under solvent), 1.51 (d, J=6.5 Hz, 3 H), 1.44-1.28 (m, 3 H), 1.04-0.91 (m, 6 H).

Description 95 methyl 4-((1S)-1-((2R)-4-fluoropiperidine-2-carboxamido)ethyl)benzoate (diastereoisomers mixture) (D95)

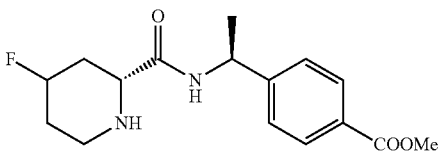

The title compound (D95) (75 mg) was prepared according to the general procedure for t-Butyl carbamate (Boc) cleavage starting from (2R)-tert-butyl 4-fluoro-2-(((S)-1-(4-(methoxycarbonyl)phenyl)ethyl)carbamoyl)piperidine-1-carboxylate (D62) (89 mg).

MS: (ES/+) m/z: 309.2 [MH⁺] C16H21FN2O3 requires 308.15

$^1$H NMR (400 MHz, CHCl3-d) δ (ppm): 8.03 (d, J=8.1 Hz, 2 H), 7.38 (d, J=8.1 Hz, 2 H), 7.20-7.07 (m, 1 H), 5.22-5.12 (m, 1 H), 5.00-4.80 (m, 1H), 3.93 (s, 3 H), 3.70-3.62 (m, 1 H), 3.13-3.01 (m, 1 H), 2.96-2.83 (m, 1 H), 2.28-2.14 (m, 1 H), 1.88-1.61 (m, 4 H), 1.52 (d, J=6.9 Hz, 3 H).

Description 96 methyl 4-(1-((2R)-4-fluoropiperidine-2-carboxamido)cyclopropyl)benzoate (diastereoisomers mixture) (D96)

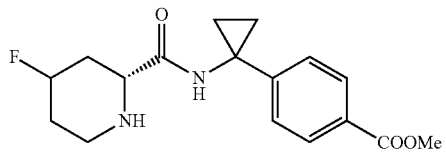 [SMILES: COC(=O)c1ccc(C2(NC(=O)[C@H]3CC(F)CCN3)CC2)cc1]

The title compound (D96) (26 mg) was prepared according to the general procedure for t-Butyl carbamate (Boc) cleavage starting from (2R)-tert-butyl 4-fluoro-2-((1-(4-(methoxycarbonyl)phenyl)cyclopropyl)carbamoyl)piperidine-1-carboxylate (D65) (39 mg).

MS: (ES/+) m/z: 321.1 [MH⁺] C17H21FN2O3 requires 320.15

$^1$H NMR (400 MHz, CHCl3-d) δ (ppm 8.05-7.86 (m, J=8.0 Hz, 2 H), 7.55 (br. s., 1H), 7.33-7.17 (m, 2 H), 5.06-4.77 (m, 1 H), 3.90 (s, 3 H), 3.71-3.58 (m, 1 H), 3.06 (d, J=11.0 Hz, 1 H), 2.98-2.83 (m, 1 H), 2.19 (d, J=9.9 Hz, 1 H), 1.98-1.43 (m, 3 H), 1.40-1.09 (m, J=6.5 Hz, 4 H).

Description 97 methyl 4-((S)-1-((R)-4,4-difluoropiperidine-2-carboxamido)ethyl)benzoate (D97)

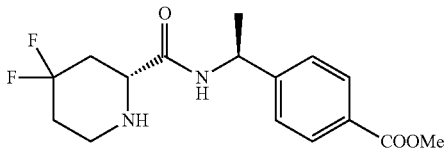 [SMILES: COC(=O)c1ccc([C@H](C)NC(=O)[C@H]2CC(F)(F)CCN2)cc1]

The title compound (D97) (66 mg) was prepared according to the general procedure for t-Butyl carbamate (Boc) cleavage starting from (R)-tert-butyl 4,4-difluoro-2-(((S)-1-(4-(methoxycarbonyl)phenyl)ethyl)carbamoyl)piperidine-1-carboxylate (D66) (98 mg).

MS: (ES/+) m/z: 327.4 [MH⁺] C16H20F2N2O3 requires 326.14

$^1$H NMR (400 MHz, CHCl3-d) δ (ppm): 8.03 (d, J=7.8 Hz, 2 H), 7.38 (d, J=7.8 Hz, 2 H), 6.98 (d, J=5.9 Hz, 1 H), 5.27-5.05 (m, 1 H), 3.93 (s, 3 H), 3.43-3.13 (m, 1 H), 2.93-2.78 (m, 1 H), 2.56-2.33 (m, 1 H), 2.15-1.94 (m, 1 H), 1.90-1.66 (m, 2 H), 1.63-1.44 (m, 4 H).

Description 98

(R)-methyl 4-(1-(4,4-difluoropiperidine-2-carboxamido)cyclopropyl)benzoate (D98)

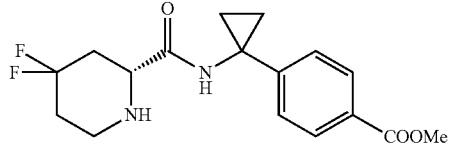 [SMILES: COC(=O)c1ccc(C2(NC(=O)[C@H]3CC(F)(F)CCN3)CC2)cc1]

The title compound (D98) (47 mg) was prepared according to the general procedure for t-Butyl carbamate (Boc) cleavage starting from (R)-tert-butyl 4,4-difluoro-2-((1-(4-(methoxycarbonyl)phenyl)cyclopropyl)carbamoyl)piperidine-1-carboxylate (D67) (68 mg).

MS: (ES/+) m/z: 339.4 [MH⁺] C17H20F2N2O3 requires 338.14

Description 99 methyl 4-(1-(4,4-difluoropiperidine-2-carboxamido)cyclopropyl)benzoate (racemic mixture) (D99)

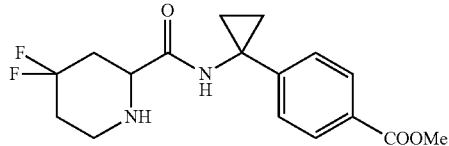 [SMILES: COC(=O)c1ccc(C2(NC(=O)C3CC(F)(F)CCN3)CC2)cc1]

The title compound (D99) (500 mg) was prepared according to the general procedure for t-Butyl carbamate (Boc) cleavage starting from tert-butyl 4,4-difluoro-2-((1-(4-(methoxycarbonyl)phenyl)cyclopropyl)carbamoyl)piperidine-1-carboxylate (D68) (685 mg)

MS: (ES/+) m/z: 339.2 [MH⁺] C17H20F2N2O3 requires 338.46

Chiral HPLC [Daicel IC; Mobile phase A: 70% n-heptane (+0.1% DEA), B: 30% EtOH; DAD: 248 nm]: Peak 1 retention time: 12.71 min, peak 2 retention time: 16.05 min.

$^1$H NMR (400 MHz, DMSO-d6) δ (ppm): 8.69 (s, 1 H), 7.85 (d, J=8.3 Hz, 2 H), 7.24 (d, J=8.3 Hz, 2 H), 3.84 (s, 3 H), 3.34-3.31 (m, 1 H), 3.09 (d, J=12.2 Hz, 1 H), 2.70-2.57 (m, 1 H), 2.25-2.07 (m, 1 H), 1.99-1.70 (m, 3 H), 1.35-1.16 (m, 4 H).

Description 100 methyl 4-(1-(3-azabicyclo[4.1.0]heptane-4-carboxamido)cyclopropyl)benzoate (diastereoisomers mixture) (D100)

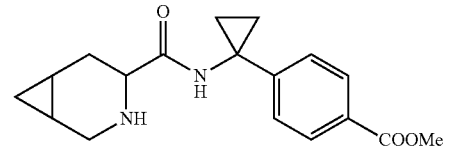 [SMILES: COC(=O)c1ccc(C2(NC(=O)C3CC4CC4CN3)CC2)cc1]

The title compound (D100) (155 mg) was prepared according to the general procedure for t-Butyl carbamate (Boc) cleavage starting from tert-butyl 4-((1-(4-(methoxycarbonyl)phenyl)cyclopropyl)carbamoyl)-3-azabicyclo[4.1.0]heptane-3-carboxylate (D69) (260 mg).

MS: (ES/+) m/z: 314.7 [MH$^+$] C18H22N2O3 requires 314.16 Chiral HPLC [Daicel AD-H; Mobile phase A: 60% n-heptane (+0.1% DEA), 40% IPA; DAD: 248 nm]: Peak 1 retention time: 13.36 min, peak 2 retention time: 19.18 min.

$^1$H NMR (400 MHz, DMSO-d6) δ (ppm): 8.46 (s, 1 H), 7.88-7.81 (m, 2 H), 7.26-7.19 (m, 2 H), 3.83 (s, 3 H), 3.33-3.31 (m, 1 H), 2.86 (dd, J=4.9, 9.8 Hz, 1 H), 2.69-2.65 (m, 1 H), 1.91-1.83 (m, 1 H), 1.83-1.73 (m, 1 H), 1.30-1.24 (m, 2 H), 1.24-1.17 (m, 2 H), 1.05-0.87 (m, 2 H), 0.59 (dt, J=4.4, 8.6 Hz, 1 H), 0.27 (q, J=4.9 Hz, 1 H).

Description 101 methyl 4-(1-((3R)-2-azabicyclo[4.1.0]heptane-3-carboxamido)cyclopropyl)benzoate (diastereoisomers mixture) (D101)

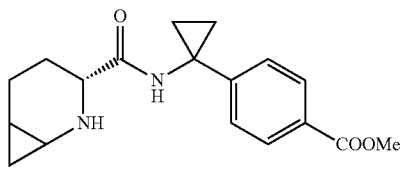 [SMILES: COC(=O)c1ccc(C2(NC(=O)[C@H]3CCC4CC4N3)CC2)cc1]

The title compound (D101) (20 mg) was prepared according to the general procedure for t-Butyl carbamate (Boc) cleavage starting from (3R)-tert-butyl 3-((1-(4-(methoxycarbonyl)phenyl)cyclopropyl)carbamoyl)-2-azabicyclo[4.1.0]heptane-2-carboxylate (D70) (28 mg).

MS: (ES/+) m/z: 315.2 [MH$^+$] C18H22N2O3 requires 314.16

Description 102 methyl 4-((1S)-1-((3R)-2-azabicyclo[4.1.0]heptane-3-carboxamido)ethyl)benzoate (diastereoisomers mixture) (D102)

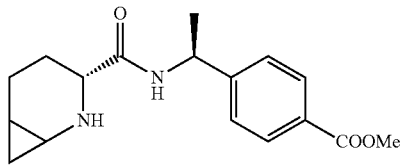 [SMILES: COC(=O)c1ccc([C@H](C)NC(=O)[C@H]2CCC3CC3N2)cc1]

The title compound (D102) (17.5 mg) was prepared according to the general procedure for t-Butyl carbamate (Boc) cleavage starting from (3R)-tert-butyl 3-(((S)-1-(4-(methoxycarbonyl)phenyl)ethyl)carbamoyl)-2-azabicyclo[4.1.0]heptane-2-carboxylate (diastereoisomers mixture) (D71) (46 mg).

MS: (ES/+) m/z: 303.1 [MH$^+$] C17H22N2O3 requires 302.16

$^1$H NMR (400 MHz, CHCl3-d) δ (ppm): 8.13-7.93 (m, 2 H), 7.57-7.33 (m, 2 H), 5.29-5.04 (m, 1 H), 3.92 (s, 3 H), 3.35-3.19 (m, 1 H), 2.41 (m, 1 H), 2.21-0.83 (m, 8 H), 0.77-0.61 (m, 1 H), 0.38 (m, 1 H).

Description 103 methyl 4-((S)-1-((R)-pyrrolidine-2-carboxamido)ethyl)benzoate (D103)

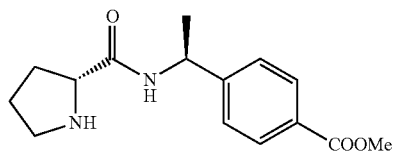

The title compound (D103) (550 mg) was prepared according to the general procedure for t-Butyl carbamate (Boc) cleavage starting from (R)-tert-butyl 2-(((S)-1-(4-(methoxycarbonyl)phenyl)ethyl)carbamoyl) pyrrolidine-1-carboxylate (D72) (815 mg).

MS: (ES/+) m/z: 277.6 [MH$^+$] C15H20N2O3 requires 276.15

Chiral HPLC [Phenomenex Lux Cellulose-1; Mobile phase A: 70% n-hexane (+0.1% DEA), 30% EtOH; DAD: 240 nm]: Peak retention time: 8.65 min.

$^1$H NMR (400 MHz, CHCl3-d) δ (ppm): 8.00 (d, J=7.3 Hz, 2 H), 7.80-7.53 (m, 1H), 7.35 (d, J=8.3 Hz, 2 H), 5.15 (br. s., 1 H), 4.35 (br. s., 1 H), 3.93 (s, 3 H), 3.37 (br. s., 2 H), 2.07 (s, 4 H), 1.50 (s, 12 H).

Description 104 methyl 4-(1-((1R,3R,5R)-2-azabicyclo[3.1.0]hexane-3-carboxamido)cyclopropyl)benzoate (syn diastereoisomer) (D104)

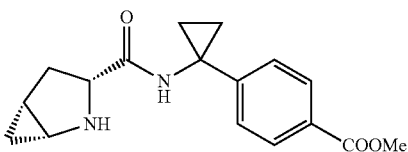 [SMILES: COC(=O)c1ccc(C2(NC(=O)[C@H]3C[C@H]4C[C@H]4N3)CC2)cc1]

The title compound (D104) (1.8 g) was prepared according to the general procedure for t-Butyl carbamate (Boc) cleavage starting from (1R,3R,5R)-tert-butyl 3-((1-(4-(methoxycarbonyl)phenyl)cyclopropyl)carbamoyl)-2-azabicyclo[3.1.0]hexane-2-carboxylate (syn diastereoisomer) (D73a) (2.6 g).

MS: (ES/+) m/z: 301 [MH$^+$] C17H20N2O3 requires 300.15

$^1$H NMR (400 MHz, DMSO-d6) δ (ppm): 8.51 (s, 1 H), 7.88-7.81 (m, 2 H), 7.23 (d, J=8.3 Hz, 2 H), 4.08 (s, 1 H), 3.87-3.78 (m, 4 H), 2.77 (dt, J=2.7, 6.2 Hz, 1 H), 2.15-1.99 (m, 2 H), 1.34-1.23 (m, 3 H), 1.21-1.13 (m, 2 H), 0.47-0.37 (m, 1 H), −0.06 (ddd, J=2.9, 4.3, 5.5 Hz, 1 H)

Description 105 methyl 4-(1-(((1S,3R,5S)-2-azabicyclo[3.1.0]hexane-3-carboxamido)cyclopropyl)benzoate (anti diastereoisomer) (D105)

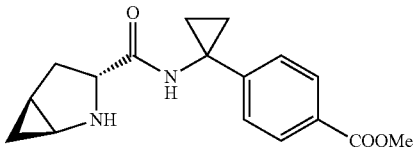 [SMILES: COC(=O)c1ccc(C2(NC(=O)[C@H]3C[C@@H]4C[C@@H]4N3)CC2)cc1]

The title compound (D106) (71.9 mg) was prepared according to the general procedure for t-Butyl carbamate (Boc) cleavage starting from (1 S,3R,5S)-tert-butyl 3-((1-(4-(methoxycarbonyl)phenyl)cyclopropyl)carbamoyl)-2-azabicyclo[3.1.0]hexane-2-carboxylate (anti diastereoisomer) (D73b) (D76) (96 mg)

MS: (ES/+) m/z: 301.3 [MH$^+$] C17H20N2O3 requires 300.15

$^1$H NMR (400 MHz, CHCl3-d) δ (ppm): 8.03 (br. s., 1 H), 7.95 (d, J=8.2 Hz, 2 H), 7.24 (d, J=8.3 Hz, 2 H), 3.91 (s, 3 H), 3.62-3.41 (m, 1 H), 3.01-2.79 (m, J=2.3 Hz, 1 H), 2.44 (dd, J=8.4, 12.7 Hz, 1 H), 2.04-1.90 (m, 1 H), 1.54-1.40 (m, 1 H), 1.40-1.25 (m, 4 H), 0.60-0.34 (m, 2 H).

Description 106 methyl 4-((1S)-1-((3R)-2-azabicyclo[3.1.0]hexane-3-carboxamido)ethyl)benzoate (diastereoisomers mixture) (D106)

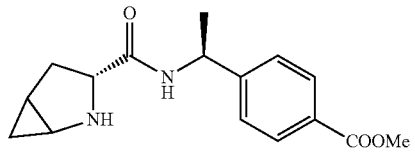 [SMILES: COC(=O)c1ccc([C@H](C)NC(=O)[C@H]2CC3CC3N2)cc1]

The title compounds (D106) (11 mg) was prepared according to the general procedure for t-Butyl carbamate (Boc) cleavage starting from (3R)-tert-butyl 3-(((S)-1-(4-(methoxycarbonyl)phenyl)ethyl)carbamoyl)-2-azabicyclo[3.1.0]hexane-2-carboxylate (diastereoisomers mixture) (D74a) (15 mg)

MS: (ES/+) m/z: 289.3 [MH$^+$] C16H20N2O3 requires 288.15

$^1$H NMR (400 MHz, CHCl3-d) δ (ppm): 8.06 (d, J=7.8 Hz, 1 H), 8.00 (d, J=7.1 Hz, 4 H), 7.93-7.85 (m, 1 H), 7.37 (dd, J=4.2, 7.7 Hz, 4 H), 5.08 (t, J=7.2 Hz, 2 H), 4.11 (d, J=7.2 Hz, 1 H), 3.92 (s, 6 H), 3.64 (s, 1 H), 2.93-2.87 (m, 2 H), 2.44-2.34 (m, 1 H), 2.28 (m, 1 H), 1.99-1.87 (m, 1 H), 1.61-1.35 (m, 9 H), 0.56-0.44 (m, 3 H), 0.05 (br. s., 1 H).

Description 107 methyl 4-((1S)-1-((3R)-2-azabicyclo[3.1.0]hexane-3-carboxamido)ethyl)benzoate (single diastereoisomer) (D107)

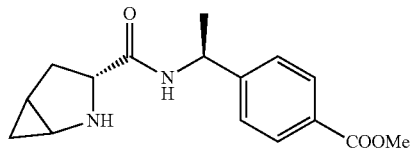 [SMILES: COC(=O)c1ccc([C@H](C)NC(=O)[C@H]2CC3CC3N2)cc1]

The title compounds (D107) (48 mg) was prepared according to the general procedure for t-Butyl carbamate (Boc) cleavage starting from (3R)-tert-butyl 3-(((S)-1-(4-(methoxycarbonyl)phenyl)ethyl)carbamoyl)-2-azabicyclo[3.1.0]hexane-2-carboxylate (single diastereoisomer) (D74b) (65 mg)

MS: (ES/+) m/z: 289.3 [MH$^+$] C16H20N2O3 requires 288.15

$^1$H NMR (400 MHz, CHCl3-d) δ (ppm): 7.99 (d, J=8.1 Hz, 2 H), 7.89 (d, J=7.7 Hz, 1 H), 7.36 (d, J=8.1 Hz, 2 H), 5.07 (t, J=7.3 Hz, 1 H), 3.90 (s, 3 H), 3.60 (t, J=8.7 Hz, 1 H), 2.90-2.80 (m, J=2.5 Hz, 1 H), 2.36 (dd, J=8.3, 12.7 Hz, 1 H), 1.97-1.81 (m, J=4.1, 4.1, 8.3 Hz, 1 H), 1.48 (d, J=7.0 Hz, 3 H), 1.45-1.39 (m, J=7.0 Hz, 1 H), 0.53-0.39 (m, 2 H).

Description 108

(R)-methyl 4-(1-(4,4-dimethylpyrrolidine-2-carboxamido)cyclopropyl)benzoate (D108)

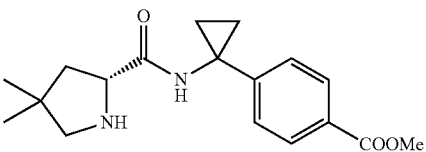 [SMILES: COC(=O)c1ccc(C2(NC(=O)[C@H]3CC(C)(C)CN3)CC2)cc1]

The title compound (D108) (70 mg) was prepared according to the general procedure for t-Butyl carbamate (Boc) cleavage starting from (R)-tert-butyl 2-((1-(4-(methoxycarbonyl)phenyl)cyclopropyl)carbamoyl)-4,4-dimethylpyrrolidine-1-carboxylate (D75) (94 mg).

MS: (ES/+) m/z: 317.3 [MH$^+$] C18H24N2O3 requires 316.18

$^1$H NMR (400 MHz, CHCl3-d) δ (ppm): 8.51 (br. s., 1 H), 7.96 (d, J=8.0 Hz, 2 H), 7.25 (br. d, J=1.0 Hz, 2 H), 4.13-4.00 (m, 1 H), 3.91 (s, 3 H), 2.86 (d, J=10.7 Hz, 1 H), 2.72 (d, J=10.6 Hz, 1 H), 2.22-2.07 (m, 1 H), 1.66 (dd, J=7.9, 12.8 Hz, 1 H), 1.35 (s, 4 H), 1.09 (d, J=8.8 Hz, 6 H).

Description 109 methyl 4-((1S)-1-(azetidine-2-carboxamido)ethyl)benzoate (diastereoisomers mixture) (D109)

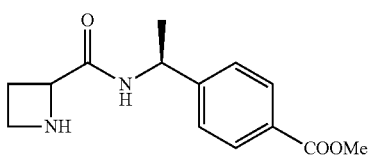 [SMILES: COC(=O)c1ccc([C@H](C)NC(=O)C2CCN2)cc1]

To a solution of methyl 4-((1S)-1-(1-benzylazetidine-2-carboxamido)ethyl)benzoate (D76) (98 mg, 0.278 mmol in EtOH (20 ml) Pd/C 10% (90 mg, 0.083 mmol) and ammonium formate (52 mg, 0.83 mmol) were added and the heterogeneous solution was left stirring at RT for 20 hrs. Further addition of Pd/C 10% (90 mg, 0.083 mmol) and ammonium formate (52 mg, 0.83 mmol) was done and the resulting mixture was stirred at RT for 5 hrs. Catalyst was filtered off and the solvent evaporated to afford the title compound (D109) (60 mg).

MS: (ES/+) m/z: 263.2 [MH$^+$] C14H18N2O3 requires 262.13

¹H NMR (400 MHz, CHCl3-d) δ (ppm): 8.24 (s, 1 H), 8.09-7.96 (m, 2 H), 7.46-7.33 (m, 2 H), 5.39-5.22 (m, 1 H), 5.22-5.05 (m, 1 H), 3.93 (d, J=2.8 Hz, 3 H), 3.89-3.70 (m, 1 H), 2.78 (dd, J=5.9, 9.2 Hz, 1 H), 2.65-2.34 (m, 1 H), 1.51 (q, J=6.8 Hz, 3 H), 1.43-1.34 (m, 1 H).

General Procedure for Esters Hydrolysis

Method A

To a solution of the selected ester (1 eq) in dioxane/water (1:1), LiOH H₂O (1.2-4 eq) was added and the resulting mixture was stirred at RT. Organic solvent was evaporated off and the aqueous solution was washed with DCM and evaporated in vacuo. The residue was loaded on a C18 cartridge eluting with H₂O/MeOH 9/1 then MeOH. Collected methanolic phases were evaporated off affording the title compound as lithium salt.

Method B

To a solution of the selected ester (1 eq) in dioxane/water (1:1), LiOH H₂O (1.2-4 eq) was added and the resulting mixture was stirred at RT. Dioxane was evaporated off and the aqueous solution was loaded onto a reverse phase Biotage SNAP-C18 column eluting with a mixture H₂O/MeCN containing 0.1% of CH₃CO₂H from 90/10 to 80/20. Collected fractions after solvent evaporation afforded the title compound Method C To a solution of the selected ester (1 eq) in dioxane/water (1:1), LiOH H₂O (1.5 eq) was added and the resulting mixture was stirred at RT for 18 hrs or heated under microwave irradiation. Organic solvent was evaporated off and the aqueous solution was acidified with acetic acid and loaded onto a reverse phase Biotage SNAP-C18 column eluting first with H₂O then MeOH. The methanolic phase was evaporated in vacuo to afford the title compound.

Method D

To a solution of the selected ester (1 eq) in dioxane/water (1:1), LiOH H₂O (1.5-4 eq) was added and the resulting mixture was stirred at RT or heated under microwave irradiation. Organic solvent was evaporated off and the aqueous solution was washed with DCM prior addition of acetic acid until the solution reached the value of pH≈4. The aqueous solution was extracted with EtOAc. The organic phases were collected and washed with NaCl sat sol, dried over Na₂SO₄ and evaporated to afford the title compound.

Method E

To a solution of the selected ester (1 eq) in dioxane/water (1:1), LiOH H₂O (1.5-4 eq) was added and the resulting mixture was stirred at RT or heated under microwave irradiation. Organic solvent was evaporated off and the aqueous solution was washed with DCM prior addition of acetic acid until the solution reached the value of pH≈4. The dolid precipitated was extracted with EtOAc. The organic phases were collected, dried over Na₂SO₄ and evaporated in vacuo to afford the title compound.

Description 110

3-(4-(trifluoromethyl)benzyl)-3-azabicyclo[3.1.0] hexane-2-carboxylic acid (syn relative stereochemistry) (D110)

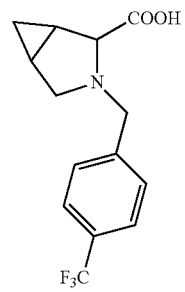 [SMILES: O=C(O)C1C2CC2CN1Cc1ccc(C(F)(F)F)cc1]

The title compound (D110) (110 mg) was prepared according to the general procedure for esters hydrolysis (Method C) starting from methyl 3-(4-(trifluoromethyl)benzyl)-3-azabicyclo[3.1.0]hexane-2-carboxylate (D77) (180 mg).

(LiOH: 1.5 eq; reaction temperature: 150° C. under microwave irradiation, reaction time: 5 min).

MS: (ES/+) m/z: 286.3 [MH⁺] C14H14F3NO2 requires 285.10

¹H NMR (400 MHz, METHANOL-d4) δ (ppm): 7.77-7.72 (m, 2 H), 7.72-7.66 (m, 2 H), 4.42 (d, J=1.0 Hz, 1 H), 4.17 (d, J=1.0 Hz, 1 H), 4.05 (d, J=4.0 Hz, 1 H), 3.38 (br. s., 2 H), 2.14-2.04 (m, 1 H), 1.81-1.70 (m, 1 H), 0.96-0.84 (m, 1 H), 0.73-0.59 (m, 1 H).

Description 111

2-(4-(trifluoromethyl)benzyl)-2-azabicyclo[2.2.2] octane-3-carboxylic acid (D111)

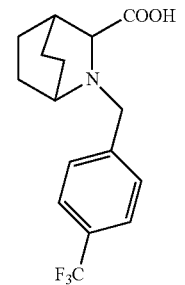 [SMILES: O=C(O)C1C2CCC(CC2)N1Cc1ccc(C(F)(F)F)cc1]

The title compound (D111) (45 mg) was prepared according to the general procedure for esters hydrolysis (Method C) starting from ethyl 2-(4-(trifluoromethyl)benzyl)-2-azabicyclo[2.2.2]octane-3-carboxylate (D78) (420 mg).

(LiOH: 2 eq; reaction time: 18 hrs; RT).

MS: (ES/+) m/z: 314.3 [MH⁺] C16H18F3NO2 requires 313.13

¹H NMR (400 MHz, MeOH-d4) δ (ppm): 7.85-7.79 (m, 2 H), 7.77-7.72 (m, 2 H), 4.48-4.36 (m, 2 H), 3.56-3.47 (m, 2H), 2.41-2.28 (m, 2 H), 2.19-2.03 (m, 1 H), 1.98-1.88 (m, 2 H), 1.88-1.77 (m, 2 H), 1.71-1.56 (m, 2 H).

Description 112 lithium (R)-2-methyl-1-(4- trifluoromethyl)benzyl) piperidine-2-carboxylate (D112)

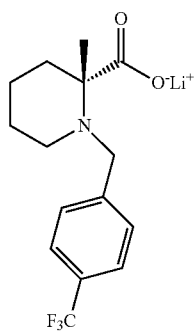

The title compound (D112) (10 mg) was prepared according to the general procedure for esters hydrolysis (Method A) starting from (R)-4-(trifluoromethyl)benzyl 2-methyl-1-(4-(trifluoromethyl)benzyl)piperidine-2-carboxylate (D79) (70 mg). (LiOH: 3 eq; Reaction time: 48 hrs; RT then 140° C. under microwave irradiation for 2 hrs).

MS: (ES/+) m/z: 302.2 [M−Li+2H$^+$] C15H17F3LiNO2 requires 307.14

Description 113 lithium (R)-2-methyl-1-(4-(trifluoromethyl)benzyl) pyrrolidine-2-carboxylate (D113)

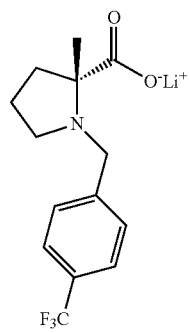

The title compound (D113) (42 mg) was prepared according to the general procedure for esters hydrolysis (Method A) starting from (R)-methyl 2-methyl-1-(4-(trifluoromethyl) benzyl)pyrrolidine-2-carboxylate (D80) (50 mg). (LiOH: 3 eq; Reaction time: 18 hrs; RT)

MS: (ES/+) m/z: 288.2 [M−Li+2H$^+$] C14H15F3LiNO2 requires 293.12

$^1$H NMR (400 MHz, MeOH-d4) δ (ppm): 7.72 (s, 4 H), 4.35 (d, J=12.7 Hz, 1 H), 4.02 (d, J=12.7 Hz, 1 H), 3.25-2.96 (m, 2 H), 2.31 (d, J=10.3 Hz, 1 H), 2.13-1.80 (m, 3 H), 1.54 (s, 3 H)

Description 114 lithium (2R,4S)-4-fluoro-1-(3-(trifluoromethyl)benzyl)pyrrolidine-2-carboxylate (D114)

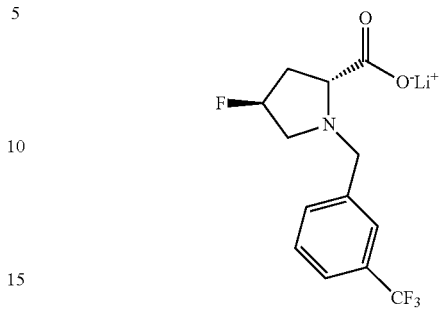

The title compound (D114) (60 mg) was prepared according to the general procedure for esters hydrolysis (Method A) starting (2R,4S)-3-(trifluoromethyl)benzyl 4-fluoro-1-(4-(trifluoromethyl)benzyl)pyrrolidine-2-carboxylate (D82) (110 mg). (LiOH: 2 eq; Reaction time: 18 hrs)

MS: (ES/+) m/z: 292.2 [M−Li+2H$^+$] C13H12F4LiNO2 requires 297.10

Description 115 lithium (R)-4,4-difluoro-1-(3-(trifluoromethyl)benzyl)pyrrolidine-2-carboxylate (D115)

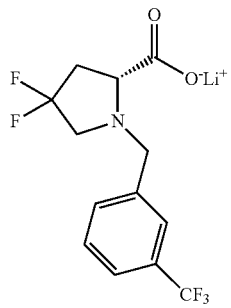

The title compound (D115) (51 mg) was prepared according to the general procedure for esters hydrolysis (Method A) starting (R)-4-(trifluoromethyl)benzyl 4,4-difluoro-1-(4-(trifluoromethyl)benzyl)pyrrolidine-2-carboxylate (D84) (81 mg). Reaction time: 18 hrs; RT.

MS: (ES/+) m/z: 310.1 [M−Li+2H$^+$] C13H11F5LiNO2 requires 315.09

Description 116

4-((1S)-1-(1-(4-(trifluoromethyl)benzyl)piperidine-2-carboxamido)ethyl)benzoate (diastereoisomers mixture) (D116)

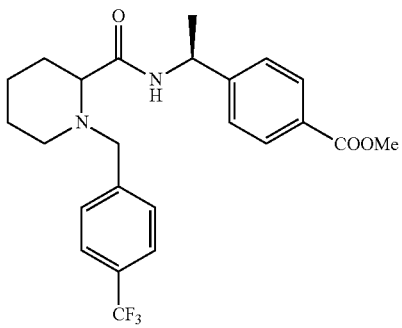 [SMILES: COC(=O)c1ccc([C@H](C)NC(=O)C2CCCCN2Cc2ccc(C(F)(F)F)cc2)cc1]

To a mixture of methyl 4-((1S)-1-(piperidine-2-carboxamido)ethyl) (diastereoisomers mixture) (D85) (50.0 mg, 0,172 mmol) and 4-(trifluoromethyl)benzaldehyde (0,028 ml, 0,207 mmol) in DCE (1.7 ml), catalytic AcOH was added and the mixture stirred 1 h at RT. NaBH(OAc)₃ (43.8 mg, 0,207 mmol) was added and the resulting mixture stirred at RT overnight. Solvents were evaporated in vacuo and the residue was purified by SPE-Si (2 g) eluting with a mixture DCM/MeOH 98/2. Collected fractions after solvent evaporation afforded the title compound (D116) (75 mg).

MS: (ES/+) m/z: 449 [MH⁺] C16H22N2O3 requires 290.16

Chiral HPLC [Phenomenex Lux Cellulose-1; Mobile phase A: 90% n-hexane (+0.1% DEA), B: 10% IPA; DAD: 237 nm]: Peak 1 retention time: 16.08 min, peak 2 retention time: 17.5 min.

¹H NMR (400 MHz, CHCl3-d) δ (ppm): 8.04 (d, 2 H) 7.84 (d, 2 H) 7.63 (d, 2 H) 7.50 (d, 2 H) 7.45 (d, 2 H) 7.39 (s, 2 H) 7.25 (d, 2 H) 7.20 (s, 2 H) 7.00 (d, 1 H) 6.95 (d, 1 H) 5.13-5.25 (m, 2 H) 3.88-4.01 (m, 7 H) 3.69 (d, 1 H) 3.32 (d, 1 H) 3.19 (d, 1 H) 2.81-2.95 (m, 4 H) 1.95-2.14 (m, 4 H) 1.78 (br. s., 2 H) 1.47-1.67 (m, 9 H) 1.43 (d, 3 H) 1.27-1.40 (m, 2 H).

Description 117 methyl 4-((S)-1-((R)-1-(4-fluorobenzyl)piperidine-2-carboxamido)ethyl)benzoate (D117)

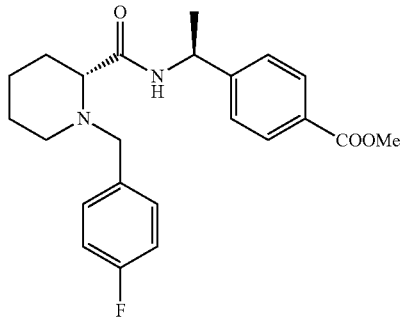 [SMILES: COC(=O)c1ccc([C@H](C)NC(=O)[C@H]2CCCCN2Cc2ccc(F)cc2)cc1]

The title compound (D117) (20 mg) was prepared according to the general procedure for substituted benzyl amines preparation starting from methyl 4-((S)-1-((R)-piperidine-2-carboxamido)ethyl)benzoate (D86) (50 mg) and 4-fluorobenzyl bromide (0.043 ml, 0.34 mmol). (Na₂CO₃: 2.5 eq; reaction time: 4 hrs; 60° C.)

MS: (ES/+) m/z: 399.3 [MH⁺] C23H27FN2O3 requires 398.20

Chiral HPLC [Phenomenex Lux Cellulose-1; Mobile phase A: 80% n-hexane (+0.1% DEA), B: 20% EtOH; DAD: 237 nm]: Peak retention time: 8.98 min.

Description 118 methyl 4-((S)-1-((R)-1-(4-(trifluoromethyl)benzyl)piperidine-2-carboxamido)ethyl)benzoate (D118)

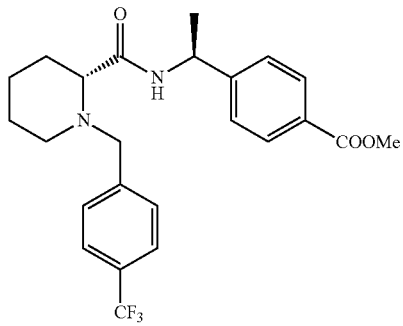 [SMILES: COC(=O)c1ccc([C@H](C)NC(=O)[C@H]2CCCCN2Cc2ccc(C(F)(F)F)cc2)cc1]

The title compound (D118) (24 mg) was prepared according to the general procedure for substituted benzyl amines preparation starting from methyl 4-((S)-1-((R)-piperidine-2-carboxamido)ethyl)benzoate (D86) (40 mg) and 4-(trifluoromethyl)benzylbromide (0.032 ml). (Na₂CO₃: 2.5 eq; reaction time: 4 hrs; 60° C.)

MS: (ES/+) m/z: 449.3 [MH⁺] C24H27F3N2O3 requires 448.20

Description 119

(R)-methyl 4-(1-(1-(4-(trifluoromethyl)benzyl)piperidine-2-carboxamido)cyclopropyl)benzoate (D119)

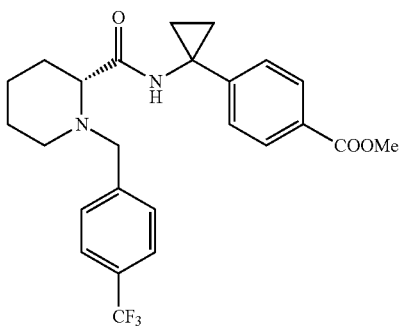 [SMILES: COC(=O)c1ccc(C2(NC(=O)[C@H]3CCCCN3Cc3ccc(C(F)(F)F)cc3)CC2)cc1]

The title compound (D119) (74 mg) was prepared according to the general procedure for substituted benzyl amines preparation starting from (R)-methyl 4-(1-(piperidine-2-carboxamido)cyclopropyl)benzoate (D87) (50 mg) and 4-(trifluoromethyl)benzylbromide (0.039 ml). (Na₂CO₃: 2.5 eq; reaction time: 6 hrs; 60° C.)

MS: (ES/+) m/z: 461.3 [MH⁺] C25H27F3N2O3 requires 460.20

¹H NMR (400 MHz, CHCl3-d) δ (ppm): 7.92 (d, J=8.1 Hz, 2 H), 7.62 (d, J=7.8 Hz, 2 H), 7.48-7.34 (m, 3 H), 7.25 (d, J=8.2 Hz, 2 H), 3.90 (s, 3 H), 3.79 (d, J. 14.4 Hz, 1 H), 3.27 (d, J=14.5 Hz, 1 H), 2.97-2.82 (m, 2 H), 2.16-1.97 (m, 2 H), 1.80 (d, J=12.7 Hz, 1 H), 1.64 (t, J=12.3 Hz, 2 H), 1.49 (d, J=12.2 Hz, 1 H), 1.43-1.26 (m, 4H), 1.13 (t, J=7.2 Hz, 1H)

Description 120

(R)-methyl 4-(1-(1-(4-chlorobenzyl)piperidine-2-carboxamido)cyclopropyl)benzoate (D120)

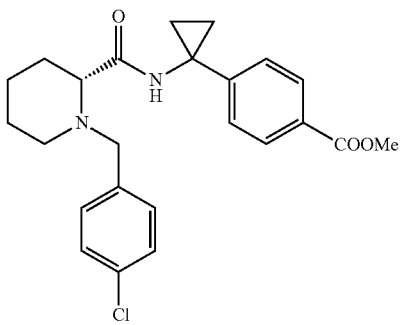 [SMILES: COC(=O)c1ccc(C2(NC(=O)[C@H]3CCCCN3Cc3ccc(Cl)cc3)CC2)cc1]

The title compound (D120) (45 mg) was prepared according to the general procedure for substituted benzyl amines preparation starting from (R)-methyl 4-(1-(piperidine-2-carboxamido)cyclopropyl)benzoate (D87) (34 mg) and 4-(Chloro)benzylbromide (35 mg). (Na₂CO₃: 4 eq; reaction time: 18 hrs; 68° C.)

MS: (ES/+) m/z: 427.3[MH⁺] C24H27ClN2O3 requires 426.17

¹H NMR (400 MHz, CHCl3-d) δ (ppm): 7.93 (d, J=8.1 Hz, 2 H), 7.40 (br. s., 1 H), 7.33 (d, J=8.1 Hz, 2 H), 7.27-7.17 (m, 4 H), 3.91 (s, 3 H), 3.72 (d, J=14.1 Hz, 1 H), 3.18 (d, J=14.1 Hz, 1 H), 2.94-2.82 (m, 2 H), 2.13-1.96 (m, 2H), 1.85-1.73 (m, 1 H), 1.63 (br. s., 2 H), 1.50-1.44 (m, 1 H), 1.43-1.27 (m, 4 H), 1.15 (br. s., 1 H).

Description 121

(R)-methyl 4-(1-(1-(4-cyanobenzyl)piperidine-2-carboxamido)cyclopropyl)benzoate (D121)

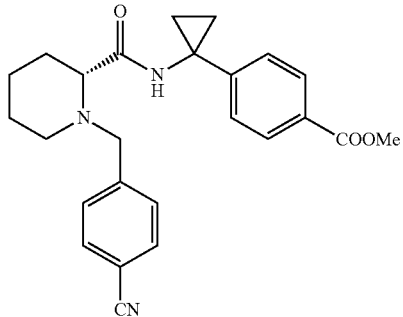 [SMILES: COC(=O)c1ccc(C2(NC(=O)[C@H]3CCCCN3Cc3ccc(C#N)cc3)CC2)cc1]

The title compound (D121) (35 mg) was prepared according to the general procedure for substituted benzyl amines preparation starting from (R)-methyl 4-(1-(piperidine-2-carboxamido)cyclopropyl)benzoate (D87) (34 mg) and 4-Cyanobenzylbromide (33 mg). (Na₂CO₃: 4 eq; reaction time: 18 hrs; 68° C.)

MS: (ES/+) m/z: 418.3 [MH⁺] C25H27N3O3 requires 417.21

Descriptions 122 a and 122b methyl 4-(1-(6-(4-(trifluoromethyl)benzyl)-6-azaspiro[2.5]octane-5-carboxamido)cyclopropyl)benzoate (enantiomer 1) (D122a) and methyl 4-(1-(6-(4-(trifluoromethyl)benzyl)-6-azaspiro[2.5]octane-5-carboxamido)cyclopropyl)benzoate (enantiomer 2) (D122b)

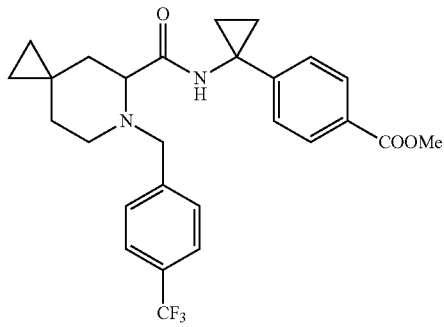

To a solution of methyl 4-(1-(6-azaspiro[2.5]octane-5-carboxamido)cyclopropyl)benzoate (racemic mixture) (D88) (230 mg, 0.70 mmol) in dry MeCN (10 ml), Na₂CO₃ (223 mg, 2.1 mmol) and 4-(trifluoromethyl)-benzylbromide (200 mg, 0.84 mmol) were added in sequence. The mixture was heated at 68° C. for 18 hrs. The solid was filtered off, MeCN was evaporated and the residue was purified by SPE-Si cartridge (10 g) eluting with a mixture DCM/EtOAc from 100/0 to 90/10. Collected fractions after solvent evaporation afforded 250 mg of racemic mixture which was submitted for chiral HPLC separation (Preparative chromatographic conditions: Column: DAICEL AD-H; Mobile phase: n-hexane/EtOH/DEA 60%/40%/0.1% v/v; Flow rate 10 ml/min; DAD: 246 nm). Collected fractions, after solvent evaporation of separated fractions afforded the two enantiomer compounds (D122a) (83.1 mg) and (D122b) (98.9 mg).

(D122a) (enantiomer 1) retention time: 8.15 min
¹H NMR (400 MHz, CHCl3-d) δ (ppm): 7.92 (d, J=8.1 Hz, 2 H), 7.63 (d, J=7.8 Hz, 2 H), 7.47-7.37 (m, 3 H), 7.25 (d, J=8.2 Hz, 2 H), 3.90 (s, 3 H), 3.84 (d, J=14.4 Hz, 1 H), 3.35 (d, J=14.4 Hz, 1 H), 3.09-3.00 (m, 1 H), 2.88 (br. s., 1 H), 2.26 (br. s., 1 H), 2.02 (br. s., 1 H), 1.89-1.78 (m, 1 H), 1.45-1.29 (m, 4 H), 1.13 (br. s., 1 H), 0.99 (br. s., 1 H), 0.49-0.35 (m, 3 H), 0.30 (d, J=6.6 Hz, 1 H).

(D122b) (enantiomer 2) retention time: 11.12 min
¹H NMR (400 MHz, CHCl3-d) δ (ppm): 7.92 (d, J=8.1 Hz, 2 H), 7.62 (d, J=7.8 Hz, 2 H), 7.48-7.39 (m, 3 H), 7.25 (d, J=8.2 Hz, 2 H), 3.90 (s, 3 H), 3.84 (d, J=14.4 Hz, 1 H), 3.35 (d, J=14.4 Hz, 1 H), 3.05 (dd, J=3.1, 10.1 Hz, 1 H), 2.89 (d, J=11.5 Hz, 1 H), 2.26 (br. s., 1 H), 2.02 (t, J=11.7 Hz, 1 H), 1.83 (br. s., 1 H), 1.44-1.27 (m, 4 H), 1.13 (t, J=7.0 Hz, 1 H), 0.97 (d, J=13.0 Hz, 1 H), 0.49-0.35 (m, 3 H), 0.30 (d, J=6.7 Hz, 1 H).

Description 123 methyl 4-(1-(6-(4-(trifluoromethyl)benzyl)-6-azaspiro[2.5]octane-5-carboxamido)cyclopropyl)benzoate (single unknown enantiomer) (D123)

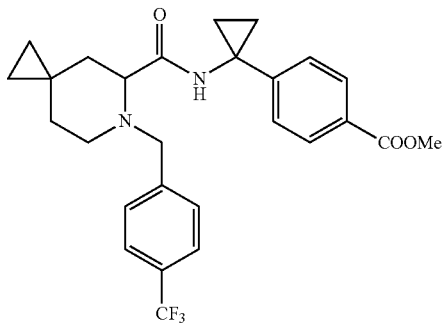 [SMILES: COC(=O)c1ccc(C2(NC(=O)C3CC4(CCN3Cc3ccc(C(F)(F)F)cc3)CC4)CC2)cc1]

To a solution of methyl 4-(1-(6-azaspiro[2.5]octane-5-carboxamido)cyclopropyl)benzoate 2,2,2-trifluoroacetate (D89) (27 g, 61.03 mmol) in dry MeCN (900 ml) Cs₂CO₃ (39.7 g, 122.05 mmol) and a solution of 4-(trifluoromethyl)-benzylbromide (14.6 g, 61.03 mmol) in MeCN (50 ml) were added in sequence. The mixture was stirred at RT for 18 hrs. The solid was filtered off and solvents were evaporated. The residue was ri-dissolved in DCM (200 ml) and washed with H₂O (3×100 ml) and NaCl sat. sol (50 ml). The organic phases were dried over Na₂SO₄ and evaporated to afford a white solid, which was triturated in cyclohexane to afford the title compound (D123) (19.7 g).

MS: (ES/+) m/z: 488.2 [MH⁺] C27H29F3N2O3 requires 486.21

¹H NMR (400 MHz, DMSO-d6) δ (ppm): 8.79-8.69 (m, 1 H), 7.87-7.76 (m, 2 H), 7.68 (s, 2 H), 7.64 (s, 2 H), 7.28-7.17 (m, 2 H), 3.89-3.71 (m, 4 H), 3.28-3.22 (m, 1 H), 2.98-2.88 (m, 1 H), 2.79-2.69 (m, 1 H), 2.16-1.99 (m, 2 H), 1.85-1.71 (m, 1 H), 1.35-1.09 (m, 5 H), 0.92-0.83 (m, 1 H), 0.43-0.20 (m, 4 H).

Description 124 methyl 4-(1-(6-(((6-(trifluoromethyl)pyridin-3-yl)methyl)-6-azaspiro[2.5]octane-5-carboxamido)cyclopropyl)benzoate (single unknown enantiomer) (D124)

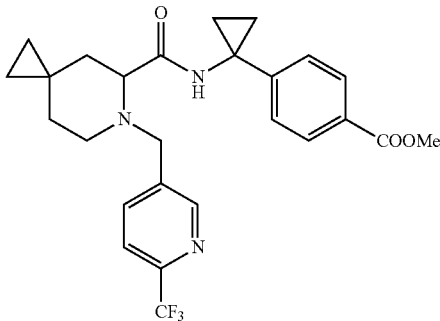 [SMILES: COC(=O)c1ccc(C2(NC(=O)C3CC4(CCN3Cc3ccc(C(F)(F)F)nc3)CC4)CC2)cc1]

The title compound (D124) (47 mg) was prepared according to the general procedure for substituted benzyl amines preparation starting from methyl 4-(1-(6-(4-(trifluoromethyl)benzyl)-6-azaspiro[2.5]octane-5-carboxamido)cyclopropyl)benzoate (D90) (50 mg) and 3-chloromethyl-6-(trifluoromethyl)piridine (38 mg). ($Cs_2CO_3$: 1.3 eq; reaction time: 18 hrs; RT)

MS: (ES/+) m/z: 488.2 [$MH^+$] $C_{26}H_{28}F_3N_3O_3$ requires 487.21

¹H NMR (400 MHz, CHCl3-d) δ (ppm): 8.68 (s, 1 H), 7.91 (d, J=8.1 Hz, 2 H), 7.77 (d, J=7.8 Hz, 1 H), 7.67 (d, J=7.9 Hz, 1 H), 7.33 (br. s., 1 H), 7.29-7.24 (m, 2 H), 3.89 (s, 3 H), 3.84 (d, J=14.5 Hz, 1 H), 3.38 (d, J=14.4 Hz, 1 H), 3.05 (dd, J=2.8, 10.0 Hz, 1 H), 2.84 (d, J=11.4 Hz, 1 H), 2.26 (t, J=10.5 Hz, 1 H), 2.05-1.95 (m, 1 H), 1.81 (t, J=10.9 Hz, 1 H), 1.45-1.24 (m, 4 H), 1.22-1.13 (m, 1 H), 0.97 (d, J=13.1 Hz, 1 H), 0.51-0.33 (m, 3 H), 0.30 (d, J=5.1 Hz, 1H).

Description 125 methyl 4-(1-(6-(3-(trifluoromethyl)benzyl)-6-azaspiro[2.5]octane-5-carboxamido)cyclopropyl)benzoate (single unknown enantiomer) (D125)

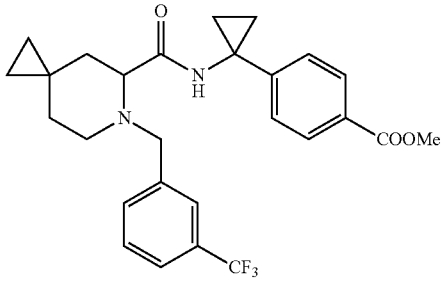 [SMILES: COC(=O)c1ccc(C2(NC(=O)C3CC4(CCN3Cc3cccc(C(F)(F)F)c3)CC4)CC2)cc1]

The title compound (D125) (60.7 mg) was prepared according to the general procedure for substituted benzyl amines preparation starting from methyl 4-(1-(6-azaspiro[2.5]octane-5-carboxamido)cyclopropyl)benzoate 2,2,2-trifluoroacetate (single unknown enantiomer) (D90) (50 mg, 0.11 mmol) and 3-(Trifluoromethyl)benzyl bromide (0.020 ml, 0.12 mmol). ($Cs_2CO_3$:2 eq; reaction time: 4 hrs; reaction temperature: RT.

MS: (ES/+) m/z: 487.6 [$MH^+$] $C_{27}H_{29}F_3N_2O_3$ requires 486.21

¹H NMR (400 MHz, DMSO-d6) δ (ppm): 8.88-8.70 (m, 1 H), 7.86-7.78 (m, 2 H), 7.77-7.68 (m, 2 H), 7.65-7.56 (m, 2 H), 7.29-7.19 (m, 2 H), 3.82 (s, 3 H), 3.81-3.75 (m, 1 H), 3.29-3.24 (m, 1 H), 2.96-2.88 (m, 1 H), 2.79-2.70 (m, 1 H), 2.18-1.97 (m, 2 H), 1.82-1.69 (m, 1 H), 1.33-1.22 (m, 2 H), 1.22-1.08 (m, 3 H), 0.94-0.84 (m, 1 H), 0.44-0.19 (m, 4 H).

Description 126 methyl 4-((1S)-1-(6-(4-fluorobenzyl)-6-azaspiro[2.5]octane-5-carboxamido)ethyl)benzoate (diastereoisomers mixture) (D126)

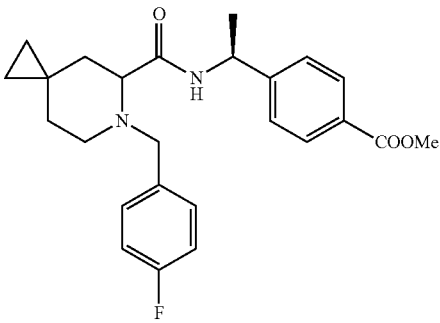 [SMILES: COC(=O)c1ccc([C@H](C)NC(=O)C2CC3(CCN2Cc2ccc(F)cc2)CC3)cc1]

The title compound (D126) (30 mg) was prepared according to the general procedure for substituted benzyl amines preparation starting from methyl 4-((1S)-1-(6-azaspiro[2.5]octane-5-carboxamido)ethyl)benzoate (D91) (60 mg) and 4-Fluorobenzylbromide (0.074 ml). ($Na_2CO_3$: 2.5 eq; reaction time: 4 hrs; 60° C.)

MS: (ES/+) m/z: 425.3 [$MH^+$] $C_{25}H_{29}FN_2O_3$ requires 424.22

Chiral HPLC [Phenomenex Lux Cellulose-2; Mobile phase A: 80% n-hexane (+0.1% DEA), B: 20% IPA; DAD: 237 nm]: Peak 1 retention time 19.73 min, peak 2 retention time 21.35 min.

Descriptions 127 a and 127b 4-((1S)-1-(6-(4-fluorobenzyl)-6-azaspiro[2.5]octane-5-carboxamido)ethyl)benzoic acid (diastereoisomer 1) (D127a) and 4-((1S)-1-(6-(4-fluorobenzyl)-6-azaspiro[2.5]octane-5-carboxamido)ethyl)benzoic acid (diastereoisomer 2) (D127b)

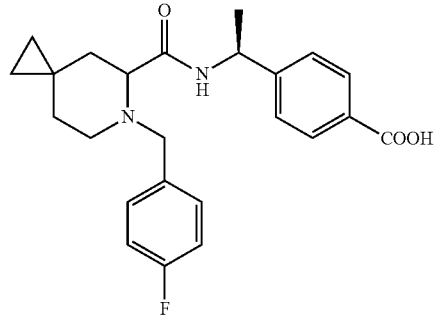 [SMILES: C[C@H](NC(=O)C1CC2(CCN1Cc1ccc(F)cc1)CC2)c1ccc(C(=O)O)cc1]

To a solution of methyl 4-((1S)-1-(6-(4-fluorobenzyl)-6-azaspiro[2.5]octane-5-carboxamido)ethyl)benzoate (D126) (80 mg, 0.19 mmol) in a mixture of H$_2$O/Dioxane (½ ml) LiOH H$_2$O (11.8 mg, 0.28 mmol) were added and the resulting mixture was stirred for 8 hrs before evaporating off the dioxane. The aqueous solution was loaded on a C18 column (10 g). Collected methanolic fractions after solvent evaporation afforded of 80 mg of diastereoisomers mixture which was submitted for chiral HPLC separation (Preparative chromatographic conditions: Column: Phenomenex Lux-1; Mobile phase: n-hexane/EtOH/TFA 65%/35%/0.5% v/v; Flow rate 10 ml/min; DAD: 235 nm). Collected fractions, after solvent evaporation afforded two separated peaks, each one of them was evaporated in vacuo, redissolved in H$_2$O/MeOH (5/1 ml), basified to pH~8 with NaHCO$_3$ and loaded on a SPE-C18 column (10 g). The methanolic phases were evaporated and the resulting residues were filtered on SPE-Si column (1 g) eluting with DCM/MeOH 90/10. Collected fractions after solvent evaporation of the separated fractions afforded the two diastereoisomers (D127a) (23 mg) and (D127b) (13 mg).

(D127a) (diastereoisomer 1): retention time: 6.7 min
MS: (ES/+) m/z: 411.3 [MH$^+$] C24H27FN2O3 requires 410.20
$^1$H NMR (400 MHz, MeOH-d4) δ (ppm): 7.99 (d, J=8.0 Hz, 2 H), 7.46 (d, J=8.0 Hz, 2 H), 7.40-7.31 (m, 2 H), 7.05 (t, J=8.5 Hz, 2 H), 5.16-5.05 (m, 1 H), 3.87 (d, J=13.1 Hz, 1 H), 3.37 (m, 1 H), 3.16-3.07 (m, 1 H), 3.01-2.91 (m, 1 H), 2.40-2.28 (m, 1 H), 2.22-2.09 (m, 1 H), 2.03-1.90 (m, 1 H), 1.49 (d, J=7.0 Hz, 3 H), 1.19-1.13 (m, 1 H), 0.97-0.87 (m, 1 H), 0.39 (d, J=5.1 Hz, 4 H).

(D127b) (diastereoisomer 2): retention time 14.42 min
MS: (ES/+) m/z: 411.3 [MH$^+$] C24H27FN2O3 requires 410.20
$^1$H NMR (400 MHz, MeOH-d4) δ (ppm): 7.92 (d, J=8.0 Hz, 2H), 7.48-7.28 (m, 4H), 7.05 (t, J=8.5 Hz, 2 H), 5.15 (m, 1 H), 3.86 (d, J=13.2 Hz, 1 H), 3.37 (1 H, under solvent), 3.20-3.07 (d, J=8.6 Hz, 1H), 2.96 (d, J=11.4 Hz, 1 H), 2.33 (m, 1 H), 2.11 (m, 1 H), 1.96 (br. s., 1 H), 1.53 (d, J=6.9 Hz, 3 H), 1.20-1.10 (m, 1 H), 0.91 (d, J=12.8 Hz, 1 H), 0.48-0.24 (m, 4 H).

Descriptions 128

4-((1S)-1-(6-azaspiro[2.5]octane-5-carboxamido)ethyl)benzoic acid (single unknown diastereoisomer) (D128)

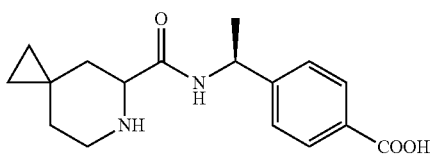 [SMILES: C[C@H](NC(=O)C1CC2(CCN1)CC2)c1ccc(C(=O)O)cc1]

4-((1S)-1-(6-(4-fluorobenzyl)-6-azaspiro[2.5]octane-5-carboxamido)ethyl)benzoic acid (single unknown enantiomer) (D127a) (14 mg, 0.034 mmol) was dissolved in EtOH (3 ml) prior addition of Pd/C 10% (18 mg, 0.017 mmol) and ammonium formate (6.5 mg, 0.102 mmol). The heterogeneous solution was left stirring at RT for 24 hrs then catalyst was filtered off and the solvent evaporated in vacuo to afford the title compound (D128) (10 mg).

$^1$H NMR (400 MHz, MeOH-d4) δ (ppm): 7.87 (d, J=7.9 Hz, 2 H), 7.36 (d, J=7.9 Hz, 2 H), 5.12-4.99 (m, 1 H), 4.00-3.89 (m, 1 H), 3.45-3.35 (m, 1 H), 3.26-3.04 (m, 1 H), 2.26-2.08 (m, 2 H), 1.55-1.40 (m, J=6.7 Hz, 4 H), 1.32 (d, J=6.8 Hz, 1 H), 1.16-1.04 (m, 1 H), 0.69-0.22 (m, 4 H).

Descriptions 129

4-(trifluoromethyl)benzyl 4-((1S)-1-(6-(4-(trifluoromethyl)benzyl)-6-azaspiro[2.5]octane-5-carboxamido)ethyl)benzoate (single unknown diastereoisomer) (D129)

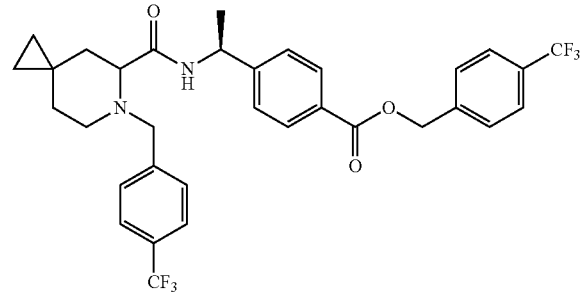 [SMILES: C[C@H](NC(=O)C1CC2(CCN1Cc1ccc(C(F)(F)F)cc1)CC2)c1ccc(C(=O)OCc2ccc(C(F)(F)F)cc2)cc1]

To a solution of 4-((1S)-1-(6-azaspiro[2.5]octane-5-carboxamido)ethyl)benzoic acid (D128) (10 mg, 33.1 µmol) in dry MeCN, Na$_2$CO$_3$ (17.5 mg, 165.4 µmol) and 4-(trifluoromethyl)-benzylbromide (24 mg, 99.2 µmol) were added in sequence. The mixture was heated at 68° C. for 18 hrs. The solid was filtered off, MeCN was evaporated and the residue was purified by Biotage SNAP-Si column (10 g) eluting with a mixture DCM/EtOAc from 100/0 to 80/20. Collected fractions after solvent evaporation afforded the title compounds (D129) (14.8 mg).

$^1$H NMR (400 MHz, CHCl3-d) δ (ppm): 8.08 (d, J=8.0 Hz, 2 H), 7.66 (dd, J=8.0, 14.4 Hz, 4 H), 7.58 (d, J=7.9 Hz, 2 H), 7.47 (d, J=7.8 Hz, 2 H), 7.39 (d, J=7.9 Hz, 2 H), 7.05 (d, J=7.7 Hz, 1 H), 5.23-5.11 (m, 1 H), 4.00 (d, J=14.4 Hz, 1 H), 3.37 (d, J=14.4 Hz, 1 H), 3.06 (dd, J=3.1, 10.6 Hz, 1H), 2.89 (d, J=11.4 Hz, 1 H), 2.31-2.18 (m, 1 H), 2.01-1.80 (m, 2 H), 1.59-1.54 (m, 1 H), 1.43 (d, J=6.8 Hz, 3 H), 0.90 (d, J=12.9 Hz, 1 H), 0.44-0.33 (m, 3 H), 0.28 (d, J=6.8 Hz, 1 H).

Description 130 methyl 4-((1S)-1-(5-methyl-6-(4-(trifluoromethyl)benzyl)-6-azaspiro[2.5]octane-5-carboxamido)ethyl)benzoate (diastereoisomers mixture) (D130)

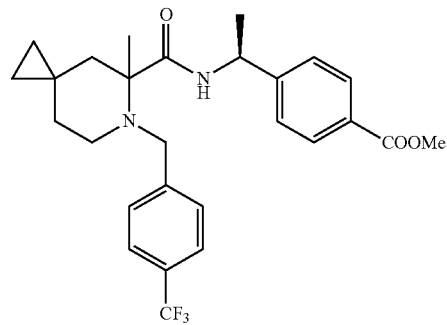 [SMILES: COC(=O)c1ccc([C@H](C)NC(=O)C2(C)CC3(CCN2Cc2ccc(C(F)(F)F)cc2)CC3)cc1]

The title compound (D130) (19 mg) was prepared according to the general procedure for substituted benzyl amines preparation starting from methyl 4-((1S)-1-(5-methyl-6-azaspiro[2.5]octane-5-carboxamido)ethyl)benzoate (D92) (16 mg) and 4-(Trifluoromethyl)benzylbromide (0.011 ml). (Na$_2$CO$_3$: 3 eq; reaction time: 18 hrs; 68° C.)

MS: (ES/+) m/z: 489 [MH$^+$] C27H31F3N2O3 requires 488.23

Descriptions 131a and 131b methyl 4-(1-(4,4-dimethyl-1-(4-(trifluoromethyl) benzyl)piperidine-2-carboxamido)cyclopropyl)benzoate (enantiomer 1) (D131a) and methyl 4-(1-(4,4-dimethyl-1-(4-(trifluoromethyl)benzyl)piperidine-2-carboxamido)cyclopropyl)benzoate (enantiomer 2) (D131 b)

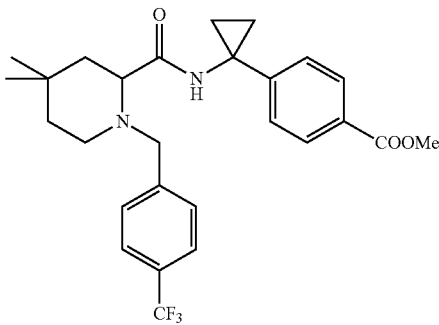 [SMILES: COC(=O)c1ccc(C2(NC(=O)C3CC(C)(C)CCN3Cc3ccc(C(F)(F)F)cc3)CC2)cc1]

To a solution of methyl 4-(1-(4,4-dimethylpiperidine-2-carboxamido)cyclopropyl)benzoate (racemic mixture) (D93) (190 mg, 057 mmol) in dry MeCN (5 ml), Cs$_2$CO$_3$ (606 mg, 1.8 mmol) and 4-(trifluoromethyl)-benzylbromide (0.115 ml, 0.74 mmol) were added in sequence and the mixture was stirred at RT for 18 hrs. The solid was filtered off, MeCN was evaporated and the residue was purified by SPE-Si cartridge (10 g) eluting with a mixture DCM/EtOAc from 100/0 to 95/5. Collected fractions after solvent evaporation afforded 236 mg of racemic mixture which was submitted for chiral HPLC separation (Preparative chromatographic conditions: Column: DAICEL AD-H; Mobile phase: n-hexane/EtOH/DEA 80%/20%/0.1% v/v; Flow rate 10 ml/min; DAD: 246 nm). Collected fractions, after solvent evaporation afforded the two enantiomer compounds (D131a) (147 mg) and (D131b) (141 mg).

(D131a) (enantiomer 1): retention time: 11.43 min $^1$H NMR (400 MHz, CHCl3-d) δ (ppm): 7.92 (d, J=8.2 Hz, 2 H), 7.61 (d, J=7.9 Hz, 2 H), 7.39 (d, J=7.8 Hz, 2 H), 7.34 (br. s., 1 H), 7.25 (d, J=8.3 Hz, 2 H), 3.90 (s, 3 H), 3.80 (d, J=14.4 Hz, 1 H), 3.26 (d, J=14.4 Hz, 1 H), 3.07 (d, J=9.2 Hz, 1 H), 2.71 (d, J=11.8 Hz, 1 H), 2.21 t, 1 H), 1.79 (d, J=13.1 Hz, 1H), 1.46 (t, J=12.5 Hz, 2H), 1.40-1.24 (m, 4H), 1.12 (d, J=7.0 Hz, 1 H), 0.99 (d, J=10.0 Hz, 6 H).

(D131b) (enantiomer 2): retention time: 16.66 min $^1$H NMR (400 MHz, CHCl3-d) δ (ppm): 7.92 (d, J=8.1 Hz, 2 H), 7.61 (d, J=7.8 Hz, 2 H), 7.39 (d, J=7.8 Hz, 2 H), 7.34 (br. s., 1 H), 7.25 (d, J=8.4 Hz, 2 H), 3.90 (s, 3 H), 3.80 (d, J=14.5 Hz, 1 H), 3.26 (d, J=14.5 Hz, 1 H), 3.07 (d, J=9.1 Hz, 1 H), 2.70 (br. d, J=1.0 Hz, 1 H), 2.21 (t, J=1.0 Hz, 1 H), 1.78 (d, J=1.0 Hz, 1 H), 1.46 (t, J=12.5 Hz, 2 H), 1.40-1.24 (m, 4 H), 1.17-1.08 (m, 1 H), 0.99 (d, J=9.9 Hz, 6 H).

Descriptions 132 a, 132b methyl 4-((1S)-1-(4,4-dimethyl-1-(4-(trifluoromethyl)benzyl)piperidine-2-carboxamido)ethyl)benzoate (diastereoisomer 1) (D132a) and methyl 4-((1S)-1-(4,4-dimethyl-1-(4-(trifluoromethyl)benzyl)piperidine-2-carboxamido)ethyl)benzoate (diastereoisomer 2) (D132b)

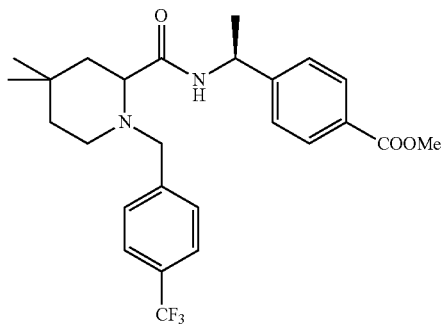 [SMILES: COC(=O)c1ccc([C@H](C)NC(=O)C2CC(C)(C)CCN2Cc2ccc(C(F)(F)F)cc2)cc1]

To a solution of methyl 4-((1S)-1-(4,4-dimethylpiperidine-2-carboxamido)ethyl)benzoate (diastereoisomers mixture) (D94) (150 mg, 047 mmol) in dry MeCN (5 ml), Cs$_2$CO$_3$ (462 mg, 1.4 mmol) and 4-(trifluoromethyl)-benzylbromide (0.08 ml, 0.56 mmol) were added in sequence and the mixture was stirred at RT for 18 hrs. The solid was filtered off, MeCN was evaporated and the residue was purified by SPE-Si cartridge (10 g) eluting with a mixture DCM/EtOAc from 100/0 to 95/5. Collected fractions after solvent evaporation afforded 140 mg of diastereoisomeric mixture which was submitted for chiral HPLC separation (Preparative chromatographic conditions: Column: DAICEL AD-H; Mobile phase: n-hexane/EtOH/DEA 80%/20%/0.1% v/v; Flow rate 10 ml/min; DAD: 246 nm). Collected fractions, after solvent evaporation of the separated fractions afforded the two diastereoisomer compounds (D132a) (71 mg) and (D132b) (68 mg).

(D132a) (diastereoisomer 1): retention time: 8.95 min $^1$H NMR (400 MHz, CHCl3-d) δ (ppm): 7.83 (d, J=8.0 Hz, 2 H), 7.48 (d, J=7.9 Hz, 2 H), 7.25 (d, J=8.1 Hz, 2 H), 7.16 (d, J=7.8 Hz, 2 H), 6.97-6.87 (m, 1 H), 5.26-5.13 (m, 1 H), 3.90 (s, 3 H), 3.75-3.65 (m, 1 H), 3.23-3.12 (m, 1 H), 3.09-3.01 (m, 1 H), 2.74-2.63 (m, 1 H), 2.25-2.12 (m, 1 H), 1.85-1.74 (m, 1 H), 1.54-1.38 (m, 5 H), 1.37-1.28 (m, 1 H), 0.98 (d, J=9.8 Hz, 6 H).

(D132b) (diastereoisomer 2): retention time: 17.94 min $^1$H NMR (400 MHz, CHCl3-d) δ (ppm): 8.05 (d, J=8.1 Hz, 2 H), 7.63 (d, J=7.9 Hz, 2 H), 7.45 (d, J=7.8 Hz, 2 H), 7.37 (d, J=8.1 Hz, 2 H), 6.98 (d, J=7.9 Hz, 1 H), 5.17 (t, J=7.2 Hz, 1 H), 4.07-3.81 (m, 4 H), 3.31 (d, J=14.4 Hz, 1 H), 3.09 (dd, J=2.7, 11.7 Hz, 1 H), 2.72 (d, J=11.8 Hz, 1 H), 2.23 (br. s., 1 H), 1.72 (d, J=13.1 Hz, 1 H), 1.51-1.25 (m, 6H), 0.96 (s, 6H).

Description 133 methyl 4-((1S)-1-((2R)-4-fluoro-1-(4-(trifluoromethyl)benzyl)piperidine-2-carboxamido)ethyl)benzoate (diastereoisomers mixture) (D133)

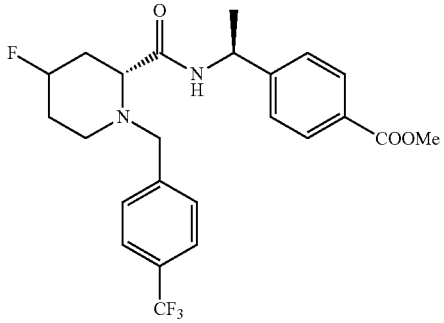 [SMILES: COC(=O)c1ccc([C@H](C)NC(=O)[C@H]2CC(F)CCN2Cc2ccc(C(F)(F)F)cc2)cc1]

The title compound (D133) (62 mg) was prepared according to the general procedure for substituted benzyl amines preparation starting from methyl 4-((1S)-1-((2R)-4-fluoropiperidine-2-carboxamido)ethyl)benzoate (D95) (75 mg) and 4-(trifluoromethyl)-benzylbromide (0.045 ml). (Cs$_2$CO$_3$: 1.3 eq; reaction time: 18 hrs; RT).

MS: (ES/+) m/z: 467.0 [MH$^+$] C24H26F4N2O3 requires 466.19

$^1$H NMR (400 MHz, CHCl3-d) δ (ppm): 8.03 (d, J=7.4 Hz, 2 H), 7.63 (d, J=7.3 Hz, 2 H), 7.44 (d, J=7.7 Hz, 2 H), 7.36 (d, J=7.9 Hz, 2 H), 6.98 (d, J=6.2 Hz, 1 H), 5.17 (t, J=7.1 Hz, 1 H), 4.99-4.72 (m, 1 H), 4.03-3.86 (m, 4 H), 3.41 (d, J=14.1 Hz, 1 H), 3.30 (d, J=8.0 Hz, 1 H), 2.71 (d, J=12.2 Hz, 1 H), 2.50 (t, J=11.3 Hz, 1 H), 2.22 (br. s., 1 H), 1.97-1.63 (m, 3 H), 1.45 (d, J=6.7 Hz, 3 H).

Description 134 methyl 4-(1-((2R)-4-fluoro-1-(4-(trifluoromethyl)benzyl)piperidine-2-carboxamido)cyclopropyl)benzoate (diastereoisomers mixture) (D134)

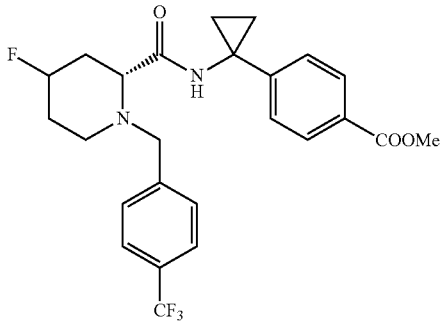 [SMILES: COC(=O)c1ccc(C2(NC(=O)[C@H]3CC(F)CCN3Cc3ccc(C(F)(F)F)cc3)CC2)cc1]

The title compound (D134) (26 mg) was prepared according to the general procedure for substituted benzyl amines preparation starting from methyl 4-(1-((2R)-4-fluoropiperidine-2-carboxamido)cyclopropyl)benzoate (D96) (39 mg) and 4-(trifluoromethyl)-benzylbromide (0.015 ml). (Cs$_2$CO$_3$: 1.3 eq; reaction time: 18 hrs; RT).

MS: (ES/+) m/z: 479.2 [MH$^+$] C25H26F4N2O3 requires 478.19

$^1$H NMR (400 MHz, CHCl3-d) δ (ppm): 7.93 (d, J=8.1 Hz, 2 H), 7.63 (d, J=7.8 Hz, 2 H), 7.42 (d, J=7.8 Hz, 2 H), 7.33 (br. s., 1 H), 7.25 (br. s., 2 H), 5.03-4.75 (m, 1 H), 3.91 (s, 3 H), 3.82 (d, J=14.2 Hz, 1 H), 3.39 (d, J=14.2 Hz, 1 H), 3.29 (dd, J=3.1, 9.8 Hz, 1 H), 2.78-2.66 (m, 1 H), 2.57-2.45 (m, 1 H), 2.27 (br. s., 1 H), 2.01-1.68 (m, 3 H), 1.41-1.27 (m, 3 H), 1.22-1.12 (m, 1 H).

Description 135 methyl 4-((S)-1-((R)-4,4-difluoro-1-(4-(trifluoromethyl)benzyl)piperidine-2-carboxamido)ethyl)benzoate (single diastereoisomer) (D135)

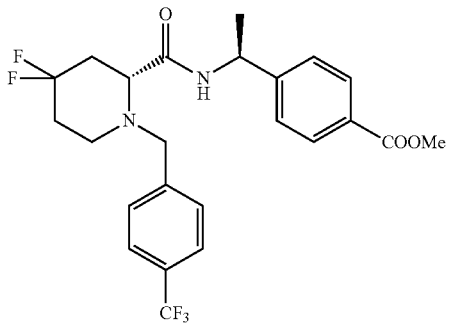 [SMILES: COC(=O)c1ccc([C@H](C)NC(=O)[C@H]2CC(F)(F)CCN2Cc2ccc(C(F)(F)F)cc2)cc1]

To a solution of methyl 4-((S)-1-((R)-4,4-difluoropiperidine-2-carboxamido)ethyl)benzoate (D97) (66 mg, 0.20 mmol) in dry MeCN (4 ml), Cs$_2$CO$_3$ (198 mg, 0.60 mmol) and the 4-(Trifluoromethyl)benzylbromide (0.037 ml, 0.24 mmol) were added in sequence and the resulting mixture was stirred at RT for 18 hrs. The solid was filtered off, the acetonitrile was evaporated and the crude was purified by flash chromatography SNAP HP_SiO2 (10 g) eluting with a gradient DCM/EtOAc from 100/0 to 90/10. Collected fractions after solvent evaporation were purified onto reverse phase column GOLD-C18 (15 g) eluting with a gradient of H$_2$O/MeCN (containing 0.1% Acetic acid) from 10/90 to 80/20. Collected fractions after solvent evaporation afforded the title compound (D135) (20 mg).

MS: (ES/+) m/z: 485.5 [MH$^+$] C24H25F5N2O3 requires 484.18

$^1$H NMR (400 MHz, CHCl3-d) δ (ppm): 8.03 (d, J=8.1 Hz, 2H), 7.64 (d, J=7.9 Hz, 2H), 7.42 (d, J=7.8 Hz, 2 H), 7.35 (d, J=8.0 Hz, 2 H), 6.85 (d, J=7.9 Hz, 1H), 5.19 (t, J=7.2 Hz, 1 H), 3.98 (d, J=14.4 Hz, 1 H), 3.95-3.89 (m, 3 H), 3.39 (d, J=14.2 Hz, 1 H), 3.27 (dd, J=3.3, 10.6 Hz, 1 H), 2.94 (d, J=11.1 Hz, 1 H), 2.51-2.30 (m, 2 H), 2.05-1.86 (m, 3 H), 1.57-1.52 (m, J=6.8 Hz, 1 H), 1.48 (d, J=6.8 Hz, 3 H).

Description 136

(R)-methyl 4-(1-(4,4-difluoro-1-(4-(trifluoromethyl)benzyl)piperidine-2-carboxamido)cyclopropyl)benzoate (single enantiomer) (D136)

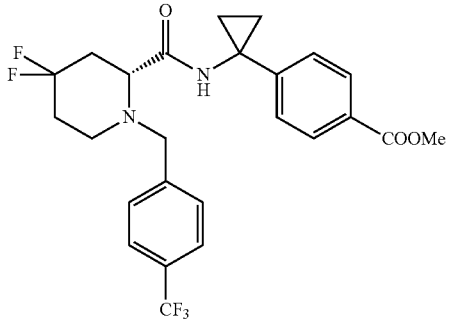 [SMILES: COC(=O)c1ccc(C2(NC(=O)[C@H]3CC(F)(F)CCN3Cc3ccc(C(F)(F)F)cc3)CC2)cc1]

The title compound (D136) (30 mg) was prepared according to the general procedure described in Description 135 starting from (R)-methyl 4-(1-(4,4-difluoropiperidine-2-carboxamido)cyclopropyl)benzoate (D98) (47 mg) and 4-(trifluoromethyl)-benzylbromide (0.027 ml).

MS: (ES/+) m/z: 497.4 [MH$^+$] C25H25F5N2O3 requires 496.18

$^1$H NMR (400 MHz, CHCl3-d) δ (ppm): 7.92 (d, J=8.2 Hz, 2 H), 7.64 (d, J=7.8 Hz, 2 H), 7.44-7.37 (m, 2 H), 7.26 (d, J=8.6 Hz, 2 H), 3.91 (s, 3 H), 3.84 (d, J=14.2 Hz, 1 H), 3.38 (d, J=14.2 Hz, 1 H), 3.31-3.19 (m, 1 H), 2.96 (d, J=11.4 Hz, 1 H), 2.54-2.33 (m, 2 H), 2.25-2.11 (m, 1 H), 2.02 (br. s., 1 H), 1.98-1.85 (m, 1H), 1.43-1.31 (m, 3 H), 1.24-1.14 (m, 1 H).

Descriptions 137 a and 137b methyl 4-(1-(4,4-difluoro-1-(4-(trifluoromethyl)benzyl)piperidine-2-carboxamido)cyclopropyl)benzoate (enantiomer 1) (D137a) and methyl 4-(1-(4,4-difluoro-1-(4-(trifluoromethyl)benzyl)piperidine-2-carboxamido)cyclopropyl)benzoate (enantiomer 2) (D137b)

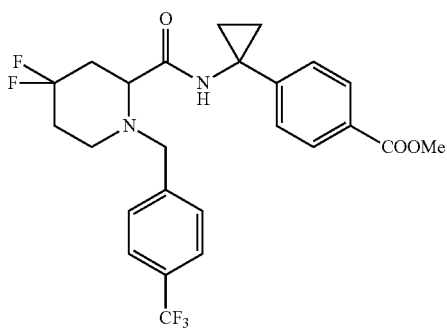 [SMILES: COC(=O)c1ccc(C2(NC(=O)C3CC(F)(F)CCN3Cc3ccc(C(F)(F)F)cc3)CC2)cc1]

To a solution of methyl 4-(1-(4,4-difluoropiperidine-2-carboxamido)cyclopropyl)benzoate (D99) (500 mg, 1.47 mmol) in dry MeCN (20 ml), Cs$_2$CO$_3$ (1.4 g, 4.43 mmol) and 4-(trifluoromethyl)-benzylbromide (0.27 ml, 1.77 mmol) were added in sequence and the resulting mixture was stirred at RT for 12 hrs. The solid was filtered off and the solvent evaporated to afford a residue which was loaded on Biotage SNAP-Si cartridges (25 g) eluting with a mixture cHex/EtOAc from 90/10 to 70/30. Collected fractions after solvent evaporation afforded 490 mg of racemic mixture which was submitted for chiral HPLC separation (Preparative chromatographic conditions: Column: DAICEL IC; Mobile phase: n-heptane/IPA/DEA 60%/40%/0.1% v/v Flow rate 10 ml/min; DAD: 248 nm). Collected fractions, after solvent evaporation of the separated fractions afforded the two enantiomer compounds (D137a) (143 mg) and (D137b) (130 mg).

(D137a) (enantiomer 1): retention time: 10.86 min.

MS: (ES/+) m/z: 497.3 [MH$^+$] C25H25F5N2O3 requires 496.18

$^1$H NMR (400 MHz, DMSO-d6) δ (ppm): 8.97 (s, 1 H), 7.86-7.77 (m, J=8.3 Hz, 2H), 7.74-7.67 (m, J=7.8 Hz, 2 H), 7.65-7.55 (m, J=7.8 Hz, 2 H), 7.27-7.17 (m, J=8.8 Hz, 2 H), 3.87-3.77 (m, 4 H), 3.39 (d, J=14.2 Hz, 1 H), 3.22-3.12 (m, 1 H), 2.86-2.76 (m, 1 H), 2.33-2.15 (m, J=7.8 Hz, 3 H), 2.00 (br. s., 2 H), 1.31-1.13 (m, 4 H).

(D137b) (enantiomer 2): retention time: 13.81 min.

MS: (ES/+) m/z: 496.8 [MH$^+$] C25H25F5N2O3 requires 496.18

$^1$H NMR (400 MHz, DMSO-d6) δ (ppm): 8.97 (s, 1 H), 7.81 (d, J=8.3 Hz, 2 H), 7.76-7.66 (m, J=8.3 Hz, 2 H), 7.66-7.56 (m, J=8.3 Hz, 2 H), 7.23 (d, J=8.3 Hz, 2 H), 3.86-3.74 (m, 4 H), 3.39 (d, J=14.2 Hz, 1 H), 3.20-3.14 (m, 1 H), 2.82 (d, J=12.2 Hz, 1 H), 2.35-2.16 (m, 3 H), 2.07-1.81 (m, 2 H), 1.34-1.13 (m, 4 H)

Descriptions 138 a and 138b methyl 4-(1-(4,4-difluoro-1-(3-(trifluoromethyl)benzyl)piperidine-2-carboxamido)cyclopropyl)benzoate (enantiomer 1) (D138a) and methyl 4-(1-(4,4-difluoro-1-(3-(trifluoromethyl)benzyl)piperidine-2-carboxamido)cyclopropyl)benzoate (enantiomer 2) (D138b)

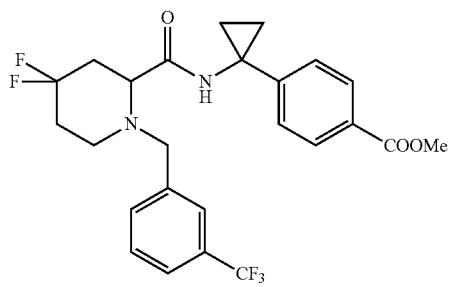 [SMILES: COC(=O)c1ccc(C2(NC(=O)C3CC(F)(F)CCN3Cc3cccc(C(F)(F)F)c3)CC2)cc1]

To a solution of methyl 4-(1-(4,4-difluoropiperidine-2-carboxamido)cyclopropyl)benzoate (D99) (50 mg, 0.15 mmol) in dry MeCN (5 ml), Cs$_2$CO$_3$ (73 mg, 0.22 mmol) and 3-(trifluoromethyl)-benzylbromide (42 mg, 0.18 mmol) were added in sequence and the resulting mixture was stirred at RT for 12 hrs. The solid was filtered off and the solvent evaporated to afford a residue which was loaded on Biotage SNAP-Si cartridges (100 g) eluting with a mixture DCM/EtOAc from 100/0 to 90/10. Collected fractions after solvent evaporation afforded 83 mg of racemic mixture which was submitted for chiral HPLC separation (Preparative chromatographic conditions: Column: DAICEL IC; Mobile phase: n-heptane/IPA/DEA 60%/40%/0.1% v/v; Flow rate 10 ml/min; DAD: 248 nm). Collected fractions, after solvent evaporation of the separated fractions afforded the two enantiomer compounds (D138a) (35 mg) and (D138b) (45 mg).

(D138a) (enantiomer 1): retention time: 10.18 min (D138b) (enantiomer 2): retention time: 15.06 min Descriptions 139 methyl 4-(1-(3-(4-(trifluoromethyl)benzyl)-3-azabicyclo[4.1.0]heptane-4-carboxamido)cyclopropyl)benzoate (racemic mixture) (D139)

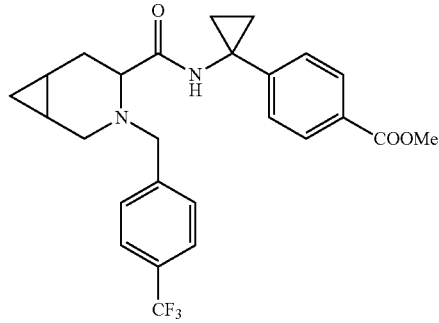 [SMILES: COC(=O)c1ccc(C2(NC(=O)C3CC4CC4CN3Cc3ccc(C(F)(F)F)cc3)CC2)cc1]

To a solution of methyl 4-(1-(3-azabicyclo[4.1.0]heptane-4-carboxamido)cyclopropyl)benzoate (racemic mixture) (D100) (155 mg, 0.49 mmol) in dry MeCN (4 ml), Cs₂CO₃ (241 mg, 0.74 mmol) and 4-(trifluoromethyl)-benzylbromide (0.09 ml, 0.59 mmol) were added in sequence and the resulting mixture was stirred at RT for 4 hrs. The residue obtained after solvent evaporation was loaded on Biotage SNAP-Si column (25 g) eluting with a mixture cHex/EtOAc from 65/35 to 40/60. Collected fractions after solvent evaporation afforded the title compound (D139) (racemic mixture) (215 mg).

MS: (ES/+) m/z: 472.7 [MH⁺] C26H27F3N2O3 requires 472.20

¹H NMR (400 MHz, DMSO-d6) δ (ppm): 8.64 (s, 1 H), 7.80 (d, J=8.3 Hz, 2 H), 7.72-7.65 (m, J=7.8 Hz, 2 H), 7.59 (d, J=7.8 Hz, 2 H), 7.22-7.15 (m, J=8.3 Hz, 2 H), 3.82 (s, 3 H), 3.70 (d, J=13.7 Hz, 1 H), 3.56 (d, J=14.2 Hz, 1 H), 3.17 (dd, J=7.1, 12.5 Hz, 1 H), 2.99 (t, J=6.1 Hz, 1 H), 2.32 (dd, J=4.2, 12.5 Hz, 1 H), 2.18 (td, J=6.7, 13.9 Hz, 1 H), 1.68 (td, J=4.3, 9.0 Hz, 1 H), 1.30-1.20 (m, 2 H), 1.20-1.08 (m, 2 H), 1.08-0.90 (m, 2 H), 0.67 (dt, J=4.2, 8.2 Hz, 1 H), 0.22 (q, J=4.4 Hz, 1 H)

Descriptions 140 a and 140b methyl 4-(1-(3-(4-(trifluoromethyl)benzyl)-3-azabicyclo[4.1.0]heptane-4-carboxamido)cyclopropyl)benzoate (enantiomer 1) (D140a) and methyl 4-(1-(3-(4-(trifluoromethyl)benzyl)-3-azabicyclo[4.1.0]heptane-4-carboxamido)cyclopropyl)benzoate (enantiomer 2) (D140b)

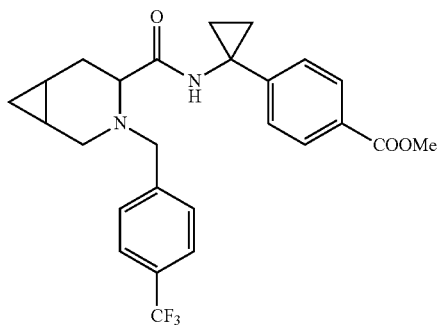 [SMILES: COC(=O)c1ccc(C2(NC(=O)C3CC4CC4CN3Cc3ccc(C(F)(F)F)cc3)CC2)cc1]

Methyl 4-(1-(3-(4-(trifluoromethyl)benzyl)-3-azabicyclo[4.1.0]heptane-4-carboxamido)cyclopropyl)benzoate (racemic mixture) (189 mg) (D139) was submitted for chiral HPLC separation (Preparative chromatographic conditions: Column: DAICEL IC; Mobile phase: n-heptane/IPA/DEA 60%/40%/0.1% v/v Flow rate 10 ml/min; DAD: 248 nm). Collected fractions, after solvent evaporation of separated fractions afforded the two diastereoisomer compounds (D140a) (78 mg) and (D140b) (82 mg).

(D140a) (enantiomer 1 with trans relative stereochemistry): retention time: 12.89 min.

MS: (ES/+) m/z: 472.7 [MH⁺] C26 H27F3N2O3 requires 472.20

Chiral HPLC: [DAICEL AD-H; Mobile phase A: 70% n-heptane (+0.1% DEA), B: 30% IPA; DAD: 248 nm]: Peak retention time: 12.9 min.

¹H NMR (400 MHz, DMSO-d6) δ (ppm): 8.65 (s, 1 H), 7.80 (d, J=8.3 Hz, 2 H), 7.72-7.65 (m, J=7.8 Hz, 2 H), 7.62-7.56 (m, J=7.8 Hz, 2 H), 7.19 (d, J=8.3 Hz, 2 H), 3.82 (s, 3 H), 3.70 (d, J=13.7 Hz, 1 H), 3.56 (d, J=14.2 Hz, 1 H), 3.17 (dd, J=7.1, 12.5 Hz, 1 H), 2.99 (t, J=6.1 Hz, 1 H), 2.32 (dd, J=4.2, 12.5 Hz, 1 H), 2.23-2.14 (m, 1 H), 1.69 (br. s., 1 H), 1.30-1.22 (m, 2 H), 1.20-1.13 (m, 1 H), 1.11 (dd, J=3.2, 6.1 Hz, 1 H), 1.05-0.93 (m, 2 H), 0.70-0.64 (m, 1 H), 0.22 (d, J=4.9 Hz, 1 H).

(D140b) (enantiomer 2 with trans relative stereochemistry): retention time: 18.26 min.

MS: (ES/+) m/z: 473.6 [MH⁺] C26H27F3N2O3 requires 472.20

Chiral HPLC: [DAICEL AD-H; Mobile phase A: 60% n-heptane (+0.1% DEA), B: 40% IPA; DAD: 248 nm]: Peak retention time: 18.2 min ¹H NMR (400 MHz, DMSO-d6) δ (ppm): 8.65 (s, 1 H), 7.83-7.77 (m, J=8.3 Hz, 2 H), 7.71-7.64 (m, J=7.8 Hz, 2 H), 7.62-7.54 (m, J=8.3 Hz, 2 H), 7.22-7.14 (m, J=8.8 Hz, 2 H), 3.82 (s, 3 H), 3.70 (d, J=13.7 Hz, 1 H), 3.56 (d, J=14.2 Hz, 1 H), 3.17 (dd, J=7.1, 12.5 Hz, 1 H), 2.99 (t, J=6.1 Hz, 1 H), 2.32 (dd, J=4.2, 12.5 Hz, 1 H), 2.23-2.11 (m, 1 H), 1.68 (d, J=12.7 Hz, 1 H), 1.30-1.21 (m, 2 H), 1.16 (dd, J=4.2, 6.1 Hz, 1 H), 1.11 (dd, J=3.2, 6.1 Hz, 1 H), 1.05-0.92 (m, 2 H), 0.68 (td, J=4.3, 8.1 Hz, 1 H), 0.22 (d, J=4.9 Hz, 1 H).

Description 141 methyl 4-(1-(3-(3-(trifluoromethyl)benzyl)-3-azabicyclo[4.1.0]heptane-4-carboxamido)cyclopropyl)benzoate (D141)

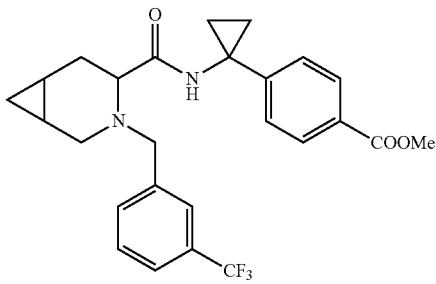 [SMILES: COC(=O)c1ccc(C2(NC(=O)C3CC4CC4CN3Cc3cccc(C(F)(F)F)c3)CC2)cc1]

The title compound (D141) (53 mg) was prepared according to the general procedure for substituted benzyl amines preparation starting from methyl 4-(1-(3-azabicyclo[4.1.0]heptane-4-carboxamido)cyclopropyl)benzoate (diastereoisomers mixture) (D100) (48 mg, 0.15 mmol) and 3-(Trifluoromethyl)benzyl bromide (0.040 ml, 0.17 mmol). (Cs₂CO₃:2 eq; reaction time: 4 hrs; reaction temperature: RT.

MS: (ES/+) m/z: 473 [MH⁺] C26H27F3N2O3 requires 472.20

Description 142 methyl 4-(1-((3R)-2-(4-(trifluoromethyl)benzyl)-2-azabicyclo[4.1.0]heptane-3-carboxamido)cyclopropyl)benzoate (diastereoisomers mixture) (D142)

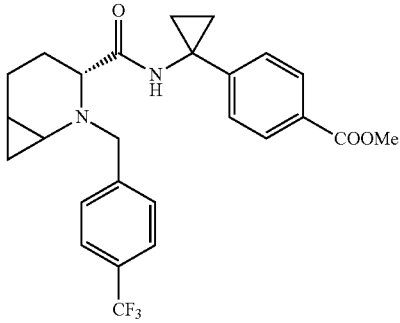 [SMILES: COC(=O)c1ccc(C2(NC(=O)[C@H]3CCC4CC4N3Cc3ccc(C(F)(F)F)cc3)CC2)cc1]

The title compound (D142) (6.8 mg) was prepared according to the general procedure for substituted benzyl amines preparation starting from methyl 4-(1-((3R)-2-azabicyclo[4.1.0]heptane-3-carboxamido)cyclopropyl)benzoate (diastereoisomers mixture) (D101) (17.5 mg) and 4-(trifluoromethyl)-benzylbromide (0.01 ml). (Cs$_2$CO$_3$: 1.5 eq; Reaction time: 20 hrs; RT).

MS: (ES/+) m/z: 473.2 [MH$^+$] C26H27F3N2O3 requires 472.20

$^1$H NMR (400 MHz, CHCl3-d) δ (ppm): 8.01-7.84 (m, J=8.3 Hz, 2 H), 7.66-7.60 (m, J=8.8, 8.8 Hz, 2 H), 7.57-7.39 (m, 3 H), 7.28-7.09 (m, J=8.1 Hz, 2 H), 4.03-3.65 (m, 5 H), 3.13-2.81 (m, 1 H), 2.06 (m, 2 H), 1.80-0.98 (8 H, under residual solvent), 0.71-0.24 (m, 2 H).

Description 143 methyl 4-((1S)-1-((3R)-2-(4-(trifluoromethyl)benzyl)-2-azabicyclo[4.1.0]heptane-3-carboxamido)ethyl)benzoate (diastereoisomers mixture) (D143)

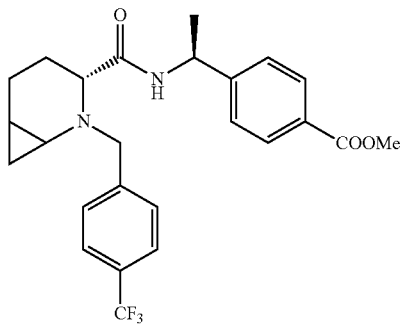 [SMILES: COC(=O)c1ccc([C@H](C)NC(=O)[C@H]2CCC3CC3N2Cc2ccc(C(F)(F)F)cc2)cc1]

The title compound (D143) (10 mg) was prepared according to the general procedure for substituted benzyl amines preparation starting from methyl 4-((1S)-1-((3R)-2-azabicyclo[4.1.0]heptane-3-carboxamido)ethyl)benzoate (diastereoisomers mixture) (D102) (20 mg) and 4-(trifluoromethyl)-benzylbromide (0.012 ml). (Cs$_2$CO$_3$: 1.5 eq; Reaction time: 20 hrs; RT).

MS: (ES/+) m/z: 461.1 [MH$^+$] C25H27F3N2O3 requires 460.20

$^1$H NMR (400 MHz, CHCl3-d) δ (ppm): 8.02 (d, J=7.0 Hz, 2 H), 7.89-7.06 (m, 7H), 5.24-5.04 (m, 1 H), 4.19-3.69 (m, 5 H), 3.13-2.76 (m, 1 H), 2.43-1.81 (m, 2 H), 1.81-1.06 (7H under residual solvent), 0.66-0.16 (m, 2 H).

Description 144 methyl 4-((S)-1-((R)-1-(4-(trifluoromethyl)benzyl)pyrrolidine-2-carboxamido)ethyl)benzoate (D144)

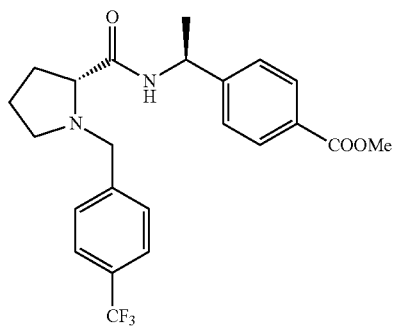 [SMILES: COC(=O)c1ccc([C@H](C)NC(=O)[C@H]2CCCN2Cc2ccc(C(F)(F)F)cc2)cc1]

The title compound (D144) (60 mg) was prepared according to the general procedure for substituted benzyl amines preparation starting from methyl 4-((S)-1-((R)-pyrrolidine-2-carboxamido)ethyl)benzoate (D103) (50 mg) and and 4-(trifluoromethyl)-benzylbromide (0.056 ml). (Na$_2$CO$_3$; reaction time: 5 hrs; 70° C.).

MS: (ES/+) m/z: 434.8 [MH$^+$] C23H25F3N2O3 requires 434.18 Chiral HPLC [Phenomenex Lux Cellulose-1; Mobile phase A: 70% n-hexane (+0.1% DEA), B: 30% IPA; DAD: 235 nm]: Peak retention time: 10.50 min.

$^1$H NMR (400 MHz, CHCl3-d) δ (ppm): 8.07 (d, J=8.3 Hz, 1 H), 8.04-7.99 (m, J=7.8 Hz, 2 H), 7.40-7.34 (m, J=8.3 Hz, 2 H), 5.14 (quin, J=7.3 Hz, 1 H), 3.93 (s, 3 H), 3.83 (dd, J=5.1, 9.0 Hz, 1 H), 3.06 (td, J=6.8, 10.3 Hz, 1 H), 2.92 (td, J=6.1, 10.3 Hz, 1 H), 2.22-2.10 (m, 1 H), 1.91 (qd, J=6.4, 12.7 Hz, 1 H), 1.77-1.67 (m, 2 H), 1.51 (d, J=7.3 Hz, 3 H).

Description 145 methyl 4-((S)-1-((R)-1-(4-fluorobenzyl)pyrrolidine-2-carboxamido)ethyl)benzoate (D145)

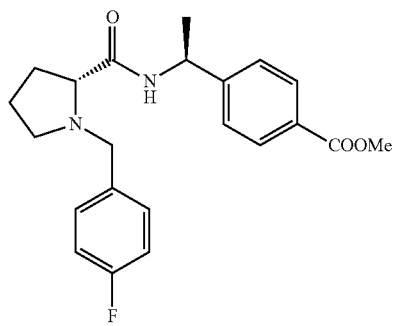 [SMILES: COC(=O)c1ccc([C@H](C)NC(=O)[C@H]2CCCN2Cc2ccc(F)cc2)cc1]

The title compound (D145) (22 mg) was prepared according to the general procedure for substituted benzyl amines preparation starting from methyl 4-((S)-1-((R)-pyrrolidine-2-carboxamido)ethyl)benzoate (D103) (50 mg) and 4-Fluorobenzyl bromide (0.045 ml). (Na$_2$CO$_3$; reaction time: 5 hrs; 70° C.).

MS: (ES/+) m/z: 385 [MH$^+$] C22H25FN2O3 requires 384.18 Chiral HPLC [Phenomenex Lux Cellulose-1; Mobile phase A: 80% n-hexane (+0.1% DEA), B: 20% IPA; DAD: 235 nm]: Peak retention time 14.18 min.

$^1$H NMR (400 MHz, CHCl3-d) δ (ppm): 8.02 (d, J=7.8 Hz, 2 H), 7.64 (d, J=7.8 Hz, 1 H), 7.34 (d, J=8.3 Hz, 2 H), 7.28-7.24 (m, 2 H), 7.10-7.02 (m, 2 H), 5.15-5.05 (m, 1 H), 3.93 (s, 3 H), 3.85 (d, J=13.2 Hz, 1 H), 3.58 (d, J=12.7 Hz, 1 H), 3.25 (dd, J=4.6, 10.5 Hz, 1 H), 3.08 (br. s., 1 H), 2.43 (d, J=5.9 Hz, 1 H), 2.29-2.16 (m, 1 H), 1.84 (d, J=10.8 Hz, 2 H), 1.74-1.61 (m, 1 H), 1.42 (d, J=6.8 Hz, 3H)

Description 146 methyl 4-(1-((3R)-2-(3-(trifluoromethyl)benzyl)-2-azabicyclo[3.1.0]hexane-3-carboxamido)cyclopropyl)benzoate (D146)

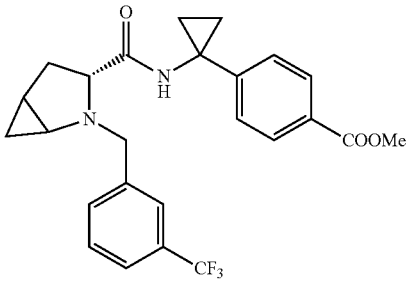 [SMILES: COC(=O)c1ccc(C2(NC(=O)[C@H]3CC4CC4N3Cc3cccc(C(F)(F)F)c3)CC2)cc1]

The title compound (D146) (67 mg) was prepared according to the general procedure for substituted benzyl amines preparation starting from methyl methyl 4-(1-((3R)-2-azabicyclo[3.1.0]hexane-3-carboxamido)cyclopropyl)benzoate (D104) (37 mg, 0.12 mmol) and 3-(Trifluoromethyl)benzyl bromide (0.029 ml, 0.19 mmol).

(Cs$_2$CO$_3$:2 eq; reaction time: 6 hrs; reaction temperature: RT.

MS: (ES/+) m/z: 459 [MH$^+$] C25H25F3N2O3 requires 458.18

Description 147 methyl 4-(1-((1R,3R,5R)-2-(4-(trifluoromethyl)benzyl)-2-azabicyclo[3.1.0]hexane-3-carboxamido)cyclopropyl)benzoate (syn diastereoisomer) (D147)

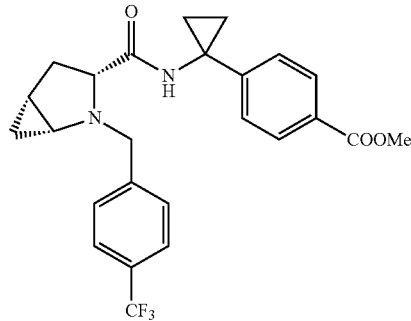 [SMILES: COC(=O)c1ccc(C2(NC(=O)[C@H]3C[C@H]4C[C@H]4N3Cc3ccc(C(F)(F)F)cc3)CC2)cc1]

To a solution of methyl 4-(1-((1R,3R,5R)-2-azabicyclo[3.1.0]hexane-3-carboxamido)cyclopropyl)benzoate (D104) (1.7 g, 5.7 mmol) in MeCN (80 ml) Cs$_2$CO$_3$ (2.8 g, 8.5 mmol) and 4-(trifloromethyl)benzylbromide (1.6 g, 6.8 mmol) were added and the resulting mixture was stirred at RT for 4 hrs. Solvent was evaporated and the residue was loaded on a SNAP-Si cartridge (100 g), eluted with a mixture DCM/AcOEt from 10/0 to DCM/AcOEt 9/1. Collected fractions after solvent evaporation afforded the title compound (D147) (2.41 g).

MS: (ES/+) m/z: 459 [MH$^+$] C25 H25F3N2O3 requires 458.18

$^1$H NMR (400 MHz, DMSO-d6) δ (ppm): 8.35 (s, 1 H), 7.81-7.74 (m, 4 H), 7.73-7.68 (m, 2 H), 7.03 (d, J=8.3 Hz, 2 H), 4.04-3.97 (m, 1 H), 3.86-3.75 (m, 4 H), 3.54 (dd, J=2.2, 10.0 Hz, 1 H), 2.77-2.69 (m, 1 H), 2.25-2.12 (m, 1 H), 2.05-1.95 (m, 1 H), 1.49-1.26 (m, 2 H), 1.22-1.04 (m, 3 H), 0.47 (q, J=7.0 Hz, 1 H), 0.22-0.14 (m, 1 H).

Description 148 methyl 4-(1-((1S,3R,5S)-2-(4-(trifluoromethyl)benzyl)-2-azabicyclo[3.1.0]hexane-3-carboxamido)cyclopropyl)benzoate (anti diastereoisomer) (D148)

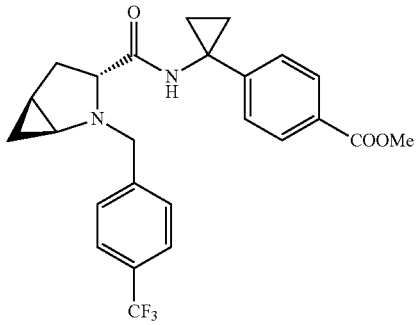 [SMILES: COC(=O)c1ccc(C2(NC(=O)[C@H]3C[C@@H]4C[C@@H]4N3Cc3ccc(C(F)(F)F)cc3)CC2)cc1]

The title compound (D148) (100.8 mg) was prepared according to the general procedure for substituted benzyl amines preparation starting from methyl 4-(1-((1S,3R,5S)-2-azabicyclo[3.1.0]hexane-3-carboxamido)cyclopropyl)benzoate (diastereoisomer trans) (D105) (71.9 mg) and 4-(trifluoromethyl)-benzylbromide (0.047 ml). (Na$_2$CO$_3$: 3 eq; Reaction time: 18 hrs; 68° C.)

MS: (ES/+) m/z: 459.4 [MH$^+$] C25H25F3N2O3 requires 458.18

$^1$H NMR (400 MHz, CHCl3-d) δ (ppm): 7.96 (d, J=8.3 Hz, 2 H), 7.85-7.72 (m, 1H), 7.65 (d, J=7.8 Hz, 2 H), 7.48 (d, J=7.5 Hz, 2 H), 7.26 (d, J=8.3 Hz, 2 H), 3.91 (s, 3 H), 3.82-3.71 (m, 1 H), 3.62-3.47 (m, 1 H), 2.98-2.85 (m, 1 H), 2.76-2.64 (m, 1 H), 2.59-2.46 (m, 1 H), 2.06-1.91 (m, 1 H), 1.53-1.44 (m, 1 H), 1.38 (br. s., 1 H), 1.34-1.13 (m, 3 H), 0.64 (br. s., 1 H), 0.32-0.19 (m, 1 H).

Description 149 methyl 4-((1S)-1-((3R)-2-(4-(trifluoromethyl)benzyl)-2-azabicyclo[3.1.0]hexane-3-carboxamido)ethyl)benzoate (diastereoisomers mixture) (D149)

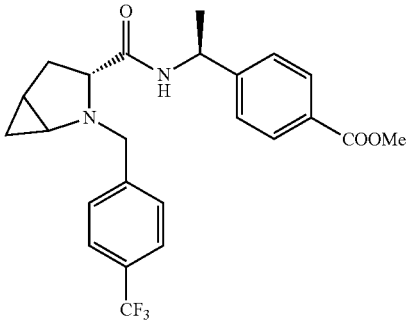 [SMILES: COC(=O)c1ccc([C@H](C)NC(=O)[C@H]2CC3CC3N2Cc2ccc(C(F)(F)F)cc2)cc1]

The title compounds (D149) (14 mg) was prepared according to the general procedure for substituted benzyl amines preparation starting from methyl 4-((1S)-1-((3R)-2-azabicyclo[3.1.0]hexane-3-carboxamido)ethyl)benzoate (D106) (11 mg) and 4-(trifluoromethyl)-benzylbromide (0.007 ml). (Na$_2$CO$_3$: 3 eq; Reaction time: 18 hrs; 68° C.)

MS: (ES/+) m/z: 447.4 [MH$^+$] C24H25F3N2O3 requires 446.18

$^1$H NMR (400 MHz, CHCl3-d) δ (ppm): 8.03 (d, J=8.1 Hz, 4 H), 7.80-7.70 (m, 1H), 7.69-7.58 (m, 4 H), 7.56-7.47 (m, 4 H), 7.47-7.41 (m, 1 H), 7.37 (d, J=8.0 Hz, 4 H), 5.13-5.04 (m, 1 H), 5.04-4.95 (m, 1 H), 3.98 (d, J=13.3 Hz, 1 H), 3.93 (s, 6 H), 3.87-3.79 (m, 1 H), 3.75 (d, J=13.3 Hz, 1 H), 3.54 (d, J=7.2 Hz, 2 H), 2.96-2.87 (m, 1 H), 2.73-2.60 (m, 2 H), 2.49-2.41 (m, 1 H), 2.26-2.20 (m, 2H), 1.95-1.84 (m, 1 H), 1.49 (d, J=4.0 Hz, 1 H), 1.45 (d, J=7.0 Hz, 3 H), 1.40 (d, J=6.9 Hz, 4 H), 0.68-0.58 (m, 1 H), 0.42 (d, J=7.6 Hz, 1 H), 0.30-0.19 (m, 1 H), 0.05-−0.05 (m, 1 H).

Description 150 methyl 4-((1S)-1-((3R)-2-(4-(trifluoromethyl)benzyl)-2-azabicyclo[3.1.0]hexane-3-carboxamido)ethyl)benzoate (single diastereoisomer) (D150)

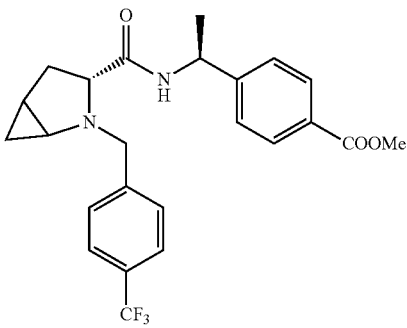 [SMILES: COC(=O)c1ccc([C@H](C)NC(=O)[C@H]2CC3CC3N2Cc2ccc(C(F)(F)F)cc2)cc1]

The title compounds (D150) (72 mg) was prepared according to the general procedure for substituted benzyl amines preparation starting from methyl 4-((1S)-1-((3R)-2-azabicyclo[3.1.0]hexane-3-carboxamido)ethyl)benzoate (D107) (48 mg) and 4-(trifluoromethyl)-benzylbromide (0.031 ml) (Na$_2$CO$_3$: 3 eq; Reaction time: 18 hrs; 68° C.)

MS: (ES/+) m/z: 447.4 [MH$^+$] C24H25F3N2O3 requires 446.18

$^1$H NMR (400 MHz, CHCl3-d) δ (ppm): 8.04 (d, J=8.1 Hz, 2 H), 7.66 (d, J=7.7 Hz, 2 H), 7.51 (d, J=7.3 Hz, 2 H), 7.46-7.41 (m, 1 H), 7.37 (d, J=8.1 Hz, 2 H), 5.14-5.03 (m, 1 H), 3.94 (s, 3 H), 3.88-3.78 (m, 1 H), 3.64-3.51 (m, 1 H), 2.97-2.88 (m, 1 H), 2.74-2.65 (m, 1 H), 2.51-2.37 (m, 1 H), 1.97-1.84 (m, 1 H), 1.56-1.51 (m, 1 H), 1.45 (d, J=6.9 Hz, 3 H), 0.68-0.59 (m, 1 H), 0.31-0.20 (m, 1 H).

Description 151

(R)-methyl 4-(1-(4,4-dimethyl-1-(4-(trifluoromethyl)benzyl)pyrrolidine-2-carboxamido)cyclopropyl)benzoate (D151)

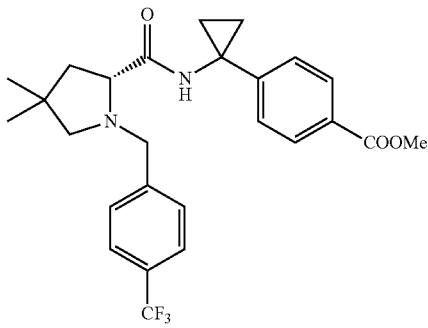 [SMILES: COC(=O)c1ccc(C2(NC(=O)[C@H]3CC(C)(C)CN3Cc3ccc(C(F)(F)F)cc3)CC2)cc1]

The title compound (D151) (100 mg) was prepared according to the general procedure for substituted benzyl amines preparation starting from (R)-methyl 4-(1-(4,4-dimethylpyrrolidine-2-carboxamido)cyclopropyl)benzoate (D108) (70 mg) and 4-(trifluoromethyl)-benzylbromide (0.041 ml). (Cs$_2$CO$_3$: 1.5 eq; reaction time: 20 hrs, RT)

MS: (ES/+) m/z: 475.4 [MH$^+$] C26H29F3N2O3 requires 474.21

$^1$H NMR (400 MHz, CHCl3-d) δ (ppm): 7.95 (d, J=8.1 Hz, 2 H), 7.88 (br. s., 1 H), 7.63 (d, J=7.7 Hz, 2 H), 7.41 (d, J=7.6 Hz, 2 H), 7.23 (d, J=8.1 Hz, 2 H), 3.91 (s, 4 H), 3.57 (d, J=13.5 Hz, 1 H), 3.37 (dd, J=6.5, 9.7 Hz, 1 H), 2.84 (d, J=9.2 Hz, 1 H), 2.29 (d, J=9.2 Hz, 1 H), 2.23-2.12 (m, 1 H), 1.73 (dd, J=6.2, 13.1 Hz, 1 H), 1.43-1.35 (m, 1 H), 1.34-1.28 (m, 2 H), 1.25-1.19 (m, 1 H), 1.11 (d, J=19.4 Hz, 6 H)

Description 152 a and 152b methyl 4-((1S)-1-(1-(4-(trifluoromethyl)benzyl)azetidine-2-carboxamido)ethyl)benzoate (diastereoisomers mixture) (D152a) and methyl 4-((1S)-1-(1-(4-(trifluoromethyl)benzyl)azetidine-2-carboxamido)ethyl)benzoate (single diastereoisomer) (D152b)

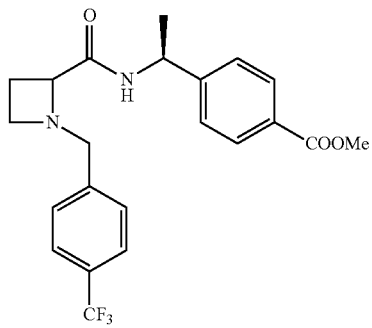 [SMILES: COC(=O)c1ccc([C@H](C)NC(=O)C2CCN2Cc2ccc(C(F)(F)F)cc2)cc1]

To a solution of methyl 4-((1S)-1-(azetidine-2-carboxamido)ethyl)benzoate (diastereoisomers mixture) (D109) (60 mg, 0.23 mmol) in dry MeCN (5 ml), Cs$_2$CO$_3$ (223.6 mg, 0.68 mmol) and the 4-(Trifluoromethyl)benzylbromide (0.042 ml, 0.27 mmol) were added in sequence and the resulting mixture was stirred at RT for 18 hrs. The solid was filtered off, solvent was evaporated and the residue was purified by Biotage SNAP HP—Si column (10 g) eluting with a gradient of DCM/EtOAc from 100/0 to 90/10. Collected fractions after solvent evaporation afforded 23 mg of diasteroisomeric mixture which was submitted for chiral HPLC separation (Preparative chromatographic conditions: Column: DAICEL AD-H; Mobile phase: n-heptane/EtOH/DEA 70%/30%/0.1% v/v Flow rate 10 ml/min; DAD: 235 nm). Collected fractions, after solvent evaporation afforded the title compound (D152a) (diastereoisomers mixture) (6 mg) and (D152b) (diastereoisomer 2) (7 mg)

(D152b) (single diastereoisomer): retention time: 15.8 min $^1$H NMR (400 MHz, CHCl3-d) δ (ppm): 8.03 (d, J=8.1 Hz, 2 H), 7.63 (d, J=7.8 Hz, 2 H), 7.41 (d, J=7.8 Hz, 2 H), 7.34 (d, J=8.1 Hz, 2 H), 7.20 (d, J=7.9 Hz, 1 H), 5.04-4.92 (m, 1 H), 3.94 (s, 3 H), 3.82-3.65 (m, 3 H), 3.44 (t, J=6.6 Hz, 1 H), 3.11 (d, J=8.0 Hz, 1 H), 2.45 (d, J=8.6 Hz, 1 H), 2.14-1.99 (m, 1 H), 1.19 (d, J=6.8 Hz, 3 H).

Description 153 methyl 4-((1S)-1-(3-(4-(trifluoromethyl)benzyl)-3-azabicyclo[3.1.0]hexane-2-carboxamido)ethyl)benzoate (syn diastereoisomers mixture) (D153)

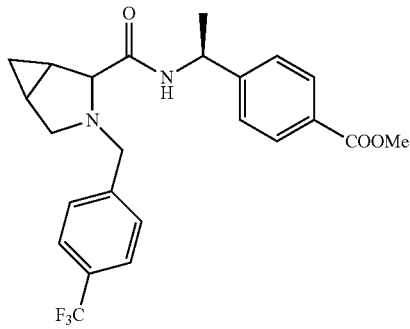 [SMILES: COC(=O)c1ccc([C@H](C)NC(=O)C2C3CC3CN2Cc2ccc(C(F)(F)F)cc2)cc1]

The title compound (D153) (85 mg) was prepared according to the general procedure for amides preparation (Method A) starting from 3-(4-(trifluoromethyl)benzyl)-3-azabicyclo[3.1.0]hexane-2-carboxylic acid (D110) (55 mg) and (S)-methyl 4-(1-aminoethyl)benzoate hydrochloride (43.3 mg). (EDC.HCl: 1.05 eq; reaction time: 18 hrs; RT)

MS: (ES/+) m/z: 447.3 [MH$^+$] C24H25F3N2O3 requires 446.18

$^1$H NMR (400 MHz, CHCl3-d) δ (ppm): 8.04 (d, J=8.0 Hz, 2 H), 7.97 (d, J=8.0 Hz, 2 H), 7.63 (d, J=7.7 Hz, 2 H), 7.49 (d, J=7.8 Hz, 2 H), 7.44-7.31 (m, 6 H), 7.27-7.05 (m, 4 H), 5.30-5.09 (m, 2 H), 3.93 (d, J=6.0 Hz, 7 H), 3.77 (d, J=13.8 Hz, 1 H), 3.55-3.39 (m, 3 H), 3.34 (d, J=13.6 Hz, 1 H), 3.05 (dd, J=9.5, 13.1 Hz, 2 H), 2.56 (t, J=9.4 Hz, 2 H), 1.86 (d, J=17.4 Hz, 2 H), 1.57 (d, J=6.8 Hz, 3 H), 1.53 (d, J=3.1 Hz, 2 H), 1.44 (d, J=6.8 Hz, 3 H), 0.76-0.59 (m, 2 H), 0.58-0.40 (m, 2 H).

Descriptions 154 a and 154b methyl 4-(1-(3-(4-(trifluoromethyl)benzyl)-3-azabicyclo[3.1.0]hexane-2-carboxamido)cyclopropyl)benzoate (enantiomer 1) (D154a) and methyl 4-(1-(3-(4-(trifluoromethyl)benzyl)-3-azabicyclo[3.1.0]hexane-2-carboxamido)cyclopropyl)benzoate (enantiomer 2) (D154b)

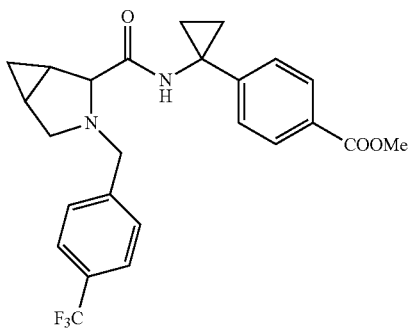 [SMILES: COC(=O)c1ccc(C2(NC(=O)C3C4CC4CN3Cc3ccc(C(F)(F)F)cc3)CC2)cc1]

To a solution of 3-(4-(trifluoromethyl)benzyl)-3-azabicyclo[3.1.0]hexane-2-carboxylic acid (D110) (55 mg, 0.19 mmol) in DCM (5 ml), HOBT.H2O (39 mg, 0.19 mmol), EDC HCl (35 mg, 0.20 mmol) were added and the mixture stirred 30 min to RT. Methyl 4-(1-aminocyclopropyl)benzoate hydrochloride (43.3 mg, 0.19 mmol) were added and the resulting mixture stirred 18 hrs at RT. The mixture was then diluted with DCM, and washed with sat. sol. NaHCO$_3$ (2×10 ml) then water (10 ml). Collected organic phases after drying over Na$_2$SO$_4$ and solvent evaporation afforded a residue which was purified by SPE-Si cartridge (5 g9 eluting with a mixture DCM/EtOAc 80/20. Collected fractions after solvent evaporation afforded the title compound 50 mg of racemic mixture which was submitted for chiral HPLC separation (Preparative chromatographic conditions: Column: DAICEL AD-H; Mobile phase: n-heptane/EtOH/DEA 60%/40%/0.1% v/v Flow rate 10 ml/min; DAD: 249 nm). Collected fractions after solvent evaporation, afforded the two enantiomers (D154a) (10 mg) and (D154b) (15 mg).

(D154a) (enantiomer 1 with syn relative stereochemistry): retention time: 10.1 min MS: (ES/+) m/z: 459 [MH$^+$] C25H25F3N2O3 requires 458.18

$^1$H NMR (400 MHz, CHCl3-d) δ (ppm): 7.96 (d, J=8.3 Hz, 2 H), 7.63 (d, J=7.8 Hz, 2 H), 7.48-7.32 (m, 2 H), 7.26 (d, J=8.8 Hz, 2 H), 3.91 (s, 4 H), 3.55-3.35 (m, 2 H), 3.19-3.00 (m, 1 H), 2.69-2.47 (m, 1 H), 2.03-1.83 (m, 1 H), 1.49-1.37 (m, 1 H), 1.36-1.24 (m, 2 H), 1.21-1.14 (m, 1 H), 0.88-0.72 (m, 1 H), 0.68-0.50 (m, 1 H)

(D154b) (enantiomer 2 with syn relative stereochemistry): retention time: 18.1 min MS: (ES/+) m/z: 459 [MH$^+$] C25H25F3N2O3 requires 458.18

Description 155 methyl 4-((1S)-1-(2-(4-(trifluoromethyl)benzyl)-2-azabicyclo[2.2.2]octane-3-carboxamido)ethyl)benzoate (D155)

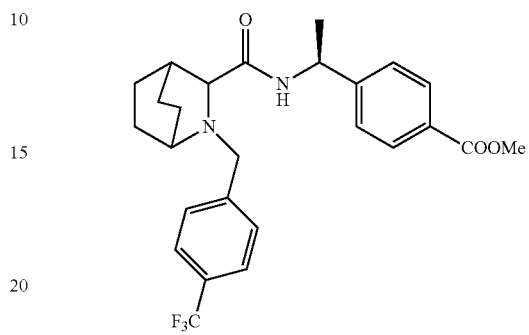

The title compound (D155) (12 mg) was prepared according to the general procedure for amides preparation (Method C) starting from 2-(4-(trifluoromethyl)benzyl)-2-azabicyclo[2.2.2]octane-3-carboxylic acid (D111) (22.5 mg) and (S)-methyl 4-(1-aminoethyl)benzoate hydrochloride (17 mg). (Reaction time: 2 hrs; 60° C.)

MS: (ES/+) m/z: 475.1 [MH$^+$] C26H29F3N2O3 requires 474.21

Description 156 methyl 4-(1-(2-(4-(trifluoromethyl)benzyl)-2-azabicyclo[2.2.2]octane-3-carboxamido)cyclopropyl)benzoate (D156)

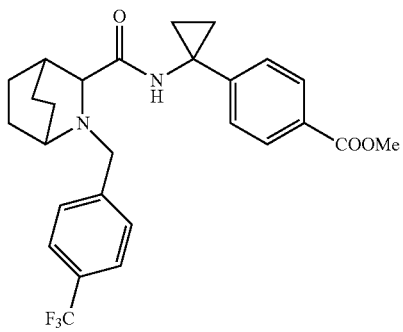 [SMILES: COC(=O)c1ccc(C2(NC(=O)C3C4CCC(CC4)N3Cc3ccc(C(F)(F)F)cc3)CC2)cc1]

The title compound (D156) (12 mg) was prepared according to the general procedure for amides preparation (Method C) starting from 2-(4-(trifluoromethyl)benzyl)-2-azabicyclo[2.2.2]octane-3-carboxylic acid (D111) (22.5 mg) and methyl 4-(1-aminocyclopropyl)benzoate hydrochloride (18 mg). (Reaction time: 2 hrs; 60° C.)

MS: (ES/+) m/z: 487.4 [MH$^+$] C27H29F3N2O3 requires 486.21

Description 157

(R)-methyl 4-(1-(2-methyl-1-(4-(trifluoromethyl)benzyl)piperidine-2-carboxamido)cyclopropyl)benzoate (D157)

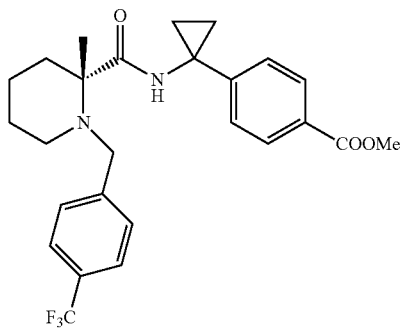 [SMILES: COC(=O)c1ccc(C2(NC(=O)[C@@]3(C)CCCCN3Cc3ccc(C(F)(F)F)cc3)CC2)cc1]

The title compound (D157) (5 mg) was prepared according to the general procedure for amides preparation (Method B) starting from lithium (R)-2-methyl-1-(4-(trifluoromethyl)benzyl)piperidine-2-carboxylate (D112) (20 mg) and methyl 4-(1-aminocyclopropyl)benzoate hydrochloride (17.2 mg).

MS: (ES/+) m/z: 475.4 [MH$^+$] C26H29F3N2O3 requires 474.21

Description 158 methyl 4-((S)-1-((R)-2-methyl-1-(4-(trifluoromethyl)benzyl)piperidine-2-carboxamido)ethyl)benzoate (D158)

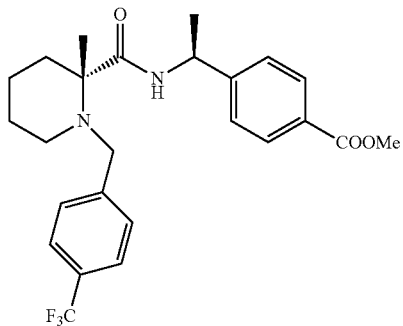 [SMILES: COC(=O)c1ccc([C@H](C)NC(=O)[C@@]2(C)CCCCN2Cc2ccc(C(F)(F)F)cc2)cc1]

The title compound (D158) (10 mg) was prepared according to the general procedure for amides preparation (Method B) starting from lithium (R)-2-methyl-1-(4-(trifluoromethyl)benzyl)piperidine-2-carboxylate (D112) (20 mg) and (S)-methyl 4-(1-aminoethyl)benzoate hydrochloride (16.32 mg).

MS: (ES/+) m/z: 463.4 [MH$^+$] C25H29F3N2O3 requires 462.21

Description 159

(R)-methyl 4-(1-(2-methyl-1-(4-(trifluoromethyl)benzyl)pyrrolidine-2-carboxamido)cyclopropyl)benzoate (D159)

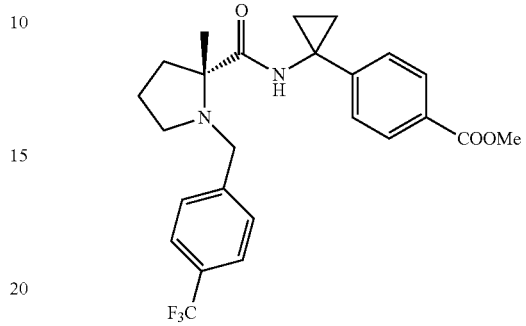

The title compound (D159) (13 mg) was prepared according to the general procedure for amides preparation (Method A) starting from lithium (R)-2-methyl-1-(4-(trifluoromethyl)benzyl)pyrrolidine-2-carboxylate (D113) (21 mg) and (S)-methyl 4-(1-aminoethyl)benzoate hydrochloride (16.3 mg).

MS: (ES/+) m/z: 461.4 [MH$^+$] C25H27F3N2O3 requires 460.20

Description 160 methyl 4-((S)-1-((2R,4S)-4-fluoro-1-(3-(trifluoromethyl)benzyl)pyrrolidine-2-carboxamido)ethyl)benzoate (D160)

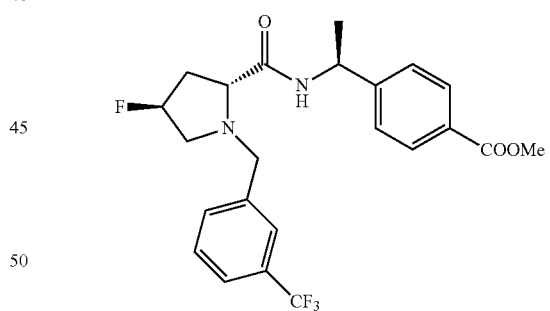

The title compound (D160) (67.3 mg) was prepared according to the general procedure for amides preparation (Method A) starting from lithium (2R,4S)-4-fluoro-1-(3-(trifluoromethyl)benzyl)pyrrolidine-2-carboxylate (D114) (60 mg) and (S)-methyl 4-(1-aminoethyl)benzoate hydrochloride (43.5 mg). (Reaction time: 18 hrs; RT)

MS: (ES/+) m/z: 475.2 [MH+Na$^+$] C23H24F4N2O3 requires 452.17

$^1$H NMR (400 MHz, CHCl3-d) δ (ppm): 8.01 (d, J=8.1 Hz, 2 H), 7.75-7.46 (m, 5 H), 7.36 (d, J=8.1 Hz, 2 H), 5.32-5.00 (m, 2 H), 4.01 (d, J=13.2 Hz, 1 H), 3.92 (s, 3 H), 3.70 (d, J=13.2 Hz, 1 H), 3.54-3.33 (m, 2 H), 2.73-2.41 (m, 2 H), 2.31-2.11 (m, 1 H), 1.42 (d, J=6.8 Hz, 3 H)

Description 161 lithium 4-((S)-1-((2R,4S)-4-fluoro-1-(3-(trifluoromethyl)benzyl)pyrrolidine-2-carboxamido)ethyl)benzoate (D161)

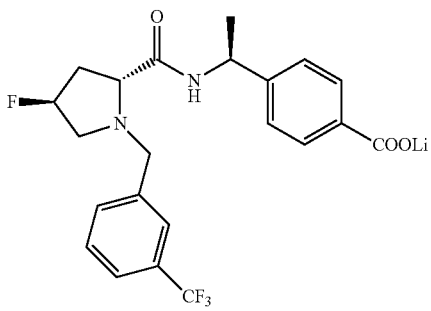

The title compound (D161) (50 mg) was prepared according to the general procedure for esters hydrolysis (Method A) starting from methyl 4-((S)-1-((2R,4S)-4-fluoro-1-(3-(trifluoromethyl)benzyl)pyrrolidine-2-carboxamido)ethyl)benzoate (D160) (67.3 mg). (LiOH H$_2$O: 4 eq; reaction time: 18 hrs).

MS: (ES/+) m/z: 439.2 [M−Li+2H$^+$] C22H21F4LiN2O3 requires 444.16

$^1$H NMR (400 MHz, MeOH-d4) δ (ppm): 7.90 (d, J=7.9 Hz, 2 H), 7.71 (s, 4 H), 7.27 (d, J=8.1 Hz, 2 H), 5.28-5.07 (m, 1 H), 4.95-4.88 (1 H under solvent), 4.00-3.90 (m, 1 H), 3.83 (s, 1 H), 3.43-3.35 (m, 2 H), 2.83-2.50 (m, 2 H), 2.16-1.98 (m, 1 H), 1.34 (d, J=7.0 Hz, 3 H)

Description 162

4-((S)-1-((2R,4S)-4-fluoropyrrolidine-2-carboxamido)ethyl)benzoic acid (D162)

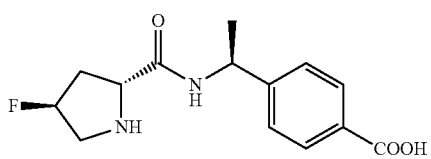 [SMILES: C[C@H](NC(=O)[C@H]1C[C@H](F)CN1)c1ccc(C(=O)O)cc1]

A suspension of lithium 4-((S)-1-((2R,4S)-4-fluoro-1-(3-(trifluoromethyl)benzyl)pyrrolidine-2-carboxamido)ethyl)benzoate (D161) (47 mg) and 10% w Pd/C (5 mg) in MeOH (5 ml) and 1M HCl (0.5 ml) was stirred under a constant current of H$_2$ for 3 hrs. Catalyst was filtered off and solvent evaporated to afford a residue which was triturated with cHex and filtered to afford the title compound (D162) (22 mg).

MS: (ES/+) m/z: 281.2 [MH$^+$] C14H17FN4O3 requires 280.12

$^1$H NMR (400 MHz, MeOH-d4) δ (ppm): 8.99-8.87 (m, 1 H), 8.09-7.98 (m, 2 H), 7.52-7.46 (m, 2 H), 5.60-5.36 (m, 1 H), 5.20-5.06 (m, 1 H), 4.55-4.44 (m, 1H), 3.86-3.72 (m, 1 H), 3.66-3.47 (m, 1 H), 2.94-2.72 (m, 1 H), 2.65-2.45 (m, 1 H), 1.54 (d, J=7.0 Hz, 3 H).

Description 163

4-(trifluoromethyl)benzyl 4-((S)-1-((2R,4S)-4-fluoro-1-(4-(trifluoromethyl)benzyl)pyrrolidine-2-carboxamido)ethyl)benzoate (D163)

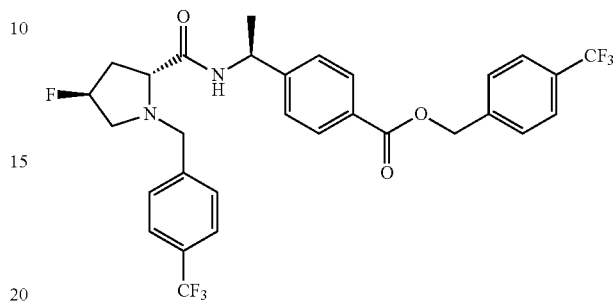

The title compound (D163) (31 mg) was prepared according to the general procedure for substituted benzylamine preparation starting from 4-((S)-1-((2R,4S)-4-fluoropyrrolidine-2-carboxamido)ethyl)benzoic acid (D162) (22 mg). (Na$_2$CO$_3$: 4 eq; reaction time: 18 hrs; 68° C.)

MS: (ES/+) m/z: 597.4 [MH$^+$] C30H27F7N2O3 requires 596.54

$^1$H NMR (400 MHz, CHCl3-d) δ (ppm): 8.05 (d, J=8.1 Hz, 2 H), 7.72-7.52 (m, 7H), 7.45 (d, J=7.8 Hz, 2 H), 7.37 (d, J=8.1 Hz, 2 H), 5.42 (s, 2 H), 5.27-4.99 (m, 2 H), 4.01 (d, J=13.3 Hz, 1 H), 3.71 (d, J=13.3 Hz, 1 H), 3.47-3.32 (m, 2 H), 2.72-2.45 (m, 2 H), 2.29-2.09 (m, 1 H), 1.40 (d, J=7.0 Hz, 3 H).

Description 164 methyl 4-((S)-1-((R)-4,4-difluoro-1-(3-(trifluoromethyl)benzyl)pyrrolidine-2-carboxamido)ethyl)benzoate (D164)

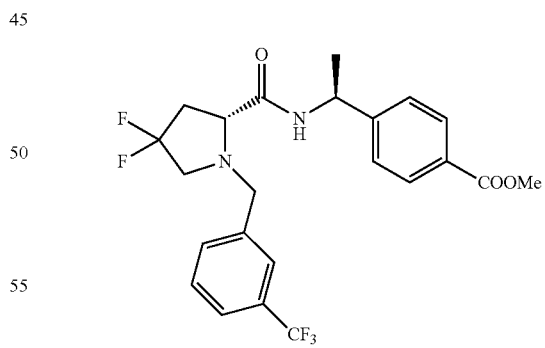

The title compound (D164) (37 mg) was prepared according to the general procedure for amides preparation (Method A) starting from lithium (R)-4,4-difluoro-1-(3-(trifluoromethyl)benzyl)pyrrolidine-2-carboxylate (D115) (51 mg) and (S)-methyl 4-(1-aminoethyl)benzoate hydrochloride (35 mg). (Reaction time: 48 hrs; RT).

MS: (ES/+) m/z: 471.2 [MH$^+$] C23H23F5N2O3 requires 470.16

Description 165 methyl 4-((S)-1-((R)-4,4-difluoropyrrolidine-2-carboxamido)ethyl)benzoate (D165)

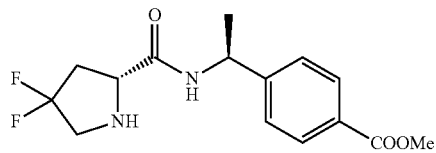 [SMILES: COC(=O)c1ccc([C@H](C)NC(=O)[C@H]2CC(F)(F)CN2)cc1]

A suspension of methyl 4-((S)-1-((R)-4,4-difluoro-1-(3-(trifluoromethyl)benzyl)pyrrolidine-2-carboxamido)ethyl)benzoate (D164) (33 mg) and 10% w Pd/C (5 mg) in MeOH (5 ml) and 1M HCl (0.5 ml) was stirred under a constant current of $H_2$ for 3 hrs. Catalyst was filtered off and solvent evaporated to afford a residue which was triturated with cHex and filtered to afford the title compound (D165) (30 mg).

MS: (ES/+) m/z: 313.2 [MH$^+$] C23H23F5N2O3 requires 312.13

Description 166 methyl 4-((S)-1-((R)-4,4-difluoro-1-(4-(trifluoromethyl)benzyl)pyrrolidine-2-carboxamido)ethyl)benzoate (D166)

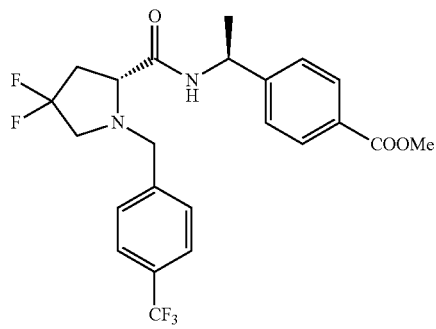 [SMILES: COC(=O)c1ccc([C@H](C)NC(=O)[C@H]2CC(F)(F)CN2Cc2ccc(C(F)(F)F)cc2)cc1]

The title compound (D166) (16.5 mg) was prepared according to the general procedure for substituted benzylamine preparation starting from methyl 4-((S)-1-((R)-4,4-difluoropyrrolidine-2-carboxamido)ethyl)benzoate (D165) (30 mg) and 4-(Trifluoromethyl)benzyl bromide (33 mg). (Na$_2$CO$_3$: 2.5 eq; reaction time: 18 hrs; 68° C.)

MS: (ES/+) m/z: 471 [MH$^+$] C23H23F5N2O3 requires 470.16

$^1$H NMR (400 MHz, CHCl3-d) δ (ppm): 8.04 (d, J=7.8 Hz, 2 H), 7.67 (d, J=7.8 Hz, 2 H), 7.43 (d, J=7.8 Hz, 2 H), 7.35 (d, J=7.8 Hz, 3 H), 5.10 (t, J=7.1 Hz, 1H), 4.01 (d, J=13.7 Hz, 1 H), 3.94 (s, 3 H), 3.68 (d, J=13.2 Hz, 1 H), 3.61-3.54 (m, 1 H), 3.36 (d, J=6.8 Hz, 1 H), 2.87 (d, J=17.1 Hz, 2 H), 2.29 (br. s., 1 H), 1.45 (d, J=6.8 Hz, 3 H)

EXAMPLES

Example 1 lithium 4-((1S)-1-(1-(4-(trifluoromethyl)benzyl)piperidine-2-carboxamido)ethyl)benzoate (diastereoisomers mixture) (E1)

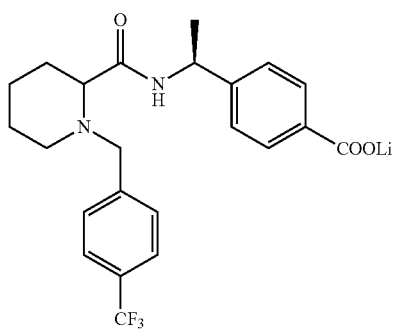

The title compound (E1) (70 mg) was prepared according to the general procedure for esters hydrolysis (Method A) starting from methyl 4-((1S)-1-(1-(4-(trifluoromethyl)benzyl)piperidine-2-carboxamido)ethyl)benzoate (D116) (75 mg).

(LiOH: 1.2 eq; reaction time: 3 hrs; RT)

MS: (ES/+) m/z: 435 [M−Li+2H$^+$] C23H24F3LiN2O3 requires 440.19

Chiral HPLC: [Phenomenex Lux Cellulose-1; Mobile phase A: 70% n-hexane (+0.5% TFA), B: 30% EtOH; DAD: 230 nm]: Peak 1 retention time: 7.51 min; peak 2 retention time: 38.92 min.

$^1$H NMR (400 MHz, DMSO-d6) δ (ppm): 8.20 (br. s., 2 H) 7.81 (d, 2 H) 7.75 (d, 2 H) 7.66 (d, 4 H) 7.50-7.61 (m, 4 H) 7.10-7.31 (m, 4 H) 4.98 (br. s., 2 H) 3.73 (t, 2 H) 3.20 (d, 2 H) 2.83 (d, 2 H) 2.74 (d, 2 H) 1.93 (br. s., 2 H) 1.56-1.82 (m, 6 H) 1.46 (d, 3 H) 1.41 (br. s., 1 H) 1.35 (dd, 6 H) 1.25 (br. s., 2 H).

Example 2 lithium 4-((S)-1-((R)-1-(4-fluorobenzyl)piperidine-2-carboxamido)ethyl)benzoate (E2)

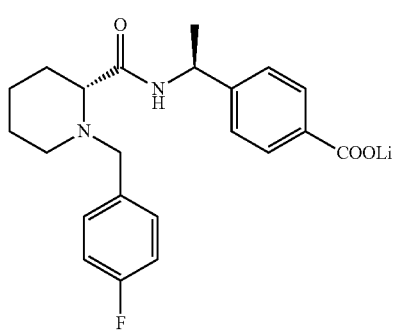

The title compound (E2) (8 mg) was prepared according to the general procedure for esters hydrolysis (Method A) starting from methyl 4-((S)-1-((R)-1-(4-fluorobenzyl)piperidine-2-carboxamido)ethyl)benzoate (D117) (10 mg).

(LiOH: 1.5 eq; Reaction time: 3 hrs; RT)

MS: (ES/+) m/z: 385.3 [M−Li+2H$^+$] C22H24FLiN2O3 requires 390.19

Chiral HPLC: [DAICEL OD-H; Mobile phase A: 60% n-hexane (+0.5% TFA), B: 40% EtOH; DAD: 235 nm]: Peak retention time: 5.68 min.

$^1$H NMR (400 MHz, MeOH-d4) δ (ppm): 7.94 (d, J=7.9 Hz, 2 H), 7.45-7.27 (m, 4H), 7.03 (t, J=8.5 Hz, 2 H), 5.11 (d, J=6.9 Hz, 1 H), 3.75 (d, J=13.1 Hz, 1 H), 3.17 (d, J=13.2 Hz, 1 H), 2.81 (br. s., 2 H), 2.05-1.94 (m, 1 H), 1.91-1.64 (m, 3H), 1.58 (br. s., 2 H), 1.48 (d, J=6.9 Hz, 3 H), 1.40-1.25 (m, 1 H)

Example 3 lithium 4-((S)-1-((R)-1-(4-(trifluoromethyl)benzyl)piperidine-2-carboxamido)ethyl)benzoate (E3)

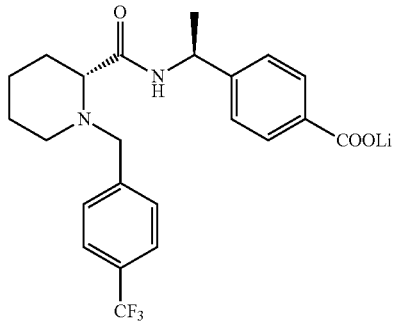

The title compound (E3) (21.3 mg) was prepared according to the general procedure for esters hydrolysis (Method A) starting from methyl 4-((S)-1-((R)-1-(4-(trifluoromethyl)benzyl)piperidine-2-carboxamido)ethyl)benzoate (D118) (24 mg).

(LiOH: 1.5 eq; Reaction time: 3 hrs; RT)

MS: (ES/+) m/z: 435.2 [M−Li+2H$^+$] C23H24F3LiN2O3 requires 440.19

Chiral HPLC [DAICEL OD-H; Mobile phase A: 60% n-hexane (+0.5% TFA), B: 40% EtOH; DAD: 235 nm]: Peak retention time: 6.09 min.

$^1$H NMR (400 MHz, MeOH-d4) δ (ppm): 7.93 (d, J=7.9 Hz, 2 H), 7.65-7.57 (m, 2H), 7.57-7.49 (m, 2 H), 7.36 (d, J=7.9 Hz, 2 H), 5.16-5.04 (m, 1 H), 3.88-3.78 (m, 1 H), 3.27 (s, 1 H), 2.86 (d, J=10.3 Hz, 2 H), 2.09-1.95 (m, 1 H), 1.94-1.65 (m, 3 H), 1.59 (br. s., 2 H), 1.46 (d, J=6.9 Hz, 3 H), 1.41-1.26 (m, 1 H).

Example 4 lithium (R)-4-(1-(1-(4-(trifluoromethyl)benzyl)piperidine-2-carboxamido)cyclopropyl)benzoate (E4)

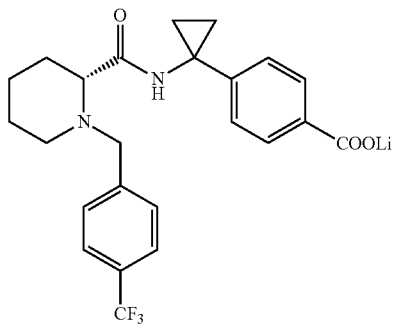

The title compound (E4) (50 mg) was prepared according to the general procedure for esters hydrolysis (Method A) starting from (R)-methyl 4-(1-(1-(4-(trifluoromethyl)benzyl)piperidine-2-carboxamido)cyclopropyl)benzoate (D119) (74 mg). (LiOH: 3 eq; Reaction time: 3 hrs; RT)

MS: (ES/+) m/z: 447.2 [M−Li+2H$^+$] C24H24F3LiN2O3 requires 452.19

Chiral HPLC: [DAICEL OD-H; Mobile phase A: 80% n-hexane (+0.2% TFA), B: 20% EtOH; DAD: 243 nm]: Peak retention time: 22.92 min.

Example 5 lithium (R)-4-(1-(1-(4-chlorobenzyl)piperidine-2-carboxamido)cyclopropyl)benzoate (E5)

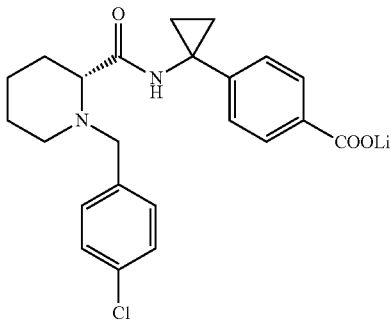

The title compound (E5) (31 mg) was prepared according to the general procedure for esters hydrolysis (Method A) starting from (R)-methyl 4-(1-(1-(4-chlorobenzyl)piperidine-2-carboxamido)cyclopropyl)benzoate (D120) (45 mg).

(LiOH: 3 eq; Reaction time: 3 hrs; RT)

MS: (ES/+) m/z: 413 [M−Li+2H$^+$] C23H24ClLiN2O3 requires 418.16

$^1$H NMR (400 MHz, MeOH-d4) δ (ppm): 7.85 (d, J=8.0 Hz, 2 H), 7.33 (d, J=4.9 Hz, 4 H), 7.23 (d, J=8.1 Hz, 2 H), 4.90-4.82 (1 H under solvent peak), 3.79-3.65 (m, 1 H), 3.21-3.07 (m, 1 H), 2.93-2.75 (m, 2 H), 2.06-1.86 (m, 2 H), 1.86-1.68 (m, 2 H), 1.66-1.50 (m, 2 H), 1.41-1.15 (m, 4 H).

Example 6 lithium (R)-4-(1-(1-(4-cyanobenzyl)piperidine-2-carboxamido)cyclopropyl)benzoate (E6)

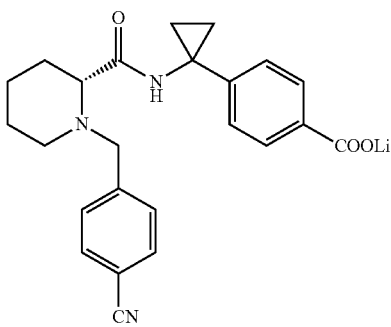

The title compound (E6) (34 mg) was prepared according to the general procedure for esters hydrolysis (Method A) starting from (R)-methyl 4-(1-(1-(4-cyanobenzyl)piperidine-2-carboxamido)cyclopropyl)benzoate (D121) (35 mg). (LiOH: 3 eq; Reaction time: 3 hrs; RT)

MS: (ES/+) m/z: 404 [M−Li+2H$^+$] C24H24LiN3O3 requires 409.20

$^1$H NMR (400 MHz, MeOH-d4) δ (ppm): 7.90-7.79 (m, 2 H), 7.74-7.65 (m, 2 H), 7.62-7.54 (m, 2 H), 7.28-7.17 (m, 2 H), 4.90-4.82 (1 H under solvent peak), 3.84-3.72 (m, 1 H), 3.28-3.19 (m, 1 H), 2.92-2.77 (m, 2 H), 2.07-1.89 (m, 2H), 1.87-1.68 (m, 2 H), 1.65-1.53 (m, 2 H), 1.43-1.10 (m, 4 H).

Example 7

4-(1-(6-(4-(trifluoromethyl)benzyl)-6-azaspiro[2.5]octane-5-carboxamido)cyclopropyl)benzoic acid (single unknown enantiomer) (E7)

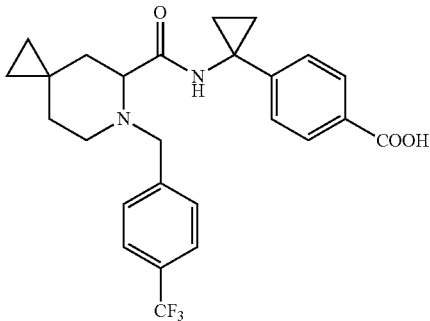 [SMILES: O=C(O)c1ccc(C2(NC(=O)C3CC4(CCN3Cc3ccc(C(F)(F)F)cc3)CC4)CC2)cc1]

Procedure A:

The title compound (E7) (54 mg) was prepared according to the general procedure for esters hydrolysis (Method B) starting from methyl 4-(1-(6-(4-(trifluoromethyl)benzyl)-6-azaspiro[2.5]octane-5-carboxamido)cyclopropyl)benzoate (D122b) (100 mg). (LiOH: 4 eq; Reaction time: 18 hrs; RT)

MS: (ES/+) m/z: 473.4 [MH$^+$] C26H27F3N2O3 requires 472.20

Chiral HPLC: [DAICEL AD-H; Mobile phase A: 90% n-heptane (+0.2% TFA), B: 10% EtOH; DAD: 245 nm]: Peak retention time: 18.97 min.

$^1$H NMR (400 MHz, CHCl3-d) δ (ppm): 7.97 (d, J=8.0 Hz, 2 H), 7.74-7.35 (m, 5H), 7.26 (br. s., 1 H), 3.86 (d, J=14.1 Hz, 1 H), 3.38 (d, J=14.1 Hz, 1 H), 3.08 (d, J=7.8 Hz, 1 H), 2.91 (d, J=9.8 Hz, 1 H), 2.27 (br. s., 1 H), 2.05 (t, J=11.2 Hz, 1H), 1.84 (br. s., 1 H), 1.50-1.24 (m, 4 H), 1.14 (br. s., 1 H), 0.98 (d, J=12.7 Hz, 1 H), 0.53-0.23 (m, 4 H)

Procedure B:

methyl 4-(1-(6-(4-(trifluoromethyl)benzyl)-6-azaspiro[2.5]octane-5-carboxamido)cyclopropyl)benzoate (D123)) (17.7 g, 36.38 mmol) was partitioned between dioxane (485 ml) and water (242 ml) prior addition of LiOH H$_2$O (6.1 g, 145.5 mmol). The mixture was stirred at RT for 10 hrs. Water (200 ml) was added followed by addition of acetic acid (5.27 ml). Dioxane was evaporated off and acetic acid was added until the pH of the aqueous solution reached the value of ~4. The white solid was filtered from the reaction and dried under vacuum overnight then 24 hrs under vacuum at 40° C. affording the title compound (E7) (16.7 g).

MS: (ES/+) m/z: 473.3 [MH$^+$] C26H27F3N2O3 requires 472.20

Chiral HPLC: [DAICEL AD-H; Mobile phase A: 90% n-heptane (+0.2% TFA), B: 10% EtOH; DAD: 245 nm]: Peak retention time: 19.07 min.

$^1$H NMR (400 MHz, DMSO-d6) δ (ppm): 12.92-12.51 (m, 1 H), 8.83-8.62 (m, 1H), 7.85-7.75 (m, 2 H), 7.74-7.57 (m, 4 H), 7.26-7.14 (m, 2 H), 3.87-3.72 (m, 1 H), 3.27-3.20 (m, 1 H), 2.99-2.86 (m, 1 H), 2.79-2.69 (m, 1 H), 2.19-1.98 (m, 2 H), 1.86-1.70 (m, 1 H), 1.32-1.07 (m, 5 H), 0.94-0.82 (m, 1 H), 0.46-0.17 (m, 4 H).

Example 8

4-(1-(6-((6-(trifluoromethyl)pyridin-3-yl)methyl)-6-azaspiro[2.5]octane-5-carboxamido)cyclopropyl)benzoic acid (single unknown enantiomer) (E8)

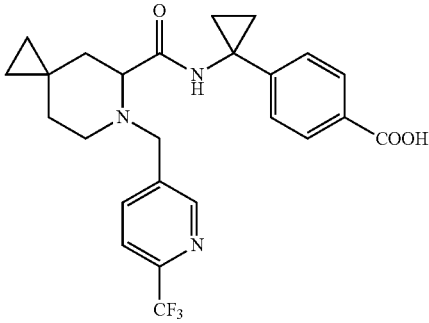 [SMILES: O=C(O)c1ccc(C2(NC(=O)C3CC4(CCN3Cc3ccc(C(F)(F)F)nc3)CC4)CC2)cc1]

The title compound (E8) (35 mg) was prepared according to the general procedure for esters hydrolysis (Method D) starting from methyl 4-(1-(6-((6-(trifluoromethyl)pyridin-3-yl)methyl)-6-azaspiro[2.5]octane-5-carboxamido)cyclopropyl)benzoate (D124) (47 mg). (LiOH: 4 eq; Reaction time: 5 hrs; RT)

MS: (ES/+) m/z: 474.2 [MH$^+$] C25H26F3N3O3 requires 473.19

$^1$H NMR (400 MHz, MeOH-d4) δ (ppm): 8.74 (s, 1 H), 8.10 (d, J=8.3 Hz, 1 H), 7.90 (d, J=8.3 Hz, 2 H), 7.79 (d, J=7.8 Hz, 1 H), 7.31 (d, J=8.3 Hz, 2 H), 3.88 (d, J=14.2 Hz, 1 H), 3.39 (d, J=14.2 Hz, 2 H), 3.06 (dd, J=2.7, 10.5 Hz, 1 H), 2.84 (d, J=11.2 Hz, 1 H), 2.37-2.12 (m, 2 H), 2.04-1.88 (m, 1 H), 1.45-1.14 (m, 6 H), 0.94 (d, J=11.2 Hz, 1 H), 0.51-0.28 (m, 4 H).

Example 9

4-(1-(6-(3-(trifluoromethyl)benzyl)-6-azaspiro[2.5]octane-5-carboxamido)cyclopropyl)benzoic acid (single unknown enantiomer) (E9)

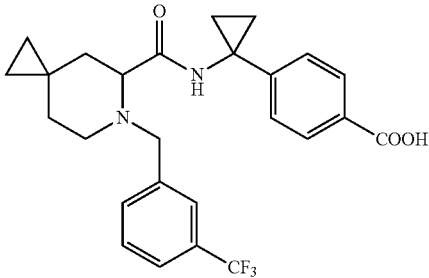 [SMILES: O=C(O)c1ccc(C2(NC(=O)C3CC4(CCN3Cc3cccc(C(F)(F)F)c3)CC4)CC2)cc1]

The title compound (E9) (39 mg) was prepared according to the general procedure for esters hydrolysis (Method D) starting from methyl 4-(1-(6-(3-(trifluoromethyl)benzyl)-6- azaspiro[2.5]octane-5-carboxamido)cyclopropyl)benzoate (single unknown enantiomer) (D125) (60.7 mg). (LiOH H₂O: 4 eq; reaction time: 18 hrs)

MS: (ES/+) m/z: 473.2 [MH⁺] C26H27F3N2O3 requires 472.20

¹H NMR (400 MHz, DMSO-d6) δ (ppm): 12.90-12.63 (m, 1 H), 8.71-8.64 (m, 1H), 7.81-7.74 (m, 2 H), 7.72-7.66 (m, 2 H), 7.64-7.55 (m, 2 H), 7.22-7.11 (m, 2 H), 3.77-3.66 (m, 1 H), 3.60-3.47 (m, 1 H), 3.22-3.11 (m, 1 H), 3.03-2.95 (m, 1 H), 2.39-2.29 (m, 1 H), 2.25-2.11 (m, 1 H), 1.76-1.64 (m, 1 H), 1.31-1.19 (m, 3 H), 1.19-1.07 (m, 3 H), 1.07-0.91 (m, 2 H), 0.73-0.59 (m, 1 H), 0.26-0.17 (m, 1 H).

Example 10

4-((1S)-1-(6-(4-(trifluoromethyl)benzyl)-6-azaspiro[2.5]octane-5-carboxamido)ethyl)benzoic acid (single unknown diastereoisomer) (E10)

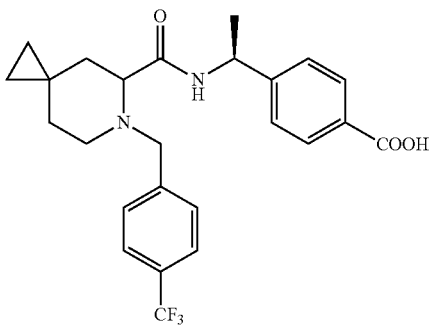 [SMILES: C[C@H](NC(=O)C1CC2(CCN1Cc1ccc(C(F)(F)F)cc1)CC2)c1ccc(C(=O)O)cc1]

The title compound (E10) (6.4 mg) was prepared according to the general procedure for esters hydrolysis (Method B) starting from starting from 4-(trifluoromethyl)benzyl 4-((1S)-1-(6-(4-(trifluoromethyl)benzyl)-6-azaspiro[2.5]octane-5-carboxamido)ethyl)benzoate (D129) (15 mg). (LiOH H₂O: 4 eq; Reaction time: 18 hrs)

MS: (ES/+) m/z: 461 [MH⁺] C25H27F3N2O3 requires 460.20

¹H NMR (400 MHz, MeOH-d4) δ (ppm): 7.98 (d, J=7.8 Hz, 2 H), 7.71-7.51 (m, 4H), 7.44 (d, J=7.6 Hz, 2 H), 5.21-5.02 (m, 1 H), 4.00-3.79 (m, 1 H), 3.11-2.96 (m, 1 H), 2.95-2.79 (m, 1 H), 2.34-2.06 (m, 2 H), 2.04-1.87 (m, 1 H), 1.47 (d, J=6.9 Hz, 3 H), 1.38-1.23 (m, 1 H), 1.23-1.08 (m, 1 H), 1.00-0.81 (m, 2 H), 0.48-0.24 (m, 4 H)

Example 11

4-((1S)-1-(5-methyl-6-(4-(trifluoromethyl)benzyl)-6-azaspiro[2.5]octane-5-carboxamido)ethyl)benzoic acid (diastereoisomers mixture) (E11)

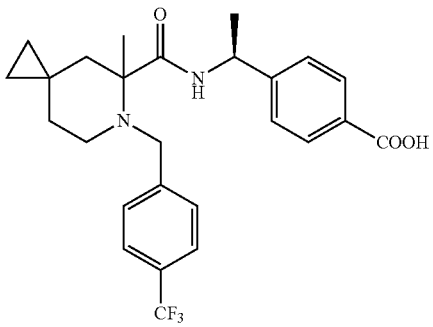 [SMILES: C[C@H](NC(=O)C1(C)CC2(CCN1Cc1ccc(C(F)(F)F)cc1)CC2)c1ccc(C(=O)O)cc1]

The title compound (E11) (4.5 mg) was prepared according to the general procedure for esters hydrolysis (Method B) starting from methyl 4-((1S)-1-(5-methyl-6-(4-(trifluoromethyl)benzyl)-6-azaspiro[2.5]octane-5-carboxamido)ethyl)benzoate (D130) (19 mg). (LiOH H₂O: 4 eq; reaction time: 18 hrs)

MS: (ES/+) m/z: 475.4 [MH⁺] C26H29F3N2O3 requires 474.21

¹H NMR (400 MHz, MeOH-d4) δ (ppm): 7.96 (d, J=7.8 Hz, 1 H), 7.76 (d, J=7.8 Hz, 1 H), 7.68 (s, 2 H), 7.56 (d, J=7.8 Hz, 1 H), 7.47-7.31 (m, 2 H), 7.15 (d, J=7.8 Hz, 1 H), 5.11-4.94 (m, 1 H), 3.51 (t, J=13.4 Hz, 1 H), 2.73 (dd, J=12.0, 19.8 Hz, 1 H), 2.65-2.46 (m, 1 H), 2.37-2.18 (m, 1 H), 2.05 (t, J=12.0 Hz, 1 H), 1.58-1.24 (m, 7 H), 1.18-1.00 (m, 1 H), 0.94 (d, J=11.2 Hz, 1 H), 0.49 (br. s., 2 H), 0.27 (d, J=6.8 Hz, 2 H).

Example 12

4-(1-(4,4-dimethyl-1-(4-(trifluoromethyl)benzyl)piperidine-2-carboxamido)cyclopropyl)benzoic acid (single unknown enantiomer) (E12)

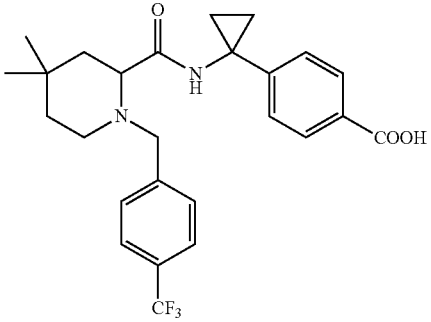 [SMILES: CC1(C)CCN(Cc2ccc(C(F)(F)F)cc2)C(C(=O)NC2(c3ccc(C(=O)O)cc3)CC2)C1]

The title compound (E12) (88.4 mg) was prepared according to the general procedure for esters hydrolysis (Method C) starting from methyl 4-(1-(4,4-dimethyl-1-(4-(trifluoromethyl)benzyl)piperidine-2-carboxamido)cyclopropyl)benzoate (enantiomer 2) (D131 b) (141 mg). (LiOH H₂O: 4 eq; reaction time: 18 hrs)

MS: (ES/+) m/z: 475.4 [MH⁺] C26H29F3N2O3 requires 474.21

Chiral HPLC: [DAICEL AD-H; Mobile phase A: 70% n-heptane (+0.1% AcOH), B: 30% EtOH; DAD: 245 nm]: Peak retention time: 11.4 min.

¹H NMR (400 MHz, CHCl3-d) δ (ppm): 7.97 (d, J=8.1 Hz, 2 H), 7.62 (d, J=7.8 Hz, 2 H), 7.41 (d, J=7.4 Hz, 3 H), 7.27 (br. s., 2 H), 3.82 (d, J=14.0 Hz, 1 H), 3.29 (d, J=13.5 Hz, 1 H), 3.10 (d, J=7.7 Hz, 1 H), 2.73 (d, J=10.0 Hz, 1 H), 2.23 (br. s., 1 H), 1.81 (d, J=13.1 Hz, 1 H), 1.49 (t, J=12.1 Hz, 2 H), 1.42-1.27 (m, 4 H), 1.13 (br. s., 1 H), 1.05-0.92 (m, 6 H)

Example 13

4-((1S)-1-(4,4-dimethyl-1-(4-(trifluoromethyl)benzyl)piperidine-2-carboxamido)ethyl)benzoic acid (single unknown diastereoisomer) (E13)

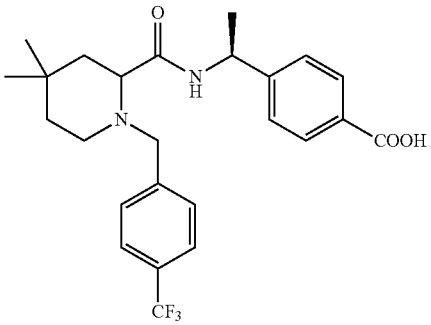 [SMILES: C[C@H](NC(=O)C1CC(C)(C)CCN1Cc1ccc(C(F)(F)F)cc1)c1ccc(C(=O)O)cc1]

The title compound (E13) (54.6 mg) was prepared according to the general procedure for esters hydrolysis (Method C) starting from methyl 4-((1S)-1-(4,4-dimethyl-1-(4-(trifluoromethyl)benzyl)piperidine-2-carboxamido)ethyl)benzoate (diastereoisomer 2) (D132b) (69 mg). (LiOH H$_2$O: 4 eq; reaction time: 18 hrs)

MS: (ES/+) m/z: 463.4 [MH$^+$] C25H29F3N2O3 requires 462.21

Chiral HPLC: [DAICEL AD-H; Mobile phase A: 70% n-heptane (+0.1% DEA), B: 30% EtOH; DAD: 235 nm]: Peak retention time: 10.4 min.

Example 14

4-((1S)-1-((2R)-4-fluoro-1-(4-(trifluoromethyl)benzyl)piperidine-2-carboxamido)ethyl)benzoic acid (diastereoisomers mixture) (E14)

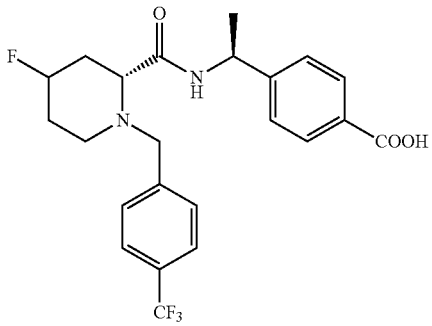 [SMILES: C[C@H](NC(=O)[C@H]1CC(F)CCN1Cc1ccc(C(F)(F)F)cc1)c1ccc(C(=O)O)cc1]

The title compound (E14) (42 mg) was prepared according to the general procedure for esters hydrolysis (Method D) starting from methyl 4-((1S)-1-((2R)-4-fluoro-1-(4-(trifluoromethyl)benzyl)piperidine-2-carboxamido)ethyl)benzoate (D133) (62 mg). (LiOH H$_2$O: 4 eq; reaction time: 5 hrs)

MS: (ES/+) m/z: 471.3 [MH$^+$] C23H24F4N2O3 requires 452.17

$^1$H NMR (400 MHz, MeOH-d4) δ (ppm): 7.99 (d, J=8.1 Hz, 2 H), 7.66-7.36 (m, 6H), 5.18-5.04 (m, 1 H), 3.88-3.76 (m, 1 H), 2.80-2.67 (m, 1 H), 2.55-2.35 (m, 1 H), 2.19-1.75 (m, 4 H), 1.49 (d, J=7.0 Hz, 3 H), 1.14 (d, J=6.1 Hz, 3 H).

Example 15

4-(1-((2R)-4-fluoro-1-(4-(trifluoromethyl)benzyl)piperidine-2-carboxamido)cyclopropyl)benzoic acid (diastereoisomers mixture) (E15)

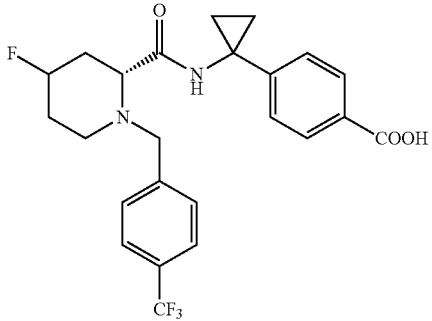 [SMILES: O=C(O)c1ccc(C2(NC(=O)[C@H]3CC(F)CCN3Cc3ccc(C(F)(F)F)cc3)CC2)cc1]

The title compound (E15) (15.8 mg) was prepared according to the general procedure for esters hydrolysis (Method D) starting from methyl 4-(1-((2R)-4-fluoro-1-(4-(trifluoromethyl)benzyl)piperidine-2-carboxamido)cyclopropyl)benzoate (D134) (25 mg). (LiOH H$_2$O: 4 eq; reaction time: 5 hrs)

MS: (ES/+) m/z: 471.3 [MH$^+$] C23H24F4N2O3 requires 452.17

$^1$H NMR (400 MHz, MeOH-d4) δ (ppm): 7.91 (d, J=8.1 Hz, 2 H), 7.69-7.53 (m, 4 H), 7.31 (d, J=8.1 Hz, 2 H), 5.06-4.91 (m, 1 H), 3.84 (d, J=13.7 Hz, 1 H), 3.24 (br. s., 1 H), 2.72 (d, J=11.8 Hz, 1 H), 2.42 (br. s., 1 H), 2.22-1.77 (m, 3 H), 1.47-1.16 (m, 6 H).

Example 16

4-((S)-1-((R)-4,4-difluoro-1-(4-(trifluoromethyl)benzyl)piperidine-2-carboxamido)ethyl)benzoic acid (E16)

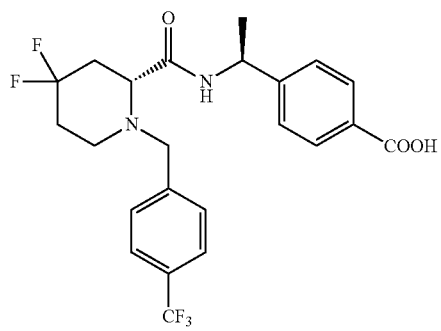

The title compound (E16) (15 mg) was prepared according to the general procedure for esters hydrolysis (Method D) starting from methyl 4-((S)-1-((R)-4,4-difluoro-1-(4-(trifluoromethyl)benzyl)piperidine-2-carboxamido)ethyl)benzoate (D135) (20 mg). (LiOH H$_2$O: 4 eq; reaction time: 18 hrs)

MS: (ES/+) m/z: 471.3 [MH$^+$] C23H23F5N2O3 requires 470.16

$^1$H NMR (400 MHz, DMSO-d6) δ (ppm): 8.63-8.54 (m, 1 H), 7.87-7.77 (m, 2 H), 7.74-7.63 (m, 2 H), 7.60-7.51 (m, 2 H), 7.40-7.27 (m, 2H), 5.06-4.92 (m, 1H), 3.76 (d, J=13.8 Hz, 1 H), 3.37-3.32 (1 H under residual solvent), 3.23-3.10 (m, J=7.1 Hz, 1 H), 2.85-2.74 (m, J=11.7 Hz, 1 H), 2.32-2.04 (m, 3 H), 2.05-1.83 (m, 2 H), 1.37 (d, J=6.8 Hz, 3 H).

Example 17

(R)-4-(1-(4,4-difluoro-1-(4-(trifluoromethyl)benzyl)piperidine-2-carboxamido)cyclopropyl)benzoic acid (E17

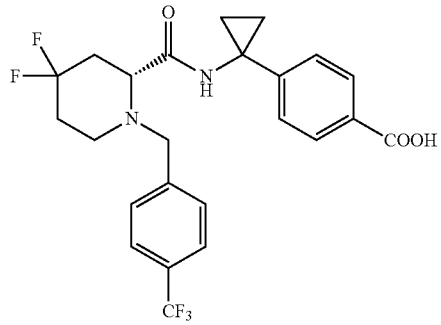 [SMILES: O=C(O)c1ccc(C2(NC(=O)[C@H]3CC(F)(F)CCN3Cc3ccc(C(F)(F)F)cc3)CC2)cc1]

Procedure A:
(R)-methyl 4-(1-(4,4-difluoro-1-(4-(trifluoromethyl)benzyl)piperidine-2-carboxamido)cyclopropyl)benzoate (D136) (30 mg, 60.4 mmol) was partitioned between dioxane (2 ml) and water (2 ml) prior addition of LiOH H$_2$O (10 mg, 242 mmol). The mixture was stirred at RT for 18 hrs then dioxane was evaporated off.

The aqueous solution was loaded onto a reverse phase Porapak cartridge (5 g) eluting with H$_2$O (with 0.1% CH$_3$CO$_2$H) then with MeCN (with 0.1% CH$_3$CO$_2$H). Collected fractions after solvent evaporation afforded a 19 mg of racemic mixture which was submitted for chiral HPLC separation (Preparative chromatographic conditions: Column: DAICEL AD-H; Mobile phase: n-heptane/EtOH/TFA 60%/40%/0.1% v/v Flow rate 10 ml/min; DAD: 245 nm). Collected fractions, after solvent evaporation afforded the title compound (E17) (11 mg).

MS: (ES/+) m/z: 483.3 [MH$^+$] C24H23F5N2O3 requires 482.16

Chiral HPLC [DAICEL AD-H; Mobile phase A: 60% n-heptane (+0.2% TFA), B: 40% IPA; DAD: 245 nm]: Peak retention time: 15.6 min.

$^1$H NMR (400 MHz, DMSO-d6) δ (ppm): 13.00-12.49 (m, 1 H), 9.18-8.93 (m, 1H), 7.81 (d, J=8.1 Hz, 2 H), 7.72 (br. s., 2 H), 7.64 (br. s., 2 H), 7.22 (d, J=8.1 Hz, 2 H), 3.99-3.84 (m, 1 H), 3.38-3.23 (m, 2 H), 2.97-2.80 (m, 1 H), 2.44-2.12 (m, 3 H), 2.10-1.89 (m, 2 H), 1.38-1.13 (m, 4 H)

Procedure B:

To a solution of methyl 4-(1-(4,4-difluoro-1-(4-(trifluoromethyl)benzyl)piperidine-2-carboxamido)cyclopropyl)benzoate (enantiomer 2) (D137b) (127 mg, 0.25 mmol) in dioxane (3 ml) and water (3 ml) LiOH H$_2$O (43 mg, 1.02 mmol) was added and the mixture was left stirring at RT for 16 hrs. Dioxane was evaporated off then acetic acid was added to the aqueous layer until the solution reached the value of pH≈4. The solid was filtered off and dissolved in DMF/DMSO. The mixture was loaded on SNAP-C18 gold cartridge (15 g) and eluted with a mixture H$_2$O containing AcOH (0.1%)/CH$_3$CN containing AcOH (0.1%) from 10/90 to 0/100. Collected fractions were evaporated in vacuo to afford a residue which was taken up in a mixture sat. sol. NH$_4$Cl/EtOAc (15/15 ml) and extracted with AcOEt (2×20 ml). The combined organic layers were evaporated in vacuo to afford the title compound (E17) (85 mg).

MS: (ES/+) m/z: 483 [MH$^+$] C24H23F5N2O3 requires 482.16

Chiral HPLC [DAICEL AD-H; Mobile phase A: 60% n-heptane (+0.2% TFA), B: 40% IPA; DAD: 245 nm]: Peak retention time: 15.6 min.

$^1$H NMR (400 MHz, DMSO-d6) δ (ppm): 12.74 (br. s., 1 H), 8.96 (s, 1 H), 7.82-7.75 (m, J=8.8 Hz, 2 H), 7.74-7.66 (m, J=7.8 Hz, 2 H), 7.66-7.58 (m, J=7.8 Hz, 2 H), 7.26-7.15 (m, J=8.8 Hz, 2 H), 3.82 (d, J=14.2 Hz, 1 H), 3.39 (d, J=14.2 Hz, 1 H), 3.20-3.09 (m, 1 H), 2.82 (m, 1 H), 2.36-2.15 (m, 3 H), 1.96 (m, 2H), 1.30-1.11 (m, 4 H).

Example 18

4-(1-(4,4-difluoro-1-(4-(trifluoromethyl)benzyl)piperidine-2-carboxamido)cyclopropyl)benzoic acid (single enantiomer) (E18)

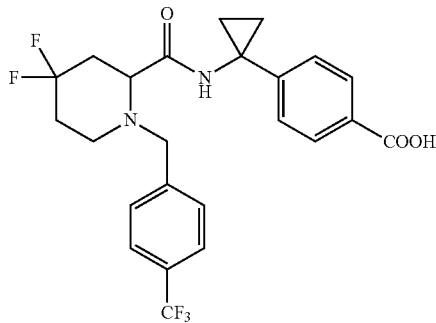 [SMILES: O=C(O)c1ccc(C2(NC(=O)C3CC(F)(F)CCN3Cc3ccc(C(F)(F)F)cc3)CC2)cc1]

To a solution of methyl 4-(1-(4,4-difluoro-1-(4-(trifluoromethyl)benzyl)piperidine-2-carboxamido)cyclopropyl)benzoate (enantiomer 1) (D137a) (140 mg, 0.28 mmol) in dioxane (3 ml) and water (3 ml) LiOH H$_2$O (47 mg, 1.12 mmol) was added and the mixture was left stirring at RT for 16 hrs. Dioxane was evaporated off then acetic acid was added to the aqueous layer until the solution reached the value of p≈4. The solid was filtered off and dried under vacuum to afford the title compound (E18) (90 mg)

MS: (ES/+) m/z: 482.8 [MH$^+$] C24H23F5N2O3 requires 482.16

Chiral HPLC [DAICEL AD-H; Mobile phase A: 60% n-heptane (+0.2% TFA), B: 40% IPA; DAD: 245 nm]: Peak retention time: 9.1 min.

$^1$H NMR (400 MHz, DMSO-d6) δ (ppm): 8.95 (s, 1 H), 7.77 (d, J=8.3 Hz, 2 H), 7.74-7.67 (m, J=8.3 Hz, 2 H), 7.67-7.58 (m, J=7.8 Hz, 2 H), 7.17 (d, J=7.8 Hz, 2 H), 3.82 (d, J=13.7 Hz, 1 H), 3.38 (d, J=14.2 Hz, 1 H), 3.16 (dd, J=5.4, 8.8 Hz, 1 H), 2.82 (d, J=12.2 Hz, 1 H), 2.36-2.14 (m, 3 H), 2.03-1.88 (m, 2 H), 1.30-1.21 (m, 2 H), 1.21-1.07 (m, 2 H)

Example 19

4-(1-(4,4-difluoro-1-(3-(trifluoromethyl)benzyl)piperidine-2-carboxamido)cyclopropyl)benzoic acid (single enantiomer) (E19)

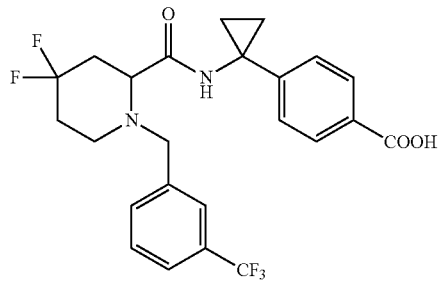 [SMILES: O=C(O)c1ccc(C2(NC(=O)C3CC(F)(F)CCN3Cc3cccc(C(F)(F)F)c3)CC2)cc1]

To a solution of methyl 4-(1-(4,4-difluoro-1-(3-(trifluoromethyl)benzyl)piperidine-2-carboxamido)cyclopropyl)benzoate (enantiomer 1) (D138a) (35 mg, 0.07 mmol) in dioxane (3 ml) and water (1 ml) LiOH H$_2$O (12 mg, 0.28 mmol) was added and the mixture was left stirring at RT for 4 hrs. Dioxane was evaporated off then HCl 2M was added to the aqueous layer until the solution reached the value of pH≈4. The aqueous phase was extracted with AcOEt (40 ml), the organics washed with water (10 ml), dried over Na$_2$SO$_4$ and evaporated to the title compound (E19) (34 mg)

MS: (ES/+) m/z: 483 [MH$^+$] C24H23F5N2O3 requires 482.16

Chiral HPLC [DAICEL AD-H; Mobile phase A: 60% n-heptane (+0.2% TFA), B: 40% IPA; DAD: 245 nm]: Peak retention time: 9.0 min.

$^1$H NMR (400 MHz, CDCl3) δ (ppm): 7.98 (d, J=8.8 Hz, 2 H), 7.60 (s, 1 H), 7.57-7.44 (m, 3 H), 7.36 (s, 1 H), 7.31 (s, 1 H), 3.83 (s, 1 H), 3.43 (s, 1 H), 3.32-3.24 (m, 1 H), 3.04-2.95 (m, 1 H), 2.52 (t, J=10.3 Hz, 1 H), 2.45-2.33 (m, 1 H), 2.31-2.14 (m, 1 H), 2.06-1.90 (m, 2 H), 1.41-1.35 (m, 2 H), 1.33-1.21 (m, 3 H)

Example 20

4-(1-(4,4-difluoro-1-(3-(trifluoromethyl)benzyl)piperidine-2-carboxamido)cyclopropyl)benzoic acid (single enantiomer) (E20)

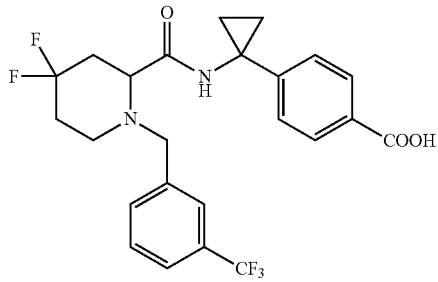 [SMILES: O=C(O)c1ccc(C2(NC(=O)C3CC(F)(F)CCN3Cc3cccc(C(F)(F)F)c3)CC2)cc1]

The title compound (E20) (37 mg) was prepared following the same procedure reported in Example 19 starting from methyl 4-(1-(4,4-difluoro-1-(3-(trifluoromethyl)benzyl)piperidine-2-carboxamido)cyclopropyl)benzoate (enantiomer 2) (D138b) (45 mg).

MS: (ES/+) m/z: 483 [MH$^+$] C24H23F5N2O3 requires 482.16

Chiral HPLC [DAICEL AD-H; Mobile phase A: 70% n-heptane (+0.2% TFA), B: 30% IPA; DAD: 245 nm]: Peak retention time: 10.2 min.

$^1$H NMR (400 MHz, CDCl3) δ (ppm): 7.98 (d, J=8.3 Hz, 2 H), 7.63-7.58 (m, 1 H), 7.56-7.44 (m, 3 H), 7.36 (s, 1 H), 7.31 (s, 1 H), 3.88-3.80 (m, 1 H), 3.45-3.37 (m, 1 H), 3.31-3.22 (m, 1 H), 3.04-2.93 (m, 1 H), 2.57-2.47 (m, 1 H), 2.44-2.32 (m, 1 H), 2.31-2.17 (m, 1 H), 2.05-1.90 (m, 2 H), 1.42-1.34 (m, 2 H), 1.33-1.20 (m, 4 H)

Example 21

4-(1-(3-(4-(trifluoromethyl)benzyl)-3-azabicyclo[4.1.0]heptane-4-carboxamido)cyclopropyl)benzoic acid (racemic mixture) (E21)

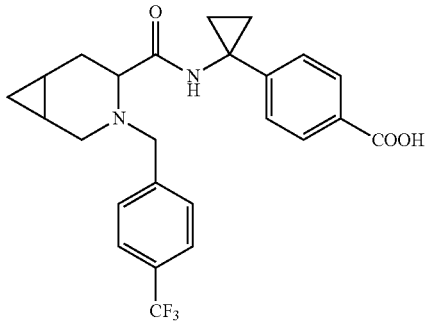 [SMILES: O=C(O)c1ccc(C2(NC(=O)C3CC4CC4CN3Cc3ccc(C(F)(F)F)cc3)CC2)cc1]

The title compound (E21) (19 mg) was prepared according to the general procedure for esters hydrolysis (Method D) starting from methyl 4-(1-(3-(4-(trifluoromethyl)benzyl)-3-azabicyclo[4.1.0]heptane-4-carboxamido)cyclopropyl)benzoate (D139) (25 mg). (LiOH H$_2$O: 4 eq; reaction time: 10 hrs)

MS: (ES/+) m/z: 457.1 [MH$^-$] C25H25F3N2O3 requires 458.18

$^1$H NMR (400 MHz, DMSO-d6) δ (ppm): 12.74 (br. s., 1 H), 8.63 (s, 1 H), 7.78 (dd, J=1.5, 8.3 Hz, 2 H), 7.68 (d, J=7.8 Hz, 2 H), 7.59 (d, J=7.8 Hz, 2 H), 7.20-7.04 (m, 2 H), 3.70 (d, J=13.7 Hz, 1 H), 3.56 (d, J=13.7 Hz, 1 H), 3.16 (dd, J=5.6, 12.5 Hz, 1 H), 2.98 (t, J=5.4 Hz, 1 H), 2.35-2.29 (m, 1 H), 2.18 (td, J=6.8, 13.3 Hz, 1 H), 1.68 (d, J=14.2 Hz, 1 H), 1.27-1.22 (m, 2 H), 1.19-1.06 (m, 2 H), 0.98 (d, J=18.6 Hz, 2 H), 0.67 (dt, J=4.4, 7.6 Hz, 1 H), 0.22 (d, J=4.4 Hz, 1 H).

Example 22

4-(1-(3-(4-(trifluoromethyl)benzyl)-3-azabicyclo[4.1.0]heptane-4-carboxamido)cyclopropyl)benzoic acid (single unknown diastereoisomer with anti relative stereochemistry) (E22)

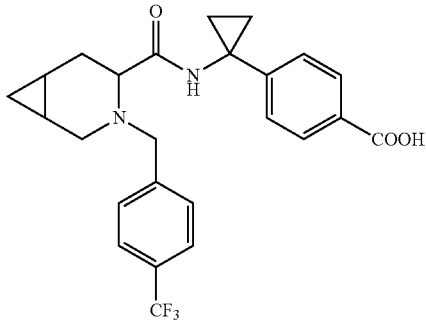 [SMILES: O=C(O)c1ccc(C2(NC(=O)C3CC4CC4CN3Cc3ccc(C(F)(F)F)cc3)CC2)cc1]

The title compound (E22) (65 mg) was prepared according to the general procedure for esters hydrolysis (Method D) starting from methyl 4-(1-(3-(4-(trifluoromethyl)benzyl)-3-azabicyclo[4.1.0]heptane-4-carboxamido)cyclopropyl)benzoate (D140a) (72 mg). (LiOH H$_2$O: 4 eq; reaction time: 10 hrs)

MS: (ES/+) m/z: 457.1 [MH$^-$] C25H25F3N2O3 requires 458.18

Chiral HPLC: [Regis Welk 01 (SS); Mobile phase A: 70% n-heptane (+0.1% AcOH), B: 30% IPA; DAD: 254 nm]: Peak retention time: 30 min $^1$H NMR (400 MHz, DMSO-d6) δ (ppm): 13.31-12.10 (m, 1 H), 8.69-8.59 (m, 1H), 7.78 (d, J=8.8 Hz, 2 H), 7.74-7.65 (m, J=7.8 Hz, 2 H), 7.65-7.55 (m, J=8.3 Hz, 2 H), 7.16 (d, J=8.3 Hz, 2 H), 3.70 (d, J=14.2 Hz, 1 H), 3.56 (d, J=14.2 Hz, 1 H), 3.16 (dd, J=6.8, 12.2 Hz, 1 H), 2.98 (t, J=6.1 Hz, 1 H), 2.31 (dd, J=3.9, 12.2 Hz, 1 H), 2.18 (td, J=6.7, 13.9 Hz, 1 H), 1.73-1.64 (m, 1 H), 1.28-1.20 (m, 2 H), 1.19-1.12 (m, 1 H), 1.09 (dt, J=3.2, 6.2 Hz, 1 H), 1.06-0.92 (m, 2 H), 0.67 (dt, J=4.4, 8.3 Hz, 1 H), 0.22 (q, J=4.4 Hz, 1 H)

Example 23

4-(1-(3-(4-(trifluoromethyl)benzyl)-3-azabicyclo[4.1.0]heptane-4-carboxamido)cyclopropyl)benzoic acid (single unknown diastereoisomer with anti relative stereochemistry) (E23)

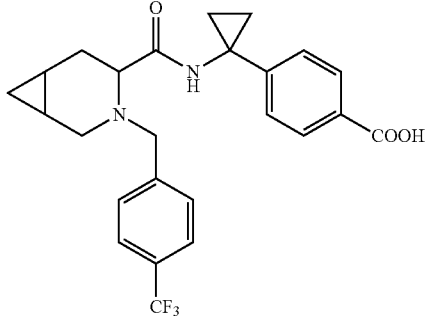 [SMILES: O=C(O)c1ccc(C2(NC(=O)C3CC4CC4CN3Cc3ccc(C(F)(F)F)cc3)CC2)cc1]

The title compound (E23) (56 mg) was prepared according to the general procedure for esters hydrolysis (Method D) starting from methyl 4-(1-(3-(4-(trifluoromethyl)benzyl)-3- azabicyclo[4.1.0]heptane-4-carboxamido)cyclopropyl)benzoate (D140b) (74 mg). (LiOH H$_2$O: 4 eq; reaction time: 10 hrs)

MS: (ES/+) m/z: 457.1 [MH$^-$] C25H25F3N2O3 requires 458.18

Chiral HPLC: [Regis Welk 01 (SS); Mobile phase A: 70% n-heptane (+0.1% AcOH), B: 30% IPA; DAD: 254 nm]: Peak retention time: 30.3 min $^1$H NMR (400 MHz, DMSO-d6) δ (ppm): 12.64 (br. s., 1 H), 8.63 (s, 1 H), 7.78 (d, J=8.8 Hz, 2 H), 7.72-7.65 (m, J=8.3 Hz, 2 H), 7.63-7.55 (m, J=8.3 Hz, 2 H), 7.16 (d, J=8.3 Hz, 2 H), 3.74-3.66 (m, 1 H), 3.61-3.53 (m, 1 H), 3.16 (dd, J=6.8, 12.2 Hz, 1 H), 2.98 (t, J=6.1 Hz, 1 H), 2.31 (dd, J=4.2, 12.5 Hz, 1 H), 2.18 (td, J=6.7, 13.9 Hz, 1 H), 1.73-1.64 (m, 1 H), 1.28-1.21 (m, 2 H), 1.19-1.13 (m, 1 H), 1.12-1.06 (m, 1 H), 1.06-0.92 (m, 2 H), 0.67 (dt, J=4.2, 8.2 Hz, 1 H), 0.22 (q, J=4.6 Hz, 1 H).

Example 24

4-(1-(3-(3-(trifluoromethyl)benzyl)-3-azabicyclo[4.1.0]heptane-4-carboxamido)cyclopropyl)benzoic acid (racemic mixture) (E24)

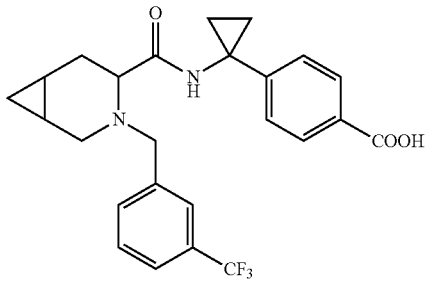 [SMILES: O=C(O)c1ccc(C2(NC(=O)C3CC4CC4CN3Cc3cccc(C(F)(F)F)c3)CC2)cc1]

The title compound (E24) (32 mg) was prepared according to the general procedure for esters hydrolysis (Method D) starting from (methyl 4-(1-(3-(3-(trifluoromethyl)benzyl)-3-azabicyclo[4.1.0]heptane-4-carboxamido)cyclopropyl)benzoate (D141) (53 mg). (LiOH H$_2$O: 4 eq; reaction time: 18 hrs)

MS: (ES/+) m/z: 459.2 [MH$^+$] C25H25F3N2O3 requires 458.18

$^1$H NMR (400 MHz, DMSO-d6) δ (ppm): 12.81-12.62 (m, 1 H), 8.77-8.56 (m, 1H), 7.99-7.45 (m, 5 H), 7.27-7.08 (m, 2 H), 3.80-3.66 (m, 1 H), 3.61-3.49 (m, 1 H), 3.24-3.11 (m, 1 H), 3.03-2.94 (m, 1 H), 2.39-2.29 (m, 1 H), 2.26-2.10 (m, 1 H), 1.75-1.58 (m, 1 H), 1.33-1.21 (m, 2 H), 1.19-1.07 (m, 2 H), 1.05-0.90 (m, 2 H), 0.73-0.61 (m, 1 H), 0.26-0.17 (m, 1 H).

Example 25

4-(1-((3R)-2-(4-(trifluoromethyl)benzyl)-2-azabicyclo[4.1.0]heptane-3-carboxamido)cyclopropyl)benzoic acid (diastereoisomers mixture) (E25)

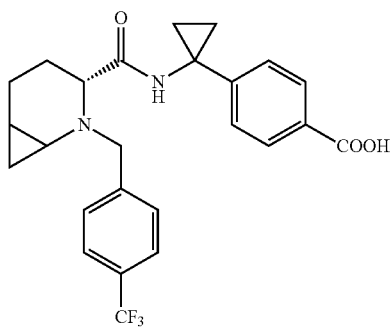 [SMILES: O=C(O)c1ccc(C2(NC(=O)[C@H]3CCC4CC4N3Cc3ccc(C(F)(F)F)cc3)CC2)cc1]

The title compound (E25 (4.9 mg) was prepared according to the general procedure for esters hydrolysis (Method D) starting from methyl 4-(1-((3R)-2-(4-(trifluoromethyl)benzyl)-2-azabicyclo[4.1.0]heptane-3-carboxamido)cyclopropyl)benzoate (diastereoisomers mixture) (D142) (6.8 mg).

(LiOH H$_2$O: 4 eq; reaction time: 10 hrs)

MS: (ES/+) m/z: 459.1 [MH$^+$] C25H25F3N2O3 requires 458.18

$^1$H NMR (400 MHz, MeOH-d4) δ (ppm): 8.02-7.84 (m, 2 H), 7.67 (m, 5 H), 7.31-7.16 (m, 2 H), 3.92 (s, 1 H), 3.85 (s, 1 H), 3.15-2.91 (m, 1 H), 2.66-0.82 (m, 10H under residual solvent), 0.64-0.39 (m, 2 H).

Example 26

4-((1S)-1-((3R)-2-(4-(trifluoromethyl)benzyl)-2-azabicyclo[4.1.0]heptane-3-carboxamido)ethyl)benzoic acid (diastereoisomers mixture) (E26)

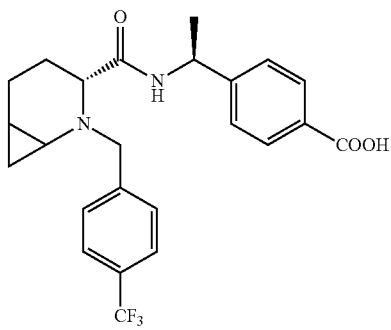 [SMILES: C[C@H](NC(=O)[C@H]1CCC2CC2N1Cc1ccc(C(F)(F)F)cc1)c1ccc(C(=O)O)cc1]

The title compound (E26) (7.2 mg) was prepared according to the general procedure for esters hydrolysis (Method D) starting from methyl 4-((1S)-1-((3R)-2-(4-(trifluoromethyl)benzyl)-2-azabicyclo[4.1.0]heptane-3-carboxamido)ethyl)benzoate (diastereoisomers mixture) (D143) (10 mg). (LiOH H$_2$O: 4 eq; reaction time: 10 hrs)

MS: (ES/+) m/z: 447.2 [MH$^+$] C24H25F3N2O3 requires 446.18

$^1$H NMR (400 MHz, MeOH-d4) δ (ppm): 7.99 (t, J=9.2 Hz, 2 H), 7.74-7.29 (m, 7H), 5.06 (m, 1 H), 4.03-3.69 (m, 2 H), 3.11-2.93 (m, 1 H), 2.58-0.77 (9 H under residual solvent), 0.52 (m, 2 H).

Example 27 lithium 4-((S)-1-((R)-1-(4-(trifluoromethyl)benzyl)pyrrolidine-2-carboxamido)ethyl)benzoate (E27)

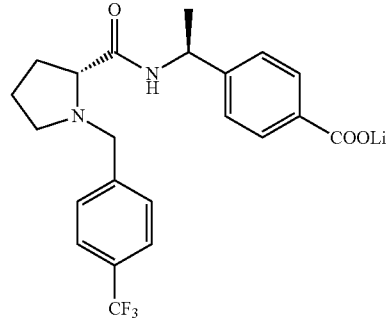

The title compound (E27) (47 mg) was prepared according to the general procedure for esters hydrolysis (Method A) starting from methyl 4-((S)-1-((R)-1-(4-(trifluoromethyl)benzyl)pyrrolidine-2-carboxamido)ethyl)benzoate (D144) (50 mg).

(LiOH H₂O: 1.2 eq; reaction time: 5 hrs; 70° C.)

MS: (ES/+) m/z: 421.2 [M−Li+2H⁺] C22H22F3LiN2O3 requires 426.17

Chiral HPLC [Phenomenex Lux Cellulose-1; Mobile phase A: 70% n-hexane (+0.5% TFA), B: 30% EtOH; DAD: 230 nm]: Peak retention time: 8.15 min.

¹H NMR (400 MHz, MeOH-d4) δ (ppm): 7.95-7.90 (m, J=8.3 Hz, 2 H), 7.69-7.63 (m, J=7.8 Hz, 2 H), 7.60-7.55 (m, J=8.3 Hz, 2 H), 7.33-7.27 (m, J=7.8 Hz, 2 H), 4.97-4.90 (m, 1 H), 3.88 (d, J=13.2 Hz, 1 H), 3.74 (d, J=12.7 Hz, 1H), 3.22 (dd, J=4.4, 9.8 Hz, 1 H), 3.18-3.11 (m, 1 H), 2.49 (d, J=6.8 Hz, 1 H), 2.21 (br. s., 1 H), 1.87-1.76 (m, 3 H), 1.36 (d, J=6.8 Hz, 3 H)

Example 28 lithium 4-((S)-1-((R)-1-(4-fluorobenzyl)pyrrolidine-2-carboxamido)ethyl)benzoate (E28)

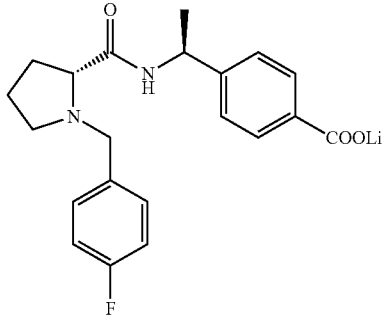

The title compound (E28) (13 mg) was prepared according to the general procedure for esters hydrolysis (Method A) starting from methyl 4-((S)-1-((R)-1-(4-fluorobenzyl)pyrrolidine-2-carboxamido)ethyl)benzoate (D145) (22 mg). (LiOH H₂O: 1.2 eq; reaction time: 5 hrs; 70° C.)

MS: (ES/+) m/z: 370.9 [M−Li+2H⁺] C21H22FLiN2O3 requires 376.18

Chiral HPLC [DAICEL OD-H; Mobile phase A: 70% n-hexane (+0.5% TFA), B: 30% EtOH; DAD: 230 nm]: Peak retention time: 8.7 min.

¹H NMR (400 MHz, MeOH-d4) δ (ppm): 7.97-7.89 (m, J=7.8 Hz, 2 H), 7.37 (dd, J=5.9, 8.3 Hz, 2 H), 7.32-7.26 (m, J=8.3 Hz, 2 H), 7.07 (t, J=8.8 Hz, 2 H), 4.96-4.90 (m, 1 H), 3.77 (d, J=12.7 Hz, 1 H), 3.66 (d, J=12.7 Hz, 1 H), 3.23-3.06 (m, 2 H), 2.57-2.37 (m, 1 H), 2.27-2.10 (m, 1 H), 1.89-1.68 (m, 3 H), 1.39 (d, J=6.8 Hz, 3 H)

Example 29

4-(1-((1R,3R,5R)-2-(3-(trifluoromethyl)benzyl)-2-azabicyclo[3.1.0]hexane-3-carboxamido)cyclopropyl)benzoic acid (syn diastereoisomer) (E29)

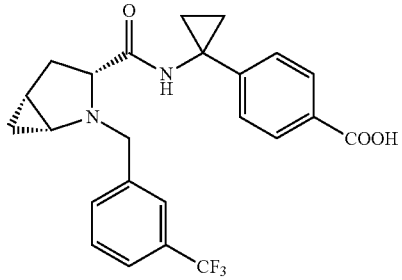 [SMILES: O=C(O)c1ccc(C2(NC(=O)[C@H]3C[C@H]4C[C@H]4N3Cc3cccc(C(F)(F)F)c3)CC2)cc1]

The title compound (E29) (52 mg) was prepared according to the general procedure for esters hydrolysis (Method D) starting from methyl 4-(1-((3R)-2-(3-(trifluoromethyl)benzyl)-2-azabicyclo[3.1.0]hexane-3-carboxamido)cyclopropyl)benzoate (D146) (60 mg). (LiOH H₂O: 4 eq; reaction time: 18 hrs)

MS: (ES/+) m/z: 445.2 [MH⁺] C24H23F3N2O3 requires 444.17

¹H NMR (400 MHz, DMSO-d6) δ (ppm): 12.85-12.69 (m, 1 H), 8.41-8.32 (m, 1H), 7.91-7.81 (m, 2 H), 7.80-7.71 (m, 2 H), 7.70-7.54 (m, 2 H), 7.06-6.96 (m, 2 H), 4.08-3.95 (m, 1 H), 3.87-3.75 (m, 1 H), 3.59-3.48 (m, 1 H), 2.80-2.70 (m, 1 H), 2.20-2.08 (m, 1 H), 2.04-1.94 (m, 1 H), 1.48-1.38 (m, 1 H), 1.32-1.23 (m, 1 H), 1.22-1.13 (m, 1 H), 1.12-1.01 (m, 2 H), 0.53-0.41 (m, 1 H), 0.25-0.12 (m, 1 H).

Example 30

4-(1-((1R,3R,5R)-2-(4-(trifluoromethyl)benzyl)-2-azabicyclo[3.1.0]hexane-3-carboxamido)cyclopropyl)benzoic acid (E30)

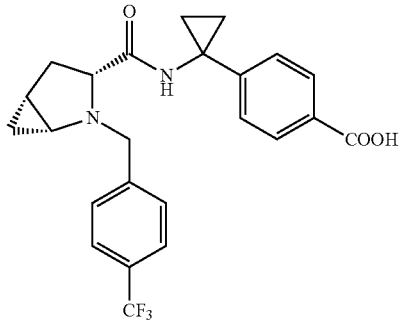 [SMILES: O=C(O)c1ccc(C2(NC(=O)[C@H]3C[C@H]4C[C@H]4N3Cc3ccc(C(F)(F)F)cc3)CC2)cc1]

The title compound (E30) (2.25 g) was prepared according to the general procedure for esters hydrolysis (Method D) starting from methyl 4-(1-((1R,3R,5R)-2-azabicyclo[3.1.0]hexane-3-carboxamido)cyclopropyl)benzoate (D147) (2.4 g)

MS: (ES/+) m/z: 445 [MH⁺] C23H23F3N2O3 requires 444.17

Chiral HPLC [Regis Welk 01(SS); Mobile phase A: 70% n-heptane (+0.1% AcOH), B: 30% IPA; DAD: 245 nm]: Peak retention time: 32.8 min.

¹H NMR (400 MHz, DMSO-d6) δ (ppm): 12.73 (br. s., 1 H), 8.34 (s, 1 H), 7.92-7.62 (m, 6 H), 7.01 (d, J=8.2 Hz, 2 H), 4.01 (d, J=13.8 Hz, 1 H), 3.79 (d, J=13.3 Hz, 1 H), 3.54 (d, J=9.5 Hz, 1 H), 2.82-2.65 (m, 1 H), 2.28-2.11 (m, 1 H), 2.09-1.92 (m, 1 H), 1.50-1.37 (m, J=3.5 Hz, 1 H), 1.35-1.24 (m, J=5.9 Hz, 1 H), 1.23-0.99 (m, 3 H), 0.55-0.38 (m, J=7.0 Hz, 1 H), 0.28-0.09 (m, 1 H)

Example 31

4-(1-((3R)-2-(4-(trifluoromethyl)benzyl)-2-azabicyclo[3.1.0]hexane-3-carboxamido)cyclopropyl)benzoic acid (single unknown diastereoisomer) (E31)

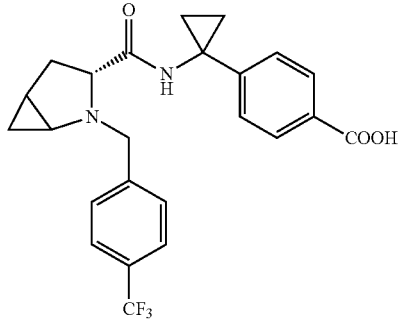

The title compound (E31) (46 mg) was prepared according to the general procedure for esters hydrolysis (Method C) starting from methyl 4-(1-((3R)-2-(4-(trifluoromethyl)benzyl)-2-azabicyclo[3.1.0]hexane-3-carboxamido)cyclopropyl)benzoate (diastereoisomer 2) (D148) (100 mg). (LiOH H₂O: 4 eq; reaction time: 18 hrs)

MS: (ES/+) m/z: 445.3 [MH⁺] C24H23F3N2O3 requires 444.17

Chiral HPLC [DAICEL AD-H; Mobile phase A: 60% n-heptane (+0.1% TFA), B: 40% IPA; DAD: 245 nm]: Peak retention time: 12.91 min.

¹H NMR (400 MHz, CHCl3-d) δ (ppm): 8.50-8.09 (br. s., 1 H), 7.98 (d, J=8.1 Hz, 2 H), 7.91-7.78 (m, 1 H), 7.63 (d, J=7.8 Hz, 2 H), 7.48 (d, J=7.7 Hz, 2 H), 7.31-7.14 (m, 2 H), 3.77 (d, J=13.0 Hz, 1 H), 3.66-3.41 (m, 1 H), 2.97 (t, J=8.7 Hz, 1 H), 2.70 (br. s., 1 H), 2.54 (dd, J=8.1, 12.5 Hz, 1 H), 2.09-1.93 (m, 1 H), 1.54-1.35 (m, 2 H), 1.36-1.21 (m, 2 H), 1.21-1.11 (m, 1 H), 0.63 (br. s., 1 H), 0.36-0.20 (m, 1 H)

Example 32

4-((1S)-1-((3R)-2-(4-(trifluoromethyl)benzyl)-2-azabicyclo[3.1.0]hexane-3-carboxamido)ethyl)benzoic acid (diastereoisomers mixture) (E32)

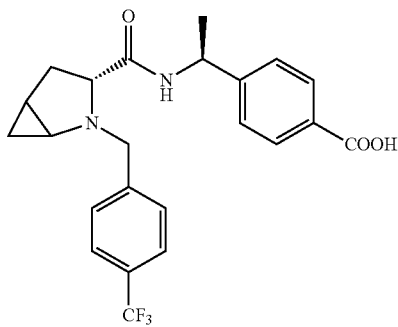 [SMILES: C[C@H](NC(=O)[C@H]1CC2CC2N1Cc1ccc(C(F)(F)F)cc1)c1ccc(C(=O)O)cc1]

The title compound (E32) (12.3 mg) was prepared according to the general procedure for esters hydrolysis (Method C) starting from methyl 4-((1S)-1-((3R)-2-(4-(trifluoromethyl)benzyl)-2-azabicyclo[3.1.0]hexane-3-carboxamido)ethyl)benzoate (D149) (14 mg). (LiOH H₂O: 4 eq; reaction time: 18 hrs)

MS: (ES/+) m/z: 433.4 [MH⁺] C23H23F3N2O3 requires 432.17

Chiral HPLC [DAICEL AD-H; Mobile phase A: 70% n-heptane 0.2% (+TFA), B: 30% EtOH; DAD: 245 nm]: Peak 1 retention time: 10.28 min; peak 2 retention time: 11.35 min.

¹H NMR (400 MHz, CHCl3-d) δ (ppm): 8.09 (d, J=7.8 Hz, 4 H), 7.80 (d, J=8.4 Hz, 1 H), 7.71-7.61 (m, 4 H), 7.57-7.46 (m, 5 H), 7.44-7.36 (m, 4 H), 5.17-4.93 (m, 2 H), 3.99 (d, J=13.3 Hz, 1 H), 3.83 (d, J=13.0 Hz, 1 H), 3.76 (d, J=13.3 Hz, 1 H), 3.64-3.47 (m, 2 H), 2.97 (t, J=8.8 Hz, 1 H), 2.75-2.60 (m, 2 H), 2.48 (dd, J=8.0, 12.6 Hz, 1 H), 2.33-2.15 (m, 2 H), 1.99-1.85 (m, 1 H), 1.54-1.48 (m, J=4.3 Hz, 1 H), 1.45 (d, J=6.7 Hz, 4 H), 1.41 (d, J=6.9 Hz, 3 H), 0.64 (br. s., 1 H), 0.44 (q, J=7.3 Hz, 1 H), 0.33-0.16 (m, 1 H), 0.02 (br. s., 1 H).

Example 33

4-((1S)-1-((3R)-2-(4-(trifluoromethyl)benzyl)-2-azabicyclo[3.1.0]hexane-3-carboxamido)ethyl)benzoic acid (single unknown diastereoisomer) (E33)

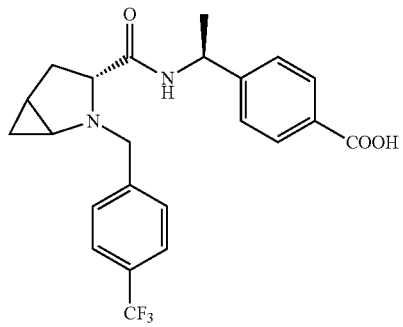 [SMILES: C[C@H](NC(=O)[C@H]1CC2CC2N1Cc1ccc(C(F)(F)F)cc1)c1ccc(C(=O)O)cc1]

The title compound (E33) (62 mg) was prepared according to the general procedure for esters hydrolysis (Method C) starting from methyl 4-((1S)-1-((3R)-2-(4-(trifluoromethyl)benzyl)-2-azabicyclo[3.1.0]hexane-3-carboxamido)ethyl)benzoate (single diastereoisomer 1) (D150) (72 mg). (LiOH H₂O: 4 eq; reaction time: 18 hrs)

MS: (ES/+) m/z: 433.4 [MH⁺] C23H23F3N2O3 requires 432.17

Chiral HPLC [DAICEL AD-H; Mobile phase A: 70% n-heptane (+0.2% TFA), B: 30% EtOH; DAD: 245 nm]: Peak retention time: 10.77 min.

¹H NMR (400 MHz, CHCl3-d) δ (ppm): 8.08 (d, J=8.0 Hz, 2 H), 7.67 (d, J=7.7 Hz, 2 H), 7.57-7.34 (m, 5 H), 5.18-4.97 (m, 1 H), 3.95-3.74 (m, 1 H), 3.70-3.46 (m, 1 H), 3.04-2.87 (m, 1 H), 2.83-2.61 (m, 1 H), 2.58-2.37 (m, 1 H), 1.98-1.87 (m, 1 H), 1.66-1.60 (m, 1 H), 1.46 (d, J=6.9 Hz, 3 H), 0.73-0.54 (m, 1H), 0.34-0.18 (m, 1 H)

Example 34

(R)-4-(1-(4,4-dimethyl-1-(4-(trifluoromethyl)benzyl)pyrrolidine-2-carboxamido)cyclopropyl)benzoic acid (E34)

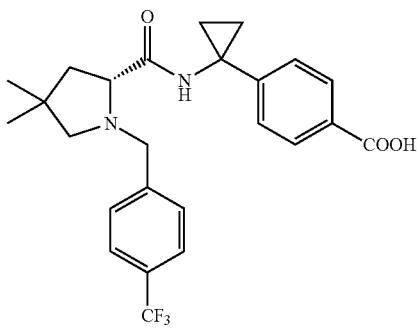 [SMILES: CC1(C)C[C@H](C(=O)NC2(c3ccc(C(=O)O)cc3)CC2)N(Cc2ccc(C(F)(F)F)cc2)C1]

(R)-methyl 4-(1-(4,4-dimethyl-1-(4-(trifluoromethyl)benzyl)pyrrolidine-2-carboxamido)cyclopropyl)benzoate (D151) (100 mg, 0.21 mmol) was partitioned between dioxane (2 ml) and water (2 ml) prior addition of LiOH H₂O (35 mg, 0.84 mmol) and the resulting mixture was stirred at RT for 18 hrs. Dioxane was evaporated off and the aqueous solution acidified with acetic acid to pH~4-5. A white solid precipitated which was filtered, dried under vacuum, then re-dissolved in dioxane (2 ml) and water (2 ml) and hydrolysed for additional 5 hrs after addition of LiOH H$_2$O (18 mg, 0.42 mmol). Dioxane was evaporated off and the aqueous solution acidified with acetic acid to pH~4-5. A white solid precipitated which was filtered and dried under vacuum, to afford the title compound (E34) (35.5 mg).

MS: (ES/+) m/z: 461.3 [MH$^+$] C25H27F3N2O3 requires 460.20

$^1$H NMR (400 MHz, MeOH-d4) δ (ppm): 7.91 (d, J=8.3 Hz, 2 H), 7.70-7.54 (m, 4H), 7.22 (d, J=7.8 Hz, 2 H), 4.92-4.74 (m, 1 H), 3.97-3.84 (m, 1 H), 3.83-3.71 (m, 1 H), 3.00-2.89 (m, 1 H), 2.48-2.37 (m, 1 H), 2.22-2.06 (m, 1 H), 1.82-1.66 (m, 1 H), 1.38-1.24 (m, 2 H), 1.19 (s, 3 H), 1.11 (s, 5 H)

Example 35

4-((1S)-1-(1-(4-(trifluoromethyl)benzyl)azetidine-2-carboxamido)ethyl)benzoic acid (diastereoisomers mixture) (E35)

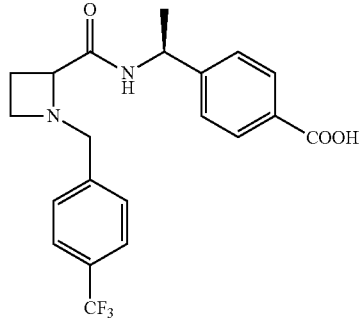 [SMILES: C[C@H](NC(=O)C1CCN1Cc1ccc(C(F)(F)F)cc1)c1ccc(C(=O)O)cc1]

The title compound (E35) (1.6 mg) was prepared according to the general procedure for esters hydrolysis (Method C) starting from methyl 4-((1S)-1-(1-(4-(trifluoromethyl)benzyl)azetidine-2-carboxamido)ethyl)benzoate (D152a) (6 mg).

(LiOH H$_2$O: 4 eq; reaction time: 18 hrs)

MS: (ES/+) m/z: 407.3 [MH$^+$] C21H21F3N2O3 requires 406.15

Example 36

4-((1S)-1-(1-(4-(trifluoromethyl)benzyl)azetidine-2-carboxamido)ethyl)benzoic acid (single unknown diastereoisomer) (E36)

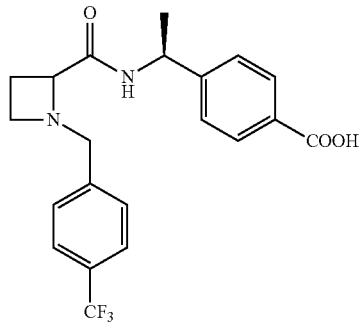 [SMILES: C[C@H](NC(=O)C1CCN1Cc1ccc(C(F)(F)F)cc1)c1ccc(C(=O)O)cc1]

The title compound (E36) (2 mg) was prepared according to the general procedure for esters hydrolysis (Method C) starting from methyl 4-((1S)-1-(1-(4-(trifluoromethyl)benzyl)azetidine-2-carboxamido)ethyl)benzoate (diastereoisomer 2) (D152b) (7 mg). (LiOH H$_2$O: 4 eq; reaction time: 18 hrs)

MS: (ES/+) m/z: 407.3 [MH$^+$] C21H21F3N2O3 requires 406.15

$^1$H NMR (400 MHz, CHCl3-d) δ (ppm): 8.02 (br. s., 2 H), 7.61 (br. s., 2 H), 7.41 (d, J=5.4 Hz, 3 H), 7.21 (br. s., 2 H), 4.96 (br. s., 1 H), 3.86-3.71 (m, 3 H), 3.43 (br. s., 1 H), 3.11 (br. s., 1 H), 2.43 (br. s., 1 H), 2.07 (br. s., 1 H), 1.16 (br. s., 3 H)

Example 37

4-((1S)-1-(3-(4-(trifluoromethyl)benzyl)-3-azabicyclo[3.1.0]hexane-2-carboxamido)ethyl)benzoic acid (diastereoisomer 2 with syn relative stereochemistry)

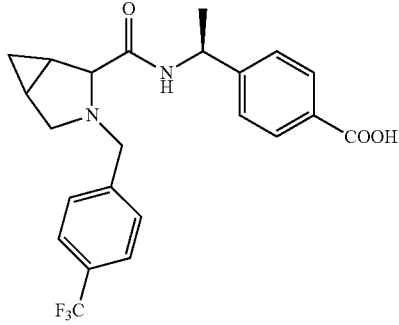 [SMILES: C[C@H](NC(=O)C1C2CC2CN1Cc1ccc(C(F)(F)F)cc1)c1ccc(C(=O)O)cc1]

To a mixture of methyl 4-((1S)-1-(3-(4-(trifluoromethyl)benzyl)-3-azabicyclo[3.1.0]hexane-2-carboxamido)ethyl)benzoate (D153) (84 mg, 0.19 mmol) in a 1:1 mixture dioxane/water, LiOH H$_2$O (12 mg, 0.28 mmol) was added and the reaction heated at 150° C. under microwave irradiation for 5 min. Dioxane was evaporated off and the aqueous phase was acidified with CH$_3$CO$_2$H. The precipitate (58 mg) was filtered off and submitted for chiral HPLC separation (Preparative chromatographic conditions: Column: DAICEL AD-H; Mobile phase: n-heptane/EtOH/TFA 60%/40%/0.2% v/v; DAD: 235 nm). Solvent evaporation of second eluted peak from chiral column, afforded the title compound (E37) (30 mg)

(E37) (diastereoisomer 2 with syn relative stereochemistry): retention time: 9.28 min MS: (ES/+) m/z: 433 [MH$^+$] C23H23F3N2O3 requires 432.17

$^1$H NMR (400 MHz, MeOH-d4) δ (ppm): 8.03 (s, 2 H), 7.66-7.55 (m, 4 H), 7.38 (s, 2 H), 5.00-4.92 (m, 1 H), 4.55-4.47 (m, 1 H), 4.45-4.38 (m, 1 H), 4.37-4.30 (m, 1 H), 3.68 (br. s., 2 H), 2.31-2.21 (m, 1 H), 2.02-1.90 (m, 1 H), 1.47 (d, J. 6.9 Hz, 3 H), 0.96-0.88 (m, 1 H), 0.88-0.79 (m, 1 H).

Example 38

4-(1-(3-(4-(trifluoromethyl)benzyl)-3-azabicyclo[3.1.0]hexane-2-carboxamido)cyclopropyl)benzoic acid (single unknown enantiomer with syn relative stereochemistry)

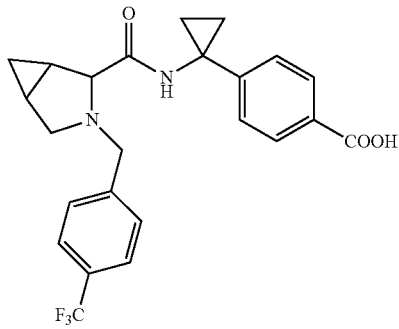 [SMILES: O=C(O)c1ccc(C2(NC(=O)C3C4CC4CN3Cc3ccc(C(F)(F)F)cc3)CC2)cc1]

The title compound (E38) (4.8 mg) was prepared according to the general procedure for esters hydrolysis (Method C) starting from methyl 4-(1-(3-(4-(trifluoromethyl)benzyl)-3-azabicyclo[3.1.0]hexane-2-carboxamido)cyclopropyl)benzoate (diastereoisomer 1) (D154a) (5 mg). (LiOH H₂O: 4 eq; reaction time: 18 hrs)

MS: (ES/+) m/z: 445 [MH⁺] C24H23F3N2O3 requires 444.17

Chiral HPLC: [ADH-Mobile phase A: 70% n-heptane (+0.2% TFA), B: 30% IPA; DAD: 235 nm]: Peak retention time: 10.5 min $^1$H NMR (400 MHz, METHANOL-d4) δ (ppm): 7.88 (d, J=8.3 Hz, 2 H), 7.64 (d, J=8.3 Hz, 2 H), 7.53 (d, J=7.8 Hz, 2 H), 7.24 (d, J=8.3 Hz, 2 H), 3.82 (d, J=13.2 Hz, 1 H), 3.51 (d, J=13.7 Hz, 1 H), 3.09 (d, J=8.8 Hz, 1 H), 2.59 (dd, J=4.4, 8.8 Hz, 1 H), 1.82 (tt, J=3.9, 7.4 Hz, 1 H), 1.62-1.53 (m, 1 H), 1.41-1.22 (m, 4 H), 1.20-1.12 (m, 2 H), 1.10-1.04 (m, 1 H), 0.55 (dt, J=4.9, 7.8 Hz, 1 H)

Example 39

4-((1S)-1-(2-(4-(trifluoromethyl)benzyl)-2-azabicyclo[2.2.2]octane-3-carboxamido)ethyl)benzoic acid (diasteroisomers mixture) (E39)

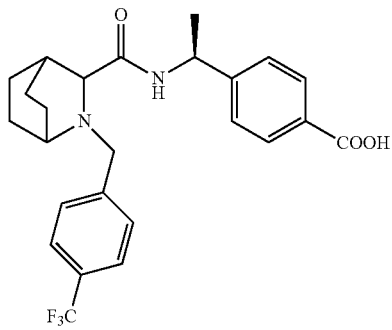 [SMILES: C[C@H](NC(=O)C1C2CCC(CC2)N1Cc1ccc(C(F)(F)F)cc1)c1ccc(C(=O)O)cc1]

The title compound (E39) (11.04 mg) was prepared according to the general procedure for esters hydrolysis (Method C) starting from methyl 4-((1S)-1-(2-(4-(trifluoromethyl)benzyl)-2-azabicyclo[2.2.2]octane-3-carboxamido)ethyl)benzoate (D155) (11.3 mg). (LiOH H₂O: 4 eq; reaction time: 18 hrs)

MS: (ES/+) m/z: 461.4 [MH⁺] C25H27F3N2O3 requires 460.20

$^1$H NMR (400 MHz, MeOH-d4) δ (ppm): 7.98 (d, J=7.5 Hz, 2 H), 7.69 (d, J=7.5 Hz, 2 H), 7.64-7.58 (m, 2 H), 7.37 (d, J=7.6 Hz, 2 H), 4.89 (d, J=7.2 Hz, 1 H), 3.96 (d, J=1.0 Hz, 1 H), 3.73 (d, J=1.0 Hz, 1 H), 3.13 (br. s., 1 H), 2.83 (br. s., 1H), 2.24-2.09 (m, 1 H), 1.89-1.56 (m, 5 H), 1.54-1.34 (m, 3 H), 1.27 (d, J=6.7 Hz, 3 H).

Example 40

4-(1-(2-(4-(trifluoromethyl)benzyl)-2-azabicyclo[2.2.2]octane-3-carboxamido)cyclopropyl)benzoic acid (diasteroisomers mixture) (E40)

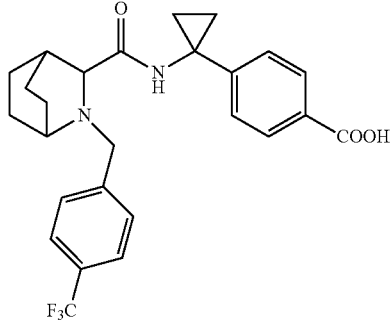 [SMILES: O=C(O)c1ccc(C2(NC(=O)C3C4CCC(CC4)N3Cc3ccc(C(F)(F)F)cc3)CC2)cc1]

The title compound (E40) (8.03 mg) was prepared according to the general procedure for esters hydrolysis (Method C) starting from methyl 4-(1-(2-(4-(trifluoromethyl)benzyl)-2-azabicyclo[2.2.2]octane-3-carboxamido)cyclopropyl)benzoate (D156) (7.6 mg). (LiOH H₂O: 4 eq; reaction time: 18 hrs)

MS: (ES/+) m/z: 473.4 [MH⁺] C26H27F3N2O3 requires 472.20

$^1$H NMR (400 MHz, MeOH-d4) δ (ppm): 7.91-7.82 (m, J=1.0 Hz, 2 H), 7.71-7.57 (m, 4 H), 7.19-7.10 (m, 2 H), 3.94 (d, J=1.0 Hz, 1 H), 3.73 (d, J=1.0 Hz, 1H), 3.13-3.08 (m, 1 H), 2.90-2.82 (m, 1 H), 2.24-2.13 (m, 1 H), 2.02-1.91 (m, 1 H), 1.90-1.56 (m, 4 H), 1.55-1.45 (m, 3 H), 1.23-1.11 (m, 2 H), 1.06-0.97 (m, 1 H), 0.96-0.91 (m, 1 H).

Example 41

(R)-4-(1-(2-methyl-1-(4-(trifluoromethyl)benzyl) piperidine-2-carboxamido)cyclopropyl)benzoic acid (E41)

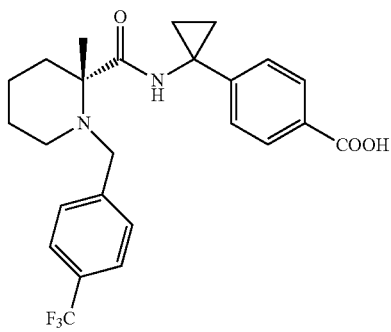 [SMILES: C[C@]1(C(=O)NC2(c3ccc(C(=O)O)cc3)CC2)CCCCN1Cc1ccc(C(F)(F)F)cc1]

The title compound (E41) (3.9 mg) was prepared according to the general procedure for esters hydrolysis (Method C) starting from (R)-methyl 4-(1-(2-methyl-1-(4-(trifluoromethyl)benzyl)piperidine-2-carboxamido)cyclopropyl)benzoate (D157) (5 mg). (LiOH H₂O: 4 eq; reaction time: 18 hrs).

MS: (ES/+) m/z: 461 [MH⁺] C25H27F3N2O3 requires 460.20

$^1$H NMR (400 MHz, MeOH-d4) δ (ppm): 7.87-7.78 (m, 2 H), 7.64 (s, 4 H), 7.22-7.07 (m, 2 H), 3.62-3.55 (m, 1 H), 3.43-3.37 (m, 1 H), 2.75-2.63 (m, 1 H), 2.43-2.31 (m, 1 H), 2.08-1.91 (m, 1 H), 1.80-1.54 (m, 5 H), 1.31 (s, 3 H), 1.25-0.85 (m, 4 H).

Example 42

4-((S)-1-((R)-2-methyl-1-(4-(trifluoromethyl)benzyl) piperidine-2-carboxamido)ethyl)benzoic acid (E42)

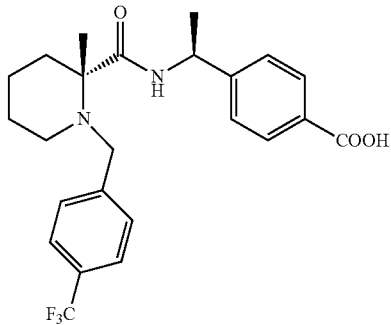 [SMILES: C[C@H](NC(=O)[C@@]1(C)CCCCN1Cc1ccc(C(F)(F)F)cc1)c1ccc(C(=O)O)cc1]

The title compound (E42) (4 mg) was prepared according to the general procedure for esters hydrolysis (Method B)

starting from methyl 4-((S)-1-((R)-2-methyl-1-(4-(trifluoromethyl)benzyl)piperidine-2-carboxamido)ethyl)benzoate (D158) (10 mg).

(LiOH H₂O: 4 eq; reaction time: 18 hrs).

MS: (ES/+) m/z: 449.4 [MH⁺] C24H27F3N2O3 requires 448.20

¹H NMR (400 MHz, MeOH-d4) δ (ppm): 7.76 (d, J=7.8 Hz, 2 H), 7.54 (br. s., 2 H), 7.40 (br. s., 2 H), 7.16 (d, J=7.8 Hz, 2 H), 5.11-5.00 (m, 1 H), 3.55-3.42 (m, 1H), 2.77-2.62 (m, 1 H), 2.40-2.26 (m, 1 H), 1.95-1.83 (m, 1 H), 1.78-1.70 (m, 1 H), 1.65 (br. s., 4 H), 1.50 (d, J=6.8 Hz, 3 H), 1.30 (s, 3 H), 0.97-0.85 (m, 1 H)

Example 43

(R)-4-(1-(2-methyl-1-(4-(trifluoromethyl)benzyl)pyrrolidine-2-carboxamido)cyclopropyl)benzoic acid (E43)

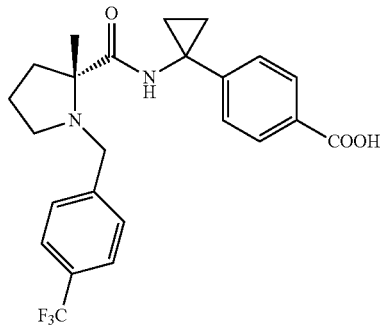 [SMILES: C[C@]1(C(=O)NC2(c3ccc(C(=O)O)cc3)CC2)CCCN1Cc1ccc(C(F)(F)F)cc1]

The title compound (E43) (11.2 mg) was prepared according to the general procedure for esters hydrolysis (Method D) starting from (R)-methyl 4-(1-(2-methyl-1-(4-(trifluoromethyl)benzyl)pyrrolidine-2-carboxamido)cyclopropyl)benzoate (D159) (13 mg). (LiOH H₂O: 4 eq; reaction time: 18 hrs).

MS: (ES/+) m/z: 449.4 [MH⁺] C24H27F3N2O3 requires 448.20

¹H NMR (400 MHz, MeOH-d4) δ (ppm): 7.90 (d, J=7.8 Hz, 2 H), 7.71-7.63 (m, 2H), 7.62-7.57 (m, 2 H), 7.25 (d, J=7.8 Hz, 2 H), 3.90 (d, J=14.2 Hz, 1 H), 3.58 (d, J=13.7 Hz, 1 H), 3.05 (d, J=4.4 Hz, 1 H), 2.54 (d, J=8.3 Hz, 1 H), 2.27-2.14 (m, 1 H), 1.96-1.82 (m, 3 H), 1.45-1.17 (m, 8 H)

Example 44 lithium 4-((S)-1-((2R,4S)-4-fluoro-1-(3-(trifluoromethyl)benzyl)pyrrolidine-2-carboxamido)ethyl)benzoate (E44)

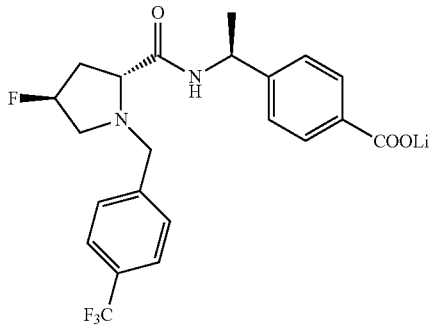

The title compound (E44) (50 mg) was prepared according to the general procedure for esters hydrolysis (Method A) starting from 4-(trifluoromethyl)benzyl 4-((S)-1-((2R,4S)-4-fluoro-1-(4-(trifluoromethyl)benzyl)pyrrolidine-2-carboxamido)ethyl)benzoate (D163) (67.3 mg). (LiOH H₂O: 3 eq; reaction time: 18 hrs).

MS: (ES/+) m/z: 439.3 [M–Li+2H⁺] C22H21F4LiN2O3 requires 444.16

¹H NMR (400 MHz, MeOH-d4) δ (ppm): 7.91 (d, J=8.1 Hz, 2 H), 7.67 (s, 2 H), 7.60 (s, 2 H), 7.29 (s, 2 H), 5.27-5.06 (m, 1 H), 4.93-4.89 (m, 1 H), 3.99-3.89 (m, 1 H), 3.87-3.77 (m, 1 H), 3.40-3.36 (m, 1 H), 2.84-2.50 (m, 2 H), 2.16-1.98 (m, 1 H), 1.33 (d, J=7.0 Hz, 3 H).

Example 45

4-((S)-1-((R)-4,4-difluoro-1-(4-(trifluoromethyl)benzyl)pyrrolidine-2-carboxamido)ethyl)benzoic acid (E45)

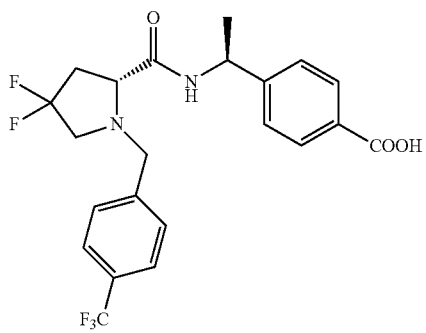 [SMILES: C[C@H](NC(=O)[C@H]1CC(F)(F)CN1Cc1ccc(C(F)(F)F)cc1)c1ccc(C(=O)O)cc1]

The title compound (E45) (12 mg) was prepared according to the general procedure for esters hydrolysis (Method D) starting from methyl 4-((S)-1-((R)-4,4-difluoro-1-(4-(trifluoromethyl)benzyl)pyrrolidine-2-carboxamido)ethyl)benzoate (D166) (16.8 mg). (LiOH H₂O: 3 eq; reaction time: 18 hrs)

MS: (ES/+) m/z: 457.3 [MH⁺] C22H21F5N2O3 requires 456.15

¹H NMR (400 MHz, MeOH-d4) δ (ppm): 8.00-7.88 (m, 2 H), 7.71-7.48 (m, 6 H), 7.40-7.25 (m, 2 H), 5.07-4.92 (br. s., 1 H), 3.97-3.47 (m, 4 H), 2.98-2.58 (m, 2 H), 2.42-2.18 (m, 1 H), 1.49-1.25 (m, 3 H).

Example 46

Determination of In Vitro Effects of the Invention Compounds

Stable Expression of Human EP₄ Receptors in the Human Embryonic Kidney (HEK293) Cell Line The cDNA clone of human EP₄ receptor (NM_000958.2) was obtained from Invitrogen™: Ultimate™ ORF Clone Collection—Clone ID 10H46525. The coding sequence was subcloned in expression vector pcDNA™6.2/V5-DEST by Gateway technology (Invitrogen™).

Human embryonic kidney cells (HEK-293) were stably transfected with expression vector for human EP₄ receptor in according to the method described in FuGENE®6 Transfection Reagent's manual (Roche Applied Science®).

Preparation of Membrane Fraction:

The EP₄ transfected cells were grown in Dulbecco's modified Eagle's medium containing 10% fetal bovine serum and 10 μg/ml Blasticidin S HCl (selection medium) at 37° C. in a humidified atmosphere of 5% CO2 in air.

For the membrane preparation, cells in flask were harvested by hypotonical/mechanical lysis with chilled (4° C.) TE buffer (5 mM TRIS, 5 mM ethylenediamine tetra-acetic acid (EDTA), pH 7.4).

Cells were detached and lysed with 10 ml of hypotonic lysis buffer and by scraping. The cell lysate was vortexed for 30 sec and centrifuged at 40000×g at 4° C. for 22 min.

a) Membrane Binding Assay[3H]-Prostaglandin E2

The membrane pellet was resuspended in the same buffer (5 mM TRIS, 5 mM ethylenediamine tetra-acetic acid (EDTA), pH 7.4), and protein concentration was determined by Bradford method (Bio-Bad® assay).

This membrane preparation was stored at −80° C. freezer until use for binding assay.

($[^3H]$-$PGE_2$) membranes binding assays toward $hEP_4$ receptors (human $EP_4$/HEK293 transfectant, see above) and $hEP_2$ receptors (human $EP_2$/HEK293 transfectant, purchased from PerkinElmer Inc) were performed in 10 mM MES-KOH buffer pH6, containing 10 mM $MgCl_2$ and 1 mM $CaCl_2$ for $EP_4$ binding assay or 50 mM Tris-Cl, BSA 0.5% for $EP_2$ binding assay (according to supplier indication).

Ten microgram of protein from membrane fractions were incubated in a total volume of 0.1 ml ($EP_4$) or 0.2 ml ($EP_2$) with 1 nM ($EP_4$) or 3 nM ($EP_2$) $[^3H]$-$PGE_2$ (PerkinElmer Inc, 171 Ci/mmol). In both assays to determine the total binding or non specific binding, 1% DMSO or 1 μM prostaglandin $E_2$ ($EP_4$) or 100 μM ($EP_2$) were added to reaction mixtures, respectively. Incubation was conducted in a polypropylene 96 multiwell for 90 min ($EP_4$) or 60 min ($EP_2$) at room temperature prior to separation of the bound and free radioligand by vacuum manifold rapid filtration on glass fiber filters (Unifilter GFB96, PerkinElmer Inc) pre-soaked in 0.3% polyethyleneimine. Filters were washed with ice cold buffer pH 7.4 (50 mM HEPES, NaCl 500 mM, BSA 0.1% for $EP_4$ binding assay or 50 mM Tris-Cl for $EP_2$ binding assays) and the residual $[^3H]$-$PGE_2$ binding determined by solid scintillation counter (TopCount, PerkinElmer Inc).

In standard competition experiments the compounds were tested in a concentration range from 1 nM to 1 μM, and $IC_{50}$ determined. The affinity (Ki) of each compound was calculated according to the Cheng-Prousoff equation: Ki=IC50/(1+([C]/Kd)). Results were expressed as pKi (−log 10 Ki (M))

Compounds of example 1 to 45 were tested according to method of example 41a in a final concentration range from 1 nM to 1 μM. All compounds showed good to excellent $EP_4$ affinities having pKi values from 6 to 8.9 at $EP_4$ receptor.

b) cAMP Assay on Human $EP_4$ Membrane of Transfected Cells.

The assay is based on the competition between endogenous cAMP and exogenously added biotinylated cAMP. The capture of cAMP is achieved by using a specific antibody conjugated to Donor beads.

Cell membranes prepared as described above, were resuspended in 1 ml stimulation buffer (HBSS 1×+BSA 0.1%+IBMX 0.5 mM+HEPES 5 mM+$MgCl_2$ 10 mM+GTP 1 nM+GDP 10 μM+ATP 100 μM−pH 7.4). Cell membranes were dispensed into white 384-well microplates at final concentration of 1 μg/well and used for the determination of cAMP with the alphascreen cAMP functional assay (EnVision-PerkinElmer). Cell membrane/anti-cAMP Acceptor beads mix (5 μl) and a mixture of analysed compounds (dissolved in 100% DMSO to a final maximal concentration of 0.01% DMSO)/PGE2 (5 μl) were incubated at room temperature (22-23° C.) for 30 min in the dark. The Biotinylated-cAMP and donor beads (15 μl) were dispensed into each well to start the competition reaction. After 1 h incubation RT (22-23° C.) in the dark the plate was read using EnVision platform to determine the cAMP level (excitation: 680 nm; emission: 520,620 nm).

In each experiment:

cAMP standard curve (concentration range from 1×10−6 to 1×10−11 M in log intervals) with a negative control (no cAMP)

a positive control: forskolin 10 μM

Antagonism studies were performed stimulating HEK293 cell membrane with PGE2 3 nM. The AlphaScreen signal is plotted as a function of log concentration of cAMP and functional IC50 is determined. IC50 value is calculated by linear regression.

Some compounds were tested according to method of example 41 b. All compounds showed good to excellent $EP_4$ antagonism having functional IC50 values from 3 μM to 4 nM at $EP_4$ receptor.

The results of membrane binding assay and cAMP assay on human $EP_4$ membrane of transfected cells selection of preferred compounds are summarised in table 1.

TABLE 1

| Example | Binding pKi | functional $IC_{50}$ (nM) |
|---------|-------------|---------------------------|
| E4  | 7.4 | 32 |
| E7  | 7.5 | 22 |
| E9  | 8.2 | 4 |
| E10 | 7.4 | 29 |
| E13 | 7.9 | 8 |
| E16 | 7.7 | 9 |
| E17 | 7.9 | 28 |
| E18 | 8.2 | 11 |
| E19 | 8.9 | 15 |
| E20 | 9.2 | 23 |
| E23 | 8   | 11.5 |
| E25 | 8.5 | 43 |
| E26 | 8.8 | 42 |
| E27 | 7.3 | 50 |
| E29 | 8.6 | 16 |
| E30 | 8.3 | 21 |

Example 47

Determination of PK of the Invention Compounds

The pharmacokinetics of compounds E7, E17 and E18, were studied in male Han Wistar rats. The rats were treated intravenously and orally (n=3 for each dose route) with compounds formulated as solutions. The rats were fitted with a jugular cannula for serial sampling. A full profile was acquired from each rat. Plasma extracts were quantitatively analyzed using a specific and sensitive LC-MS/MS bioanalytical method. Inter-individual variations between the three rats in each group were limited (CV for pharmacokinetic parameters was below 50%).

After intravenous injection all compounds showed moderate volume of distribution (Vss) ranging between 400 and 2000 ml. A range of clearance values were obtained for the different structure, ranging from low to moderate values (from 43 to 250 ml/h).

After oral administration, absorption was quite fast with a clear maximum concentration reached by the first sampling time-point of 15 minutes for all compounds. The absolute oral bioavailability was good for all compounds with F % around or in excess of 80%.

| Ex | Route | Dose (mg/kg) | CLp* (ml/h) | Vss* (ml) | t½* (h) | AUC 0-t (ng·h/ml) | AUC inf* (ng·h/ml) | F % | Cmax (ng/ml) | Tmax (h) | Tlast (h) |
|---|---|---|---|---|---|---|---|---|---|---|---|
| E7 | iv | 5 | 43 | 395 | 7.4 | 29200 | 31800 | | | | 24 |
| | po | 5 | | | 6.7 | 22900 | 24900 | 78 | 5330 | 0.5 | 24 |
| E17 | iv | 1 | 253 | 1790 | 7.3 | 966 | 1040 | | | | 24 |
| | po | 1 | | | 14.1 | 823 | 1080 | 85 | 318 | 0.5 | 24 |
| E18 | iv | 1 | 190 | 1700 | 9.3 | 1260 | 1390 | | | | 24 |
| | po | 1 | | | 5.1 | 1170 | 1200 | 93 | 556 | 0.5 | 24 |

*Clearance, volume, half-life and AUC inf expressions may automatically be taken from calculations extrapolated to infinity from unrevised regression, indicative only; clearance values and AUC will usually never be much affected by error, volumes of distribution and half-life may or may not be precisely assessable from the data collected.
In summary tables for preliminary communications volumes may be taken from data until tlast, in which case it will be approximated by default due to lack of terminal phase data.

What is claimed is:

1. A cyclic amine compound of Formula (I):

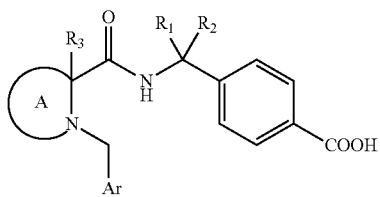

(I)

or a pharmaceutically acceptable salt or derivative thereof, wherein:

A is selected from the group consisting of

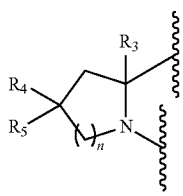  B

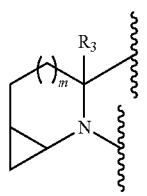  C

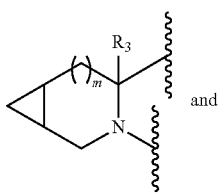  D

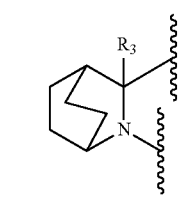  and

E wherein
n=0, 1 or 2
m=0 or 1

$R_1$ and $R_2$ are independently hydrogen, linear or branched $C_{1-3}$ alkyl or are joined together to form a cyclopropyl ring;

$R_3$ is H or linear or branched $C_{1-3}$ alkyl $R_4$ and $R_5$ are independently hydrogen, fluorine, linear or branched $C_{1-3}$ alkyl or are joined together to form a cyclopropyl ring, Ar is
phenyl having:
i. in 4-position one substituent selected from the group consisting of halogen, cyano, trifluoromethyl, or
ii. in 3-position one substituent selected from the group consisting of halogen, cyano, trifluoromethyl, provided that
  ii.a. when A is B, both $R_4$ and $R_5$ are fluorine, linear or branched $C_{1-3}$ alkyl or joined together they form a cyclopropyl ring,
  ii.b. A is C and m is 0
  ii.c. A is D and m is 1,
    a 5-membered heteroaromatic ring containing 1 to 3 heteroatoms wherein said heteroatoms independently of each others are S, O or N; or
    a 6-membered heteroaromatic ring containing 1 to 3 N.

2. A cyclic amine compound of formula (I) according to claim 1 wherein Ar is phenyl having in 4 position one substituent selected from fluorine, cyano or trifluoromethyl.

3. A cyclic amine compound of formula (I) according to claim 2 wherein $R_1$ is hydrogen and $R_2$ is methyl or both $R_1$ and $R_2$ are fused together to form a cyclopropyl ring.

4. A cyclic amine compound according to claim 1 wherein A is B and is of the formula IB

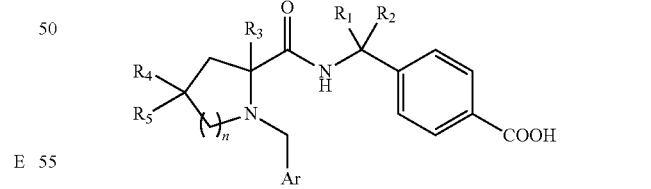

(IB)

and/or pharmaceutically acceptable derivatives or salts thereof, wherein
n=0, 1 or 2
$R_1$ and $R_2$ are independently hydrogen, linear o branched $C_{1-3}$ alkyl, or are joined together to form a cyclopropyl ring,
$R_3$ is H or linear or branched $C_{1-3}$ alkyl,
$R_4$ and $R_5$ are independently hydrogen, fluorine, linear or branched $C_{1-3}$ alkyl or are joined together to form a cyclopropyl ring, Ar is
   phenyl having:
   i. in 4-position one substituent selected from the group consisting of halogen, cyano, trifluoromethyl, or
   ii. in 3-position one substituent selected from the group consisting of halogen, cyano, trifluoromethyl, provided that both $R_4$ and $R_5$ are fluorine, linear or branched $C_{1-3}$ alkyl or are joined together to form a cyclopropyl ring,
   a 5-membered heteroaromatic ring containing 1 to 3 heteroatoms wherein said heteroatoms independently of each others are S, O or N; or
   a 6-membered heteroaromatic ring containing 1 to 3 N.

5. A cyclic amine compound of formula (IB) according to claim 4 wherein Ar is phenyl having in 4-position at least one substituent selected from the group consisting of: fluorine, cyano and trifluoromethyl.

6. A cyclic amine compound of formula (IB) according to claim 4 wherein $R_1$ and $R_2$ are methyl or are linked together to form a cyclopropyl ring.

7. A cyclic amine compound of formula (IB) according to anyone of claim 4 wherein $R_3$ is hydrogen.

8. A cyclic amine compound of formula (IB) according to claim 4 wherein $R_4$ and $R_5$ are independently selected from hydrogen, fluorine, methyl or are fused together to form a cyclopropyl ring.

9. A cyclic amine compound of formula (IB) according to claim 4 wherein n is 1 and $R_4$ and $R_5$ are independently selected from hydrogen, fluorine, methyl.

10. A cyclic amine compound of formula (IB) according to claim 4 wherein n is 2 and Ar is phenyl substituted in 4 position with at least one substituent selected from the group consisting of: fluorine, cyano and trifluoromethyl.

11. A cyclic amine compound of formula (IB) according to claim 4 wherein n is 2, both $R_4$ and $R_5$ are fluorine or are fused together to form a cyclopropyl ring.

12. A cyclic amine compound according to claim 1 wherein A is C and is of the formula IC

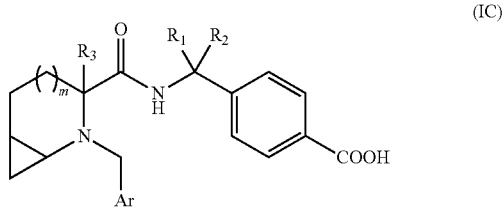

(IC)

and/or pharmaceutically acceptable salts or derivatives thereof wherein
   m=0 or 1
   $R_1$ and $R_2$ are independently hydrogen, linear o branched $C_{1-3}$ alkyl, or joined together they form a cyclopropyl ring,
   $R_3$ is H or linear or branched $(C_{1-3})$ alkyl,
   Ar is
      phenyl having
         i) in 4-position halogen, cyano or trifluoromethyl, or
         ii) in 3-position halogen, cyano, trifluoromethyl, provided that m is 0,
      a 5-membered heteroaromatic ring containing 1 to 3 heteroatoms wherein said heteroatoms independently of each others are S, O or N; or
      a 6-membered heteroaromatic ring containing 1 to 3 N.

13. A cyclic amine compound of formula (IC) according to claim 12 wherein Ar is phenyl having in 4-position at least one substituent selected from the group consisting of: fluorine, cyano and trifluoromethyl.

14. A cyclic amine compound of formula (IC) according to claim 12 wherein $R_1$ and $R_2$ are linked together to form a cyclopropyl ring.

15. A cyclic amine compound of formula (IC) according to claim 12 wherein $R_3$ is hydrogen or methyl.

16. A cyclic amine compound of formula (IC) according to claim 12 wherein m is 0 and Ar is phenyl substituted in 4 position with at least one substituent selected from the group consisting of: fluorine, cyano and trifluoromethyl.

17. A cyclic amine compound according to claim 1 wherein A is D and is of the formula (ID)

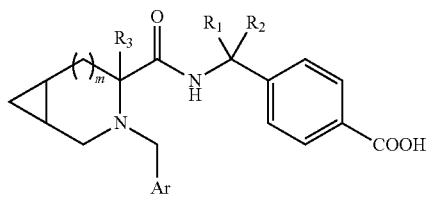

(ID)

and/or pharmaceutically acceptable salts or derivatives thereof wherein
   m=0 or 1
   $R_1$ and $R_2$ are independently hydrogen, linear o branched $C_{1-3}$ alkyl, or joined together they form a cyclopropyl ring,
   $R_3$ is H or linear or branched $C_{1-3}$ alkyl,
   Ar is
      phenyl having
         i) in 4-position halogen, cyano or trifluoromethyl, or
         ii) in 3-position halogen, cyano or trifluoromethyl provided that m is 1,
      a 5-membered heteroaromatic ring containing 1 to 3 heteroatoms wherein said heteroatoms independently of each others are S, O or N; or
      a 6-membered heteroaromatic ring containing 1 to 3 N.

18. A cyclic amine compound of formula (ID) according to claim 17 wherein Ar is phenyl having in 4-position fluorine, cyano or trifluoromethyl.

19. A cyclic amine compound of formula (ID) according to claim 17 wherein $R_1$ and $R_2$ are linked together to form a cyclopropyl ring.

20. A cyclic amine compound of formula (ID) according to claim 17 wherein $R_3$ is hydrogen or methyl.

21. A cyclic amine compound of formula (ID) according to claim 17 wherein m is 1 and Ar is phenyl substituted in 4 position with at least one substituent selected from the group consisting of: fluorine, chlorine, cyano and trifluoromethyl.

22. A cyclic amine compound according to claim 1 wherein A is E and is of the formula (IE)

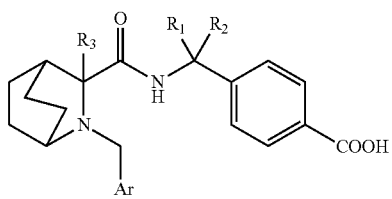

(IE)

and/or pharmaceutically acceptable salts or derivatives thereof wherein $R_1$ and $R_2$ are independently hydrogen, linear o branched $C_{1-3}$ alkyl, or joined together they form a cyclopropyl ring, $R_3$ is H or linear or branched $C_{1-3}$ alkyl, Ar is phenyl having in 3 or 4-position halogen, cyano or trifluoromethyl, a 5-membered heteroaromatic ring containing 1 to 3 heteroatoms wherein said heteroatoms independently of each others are S, O or N; or a 6-membered heteroaromatic ring containing 1 to 3 N.

23. A cyclic amine compound of formula (IE) according to claim 22 wherein Ar is phenyl having in 4-position at least one substituent selected from the group consisting of: fluorine, cyano and trifluoromethyl.

24. A cyclic amine compound of formula (IE) according to claim 22 wherein $R_1$ is hydrogen and $R_2$ is methyl or both $R_1$ and $R_2$ are linked together to form a cyclopropyl ring.

25. A cyclic amine compound of formula (IE) according to claim 22 wherein $R_3$ is hydrogen or methyl.

26. A compound according to claim 1 selected from the group consisting of:

lithium (R)-4-(1-(1-(4-(trifluoromethyl)benzyl)piperidine-2carboxamido)cyclo propyl)benzoate, 4-(1-(6-(4-(trifluoromethyl)benzyl)-6-azaspiro [2.5]octane-5-carboxamido)cyclo propyl) benzoic acid carboxamido)cyclopropyl)benzoic acid, 4-((1S)-1-(6-(4-(trifluoromethyl)benzyl)-6-azaspiro[2.5] octane-5-carboxamido) ethyl)benzoic acid, 4-((1S)-1-(4,4-dimethyl-1-(4-trifluoromethyl)benzyl)piperidine-2-carboxamido) ethyl)benzoic acid, 4-((S)-1-((R)-4,4-difluoro-1-(4-(trifluoromethyl)benzyl) piperidine-2-carboxamido)ethyl)benzoic acid, (R)-4-(1-(4,4-difluoro-1-(4-(trifluoromethyl)benzyl)piperidine-2-carboxamido) cyclopropyl)benzoic acid, 4-(1-(4,4-difluoro-1-(4-(trifluoromethyl)benzyl)piperidine-2-carboxamido)cyclo propyl)benzoic acid, 4-(1-(4,4-difluoro-1-(3-(trifluoromethyl)benzyl)piperidine-2-carboxamido)cyclo propyl)benzoic acid, 4-(1-(4,4-difluoro-1-(3-(trifluoromethyl)benzyl)piperidine-2-carboxamido)cyclo -propyl)benzoic acid, 4-(1-(3-(4-(trifluoromethyl)benzyl)-3-azabicyclo[4.1.0] heptane-4-carboxamido) cyclopropyl) benzoic acid, 4-(1-((3R)-2-(4-(trifluoromethyl) benzyl)-2-azabicyclo [4.1.0]heptane-3-carboxamido)cyclopropyl)benzoic acid, 4-((1 S)-1(3R)-2-(4-(trifluoromethyl)benzyl)-2-azabicyclo[4.1.0]heptane-3-carboxamido)ethyl)benzoic acid, lithium 4-((S)-1-((R)-1-(4-(trifluoromethyl)benzyl)pyrrolidine-2-carboxamido) ethyl) benzoate, 4-(1-((1R,3R,5R)-2-(3-(trifluoromethyl)benzyl)-2-azabicyclo[3.1.0]hexane-3-carboxamido)cyclopropyl)benzoic acid, and 4-(1-((1R,3R,5R)-2-(4-(trifluoromethyl) benzyl)-2-azabicyclo[3.1.0]hexane-3-carboxannido) cyclopropyl)benzoic acid.

27. A pharmaceutical composition comprising a compound of formula (I) according to claim 1 or a pharmaceutically acceptable salt thereof and a pharmaceutically acceptable carrier and/or excipient.

28. A method of treatment of at least one disorder selected from the group consisting of: acute and chronic pain, inflammatory pain, osteoarthritis and rheumatoid arthritis, wherein said method comprises:

identifying a subject patient suffering from acute and chronic pain, inflammatory pain, osteoarthritis and rheumatoid arthritis and any combinations of the foregoing; and administering an effective amount of a compound of formula (I) according to claim 1 to the subject patient.

* * * * *